US012618072B2

(12) United States Patent
Motel et al.

(10) Patent No.: US 12,618,072 B2
(45) Date of Patent: May 5, 2026

(54) METHODS OF TREATMENT OF SCN2A-RELATED DISORDERS

(71) Applicant: Praxis Precision Medicines, Inc., Boston, MA (US)

(72) Inventors: William Motel, Baltimore, MD (US); Alyssa Wyant, Califon, NJ (US); Marjie Hard, Lexington, MA (US)

(73) Assignee: Praxis Precision Medicines, Inc., Boston, MA (US)

( * ) Notice: Subject to any disclaimer, the term of this patent is extended or adjusted under 35 U.S.C. 154(b) by 0 days.

(21) Appl. No.: 18/885,261

(22) Filed: Sep. 13, 2024

(65) Prior Publication Data

US 2025/0092405 A1 Mar. 20, 2025

Related U.S. Application Data

(60) Provisional application No. 63/689,297, filed on Aug. 30, 2024, provisional application No. 63/686,359, filed on Aug. 23, 2024, provisional application No. 63/672,118, filed on Jul. 16, 2024, provisional application No. 63/651,681, filed on May 24, 2024, provisional application No. 63/604,103, filed on Nov. 29, 2023, provisional application No. 63/542,017, filed on Oct. 2, 2023, provisional application No. 63/538,713, filed on Sep. 15, 2023.

(51) Int. Cl.
*C12N 15/113* (2010.01)
*A61P 25/08* (2006.01)

(52) U.S. Cl.
CPC .......... *C12N 15/1138* (2013.01); *A61P 25/08* (2018.01); *C12N 2310/315* (2013.01); *C12N 2310/321* (2013.01); *C12N 2310/3341* (2013.01); *C12N 2310/341* (2013.01); *C12N 2320/34* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Clercq et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohtsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |

(Continued)

FOREIGN PATENT DOCUMENTS

| | | | |
|---|---|---|---|
| WO | 2003/060525 | A1 | 7/2003 |
| WO | 2004/016754 | A2 | 2/2004 |

(Continued)

OTHER PUBLICATIONS

Bergren et al. Mammalian Genome vol. 16, pp. 683-690 (Year: 2005).*

ClinVar Miner, GeneDx. clinvarminer.genetics.utah.edu/variants-by-gene/SCN2A/submitter/26957/likely%20pathogenic, retrieved on line on Nov. 14, 2023, pp. 1-5 (Year: 2024).*

Nair et al. Journal of Basic and Clinical Pharmacology vol. 7, pp. 27-31 (Year: 2016).*

(Continued)

*Primary Examiner* — Brian Whiteman

(74) *Attorney, Agent, or Firm* — McCarter & English, LLP; Jonathan M. Sparks; Yelena Margolin

(57) ABSTRACT

Provided are methods of treating a subject with a SCN2A-related disorder, e.g., Developmental and Epileptic Encephalopathies (DEE), comprising administering to the subject an oligomeric compound. Also provided are methods of reducing frequency of seizures experienced by a subject with a SCN2A-related disorder, comprising administering to the subject an oligomeric compound.

22 Claims, 29 Drawing Sheets

Specification includes a Sequence Listing.

(56) References Cited

U.S. PATENT DOCUMENTS

| | | | | |
|---|---|---|---|---|
| 5,386,023 | A | 1/1995 | Sanghvi et al. | |
| 5,393,878 | A | 2/1995 | Leumann | |
| 5,399,676 | A | 3/1995 | Froehler | |
| 5,403,711 | A | 4/1995 | Walder et al. | |
| 5,405,938 | A | 4/1995 | Summerton et al. | |
| 5,405,939 | A | 4/1995 | Suhadolnik et al. | |
| 5,432,272 | A | 7/1995 | Benner | |
| 5,434,257 | A | 7/1995 | Matteucci et al. | |
| 5,446,137 | A | 8/1995 | Maag et al. | |
| 5,453,496 | A | 9/1995 | Caruthers et al. | |
| 5,455,233 | A | 10/1995 | Spielvogel et al. | |
| 5,457,187 | A | 10/1995 | Gmeiner et al. | |
| 5,457,191 | A | 10/1995 | Cook et al. | |
| 5,459,255 | A | 10/1995 | Cook et al. | |
| 5,466,677 | A | 11/1995 | Baxter et al. | |
| 5,466,786 | A | 11/1995 | Buhr et al. | |
| 5,470,967 | A | 11/1995 | Huie et al. | |
| 5,476,925 | A | 12/1995 | Letsinger et al. | |
| 5,484,908 | A | 1/1996 | Froehler et al. | |
| 5,489,677 | A | 2/1996 | Sanghvi et al. | |
| 5,491,133 | A | 2/1996 | Walder et al. | |
| 5,502,177 | A | 3/1996 | Matteucci et al. | |
| 5,508,270 | A | 4/1996 | Baxter et al. | |
| 5,514,785 | A | 5/1996 | Van Ness et al. | |
| 5,519,126 | A | 5/1996 | Hecht | |
| 5,519,134 | A | 5/1996 | Acevedo et al. | |
| 5,525,711 | A | 6/1996 | Hawkins et al. | |
| 5,527,899 | A | 6/1996 | Froehler | |
| 5,536,821 | A | 7/1996 | Agrawal et al. | |
| 5,541,306 | A | 7/1996 | Agrawal et al. | |
| 5,541,307 | A | 7/1996 | Cook et al. | |
| 5,550,111 | A | 8/1996 | Suhadolnik et al. | |
| 5,552,540 | A | 9/1996 | Haralambidis | |
| 5,561,225 | A | 10/1996 | Maddry et al. | |
| 5,563,253 | A | 10/1996 | Agrawal et al. | |
| 5,565,350 | A | 10/1996 | Kmiec | |
| 5,565,555 | A | 10/1996 | Froehler et al. | |
| 5,567,811 | A | 10/1996 | Misiura et al. | |
| 5,571,799 | A | 11/1996 | Tkachuk et al. | |
| 5,576,427 | A | 11/1996 | Cook et al. | |
| 5,587,361 | A | 12/1996 | Cook et al. | |
| 5,587,469 | A | 12/1996 | Cook et al. | |
| 5,587,470 | A | 12/1996 | Cook et al. | |
| 5,591,722 | A | 1/1997 | Montgomery et al. | |
| 5,594,121 | A | 1/1997 | Froehler et al. | |
| 5,596,086 | A | 1/1997 | Matteucci et al. | |
| 5,596,091 | A | 1/1997 | Switzer | |
| 5,597,909 | A | 1/1997 | Urdea et al. | |
| 5,602,240 | A | 2/1997 | De Mesmaeker et al. | |
| 5,608,046 | A | 3/1997 | Cook et al. | |
| 5,610,289 | A | 3/1997 | Cook et al. | |
| 5,610,300 | A | 3/1997 | Altmann et al. | |
| 5,614,617 | A | 3/1997 | Cook et al. | |
| 5,618,704 | A | 4/1997 | Sanghvi et al. | |
| 5,623,065 | A | 4/1997 | Cook et al. | |
| 5,623,070 | A | 4/1997 | Cook et al. | |
| 5,625,050 | A | 4/1997 | Beaton et al. | |
| 5,627,053 | A | 5/1997 | Usman et al. | |
| 5,633,360 | A | 5/1997 | Bischofberger et al. | |
| 5,639,873 | A | 6/1997 | Barascut et al. | |
| 5,645,985 | A | 7/1997 | Froehler et al. | |
| 5,646,265 | A | 7/1997 | McGee | |
| 5,646,269 | A | 7/1997 | Matteucci et al. | |
| 5,652,355 | A | 7/1997 | Metelev et al. | |
| 5,652,356 | A | 7/1997 | Agrawal | |
| 5,663,312 | A | 9/1997 | Chaturvedula | |
| 5,670,633 | A | 9/1997 | Cook et al. | |
| 5,672,697 | A | 9/1997 | Buhr et al. | |
| 5,677,437 | A | 10/1997 | Teng et al. | |
| 5,677,439 | A | 10/1997 | Weis et al. | |
| 5,681,941 | A | 10/1997 | Cook et al. | |
| 5,698,685 | A | 12/1997 | Summerton et al. | |
| 5,700,920 | A | 12/1997 | Altmann et al. | |
| 5,700,922 | A | 12/1997 | Cook | |
| 5,721,218 | A | 2/1998 | Froehler | |
| 5,750,692 | A | 5/1998 | Cook et al. | |
| 5,763,588 | A | 6/1998 | Matteucci et al. | |
| 5,792,608 | A | 8/1998 | Swaminathan et al. | |
| 5,792,847 | A | 8/1998 | Buhr et al. | |
| 5,801,154 | A | 9/1998 | Baracchini et al. | |
| 5,808,027 | A | 9/1998 | Cook et al. | |
| 5,830,653 | A | 11/1998 | Froehler et al. | |
| 5,859,221 | A | 1/1999 | Cook et al. | |
| 5,948,903 | A | 9/1999 | Cook et al. | |
| 5,994,517 | A | 11/1999 | Ts'o et al. | |
| 6,005,087 | A | 12/1999 | Cook et al. | |
| 6,005,096 | A | 12/1999 | Matteucci et al. | |
| 6,166,199 | A | 12/2000 | Cook et al. | |
| 6,300,319 | B1 | 10/2001 | Manoharan | |
| 6,426,220 | B1 | 7/2002 | Bennett et al. | |
| 6,525,191 | B1 | 2/2003 | Ramasamy | |
| 6,531,584 | B1 | 3/2003 | Cook et al. | |
| 6,582,908 | B2 | 6/2003 | Fodor et al. | |
| 6,600,032 | B1 | 7/2003 | Manoharan et al. | |
| 6,660,720 | B2 | 12/2003 | Manoharan | |
| 6,770,748 | B2 | 8/2004 | Imanishi et al. | |
| 7,015,315 | B1 | 3/2006 | Cook et al. | |
| 7,053,207 | B2 | 5/2006 | Wengel | |
| 7,101,993 | B1 | 9/2006 | Cook et al. | |
| 7,262,177 | B2 | 8/2007 | Ts'O et al. | |
| 7,399,845 | B2 | 7/2008 | Seth et al. | |
| 7,427,672 | B2 | 9/2008 | Imanishi et al. | |
| 7,491,805 | B2 | 2/2009 | Vargeese et al. | |
| 7,547,684 | B2 | 6/2009 | Seth et al. | |
| 7,569,686 | B1 | 8/2009 | Bhat et al. | |
| 7,666,854 | B2 | 2/2010 | Seth et al. | |
| 7,696,345 | B2 | 4/2010 | Allerson et al. | |
| 7,723,509 | B2 | 5/2010 | Manoharan et al. | |
| 7,741,457 | B2 | 6/2010 | Seth et al. | |
| 7,750,131 | B2 | 7/2010 | Seth et al. | |
| 7,875,733 | B2 | 1/2011 | Bhat et al. | |
| 7,939,677 | B2 | 5/2011 | Bhat et al. | |
| 8,022,193 | B2 | 9/2011 | Seth et al. | |
| 8,030,467 | B2 | 10/2011 | Seth et al. | |
| 8,080,644 | B2 | 12/2011 | Wengel et al. | |
| 8,088,746 | B2 | 1/2012 | Seth et al. | |
| 8,088,904 | B2 | 1/2012 | Swayze et al. | |
| 8,106,022 | B2 | 1/2012 | Manoharan et al. | |
| 8,124,745 | B2 | 2/2012 | Allerson et al. | |
| 8,143,005 | B2 | 3/2012 | Rouleau et al. | |
| 8,153,365 | B2 | 4/2012 | Wengel et al. | |
| 8,268,980 | B2 | 9/2012 | Seth et al. | |
| 8,278,283 | B2 | 10/2012 | Seth et al. | |
| 8,278,425 | B2 | 10/2012 | Prakash et al. | |
| 8,278,426 | B2 | 10/2012 | Seth et al. | |
| 8,440,803 | B2 | 5/2013 | Swayze et al. | |
| 8,501,805 | B2 | 8/2013 | Seth et al. | |
| 8,530,640 | B2 | 9/2013 | Seth et al. | |
| 8,546,556 | B2 | 10/2013 | Seth et al. | |
| RE44,779 | E | 2/2014 | Imanishi et al. | |
| 8,828,956 | B2 | 9/2014 | Manoharan et al. | |
| 9,005,906 | B2 | 4/2015 | Swayze et al. | |
| 9,012,421 | B2 | 4/2015 | Migawa et al. | |
| 9,127,276 | B2 | 9/2015 | Prakash et al. | |
| 9,290,760 | B2 | 3/2016 | Rajeev et al. | |
| 12,227,746 | B2 * | 2/2025 | Jafar-Nejad ......... | C12N 15/113 |
| 2001/0053519 | A1 | 12/2001 | Fodor et al. | |
| 2003/0158403 | A1 | 8/2003 | Manoharan et al. | |
| 2003/0175906 | A1 | 9/2003 | Manoharan et al. | |
| 2003/0228597 | A1 | 12/2003 | Cowsert et al. | |
| 2004/0171570 | A1 | 9/2004 | Allerson et al. | |
| 2005/0130923 | A1 | 6/2005 | Bhat et al. | |
| 2006/0148740 | A1 | 7/2006 | Platenburg | |
| 2007/0031844 | A1 | 2/2007 | Khvorova et al. | |
| 2008/0039618 | A1 | 2/2008 | Allerson et al. | |
| 2010/0190837 | A1 | 7/2010 | Migawa et al. | |
| 2010/0197762 | A1 | 8/2010 | Swayze | |
| 2013/0130378 | A1 | 5/2013 | Manoharan et al. | |
| 2014/0107330 | A1 | 4/2014 | Freier et al. | |
| 2015/0018540 | A1 | 1/2015 | Prakash et al. | |
| 2015/0184153 | A1 | 7/2015 | Freier et al. | |
| 2015/0191727 | A1 | 7/2015 | Migawa et al. | |
| 2015/0267195 | A1 | 9/2015 | Seth et al. | |
| 2015/0275212 | A1 | 10/2015 | Albaek et al. | |

(56) References Cited

U.S. PATENT DOCUMENTS

| | | | | |
|---|---|---|---|---|
| 2017/0020851 | A1 | 1/2017 | Kalafer et al. | |
| 2019/0192691 | A1 | 6/2019 | Barrett et al. | |
| 2021/0324386 | A1* | 10/2021 | Petrou | C12N 15/1138 |
| 2022/0056455 | A1 | 2/2022 | Petrou et al. | |
| 2024/0026353 | A1 | 1/2024 | Jafar-Nejad et al. | |
| 2024/0102012 | A1 | 3/2024 | Jafar-Nejad et al. | |
| 2025/0179503 | A1 | 6/2025 | Oldham et al. | |
| 2025/0270556 | A1 | 8/2025 | Jafar-Nejad et al. | |

FOREIGN PATENT DOCUMENTS

| | | | |
|---|---|---|---|
| WO | 2004/045543 | A2 | 6/2004 |
| WO | 2005/116204 | A1 | 8/2005 |
| WO | 2016/027168 | A2 | 2/2016 |
| WO | 2019/084050 | A1 | 5/2019 |
| WO | 2019/143831 | A1 | 7/2019 |
| WO | 2020/041348 | A1 | 2/2020 |
| WO | 2020/154462 | A1 | 7/2020 |
| WO | 2020/227406 | A1 | 11/2020 |
| WO | 2021/222342 | A1 | 11/2021 |
| WO | 2022/032060 | A2 | 2/2022 |
| WO | 2023/192885 | A2 | 10/2023 |

OTHER PUBLICATIONS

Barret et al., Oligodendroglial excitability mediated by glutamatergic inputs and Nav1.2 activation. Nat Commun. Sep. 15, 2017;8(1):557, 15 pages.

Branch, A good antisense molecule is hard to find. Trends Biochem Sci. Feb. 1998;23(2):45-50.

Chin, On the Preparation and Utilization of Isolated and Purified Oligonucleotides. University of North Carolina School of Law. 1 page, Mar. 9, 2002.

Cooke, Antisense Drug Technology, Principles, Strategies, and Application, Second Edition. CRC Press. pp. 414, (2008).

Cooke, Basic Principles of Antisense Therapeutics. Antisense Research and Application. Chapter 1, pp. 1-50, (1998).

De Lera Ruiz et al., Voltage-Gated Sodium Channels: Structure, Function, Pharmacology, and Clinical Indications. J Med Chem. Sep. 24, 2015;58(18):7093-118.

Egli et al., Synthesis, improved antisense activity and structural rationale for the divergent RNA affinities of 3'-fluoro hexitol nucleic acid (FHNA and Ara-FHNA) modified oligonucleotides. J Am Chem Soc. Oct. 19, 2011;133(41):16642-9.

Gautschi et al., Activity of a novel bcl-2/bcl-xL-bispecific antisense oligonucleotide against tumors of diverse histologic origins. J Natl Cancer Inst. Mar. 21, 2001;93(6):463-71.

Heintz, BAC to the future: the use of bac transgenic mice for neuroscience research. Nat Rev Neurosci. Dec. 2001;2 (12):861-70.

Li et al., Antisense Oligonucleotide Therapy for Scn2a Gain-of-function Epilepsies. Society for Neuroscience, Chicago, IL. 1 page, poster presentation, Oct. 19-23, 2019.

Li et al., Antisense oligonucleotide therapy for SCN2A gain-of-function epilepsy. bioRxiv, doi:https://doi.org/10.1101/2020.09.09.289900. 28 pages, Sep. 11, 2020.

Li et al., Antisense oligonucleotide therapy reduces seizures and extends life span in an SCN2A gain-of-function epilepsy model. J Clin Invest. Dec. 1, 2021;131(23):e152079, 13 pages.

Maher et al., Comparative hybrid arrest by tandem antisense oligodeoxyribonucleotides or oligodeoxyribonucleoside methylphosphonates in a cell-free system. Nucleic Acids Res. Apr. 25, 1988;16(8):3341-58.

New England BioLabs, Inc., Nucleic Acids, Linkers and Primers. Catalog, pp. 121, 284, 1998/1999.

Reynolds et al., Rational siRNA design for RNA interference. Nat Biotechnol. Mar. 2004;22(3):326-30.

Sanders et al., Progress in Understanding and Treating SCN2A-Mediated Disorders. Trends Neurosci. Jul. 2018;41 (7):442-456.

Sanghvi, Heterocyclic Base Modifications in Nucleic Acids and Their Applications in Antisense Oligonucleotides. Antisense Research and Applications, Chapter 15. CRC Press, Boca Raton. Stanley T. Crooke (Ed.). pp. 273-288, (1993).

Schwarz et al., Clinical and genetic spectrum of SCN2A-associated episodic ataxia. Eur J Paediatr Neurol. May 2019;23(3):438-447.

Seth et al., Short antisense oligonucleotides with novel 2'-4' conformationaly restricted nucleoside analogues show improved potency without increased toxicity in animals. J Med Chem. Jan. 8, 2009;52(1):10-3.

Wolff et al., Genetic and phenotypic heterogeneity suggest therapeutic implications in SCN2A-related disorders. Brain. May 1, 2017;140(5):1316-1336.

Wolff et al., Phenotypic spectrum and genetics of SCN2A-related disorders, treatment options, and outcomes in epilepsy and beyond. Epilepsia. Dec. 2019;60 Suppl 3:S59-S67.

Woolf et al., Specificity of antisense oligonucleotides in vivo. Proc Natl Acad Sci U S A. Aug. 15, 1992;89(16):7305-9.

International Search Report and Written Opinion for Application No. PCT/US2021/044887, dated Jan. 28, 2022, 11 pages.

International Search Report and Written Opinion for Application No. PCT/US2023/065074, dated Nov. 28, 2023, 18 pages.

Evers et al., Antisense oligonucleotides in therapy for neurodegenerative disorders. Adv Drug Deliv Rev. Jun. 29, 2015;87:90-103.

Frizzo, Embrave: A Clinical Trial of PRAX-222, a Novel Antisense Oligonucleotide, in Pediatric Participants with Early Onset SCN2A Developmental and Epileptic Encephalopathy. Praxis Precision Medicine. 2 pages, Abstract No. 3.198, Dec. 4, 2023.

Chilean Office Action for Application No. 2023-00393, dated Oct. 11, 2024, 20 pages.

International Preliminary Report on Patentability for Application No. PCT/US2023/065074, dated Oct. 10, 2024, 8 pages.

International Search Report and Written Opinion for Application No. PCT/US2024/046682, dated Feb. 19, 2025, 26 pages.

* cited by examiner

A

C

A

Subject 2001

B

Subject 2002

C

Subject 2003

D

C

B

C

F

F

METHODS OF TREATMENT OF SCN2A-RELATED DISORDERS

RELATED APPLICATIONS

This application claims priority to U.S. Provisional Patent Application No. 63/689,297, filed on Aug. 30, 2024; U.S. Provisional Patent Application No. 63/686,359, filed on Aug. 23, 2024; U.S. Provisional Patent Application No. 63/672,118, filed on Jul. 16, 2024; U.S. Provisional Patent Application No. 63/651,681, filed on May 24, 2024; U.S. Provisional Patent Application No. 63/604,103, filed on Nov. 29, 2023; U.S. Provisional Patent Application No. 63/542,017, filed on Oct. 2, 2023; and U.S. Provisional Patent Application No. 63/538,713, filed on Sep. 15, 2023. The entire contents of each of the foregoing applications are hereby incorporated herein by reference.

SEQUENCE LISTING

The instant application contains a Sequence Listing which has been submitted electronically in XML file format and is hereby incorporated by reference in its entirety. Said XML copy, created on Sep. 13, 2024, is named 137486-09408_SL.xml and is 69,914 bytes in size.

BACKGROUND

The human gene SCN2A encodes human SCN2A protein, the alpha-1 subunit of the voltage-gated sodium channel NaV1.2. Mutations in SCN2A are associated with a variety of neurodevelopmental and intellectual diseases and disorders, such as Developmental and Epileptic Encephalopathies (DEE), including Early Seizure Onset Epileptic Encephalopathy (EE), Late Seizure Onset Epileptic Encephalopathy, and Benign Familial Neonatal-Infantile Seizures (BFNIS). Mutations in SCN2A are also associated with intellectual disability (ID) and/or autism spectrum disorder (ASD), with or without seizures (Wolff, M., et al., 2019, *Epilepsia* 60, S59-S67; Sanders, S., et al., 2018, *Trends in Neurosciences* 41, 442-456; Wolff, M., et al., 2017, *Brain* 140, 1316-1336). DEEs include a broad range of diseases that include neonatal and early infantile DEE, for example Ohtahara Syndrome and epilepsy with migrating focal seizures of infancy (EIMFS); infantile and childhood DEE, for example West Syndrome and Lennon-Gastaut Syndrome; Dravet Syndrome; Idiopathic/Generic Generalized Epilepsies (IGE/GGE); Temporal Lobe Epilepsy; Myoclonic Astatic Epilepsy (MAE); Migrating Partial Epilepsy of Infancy (MMPSI); and familial hemiplegic migraines, with or without epilepsy (Wolff, M., et al., 2019; Harkin, L. A., et al., 2007, *Brain* 130, 843-852; Escayg, A., et al., 2010, *Epilepsia* 51, 1650-1658; Miller I. O, et al., 2007 Nov. 29 [Updated 2019 Apr. 18]. In: Adam M P, Ardinger H H, Pagon R A, et al., editors. GeneReviews® [Internet]. Seattle (WA): University of Washington, Seattle; 1993-2020. Available from: www.ncbi.nlm.nih.gov/books/NBK1318/).

Symptoms and hallmarks associated with DEEs include seizures, hypotonia, sensory integration disorders, motor development delays and dysfunctions, intellectual and cognitive dysfunctions, movement and balance dysfunctions, visual dysfunctions, delayed language and speech, gastrointestinal disorders, neurodevelopmental delays, sleep problems, and sudden unexpected death in epilepsy. Seizures include focal, clonic, tonic, and generalized tonic and clonic seizures, prolonged seizures (often lasting longer than 10 minutes), and frequent seizures (for example, convulsive, myoclonic, absence, focal, obtundation status, and tonic seizures) (Guzzetta, F., 2011, *Epilepsia* 52:S2, 35-38; Anwar et al., 2019, *Cureus* 11, e5006, Wolff et al., 2019). Symptoms and hallmarks associated with ID and ASD include motor development delays, delayed social and language milestones, repetitive actions, uncoordinated oral movements, gastrointestinal disorders, sleep problems, and seizures (Wolff et al., 2019).

Currently there is a lack of acceptable options for treating DEEs such as EEs, Late Onset EEs, and BFNIS; and for treating ID and ASD. It is therefore an object herein to provide methods for the treatment of such diseases and disorders.

SUMMARY OF THE INVENTION

In one aspect, disclosed herein is a method of reducing frequency of seizures experienced by a subject with a SCN2A-related disorder, said method comprising administering to said subject an effective amount of an oligomeric compound, wherein: the SCN2A-related disorder is caused by a gain-of-function mutation in SCN2A gene; the oligomeric compound comprises a 6-10-4 MOE gapmer having a sequence (from 5' to 3') of CCACGACATATTTTTCTACA (SEQ ID NO: 3); wherein each of nucleosides 1-6 and 17-20 (from 5' to 3') are 2'-MOE nucleosides and each of nucleosides 7-16 are 2'-β-D-deoxynucleosides; wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages; and each cytosine is a 5-methyl cytosine.

In some embodiments, the oligomeric compound is administered at a dose of about 0.1 mg to about 20 mg. In some embodiments, the oligomeric compound is administered at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg or about 20 mg. In some embodiments, the oligomeric compound is administered at a dose of about 0.5 mg, about 1 mg, about 1.5 mg, about 2 mg, about 2.5 mg, about 3 mg, about 3.5 mg, about 4 mg, about 5 mg, about 8 mg, about 12 mg or about 15 mg. In some embodiments, the oligomeric compound is administered at a dose of about 1 mg. In some embodiments, the oligomeric compound is administered at a dose of about 8 mg.

In some embodiments, the oligomeric compound is administered at a dose of about 0.5 mg to about 8 mg, e.g., about 0.5 mg, about 1 mg, about 1.5 mg, about 2 mg, about 2.5 mg, about 3 mg, about 3.5 mg, about 4 mg, about 5 mg, about 6 mg, about 7 mg or about 8 mg. Is some embodiments, the oligomeric compound is administered at a dose of about 0.5 mg to about 8 mg, e.g., about 0.5 mg, about 1 mg, about 1.5 mg, about 2 mg, about 2.5 mg, about 3 mg, about 3.5 mg, about 4 mg, about 5 mg, about 6 mg, about 7 mg or about 8 mg, every 2-6 weeks, e.g., every 2 weeks, every 3 weeks, every 4 weeks, every 5 weeks or every 6 weeks. Intervals between administrations may be approximate and may be varied by a clinician based upon medical judgment and/or clinical indications such as for example patient travel, availability of medical personnel and drug, illness, or adverse event in a patient.

In some embodiments, the oligomeric compound is administered at a total dose of about 15 mg to about 30 mg over about 20-25 weeks, e.g., about 15 mg, about 20 mg, about 22.5 mg, about 25 mg or about 30 mg over 20 weeks, 21 weeks, 22 weeks, 23 weeks, 24 weeks or 25 weeks. In some embodiments, the oligomeric compound is administered at a total dose of about 22.5 mg over 23 weeks.

In some embodiments, the oligomeric compound is administered once per month. In other embodiments, the oligomeric compound is administered more than once per month. In further embodiments, the oligomeric compound is administered once every two, three, four, five, or six months, or once per year.

In some embodiments, the seizures are selected from the group consisting of focal motor seizures, tonic seizures, generalized tonic-clonic seizures and myoclonic seizures.

In some embodiments, administration of the oligomeric compound results in a decrease in the average number of daily seizures experienced by the subject in a 28-day period, as compared to the average number of daily seizures experienced by the subject prior to administration of the oligomeric compound.

In some embodiments, administration of the oligomeric compound results in a reduction in the number of seizures experienced by the subject in a 28-day period by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, as compared to the number of seizures experienced by the subject prior to administration of the oligomeric compound.

In one aspect, disclosed herein is a method of treating a subject with a SCN2A-related disorder, said method comprising administering to said subject an oligomeric compound at a dose of about 0.1 mg to about 20 mg, wherein: the SCN2A-related disorder is caused by a gain-of-function mutation in SCN2A gene; the oligomeric compound comprises a 6-10-4 MOE gapmer having a sequence (from 5' to 3') of CCACGACATATTTTTCTACA (SEQ ID NO: 3); each of nucleosides 1-6 and 17-20 (from 5' to 3') are 2'-MOE nucleosides and each of nucleosides 7-16 are 2'-β-D-deoxynucleosides; the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages; and each cytosine is a 5-methyl cytosine.

In some embodiments, the oligomeric compound is administered at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg or about 20 mg. In some embodiments, the oligomeric compound is administered at a dose of about 0.5 mg, about 1 mg, about 1.5 mg, about 3 mg, about 3.5 mg, about 4 mg, about 5 mg, about 8 mg, about 12 mg or about 15 mg. In some embodiments, the oligomeric compound is administered at a dose of about 1 mg. In some embodiments, the oligomeric compound is administered at a dose of about 8 mg.

In some embodiments, the oligomeric compound is administered about once per month. In other embodiments, the oligomeric compound is administered more frequently than about once per month. In other embodiments, the oligomeric compound is administered about once every two, three, four, five, or six months, or once per year.

In some embodiments, administration of the oligomeric compound results in a decrease in the frequency of seizures experienced by the subject, as compared to the frequency of seizures experienced by the subject prior to administration of the oligomeric compound.

In some embodiments, administration of the oligomeric compound results in a reduction in the average number of daily seizures experienced by the subject in a 28-day period, as compared to the average number of daily seizures experienced by the subject in a 28-day period prior to administration of the oligomeric compound.

In some embodiments, administration of the oligomeric compound results in a reduction in the number of seizures experienced by the subject in a 28-day period by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80% or at least about 85%, as compared to the number of seizures experienced by the subject prior to administration of the oligomeric compound.

In some embodiments, administration of the oligomeric compound results in an increase in the number of seizure-free days experienced by the subject, as compared to the number of seizure-free days experienced by the subject prior to administration of the oligomeric compound.

In some embodiments, administration of the oligomeric compound results in an increase in the number of seizure-free days in a time period experienced by the subject, as compared to the number of seizure-free days experienced by the subject in the same time period prior to administration of the oligomeric compound In some embodiments, administration of the oligomeric compound results in an increase in % of seizure-free days per 28-day period experienced by the subject, as compared to % of seizure-free days per 28-day period experienced by the subject prior to administration of the oligomeric compound.

In some embodiments, the seizures are selected from the group consisting of focal motor seizures, tonic seizures, generalized tonic-clonic seizures and myoclonic seizures.

In some embodiments, the subject is a human. In some embodiments, the subject is between 2 and 18 years old. In some embodiments, the subject is between 0 and 24 months old. In some embodiments, the subject is a newborn. In some embodiments, the newborn is a premature newborn. In some embodiments, the newborn has low birth weight with or without prematurity.

In some embodiments, the SCN2A-related disorder is SCN2A developmental and epileptic encephalopathy (SCN2A DEE). In some embodiments, the SCN2A-related disorder is early seizure onset epileptic encephalopathy (EE).

In some embodiments, the gain-of-function mutation in SCN2A gene is selected from the group consisting of L210Q, A263V, E430A, R1882Q, G879R, Q1479H, V423L, G1593R, K1502N, V1601L, G211D, S1780I, D343H and A1329D. In some embodiments, the gain-of-function mutation is A1329D.

In some embodiments, the oligomeric compound comprises a modified oligonucleotide represented by the following chemical notation: mCesmCeoAeomCeoGeoAeomCdsAdsTdsAdsTdsTdsTdsTdsTdsmCdsTeoAesmCesAe (SEQ ID NO: 3), wherein: A=an adenine nucleobase, mC=a 5-methyl cytosine nucleobase, G=a guanine nucleobase, T=a thymine nucleobase, e=a 2'-MOE sugar moiety, d=a 2'-β-D-deoxyribosyl sugar moiety, s=a phosphorothioate internucleoside linkage, and o=a phosphodiester internucleoside linkage.

In some embodiments, the oligomeric compound is a modified oligonucleotide represented by the following chemical structure:

(SEQ ID NO: 3)

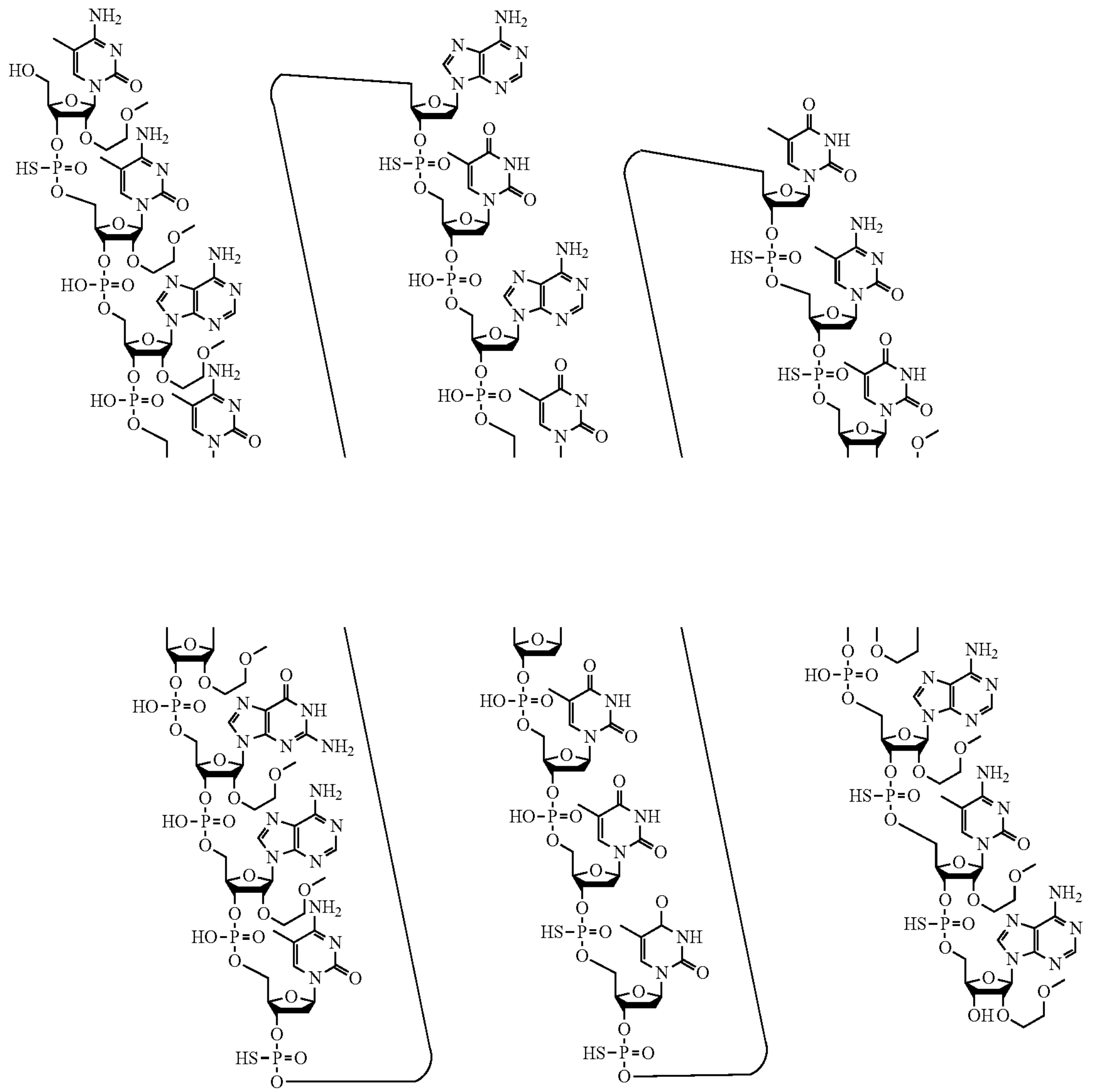

In some embodiments, the modified oligonucleotide is a sodium salt or a potassium salt. In some embodiments, the modified oligonucleotide is a sodium salt.

In some embodiments, the modified oligonucleotide represented by the following chemical structure:

(SEQ ID NO: 3)

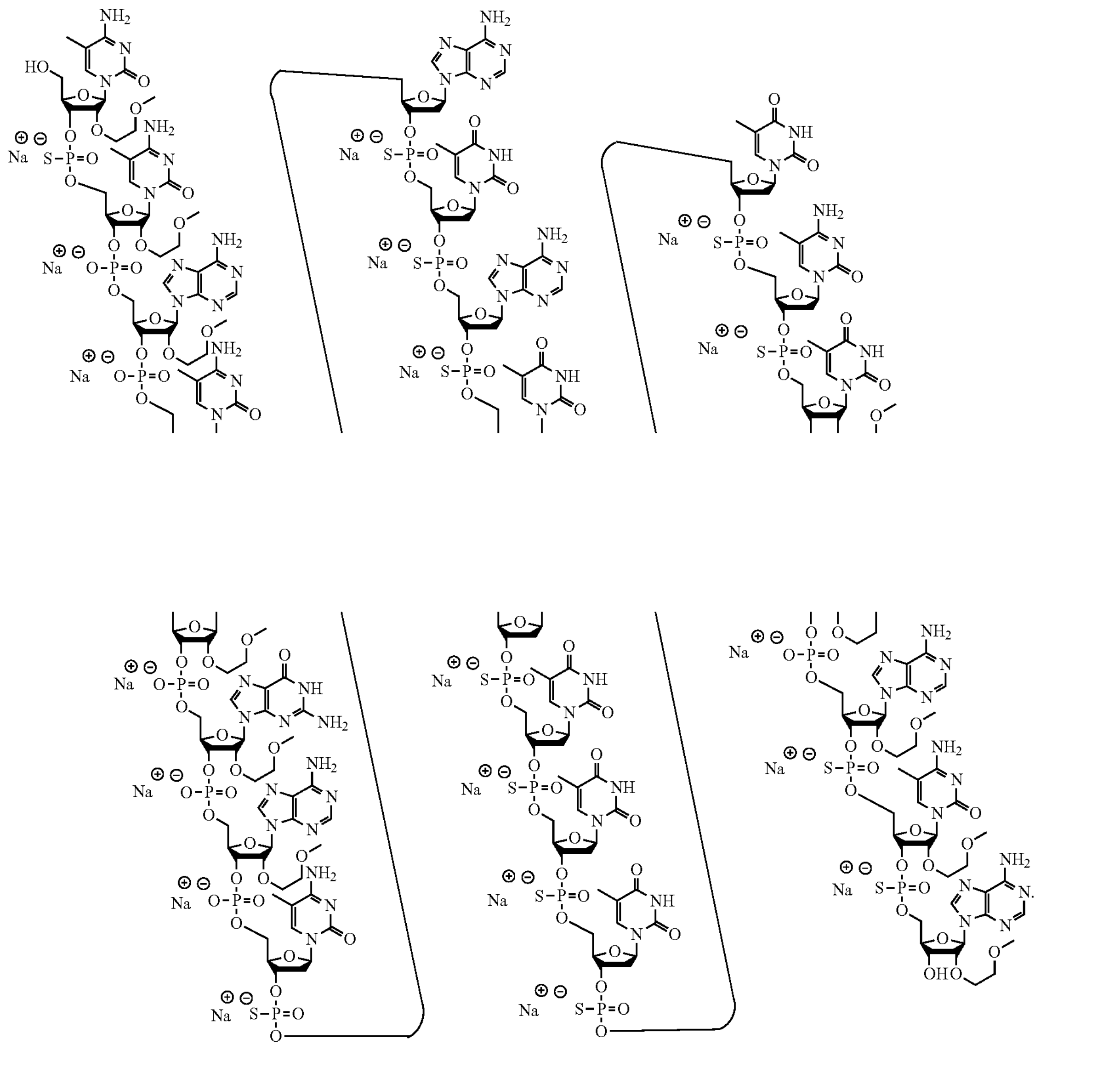

In some embodiments, the oligomeric compound is administered as a part of a pharmaceutical composition comprising the oligomeric compound and a pharmaceutically acceptable diluent or carrier. In some embodiments, the pharmaceutically acceptable diluent is artificial CSF (aCSF) or phosphate-buffered saline (PBS). In some embodiments, the pharmaceutically acceptable diluent is aCSF.

In some embodiments, the oligomeric compound is administered intrathecally.

BRIEF DESCRIPTION OF THE DRAWINGS

FIG. 4, Panel B is a boxplot showing daily seizure frequency by dosing period (28 days) for subject 2002 after 3 doses.

FIG. 4, Panel C is a boxplot showing daily seizure frequency by dosing period (28 days) for subject 2003 after 3 doses.

FIG. 4, Panel D is a boxplot showing daily seizure frequency by dosing period (28 days) for subject 2004 after 3 doses.

FIG. 5, Panel B is a graph showing daily seizure frequency per dose period for subject 2002 after 3 doses.

FIG. 5, Panel C is a graph showing daily seizure frequency per dose period for subject 2003 after 3 doses.

FIG. 5, Panel D is a graph showing daily seizure frequency per dose period for subject 2004 after 3 doses.

FIG. 6, Panel B is a bar graph showing mean and median relative percentage change from baseline in seizure-free days for 4 subjects. The results represent overall relative percentage increase in proportion of seizure-free days for 4 subjects.

FIG. 7, Panel B shows representative aEEG traces in the subject demonstrating seizure reduction after several loading doses of phenytoin (arrow) in week three.

FIG. 7, Panel C shows representative aEEG traces demonstrating that seizure reduction was not sustainable as status pattern reoccurred even when phenytoin levels were >40 g/mL. Seizures were subclinical or motor seizures.

FIG. 8, Panel B shows zoomed-in views of S4-$5_{DIII}$ region, before and after in silico mutagenesis (top, WT; bottom, A1329D). The D1329-F1489 interaction is likely to affect the binding of the IFM inactivation motif to its receptor pocket, resulting in delayed inactivation and persistent current.

FIG. 9, Panel B shows persistent inward $I_{Na}$-voltage relationships. Representative $I_{Na}$ traces elicited by −10 mV depolarizations are shown on the left.

FIG. 9, Panel C shows voltage dependence of activation.

FIG. 9, Panel D shows voltage dependence of inactivation.

FIG. 9, Panel E shows dependence of the time course of $I_{Na}$ inactivation on the membrane potential. Representative WT and A1329D INa traces elicited by −25 mV and −5 mV voltages are shown on the left.

FIG. 9, Panel F shows input-output relationships for WT and A1329D variant.

FIG. 10, Panel B is a bar graph showing the number of seizures per hour per medication level of phenytoin (PHT) and carbamazepine (CBZ). A total of seven Compound 1 intrathecal doses were administered (30.5 mg total dose).

FIG. 10, Panel C shows aEEG traces 1 day before the first administration of Compound 1 showing peak seizure frequency (status epilepticus).

FIG. 10, Panel D shows aEEG traces 1 week after first administration of Compound 1.

FIG. 10, Panel E shows aEEG traces 7 weeks after first administration of Compound 1.

FIG. 10, Panel F shows aEEG traces 10 weeks after first administration of Compound 1.

DETAILED DESCRIPTION OF THE INVENTION

Definitions

Figure 1:
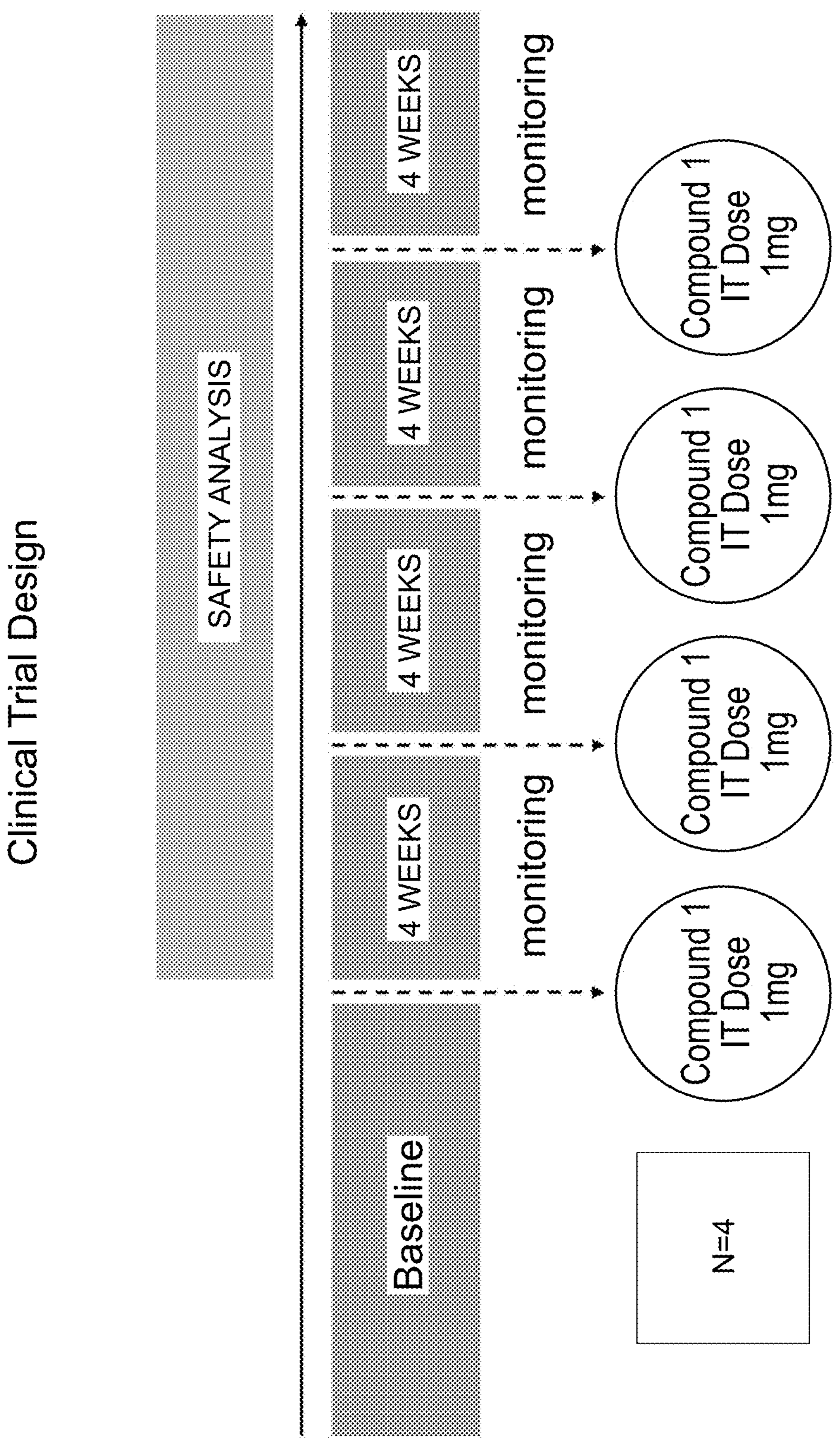
FIG. 1 is a schematic illustrating dosing of the subjects in the clinical trial.

As used herein, the terms "about" and "approximately" refer to a value that is within 10% above or below the value being described.

As used herein, the term "SCN2A" refers to $Na_v1.2$, the alpha subunit of a voltage-gated sodium channel that is expressed in the brain, having an amino acid sequence from any vertebrate or mammalian source, including, but not limited to, human, bovine, chicken, rodent, mouse, rat, porcine, ovine, primate, monkey, and guinea pig, unless specified otherwise. SCN2A can, in some embodiments, include one or more mutations that lead to neurological diseases such as epileptic encephalitis. SCN2A is encoded by the SCN2A gene. In certain embodiments, SCN2A is a human SCN2A represented by SEQ ID NO: 1 as described herein.

Example accession numbers for human SCN2A mRNA transcript and human SCN2A protein are detailed below:

```
SCN2A mRNA transcript: NM_001040142.2 (SEQ ID NO: 4;
aacagacattgggtaccatcgaatgactgtcagaacagaaagctaaggcaaaggagggaggatgctgtggtcatcctttcttgtttttttcttct

ttaatgaggatagagcacatgtgagattttactttctactccagtaaaaattctgaagaattgcattggagactgttatattcaacacatacgtgga

ttctgtgttatgatttacatttttctttatttcagcactttcttatgcaaggagctaaacagtgattaaaggagcaggatgaaaagatggcacagtca

gtgctggtaccgccaggacctgacagcttccgcttctttaccagggaatcccttgctgctattgaacaacgcattgcagaagagaaagctaa

gagacccaaacaggaacgcaaggatgaggatgatgaaaatggcccaaagccaaacagtgacttggaagcaggaaaatctcttccatttatt

tatggagacattcctccagagatggtgtcagtgcccctggaggatctggacccctactatatcaataagaaaacgtttatagtattgaataaag

ggaaagcaatctctcgattcagtgccacccctgccctttacattttaactcccttcaaccctattagaaaattagctattaagattttggtacattctt

tattcaatatgctcattatgtgcacgattcttaccaactgtgtatttatgaccatgagtaaccctccagactggacaaagaatgtggagtatacctt

tacaggaatttatacttttgaatcacttattaaaatacttgcaaggggcttttgtttagaagatttcacatttttacgggatccatggaattggttgga

tttcacagtcattacttttgcatatgtgacagagtttgtggacctgggcaatgtctcagcgttgagaacattcagagttctccgagcattgaaaac

aatttcagtcattccaggcctgaagaccattgtgggggccctgatccagtcagtgaagaagctttctgatgtcatgatcttgactgtgttctgtct
```

-continued aagcgtgtttgcgctaataggattgcagttgttcatgggcaacctacgaaataaatgtttgcaatggcctccagataattcttcctttgaaataaa tatcacttccttctttaacaattcattggatgggaatggtactactttcaataggacagtgagcatatttaactgggatgaatatattgaggataaa agtcacttttatttttagaggggcaaaatgatgctctgctttgtggcaacagctcagatgcaggccagtgtcctgaaggatacatctgtgtgaa ggctggtagaaaccccaactatggctacacgagctttgacacctttagttgggcctttttgtccttatttcgtctcatgactcaagacttctggga aaacctttatcaactgacactacgtgctgctgggaaaacgtacatgatatttttgtgctggtcattttcttgggctcattctatctaataaatttgat cttggctgtggtggccatggcctatgaggaacagaatcaggccacattggaagaggctgaacagaaggaagctgaatttcagcagatgct cgaacagttgaaaaagcaacaagaagaagctcaggcggcagctgcagccgcatctgctgaatcaagagacttcagtggtgctggtggga taggagtttttcagagagttcttcagtagcatctaagttgagctccaaaagtgaaaaagagctgaaaaacagaagaaagaaaaagaaacag aaagaacagtctggagaagaagagaaaaatgacagagtccgaaaatcggaatctgaagacagcataagaagaaaaggtttccgtttttcct tggaaggaagtaggctgacatatgaaaagagattttcttctccacaccagtccttactgagcatccgtggctccctttctctccaagacgcaa cagtagggcgagccttttcagcttcagaggtcgagcaaaggacattggctctgagaatgactttgctgatgatgagcacagcacctttgagg acaatgacagccgaagagactctctgttcgtgccgcacagacatggagaacggcgccacagcaatgtcagccaggccagccgtgcctcc agggtgctccccatcctgcccatgaatgggaagatgcatagcgctgtggactgcaatggtgtggtctccctggtcgggggcccttctaccct cacatctgctgggcagctcctaccagagggcacaactactgaaacagaaataagaaagagacggtccagttcttatcatgtttccatggattt attggaagatcctacatcaaggcaaagagcaatgagtatagccagtattttgaccaacaccatggaagaacttgaagaatccagacagaaat gcccaccatgctggtataaatttgctaatatgtgtttgatttgggactgttgtaaaccatggttaaaggtgaaacaccttgtcaacctggttgtaat ggacccatttgttgacctggccatcaccatctgcattgtcttaaatacactcttcatggctatggagcactatcccatgacggagcagttcagca gtgtactgtctgttggaaacctggtcttcacagggatcttcacagcagaaatgtttctcaagataattgccatggatccatattattactttcaaga aggctggaatatttttgatggttttattgtgagccttagtttaatggaacttggtttggcaaatgtggaaggattgtcagttctccgatcattccggc tgctccgagttttcaagttggcaaaatcttggccaactctaaatatgctaattaagatcattggcaattctgtggggggctctaggaaacctcacct tggtattggccatcatcgtcttcatttttgctgtggtcggcatgcagctctttggtaagagctacaaagaatgtgtctgcaagatttccaatgattg tgaactcccacgctggcacatgcatgactttttccactccttcctgatcgtgttccgcgtgctgtgtggagagtggatagagaccatgtgggac tgtatggaggtcgctggccaaaccatgtgccttactgtcttcatgatggtcatggtgattggaaatctagtggttctgaacctcttcttggccttg cttttgagttccttcagttctgacaatcttgctgccactgatgatgataacgaaatgaataatctccagattgctgtgggaaggatgcagaaagg aatcgattttgttaaaagaaaaatacgtgaatttattcagaaagcctttgttaggaagcagaaagctttagatgaaattaaaccgcttgaagatct aaataataaaaaagacagctgtatttccaaccataccaccatagaaataggcaaagacctcaattatctcaaagacggaaatggaactacta gtggcataggcagcagtgtagaaaaatatgtcgtggatgaaagtgattacatgtcatttataaacaaccctagcctcactgtgacagtaccaat tgctgttggagaatctgactttgaaaatttaaatactgaagaattcagcagcgagtcagatatggaggaaagcaaagagaagctaaatgcaa ctagttcatctgaaggcagcacggttgatattggagctcccgccgagggagaacagcctgaggttgaacctgaggaatcccttgaacctga agcctgttttacagaagactgtgtacggaagttcaagtgttgtcagataagcatagaagaaggcaaagggaaactctggtggaatttgagga aaacatgctataagatagtggagcacaattggttcgaaaccttcattgtcttcatgattctgctgagcagtggggctctggcctttgaagatatat acattgagcagcgaaaaaccattaagaccatgttagaatatgctgacaaggttttcacttacatattcattctggaaatgctgctaaagtgggtt gcatatggttttcaagtgtattttaccaatgcctggtgctggctagacttcctgattgttgatgtctcactggttagcttaactgcaaatgccttggg ttactcagaacttggtgccatcaaatccctcagaacactaagagctctgaggccactgagagctttgtcccggtttgaaggaatgagggttgtt gtaaatgctcttttaggagccattccatctatcatgaatgtacttctggtttgtctgatcttttggctaatattcagtatcatgggagtgaatctctttg ctggcaagttttaccattgtattaattacaccactggagagatgtttgatgtaagcgtggtcaacaactacagtgagtgcaaagctctcattgag agcaatcaaactgccaggtggaaaaatgtgaaagtaaactttgataacgtaggacttggatatctgtctctacttcaagtagccacgtttaagg gatggatggatattatgtatgcagctgttgattcacgaaatgtagaattacaacccaagtatgaagacaacctgtacatgtatctttattttgtcat ctttattattttttggttcattctttaccttgaatcttttcattggtgtcatcatagataacttcaaccaacagaaaaagaagtttggaggtcaagacatt tttatgacagaagaacagaagaaatactacaatgcaatgaaaaaactgggttcaaagaaaccacaaaaacccatacctcgacctgctaaca -continued aattccaaggaatggtctttgattttgtaaccaaacaagtctttgatatcagcatcatgatcctcatctgccttaacatggtcaccatgatggtgga aaccgatgaccagagtcaagaaatgacaaacattctgtactggattaatctggtgtttattgttctgttcactggagaatgtgtgctgaaactgat ctctcttcgttactactatttcactattggatggaatatttttgattttgtggtggtcattctctccattgtaggaatgtttctggctgaactgatagaa aagtattttgtgtcccctaccctgttccgagtgatccgtcttgccaggattggccgaatcctacgtctgatcaaaggagcaaaggggatccgca cgctgctctttgctttgatgatgtcccttcctgcgttgtttaacatcggcctccttcttttcctggtcatgttcatctacgccatctttgggatgtccaa ttttgcctatgttaagagggaagttgggatcgatgacatgttcaactttgagacctttggcaacagcatgatctgcctgttccaaattacaacctc tgctggctgggatggattgctagcacctattcttaatagtggacctccagactgtgaccctgacaaagatcaccctggaagctcagttaaagg agactgtgggaacccatctgttgggatttctttttttgtcagttacatcatcatatccttcctggttgtggtgaacatgtacatcgcggtcatcctgg agaacttcagtgttgctactgaagaaagtgcagagcctctgagtgaggatgactttgagatgttctatgaggtttgggagaagtttgatcccga tgcgacccagtttatagagtttgccaaactttctgattttgcagatgccctggatcctcctcttctcatagcaaaacccaacaaagtccagctcat tgccatggatctgcccatggtgagtggtgaccggatccactgtcttgacatcttatttgcttttacaaagcgtgttttgggtgagagtggagaga tggatgcccttcgaatacagatggaagagcgattcatggcatcaaacccctccaaagtctcttatgagcccattacgaccacgttgaaacgc aaacaagaggaggtgtctgctattattatccagagggcttacagacgctacctcttgaagcaaaaagttaaaaaggtatcaagtatatacaag aaagacaaaggcaaagaatgtgatggaacacccatcaaagaagatactctcattgataaactgaatgagaattcaactccagagaaaaccg atatgacgccttccaccacgtctccaccctcgtatgatagtgtgaccaaaccagaaaaagaaaaatttgaaaaagacaaatcagaaaagga agacaaagggaaagatatcagggaaagtaaaaagtaaaaagaaaccaagaattttccattttgtgatcaattgtttacagcccgtgatggtga tgtgtttgtgtcaacaggactcccacaggaggtctatgccaaactgactgtttttacaaatgtatacttaaggtcagtgcctataacaagacaga gacctctggtcagcaaactggaactcagtaaactggagaaatagtatcgatgggaggtttctattttcacaaccagctgacactgctgaagag cagaggcgtaatggctactcagacgataggaaccaatttaaagggggagggaagttaaatttttatgtaaattcaacatgtgacacttgata atagtaattgtcaccagtgtttatgttttaactgccacacctgccatatttttacaaaacgtgtgctgtgaatttatcacttttctttttaattcacag gttgtttactattatatgtgactatttttgtaaatgggtttgtgtttggggagagggattaaagggagggaattctacatttctctattgtattgtata actggatatattttaaatggaggcatgctgcaattctcattcacacataaaaaaatcacatcacaaaagggaagagtttacttcttgtttcaggatgtt tttagatttttgaggtgcttaaatagctattcgtatttttaaggtgtctcatccagaaaaaatttaatgtgcctgtaaatgttccatagaatcacaagc attaaagagttgttttatttttacataacccattaaatgtacatgtatatatgtatatatgtatatgtgcgtgtatatacatatatatgtatacacaca tgcacacacagagatatacacataccattacattgtcattcacagtcccagcagcatgactatcacatttttgataagtgtcctttggcataaaataaa aatatcctatcagtcctttctaagaagcctgaattgaccaaaaaacatccccaccaccactttataaagttgattctgctttatcctgcagtattgttta gccatcttctgctcttggtaaggttgacatagtatatgtcaatttaaaaaataaaagtctgctttgtaaatagtaatttacccagtggtgcatgtttg agcaaacaaaaatgatgatttaagcacactacttattgcatcaaatatgtaccacagtaagtatagtttgcaagctttcaacaggtaatatgatgt aattggttccattatagtttgaagctgtcactgctgcatgtttatcttgcctatgctgctgtatcttattccttccactgttcagaagtctaatatggga agccatatatcagtggtaaagtgaagcaaattgttctaccaagacctcattcttcatgtcattaagcaataggttgcagcaaacaaggaagagc ttcttgcttttattcttccaaccttaattgaacactcaatgatgaaaagcccgactgtacaaacatgttgcaagctgcttaaatctgtttaaaatata tggttagagttttctaagaaaatataaatactgtaaaaagttcattttattttatttttcagccttttgtacgtaaaatgagaaattaaaagtatcttca ggtggatgtcacagtcactattgttagtttctgttcctagcacttttaaattgaagcacttcacaaaataagaagcaaggactaggatgcagtgtag gtttctgctttttttattagtactgtaaacttgcacacatttcaatgtgaaacaaatctcaaactgagttcaatgtttatttgctttcaatagtaatgcct tatcattgaaagaggcttaaagaaaaaaaaaatcagctgatactcttggcattgcttgaatccaatgtttccacctagtctttttattcagtaatcatc agtcttttccaatgtttgtttacacagatagatcttattgacccatatggcactagaactgtatcagatataatatgggatcccagctttttttcctctc ccacaaaaccaggtagtgaagttatattaccagttacagcaaaatactttgtgtttcacaagcaacaataaatgtagattctttatactgaagcta ttgacttgtagtgtgttggtgaaatgcatgcaggaaaatgctgttaccataaagaacggtaaaccacattacaatcaagccaaaagaataaag gtttcgcttttgtttttgtatttaattgttgtctttgtttctatctttgaaatgccatttaaaggtagatttctatcatgtaaaaataatctatctgaa -continued aaacaaatgtaaagaacacacattaattactataattcatctttcaatttttttcatggaatggaagttaattaagaagagtgtattggataactacttt aatattggccaaaaagctagatatggcatcaggtagactagtggaaagttacaaaaattaataaaaaattgactaaca), NM_001040143.2 (SEQ ID NO: 5;
aacagacattgggtaccatcgaatgactgtcagaacagaaagctaaggcaaaggagggaggatgctgtggtcatcctttcttgtttttttcttct ttaatgaggatagagcacatgtgagattttactttctactccagtaaaaattctgaagaattgcattggagactgttatattcaacacatacgtgga ttctgtgttatgatttacattttctttatttcaggggtttttctccctttgcttgacacttctctgtcctgacaccttgagaagaaggatgtgtttgc ttacccttccgccatgattgtaaatttcctgaggccttcccagccatgcagcactcactttcttatgcaaggagctaaacagtgattaaaggagcagg atgaaaagatggcacagtcagtgctggtaccgccaggacctgacagcttccgcttctttaccagggaatcccttgctgctattgaacaacgc attgcagaagagaaagctaagagacccaaacaggaacgcaaggatgaggatgatgaaaatggcccaaagccaaacagtgacttggaag caggaaaatctcttccatttatttatggagacattcctccagagatggtgtcagtgcccctggaggatctggacccctactatatcaataagaaa acgtttatagtattgaataaagggaaagcaatctctcgattcagtgccacccctgccctttacattttaactcccttcaaccctattagaaaattag ctattaagattttggtacattctttattcaatatgctcattatgtgcacgattcttaccaactgtgtatttatgaccatgagtaaccctccagactgga caaagaatgtggagtatacctttacaggaatttatactttgaatcacttattaaaatacttgcaaggggcttttgtttagaagatttcacatttttac gggatccatggaattggttggatttcacagtcattacttttgcgtatgtaacagaatttgtaaacctaggcaatgtttcagctcttcgaactttcag agtcttgagagctttgaaaactatttctgtaattccaggcctgaagaccattgtgggggccctgatccagtcagtgaagaagctttctgatgtca tgatcttgactgtgttctgtctaagcgtgtttgcgctaataggattgcagttgttcatgggcaacctacgaaataaatgtttgcaatggcctccag ataattcttcctttgaaataaatatcacttccttctttaacaattcattggatgggaatggtactactttcaataggacagtgagcatatttaactggg atgaatatattgaggataaaagtcacttttatttttttagaggggcaaaatgatgctctgctttgtggcaacagctcagatgcaggccagtgtcctg aaggatacatctgtgtgaaggctggtagaaaccccaactatggctacacgagctttgacacctttagttgggcctttttgtccttatttcgtctcat gactcaagacttctgggaaaacctttatcaactgacactacgtgctgctgggaaaacgtacatgatatttttttgtgctggtcatttttcttgggctca ttctatctaataaatttgatcttggctgtggtggccatggcctatgaggaacagaatcaggccacattggaagaggctgaacagaaggaagct gaatttcagcagatgctcgaacagttgaaaaagcaacaagaagaagctcaggcggcagctgcagccgcatctgctgaatcaagagacttc agtggtgctggtgggataggagtttttttcagagagttcttcagtagcatctaagttgagctccaaaagtgaaaaagagctgaaaaacagaaga aagaaaaagaaacagaaagaacagtctggagaagaagagaaaaatgacagagtccgaaaatcggaatctgaagacagcataagaagaa aaggtttccgtttttccttggaaggaagtaggctgacatatgaaaagagatttcttctccacaccagtccttactgagcatccgtggctcccttttt ctctccaagacgcaacagtagggcgagccttttcagcttcagaggtcgagcaaaggacattggctctgagaatgactttgctgatgatgagc acagcacctttgaggacaatgacagccgaagagactctctgttcgtgccgcacagacatggagaacggcgccacagcaatgtcagccag gccagccgtgcctccagggtgctccccatcctgcccatgaatgggaagatgcatagcgctgtggactgcaatggtgtggtctccctggtcg gggggcccttctaccctcacatctgctgggcagctcctaccagagggcacaactactgaaacagaaataagaaagagacggtccagttctta tcatgtttccatggatttattggaagatcctacatcaaggcaaagagcaatgagtatagccagtattttgaccaacaccatggaagaacttgaa gaatccagacagaaatgcccaccatgctggtataaatttgctaatatgtgtttgatttgggactgttgtaaaccatggttaaaggtgaaacacctt gtcaacctggttgtaatggacccatttgttgacctggccatcaccatctgcattgtcttaaatacactcttcatggctatggagcactatcccatg acggagcagttcagcagtgtactgtctgttggaaacctggtcttcacagggatcttcacagcagaaatgtttctcaagataattgccatggatc catattattactttcaagaaggctggaatatttttgatggttttattgtgagccttagtttaatggaacttggtttggcaaatgtggaaggattgtcag ttctccgatcattccggctgctccgagttttcaagttggcaaaatcttggccaactctaaatatgctaattaagatcattggcaattctgtggggg ctctaggaaacctcaccttggtattggccatcatcgtcttcatttttgctgtggtcggcatgcagctctttggtaagagctacaaagaatgtgtct gcaagatttccaatgattgtgaactcccacgctggcacatgcatgactttttccactccttcctgatcgtgttccgcgtgctgtgtggagagtgg atagagaccatgtgggactgtatggaggtcgctggccaaaccatgtgccttactgtcttcatgatggtcatggtgattggaaatctagtggttct gaacctcttcttggccttgcttttgagttccttcagttctgacaatcttgctgccactgatgatgataacgaaatgaataatctccagattgctgtgg gaaggatgcagaaaggaatcgattttgttaaaagaaaaatacgtgaatttattcagaaagcctttgttaggaagcagaaagctttagatgaaat -continued taaaccgcttgaagatctaaataataaaaaagacagctgtatttccaaccataccaccatagaaataggcaaagacctcaattatctcaaaga cggaaatggaactactagtggcataggcagcagtgtagaaaaatatgtcgtggatgaaagtgattacatgtcatttataaacaaccctagcct cactgtgacagtaccaattgctgttggagaatctgactttgaaaatttaaatactgaagaattcagcagcgagtcagatatggaggaaagcaa agagaagctaaatgcaactagttcatctgaaggcagcacggttgatattggagctcccgccgagggagaacagcctgaggttgaacctga ggaatcccttgaacctgaagcctgttttacagaagactgtgtacggaagttcaagtgttgtcagataagcatagaagaaggcaaagggaaac tctggtggaatttgaggaaaacatgctataagatagtggagcacaattggttcgaaaccttcattgtcttcatgattctgctgagcagtggggct ctggcctttgaagatatatacattgagcagcgaaaaaccattaagaccatgttagaatatgctgacaaggttttcacttacatattcattctggaa atgctgctaaagtgggttgcatatggttttcaagtgtattttaccaatgcctggtgctggctagacttcctgattgttgatgtctcactggttagctt aactgcaaatgccttgggttactcagaacttggtgccatcaaatccctcagaacactaagagctctgaggccactgagagctttgtcccggttt gaaggaatgagggttgttgtaaatgctcttttaggagccattccatctatcatgaatgtacttctggtttgtctgatcttttggctaatattcagtatc atgggagtgaatctctttgctggcaagttttaccattgtattaattacaccactggagagatgtttgatgtaagcgtggtcaacaactacagtgag tgcaaagctctcattgagagcaatcaaactgccaggtggaaaaatgtgaaagtaaactttgataacgtaggacttggatatctgtctctacttca agtagccacgtttaagggatggatggatattatgtatgcagctgttgattcacgaaatgtagaattacaacccaagtatgaagacaacctgtac atgtatctttattttgtcatctttattatttttggttcattctttaccttgaatcttttcattggtgtcatcatagataacttcaaccaacagaaaaag aagtttggaggtcaagacatttttatgacagaagaacagaagaaatactacaatgcaatgaaaaaactgggttcaaagaaaccacaaaaacccata cctcgacctgctaacaaattccaaggaatggtctttgattttgtaaccaaacaagtctttgatatcagcatcatgatcctcatctgccttaacatgg tcaccatgatggtggaaaccgatgaccagagtcaagaaatgacaaacattctgtactggattaatctggtgtttattgttctgttcactggagaa tgtgtgctgaaactgatctctcttcgttactactatttcactattggatggaatatttttgattttgtggtggtcattctctccattgtaggaatgttt ctggctgaactgatagaaaagtattttgtgtcccctaccctgttccgagtgatccgtcttgccaggattggccgaatcctacgtctgatcaaaggag caaaggggatccgcacgctgctctttgctttgatgatgtcccttcctgcgttgtttaacatcggcctccttcttttcctggtcatgttcatctacgcc atctttgggatgtccaattttgcctatgttaagagggaagttgggatcgatgacatgttcaactttgagacctttggcaacagcatgatctgcctg ttccaaattacaacctctgctggctgggatggattgctagcacctattcttaatagtggacctccagactgtgaccctgacaaagatcaccctg gaagctcagttaaaggagactgtgggaacccatctgttgggatttttctttttttgtcagttacatcatcatatccttcctggttgtggtgaacatgtac atcgcggtcatcctggagaacttcagtgttgctactgaagaaagtgcagagcctctgagtgaggatgactttgagatgttctatgaggtttggg agaagtttgatcccgatgcgacccagtttatagagtttgccaaactttctgattttgcagatgccctggatcctcctcttctcatagcaaaaccca acaaagtccagctcattgccatggatctgcccatggtgagtggtgaccggatccactgtcttgacatcttatttgcttttacaaagcgtgttttgg gtgagagtggagagatggatgcccttcgaatacagatggaagagcgattcatggcatcaaacccctccaaagtctcttatgagcccattacg accacgttgaaacgcaaacaagaggaggtgtctgctattattatccagagggcttacagacgctacctcttgaagcaaaaagttaaaaaggt atcaagtatatacaagaaagacaaaggcaaagaatgtgatggaacacccatcaaagaagatactctcattgataaactgaatgagaattcaa ctccagagaaaaccgatatgacgccttccaccacgtctccaccctcgtatgatagtgtgaccaaaccagaaaaagaaaaatttgaaaaaga caaatcagaaaaggaagacaaagggaaagatatcagggaaagtaaaaagtaaaaagaaaccaagaattttccattttgtgatcaattgtttac agcccgtgatggtgatgtgtttgtgtcaacaggactcccacaggaggtctatgccaaactgactgtttttacaaatgtatacttaaggtcagtgc ctataacaagacagagacctctggtcagcaaactggaactcagtaaactggagaaatagtatcgatgggaggtttctattttcacaaccagct gacactgctgaagagcagaggcgtaatggctactcagacgataggaaccaatttaaagggggggagggaagttaaatttttatgtaaattcaa catgtgacacttgataatagtaattgtcaccagtgtttatgttttaactgccacacctgccatatttttacaaaacgtgtgctgtgaatttatcacttt tctttttaattcacaggttgtttactattatatgtgactatttttgtaaatgggtttgtgtttggggagagggattaaagggagggaattctacatttc tctattgtattgtataactggatatattttaaatggaggcatgctgcaattctcattcacacataaaaaaatcacatcacaaaagggaagagtttactt cttgtttcaggatgtttttagatttttgaggtgcttaaatagctattcgtatttttaaggtgtctcatccagaaaaaatttaatgtgcctgtaaatgtt ccatagaatcacaagcattaaagagttgttttatttttacataacccattaaatgtacatgtatatatgtatatatgtatatgtgcgtgtatatacata tatatgtatacacacatgcacacacagagatatacacataccattacattgtcattcacagtcccagcagcatgactatcacatttttgataagtgtcc -continued tttggcataaaataaaaatatcctatcagtcctttctaagaagcctgaattgaccaaaaaacatccccaccaccactttataaagttgattctgcttt atcctgcagtattgtttagccatcttctgctcttggtaaggttgacatagtatatgtcaatttaaaaaataaaagtctgctttgtaaatagtaattta cccagtggtgcatgtttgagcaaacaaaaatgatgatttaagcacactacttattgcatcaaatatgtaccacagtaagtatagtttgcaagctttc aacaggtaatatgatgtaattggttccattatagtttgaagctgtcactgctgcatgtttatcttgcctatgctgctgtatcttattccttccactgtt cagaagtctaatatgggaagccatatatcagtggtaaagtgaagcaaattgttctaccaagacctcattcttcatgtcattaagcaataggttgca gcaaacaaggaagagcttcttgctttttattcttccaaccttaattgaacactcaatgatgaaaagcccgactgtacaaacatgttgcaagctgc ttaaatctgtttaaaatatatggttagagttttctaagaaaatataaatactgtaaaaagttcattttattttatttttcagccttttgtacgtaaaa tgagaaattaaaagtatcttcaggtggatgtcacagtcactattgttagtttctgttcctagcacttttaaattgaagcacttcacaaaataagaagca aggactaggatgcagtgtaggtttctgctttttttattagtactgtaaacttgcacacatttcaatgtgaaacaaatctcaaactgagttcaatgtttat ttgctttcaatagtaatgccttatcattgaaagaggcttaaagaaaaaaaaaatcagctgatactcttggcattgcttgaatccaatgtttccaccta gtctttttattcagtaatcatcagtcttttccaatgtttgtttacacagatagatcttattgacccatatggcactagaactgtatcagatataatatg ggatcccagctttttttcctctcccacaaaaccaggtagtgaagttatattaccagttacagcaaaatactttgtgtttcacaagcaacaataaatgt agattctttatactgaagctattgacttgtagtgtgttggtgaaatgcatgcaggaaaatgctgttaccataaagaacggtaaaccacattacaat caagccaaaagaataaaggtttcgcttttgtttttgtatttaattgttgtctttgtttctatctttgaaatgccatttaaaggtagatttctatcatgt aaaaataatctatctgaaaaacaaatgtaaagaacacacattaattactataattcatctttcaatttttttcatggaatggaagttaattaagaagagt gtattggataactactttaatattggccaaaaagctagatatggcatcaggtagactagtggaaagttacaaaaattaataaaaaattgactaaca), NM_001371246.1 (SEQ ID NO: 6;
aacagacattgggtaccatcgaatgactgtcagaacagaaagctaaggcaaaggagggaggatgctgtggtcatcctttcttgtttttttcttct ttaatgaggatagagcacatgtgagattttactttctactccagtaaaaattctgaagaattgcattggagactgttatattcaacacatacgtgga ttctgtgttatgatttacatttttctttatttcagcactttcttatgcaaggagctaaacagtgattaaaggagcaggatgaaaagatggcacagtca gtgctggtaccgccaggacctgacagcttccgcttctttaccagggaatcccttgctgctattgaacaacgcattgcagaagagaaagctaa gagacccaaacaggaacgcaaggatgaggatgatgaaaatggcccaaagccaaacagtgacttggaagcaggaaaatctcttccatttatt tatggagacattcctccagagatggtgtcagtgcccctggaggatctggacccctactatatcaataagaaaacgtttatagtattgaataaag ggaaagcaatctctcgattcagtgccacccctgccctttacattttaactcccttcaaccctattagaaaattagctattaagattttggtacattctt tattcaatatgctcattatgtgcacgattcttaccaactgtgtatttatgaccatgagtaaccctccagactggacaaagaatgtggagtatacctt tacaggaatttatacttttgaatcacttattaaaatacttgcaaggggcttttgtttagaagatttcacatttttacgggatccatggaattggttgga tttcacagtcattacttttgcgtatgtaacagaatttgtaaacctaggcaatgtttcagctcttcgaactttcagagtcttgagagctttgaaaactat ttctgtaattccaggcctgaagaccattgtgggggccctgatccagtcagtgaagaagctttctgatgtcatgatcttgactgtgttctgtctaag cgtgtttgcgctaataggattgcagttgttcatgggcaacctacgaaataaatgtttgcaatggcctccagataattcttcctttgaaataaatatc acttccttctttaacaattcattggatgggaatggtactactttcaataggacagtgagcatatttaactgggatgaatatattgaggataaaagtc acttttatttttttagaggggcaaaatgatgctctgctttgtggcaacagctcagatgcaggccagtgtcctgaaggatacatctgtgtgaaggct ggtagaaaccccaactatggctacacgagctttgacacctttagttgggcctttttgtccttatttcgtctcatgactcaagacttctgggaaaac ctttatcaactgacactacgtgctgctgggaaaacgtacatgatatttttttgtgctggtcattttcttgggctcattctatctaataaatttgatcttg gctgtggtggccatggcctatgaggaacagaatcaggccacattggaagaggctgaacagaaggaagctgaatttcagcagatgctcgaac agttgaaaaagcaacaagaagaagctcaggcggcagctgcagccgcatctgctgaatcaagagacttcagtggtgctggtgggatagga gtttttttcagagagttcttcagtagcatctaagttgagctccaaaagtgaaaaagagctgaaaaacagaagaaagaaaaagaaacagaaaga acagtctggagaagaagagaaaaatgacagagtccgaaaatcggaatctgaagacagcataagaagaaaaggtttccgtttttccttggaa ggaagtaggctgacatatgaaaagagattttcttctccacaccagtccttactgagcatccgtggctccctttttctctccaagacgcaacagta gggcgagccttttcagcttcagaggtcgagcaaaggacattggctctgagaatgactttgctgatgatgagcacagcacctttgaggacaat gacagccgaagagactctctgttcgtgccgcacagacatggagaacggcgccacagcaatgtcagccaggccagccgtgcctccaggg -continued tgctccccatcctgcccatgaatgggaagatgcatagcgctgtggactgcaatggtgtggtctccctggtcgggggcccttctaccctcacat ctgctgggcagctcctaccagagggcacaactactgaaacagaaataagaaagagacggtccagttcttatcatgtttccatggatttattgg aagatcctacatcaaggcaaagagcaatgagtatagccagtattttgaccaacaccatggaagaacttgaagaatccagacagaaatgccc accatgctggtataaatttgctaatatgtgtttgatttgggactgttgtaaaccatggttaaaggtgaaacaccttgtcaacctggttgtaatggac ccatttgttgacctggccatcaccatctgcattgtcttaaatacactcttcatggctatggagcactatcccatgacggagcagttcagcagtgt actgtctgttggaaacctggtcttcacagggatcttcacagcagaaatgtttctcaagataattgccatggatccatattatttactttcaagaagg ctggaatatttttgatggttttattgtgagccttagtttaatggaacttggtttggcaaatgtggaaggattgtcagttctccgatcattccggctgct ccgagttttcaagttggcaaaatcttggccaactctaaatatgctaattaagatcattggcaattctgtgggggctctaggaaacctcaccttggt attggccatcatcgtcttcatttttgctgtggtcggcatgcagctctttggtaagagctacaaagaatgtgtctgcaagatttccaatgattgtgaa ctcccacgctggcacatgcatgactttttccactccttcctgatcgtgttccgcgtgctgtgtggagagtggatagagaccatgtgggactgtat ggaggtcgctggccaaaccatgtgccttactgtcttcatgatggtcatggtgattggaaatctagtggttctgaacctcttcttggccttgcttttg agttccttcagttctgacaatcttgctgccactgatgatgataacgaaatgaataatctccagattgctgtgggaaggatgcagaaaggaatcg attttgttaaaagaaaaatacgtgaatttattcagaaagcctttgttaggaagcagaaagctttagatgaaattaaaccgcttgaagatctaaata ataaaaaagacagctgtatttccaaccataccaccatagaaataggcaaagacctcaattatctcaaagacggaaatggaactactagtggc ataggcagcagtgtagaaaaatatgtcgtggatgaaagtgattacatgtcatttataaacaaccctagcctcactgtgacagtaccaattgctgt tggagaatctgactttgaaaatttaaatactgaagaattcagcagcgagtcagatatggaggaaagcaaagagaagctaaatgcaactagtt catctgaaggcagcacggttgatattggagctcccgccgagggagaacagcctgaggttgaacctgaggaatcccttgaacctgaagcct gttttacagaagactgtgtacggaagttcaagtgttgtcagataagcatagaagaaggcaaagggaaactctggtggaatttgaggaaaaca tgctataagatagtggagcacaattggttcgaaaccttcattgtcttcatgattctgctgagcagtggggctctggcctttgaagatatatacatt gagcagcgaaaaaccattaagaccatgttagaatatgctgacaaggttttcacttacatattcattctggaaatgctgctaaagtgggttgcata tggttttcaagtgtattttaccaatgcctggtgctggctagacttcctgattgttgatgtctcactggttagcttaactgcaaatgccttgggttactc agaacttggtgccatcaaatccctcagaacactaagagctctgaggccactgagagctttgtcccggtttgaaggaatgagggttgttgtaaa tgctcttttaggagccattccatctatcatgaatgtacttctggtttgtctgatcttttggctaatattcagtatcatgggagtgaatctctttgctgg caagttttaccattgtattaattacaccactggagagatgtttgatgtaagcgtggtcaacaactacagtgagtgcaaagctctcattgagagcaa tcaaactgccaggtggaaaaatgtgaaagtaaactttgataacgtaggacttggatatctgtctctacttcaagtagccacgtttaagggatgg atggatattatgtatgcagctgttgattcacgaaatgtagaattacaacccaagtatgaagacaacctgtacatgtatctttatttttgtcatctttatt atttttggttcattctttaccttgaatcttttcattggtgtcatcatagataacttcaaccaacagaaaaagaagtttggaggtcaagacatttttatg acagaagaacagaagaaatactacaatgcaatgaaaaaactgggttcaaagaaaccacaaaaacccatacctcgacctgctaacaaattcca aggaatggtctttgattttgtaaccaaacaagtctttgatatcagcatcatgatcctcatctgccttaacatggtcaccatgatggtggaaaccga tgaccagagtcaagaaatgacaaacattctgtactggattaatctggtgtttattgttctgttcactggagaatgtgtgctgaaactgatctctctt cgttactactatttcactattggatggaatatttttgattttgtggtggtcattctctccattgtaggaatgtttctggctgaactgatagaaaagtat tttgtgtcccctaccctgttccgagtgatccgtcttgccaggattggccgaatcctacgtctgatcaaaggagcaaaggggatccgcacgctgc tctttgctttgatgatgtcccttcctgcgttgtttaacatcggcctccttcttttcctggtcatgttcatctacgccatctttgggatgtccaattttg cctatgttaagagggaagttgggatcgatgacatgttcaactttgagacctttggcaacagcatgatctgcctgttccaaattacaacctctgctggc tgggatggattgctagcacctattcttaatagtggacctccagactgtgaccctgacaaagatcaccctggaagctcagttaaaggagactgt gggaacccatctgttgggattttctttttgtcagttacatcatcatatccttcctggttgtggtgaacatgtacatcgcggtcatcctggagaactt cagtgttgctactgaagaaagtgcagagcctctgagtgaggatgactttgagatgttctatgaggtttgggagaagtttgatcccgatgcgac ccagtttatagagtttgccaaactttctgattttgcagatgccctggatcctcctcttctcatagcaaaacccaacaaagtccagctcattgccat ggatctgcccatggtgagtggtgaccggatccactgtcttgacatcttatttgcttttacaaagcgtgttttgggtgagagtgga gagatggatg -continued cccttcgaatacagatggaagagcgattcatggcatcaaacccctccaaagtctcttatgagcccattacgaccacgttgaaacgcaaacaa gaggaggtgtctgctattattatccagagggcttacagacgctacctcttgaagcaaaaagttaaaaaggtatcaagtatatacaagaaagac aaaggcaaagaatgtgatggaacacccatcaaagaagatactctcattgataaactgaatgagaattcaactccagagaaaaccgatatgac gccttccaccacgtctccaccctcgtatgatagtgtgaccaaaccagaaaaagaaaaatttgaaaaagacaaatcagaaaaggaagacaaa gggaaagatatcagggaaagtaaaaagtaaaaagaaaccaagaattttccatttgtgatcaattgtttacagcccgtgatggtgatgtgtttgt gtcaacaggactcccacaggaggtctatgccaaactgactgtttttacaaatgtatacttaaggtcagtgcctataacaagacagagacctctg gtcagcaaactggaactcagtaaactggagaaatagtatcgatgggaggtttctattttcacaaccagctgacactgctgaagagcagaggc gtaatggctactcagacgataggaaccaatttaaagggggggagggaagttaaatttttatgtaaattcaacatgtgacacttgataatagtaatt gtcaccagtgtttatgttttaactgccacacctgccatatttttacaaaacgtgtgctgtgaatttatcacttttctttttaattcacaggttgttt actattatatgtgactattttttgtaaatgggtttgtgtttggggagagggattaaagggagggaattctacatttctctattgtattgtataactgga tatattttaaatggaggcatgctgcaattctcattcacacataaaaaaatcacatcacaaaagggaagagtttacttcttgtttcaggatgtttttaga tttttgaggtgcttaaatagctattcgtattttttaaggtgtctcatccagaaaaaatttaatgtgcctgtaaatgttccatagaatcacaagcattaa agagttgttttattttttacataacccattaaatgtacatgtatatatgtatatatgtatatgtgcgtgtatatacatatatatgtatacacacatgca cacacagagatatacacataccattacattgtcattcacagtcccagcagcatgactatcacatttttgataagtgtcctttggcataaaataaaaata tcctatcagtcctttctaagaagcctgaattgaccaaaaaacatccccaccaccactttataaagttgattctgctttatcctgcagtattgtttagcc atcttctgctcttggtaaggttgacatagtatatgtcaatttaaaaaataaaagtctgctttgtaaatagtaattttacccagtggtgcatgtttgagc aaacaaaaatgatgatttaagcacactacttattgcatcaaatatgtaccacagtaagtatagtttgcaagctttcaacaggtaatatgatgtaattgg ttccattatagtttgaagctgtcactgctgcatgtttatcttgcctatgctgctgtatcttattccttccactgttcagaagtctaatatgggaagcc atatatcagtggtaaagtgaagcaaattgttctaccaagacctcattcttcatgtcattaagcaataggttgcagcaaacaaggaagagcttcttgctt tttattcttccaaccttaattgaacactcaatgatgaaaagcccgactgtacaaacatgttgcaagctgcttaaatctgtttaaaatatatggttaga gttttctaagaaaatataaatactgtaaaaagttcattttatttttatttttcagccttttgtacgtaaaatgagaaattaaaagtatcttcaggtggat gtcacagtcactattgttagtttctgttcctagcacttttaaattgaagcacttcacaaaataagaagcaaggactaggatgcagtgtaggtttctgct tttttattagtactgtaaacttgcacacatttcaatgtgaaacaaatctcaaactgagttcaatgtttatttgctttcaatagtaatgccttatcattg aaagaggcttaaagaaaaaaaaaatcagctgatactcttggcattgcttgaatccaatgtttccacctagtctttttattcagtaatcatcagtctttt ccaatgtttgtttacacagatagatcttattgacccatatggcactagaactgtatcagatataatatgggatcccagctttttttcctctcccacaaa accaggtagtgaagttatattaccagttacagcaaaatactttgtgtttcacaagcaacaataaatgtagattctttatactgaagctattgacttgt agtgtgttggtgaaatgcatgcaggaaaatgctgttaccataaagaacggtaaaccacattacaatcaagccaaaagaataaaggtttcgctt ttgtttttgtatttaattgttgtctttgtttctatctttgaaatgccatttaaaggtagatttctatcatgtaaaaataatctatctgaaaaacaaat gtaaagaacacacattaattactataattcatctttcaatttttttcatggaatggaagttaattaagaagagtgtattggataactactttaata ttggccaaaaagctagatatggcatcaggtagactagtggaaagttacaaaaattaataaaaaattgactaaca), NM_001371247.1 (SEQ ID NO: 7;
atagcagtaacacaattcacctctagtgtgaacatatcaggatggcatagaccagcactttcttatgcaaggagctaaacagtgattaaagga gcaggatgaaaagatggcacagtcagtgctggtaccgccaggacctgacagcttccgcttctttaccagggaatcccttgctgctattgaac aacgcattgcagaagagaaagctaagagacccaaacaggaacgcaaggatgaggatgatgaaaatggcccaaagccaaacagtgactt ggaagcaggaaaatctcttccatttatttatggagacattcctccagagatggtgtcagtgccccctggaggatctggacccctactatatcaat aagaaaacgtttatagtattgaataaagggaaagcaatctctcgattcagtgccacccctgccctttacattttaactcccttcaaccctattaga aaattagctattaagattttggtacattctttattcaatatgctcattatgtgcacgattcttaccaactgtgtatttatgaccatgagtaaccctcca gactggacaaagaatgtggagtatacctttacaggaatttatacttttgaatcacttattaaaatacttgcaaggggcttttgtttagaagatttcaca tttttacgggatccatggaattggttggatttcacagtcattacttttgcatatgtgacagagtttgtggacctgggcaatgtctcagcgttgagaa cattcagagttctccgagcattgaaaacaatttcagtcattccaggcctgaagaccattgtgggggccctgatccagtcagtgaagaagctttc -continued tgatgtcatgatcttgactgtgttctgtctaagcgtgtttgcgctaataggattgcagttgttcatgggcaacctacgaaataaatgtttgcaatgg cctccagataattcttcctttgaaataaatatcacttccttctttaacaattcattggatgggaatggtactactttcaataggacagtgagcatattt aactgggatgaatatattgaggataaaagtcacttttatttttagaggggcaaaatgatgctctgctttgtggcaacagctcagatgcaggcca gtgtcctgaaggatacatctgtgtgaaggctggtagaaaccccaactatggctacacgagctttgacacctttagttgggcctttttgtccttatt tcgtctcatgactcaagacttctgggaaaacctttatcaactgacactacgtgctgctgggaaaacgtacatgatatttttgtgctggtcattttct tgggctcattctatctaataaatttgatcttggctgtggtggccatggcctatgaggaacagaatcaggccacattggaagaggctgaacaga aggaagctgaatttcagcagatgctcgaacagttgaaaaagcaacaagaagaagctcaggcggcagctgcagccgcatctgctgaatcaa gagacttcagtggtgctggtgggataggagtttttcagagagttcttcagtagcatctaagttgagctccaaaagtgaaaaagagctgaaaa acagaagaaagaaaaagaaacagaaagaacagtctggagaagaagagaaaaatgacagagtccgaaaatcggaatctgaagacagcat aagaagaaaaggtttccgtttttccttggaaggaagtaggctgacatatgaaaagagattttcttctccacaccagtccttactgagcatccgtg gctcccttttctctccaagacgcaacagtagggcgagccttttcagcttcagaggtcgagcaaaggacattggctctgagaatgactttgctg atgatgagcacagcacctttgaggacaatgacagccgaagagactctctgttcgtgccgcacagacatggagaacggcgccacagcaat gtcagccaggccagccgtgcctccagggtgctccccatcctgcccatgaatgggaagatgcatagcgctgtggactgcaatggtgtggtct ccctggtcgggggcccttctaccctcacatctgctgggcagctcctaccagagggcacaactactgaaacagaaataagaaagagacggt ccagttcttatcatgtttccatggatttattggaagatcctacatcaaggcaaagagcaatgagtatagccagtattttgaccaacaccatggaa gaacttgaagaatccagacagaaatgcccaccatgctggtataaatttgctaatatgtgtttgatttgggactgttgtaaaccatggttaaaggt gaaacaccttgtcaacctggttgtaatggacccatttgttgacctggccatcaccatctgcattgtcttaaatacactcttcatggctatggagca ctatcccatgacggagcagttcagcagtgtactgtctgttggaaacctggtcttcacagggatcttcacagcagaaatgtttctcaagataattg ccatggatccatattattactttcaagaaggctggaatatttttgatggttttattgtgagccttagtttaatggaacttggtttggcaaatgtggaag gattgtcagttctccgatcattccggctgctccgagttttcaagttggcaaaatcttggccaactctaaatatgctaattaagatcattggcaattc tgtgggggctctaggaaacctcaccttggtattggccatcatcgtcttcatttttgctgtggtcggcatgcagctctttggtaagagctacaaag aatgtgtctgcaagatttccaatgattgtgaactcccacgctggcacatgcatgactttttccactccttcctgatcgtgttccgcgtgctgtgtgg agagtggatagagaccatgtgggactgtatggaggtcgctggccaaaccatgtgccttactgtcttcatgatggtcatggtgattggaaatct agtggttctgaacctcttcttggccttgcttttgagttccttcagttctgacaatcttgctgccactgatgatgataacgaaatgaataatctccaga ttgctgtgggaaggatgcagaaaggaatcgattttgttaaaagaaaaatacgtgaatttattcagaaagcctttgttaggaagcagaaagcttt agatgaaattaaaccgcttgaagatctaaataataaaaaagacagctgtatttccaaccataccaccatagaaataggcaaagacctcaattat ctcaaagacggaaatggaactactagtggcataggcagcagtgtagaaaaatatgtcgtggatgaaagtgattacatgtcatttataaacaac cctagcctcactgtgacagtaccaattgctgttggagaatctgactttgaaaatttaaatactgaagaattcagcagcgagtcagatatggagg aaagcaaagagaagctaaatgcaactagttcatctgaaggcagcacggttgatattggagctcccgccgagggagaacagcctgaggttg aacctgaggaatcccttgaacctgaagcctgttttacagaagactgtgtacggaagttcaagtgttgtcagataagcatagaagaaggcaaa gggaaactctggtggaatttgaggaaaacatgctataagatagtggagcacaattggttcgaaaccttcattgtcttcatgattctgctgagca gtggggctctggcctttgaagatatatacattgagcagcgaaaaaccattaagaccatgttagaatatgctgacaaggttttcacttacatattc attctggaaatgctgctaaagtgggttgcatatggttttcaagtgtattttaccaatgcctggtgctggctagacttcctgattgttgatgtctcact ggttagcttaactgcaaatgccttgggttactcagaacttggtgccatcaaatccctcagaacactaagagctctgaggccactgagagctttg tcccggtttgaaggaatgagggttgttgtaaatgctcttttaggagccattccatctatcatgaatgtacttctggtttgtctgatcttttggctaata ttcagtatcatgggagtgaatctctttgctggcaagttttaccattgtattaattacaccactggagagatgtttgatgtaagcgtggtcaacaact acagtgagtgcaaagctctcattgagagcaatcaaactgccaggtggaaaaatgtgaaagtaaactttgataacgtaggacttggatatctgt ctctacttcaagtagccacgtttaagggatggatggatattatgtatgcagctgttgattcacgaaatgtagaattacaacccaagtatgaagac aacctgtacatgtatctttattttgtcatctttattatttttggttcattctttaccttgaatcttttcattggtgtcatcatagataacttcaacca acagaaaaagaagtttggaggtcaagacatttttatgacagaagaacagaagaaatactacaatgcaatgaaaaaactgggttcaaagaaaccacaa -continued aaacccatacctcgacctgctaacaaattccaaggaatggtctttgattttgtaaccaaacaagtctttgatatcagcatcatgatcctcatctgc cttaacatggtcaccatgatggtggaaaccgatgaccagagtcaagaaatgacaaacattctgtactggattaatctggtgtttattgttctgttc actggagaatgtgtgctgaaactgatctctcttcgttactactatttcactattggatggaatatttttgattttgtggtggtcattctctccattgt aggaatgtttctggctgaactgatagaaaagtattttgtgtcccctaccctgttccgagtgatccgtcttgccaggattggccgaatcctacgtctga tcaaaggagcaaaggggatccgcacgctgctctttgctttgatgatgtcccttcctgcgttgtttaacatcggcctccttcttttcctggtcatgtt catctacgccatctttgggatgtccaattttgcctatgttaagagggaagttgggatcgatgacatgttcaactttgagacctttggcaacagcat gatctgcctgttccaaattacaacctctgctggctgggatggattgctagcacctattcttaatagtggacctccagactgtgaccctgacaaa gatcaccctggaagctcagttaaaggagactgtgggaacccatctgttgggatttctttttttgtcagttacatcatcatatccttcctggttgtggt gaacatgtacatcgcggtcatcctggagaacttcagtgttgctactgaagaaagtgcagagcctctgagtgaggatgactttgagatgttctat gaggtttgggagaagtttgatcccgatgcgacccagtttatagagtttgccaaactttctgattttgcagatgccctggatcctcctcttctcata gcaaaacccaacaaagtccagctcattgccatggatctgcccatggtgagtggtgaccggatccactgtcttgacatcttatttgcttttacaaa gcgtgttttgggtgagagtggagagatggatgcccttcgaatacagatggaagagcgattcatggcatcaaacccctccaaagtctcttatga gcccattacgaccacgttgaaacgcaaacaagaggaggtgtctgctattattatccagagggcttacagacgctacctcttgaagcaaaaag ttaaaaaggtatcaagtatatacaagaaagacaaaggcaaagaatgtgatggaacacccatcaaagaagatactctcattgataaactgaat gagaattcaactccagagaaaaccgatatgacgccttccaccacgtctccaccctcgtatgatagtgtgaccaaaccagaaaaagaaaaatt tgaaaaagacaaatcagaaaaggaagacaaagggaaagatatcagggaaagtaaaaagtaaaaagaaaccaagaattttccattttgtgat caattgtttacagcccgtgatggtgatgtgtttgtgtcaacaggactcccacaggaggtctatgccaaactgactgtttttacaaatgtatactta aggtcagtgcctataacaagacagagacctctggtcagcaaactggaactcagtaaactggagaaatagtatcgatgggaggtttctattttc acaaccagctgacactgctgaagagcagaggcgtaatggctactcagacgataggaaccaatttaaagggggagggaagttaaattttta tgtaaattcaacatgtgacacttgataatagtaattgtcaccagtgtttatgttttaactgccacacctgccatatttttacaaaacgtgtgctgtga atttatcacttttctttttaattcacaggttgtttactattatatgtgactatttttgtaaatgggtttgtgtttggggagagggattaaagggaggga attctacatttctctattgtattgtataactggatatattttaaatggaggcatgctgcaattctcattcacacataaaaaaatcacatcacaaaaggg aagagtttacttcttgtttcaggatgtttttagatttttgaggtgcttaaatagctattcgtatttttaaggtgtctcatccagaaaaaatttaatgtg cctgtaaatgttccatagaatcacaagcattaaagagttgttttatttttacataacccattaaatgtacatgtatatatgtatatatgtatatgtgcg tgtatatacatatatatgtatacacacatgcacacacagagatatacacataccattacattgtcattcacagtcccagcagcatgactatcacatttt tgataagtgtcctttggcataaaataaaaatatcctatcagtcctttctaagaagcctgaattgaccaaaaaacatccccaccaccactttataaagt tgattctgctttatcctgcagtattgtttagccatcttctgctcttggtaaggttgacatagtatatgtcaatttaaaaaataaaagtctgctttgtaa atagtaattttacccagtggtgcatgtttgagcaaacaaaaatgatgatttaagcacactacttattgcatcaaatatgtaccacagtaagtatagttt gcaagctttcaacaggtaatatgatgtaattggttccattatagtttgaagctgtcactgctgcatgtttatcttgcctatgctgctgtatcttattcc ttccactgttcagaagtctaatatgggaagccatatatcagtggtaaagtgaagcaaattgttctaccaagacctcattcttcatgtcattaagcaa taggttgcagcaaacaaggaagagcttcttgctttttattcttccaaccttaattgaacactcaatgatgaaaagcccgactgtacaaacatgttg caagctgcttaaatctgtttaaaatatatggttagagttttctaagaaaatataaatactgtaaaaagttcattttattttatttttcagccttttgt acgtaaaatgagaaattaaaagtatcttcaggtggatgtcacagtcactattgttagtttctgttcctagcacttttaaattgaagcacttcacaaaat aagaagcaaggactaggatgcagtgtaggtttctgctttttttattagtactgtaaacttgcacacatttcaatgtgaaacaaatctcaaactgagttca atgtttatttgctttcaatagtaatgccttatcattgaaagaggcttaaagaaaaaaaaaatcagctgatactcttggcattgcttgaatccaatgtt tccacctagtctttttattcagtaatcatcagtcttttccaatgtttgtttacacagatagatcttattgacccatatggcactagaactgtatcagat ataatatgggatcccagctttttttcctctcccacaaaaccaggtagtgaagttatattaccagttacagcaaaatactttgtgtttcacaagcaaca ataaatgtagattctttatactgaagctattgacttgtagtgtgttggtgaaatgcatgcaggaaaatgctgttaccataaagaacggtaaaccac attacaatcaagccaaaagaataaaggtttcgcttttgtttttgtatttaattgttgtctttgtttctatctttgaaatgccatttaaaggtagatttc -continued tatcatgtaaaaataatctatctgaaaaacaaatgtaaagaacacacattaattactataattcatctttcaatttttttcatggaatggaagttaatt aagaagagtgtattggataactactttaatattggccaaaaagctagatatggcatcaggtagactagtggaaagttacaaaaattaataaaaaattga ctaaca),
and NM_021007.3 (SEQ ID NO: 2;
aagcatgatggaattttagctgcagtcttcttggtgccagcttatcaatcccaaactctgggtgtaaaagattctacagggcactttcttatgcaa ggagctaaacagtgattaaaggagcaggatgaaaagatggcacagtcagtgctggtaccgccaggacctgacagcttccgcttctttacca gggaatcccttgctgctattgaacaacgcattgcagaagagaaagctaagagacccaaacaggaacgcaaggatgaggatgatgaaaat ggcccaaagccaaacagtgacttggaagcaggaaaatctcttccatttatttatggagacattcctccagagatggtgtcagtgcccctggag gatctggacccctactatatcaataagaaaacgtttatagtattgaataaagggaaagcaatctctcgattcagtgccacccctgccctttacatt ttaactcccttcaaccctattagaaaattagctattaagattttggtacattctttattcaatatgctcattatgtgcacgattcttaccaactgtgta tttatgaccatgagtaaccctccagactggacaaagaatgtggagtatacctttacaggaatttatacttttgaatcacttattaaaatacttgcaagg ggcttttgtttagaagatttcacatttttacgggatccatggaattggttggatttcacagtcattacttttgcatatgtgacagagtttgtggacctg ggcaatgtctcagcgttgagaacattcagagttctccgagcattgaaaacaatttcagtcattccaggcctgaagaccattgtgggggccctg atccagtcagtgaagaagctttctgatgtcatgatcttgactgtgttctgtctaagcgtgtttgcgctaataggattgcagttgttcatgggcaacc tacgaaataaatgtttgcaatggcctccagataattcttcctttgaaataaatatcacttccttctttaacaattcattggatgggaatggtactactt tcaataggacagtgagcatatttaactgggatgaatatattgaggataaaagtcacttttatttttttagaggggcaaaatgatgctctgctttgtgg caacagctcagatgcaggccagtgtcctgaaggatacatctgtgtgaaggctggtagaaaccccaactatggctacacgagctttgacacct ttagttgggcctttttgtccttatttcgtctcatgactcaagacttctgggaaaacctttatcaactgacactacgtgctgctgggaaaacgtacat gatatttttttgtgctggtcatttcttgggctcattctatctaataaatttgatcttggctgtggtggccatggcctatgaggaacagaatcaggcca cattggaagaggctgaacagaaggaagctgaatttcagcagatgctcgaacagttgaaaaagcaacaagaagaagctcaggcggcagct gcagccgcatctgctgaatcaagagacttcagtggtgctggtgggataggagtttttttcagagagttcttcagtagcatctaagttgagctcca aaagtgaaaaagagctgaaaaacagaagaaagaaaaagaaacagaaagaacagtctggagaagaagagaaaaatgacagagtccgaa aatcggaatctgaagacagcataagaagaaaaggtttccgtttttccttggaaggaagtaggctgacatatgaaaagagattttcttctccaca ccagtccttactgagcatccgtggctcccttttctctccaagacgcaacagtagggcgagccttttcagcttcagaggtcgagcaaaggacat tggctctgagaatgactttgctgatgatgagcacagcacctttgaggacaatgacagccgaagagactctctgttcgtgccgcacagacatg gagaacggcgccacagcaatgtcagccaggccagccgtgcctccagggtgctccccatcctgcccatgaatgggaagatgcatagcgct gtggactgcaatggtgtggtctccctggtcgggggcccttctaccctcacatctgctgggcagctcctaccagagggcacaactactgaaac agaaataagaaagagacggtccagttcttatcatgtttccatggatttattggaagatcctacatcaaggcaaagagcaatgagtatagccagt attttgaccaacaccatggaagaacttgaagaatccagacagaaatgcccaccatgctggtataaatttgctaatatgtgtttgatttgggactg ttgtaaaccatggttaaaggtgaaacaccttgtcaacctggttgtaatggacccatttgttgacctggccatcaccatctgcattgtcttaaatac actcttcatggctatggagcactatcccatgacggagcagttcagcagtgtactgtctgttggaaacctggtcttcacagggatcttcacagca gaaatgtttctcaagataattgccatggatccatattattactttcaagaaggctggaatatttttgatggttttattgtgagccttagtttaatggaa cttggtttggcaaatgtggaaggattgtcagttctccgatcattccggctgctccgagttttcaagttggcaaaatcttggccaactctaaatatg ctaattaagatcattggcaattctgtgggggctctaggaaacctcaccttggtattggccatcatcgtcttcattttttgctgtggtcggcatgcag ctctttggtaagagctacaaagaatgtgtctgcaagatttccaatgattgtgaactcccacgctggcacatgcatgactttttccactccttcctg atcgtgttccgcgtgctgtgtggagagtggatagagaccatgtgggactgtatggaggtcgctggccaaaccatgtgccttactgtcttcatg atggtcatggtgattggaaatctagtggttctgaacctcttcttggccttgcttttgagttccttcagttctgacaatcttgctgccactgatgatgat aacgaaatgaataatctccagattgctgtgggaaggatgcagaaaggaatcgattttgttaaaagaaaaatacgtgaatttattcagaaagcct ttgttaggaagcagaaagctttagatgaaattaaaccgcttgaagatctaaataataaaaaagacagctgtatttccaaccataccaccataga aataggcaaagacctcaattatctcaaagacggaaatggaactactagtggcataggcagcagtgtagaaaaatatgtcgtggatgaaagt -continued gattacatgtcatttataaacaaccctagcctcactgtgacagtaccaattgctgttggagaatctgactttgaaaatttaaatactgaagaattca gcagcgagtcagatatggaggaaagcaaagagaagctaaatgcaactagttcatctgaaggcagcacggttgatattggagctcccgccg agggagaacagcctgaggttgaacctgaggaatcccttgaacctgaagcctgttttacagaagactgtgtacggaagttcaagtgttgtcag ataagcatagaagaaggcaaagggaaactctggtggaatttgaggaaaacatgctataagatagtggagcacaattggttcgaaaccttcat tgtcttcatgattctgctgagcagtggggctctggcctttgaagatatatacattgagcagcgaaaaaccattaagaccatgttagaatatgctg acaaggttttcacttacatattcattctggaaatgctgctaaagtgggttgcatatggttttcaagtgtattttaccaatgcctggtgctggctagac ttcctgattgttgatgtctcactggttagcttaactgcaaatgccttgggttactcagaacttggtgccatcaaatccctcagaacactaagagct ctgaggccactgagagctttgtcccggtttgaaggaatgagggttgttgtaaatgctcttttaggagccattccatctatcatgaatgtacttctg gtttgtctgatcttttggctaatattcagtatcatgggagtgaatctctttgctggcaagttttaccattgtattaattacaccactggagagatgttt gatgtaagcgtggtcaacaactacagtgagtgcaaagctctcattgagagcaatcaaactgccaggtggaaaaatgtgaaagtaaactttgat aacgtaggacttggatatctgtctctacttcaagtagccacgtttaagggatggatggatattatgtatgcagctgttgattcacgaaatgtagaa ttacaacccaagtatgaagacaacctgtacatgtatctttattttgtcatctttattattttttggttcattctttaccttgaatcttttcattggtgt catcatagataacttcaaccaacagaaaaagaagtttggaggtcaagacatttttatgacagaagaacagaagaaatactacaatgcaatgaaaaaac tgggttcaaagaaaccacaaaaacccatacctcgacctgctaacaaattccaaggaatggtctttgattttgtaaccaaacaagtctttgatatc agcatcatgatcctcatctgccttaacatggtcaccatgatggtggaaaccgatgaccagagtcaagaaatgacaaacattctgtactggatta atctggtgtttattgttctgttcactggagaatgtgtgctgaaactgatctctcttcgttactactatttcactattggatggaatatttttgatttt gtggtggtcattctctccattgtaggaatgtttctggctgaactgatagaaaagtattttgtgtcccctaccctgttccgagtgatccgtcttgccag gattggccgaatcctacgtctgatcaaaggagcaaaggggatccgcacgctgctctttgctttgatgatgtcccttcctgcgttgtttaacatcggcc tccttcttttcctggtcatgttcatctacgccatctttgggatgtccaatttttgcctatgttaagagggaagttgggatcgatgacatgttcaactttg agacctttggcaacagcatgatctgcctgttccaaattacaacctctgctggctgggatggattgctagcacctattcttaatagtggacctcca gactgtgaccctgacaaagatcaccctggaagctcagttaaaggagactgtgggaacccatctgttgggatttctttttttgtcagttacatcat catatccttcctggttgtggtgaacatgtacatcgcggtcatcctggagaacttcagtgttgctactgaagaaagtgcagagcctctgagtgag gatgactttgagatgttctatgaggtttgggagaagtttgatcccgatgcgacccagtttatagagtttgccaaactttctgattttgcagatgccc tggatcctcctcttctcatagcaaaacccaacaaagtccagctcattgccatggatctgcccatggtgagtggtgaccggatccactgtcttga catcttatttgcttttacaaagcgtgttttgggtgagagtggagagatggatgcccttcgaatacagatggaagagcgattcatggcatcaaac ccctccaaagtctcttatgagcccattacgaccacgttgaaacgcaaacaagaggaggtgtctgctattattatccagagggcttacagacgc tacctcttgaagcaaaaagttaaaaaggtatcaagtatatacaagaaagacaaaggcaaagaatgtgatggaacacccatcaaagaagata ctctcattgataaactgaatgagaattcaactccagagaaaaccgatatgacgccttccaccacgtctccaccctcgtatgatagtgtgaccaa accagaaaaagaaaaatttgaaaaagacaaatcagaaaaggaagacaaagggaaagatatcagggaaagtaaaaagtaaaaagaaacc aagaattttccattttgtgatcaattgtttacagcccgtgatggtgatgtgtttgtgtcaacaggactcccacaggaggtctatgccaaactgact gtttttacaaatgtatacttaaggtcagtgcctataacaagacagagacctctggtcagcaaactggaactcagtaaactggagaaatagtatc gatgggaggtttctattttcacaaccagctgacactgctgaagagcagaggcgtaatggctactcagacgataggaaccaatttaaagggg ggagggaagttaaatttttatgtaaattcaacatgtgacacttgataatagtaattgtcaccagtgtttatgttttaactgccacacctgccatatttt tacaaaacgtgtgctgtgaatttatcactttttcttttttaattcacaggttgtttactattatatgtgactatttttgtaaatgggtttgtgtttgggga gagggattaaagggagggaattctacatttctctattgtattgtataactggatatattttaaatggaggcatgctgcaattctcattcacacataaaa aaatcacatcacaaaagggaagagtttacttcttgtttcaggatgtttttagatttttgaggtgcttaaatagctattcgtatttttaaggtgtctcat ccagaaaaaatttaatgtgcctgtaaatgttccatagaatcacaagcattaaagagttgttttatttttacataacccattaaatgtacatgtatatat gtatatatgtatatgtgcgtgtatatacatatatatgtatacacacatgcacacacagagatatacacataccattacattgtcattcacagtcccagc agcatgactatcacatttttgataagtgtcctttggcataaaataaaaatatcctatcagtcctttctaagaagcctgaattgaccaaaaaacatcc -continued ccaccaccactttataaagttgattctgctttatcctgcagtattgtttagccatcttctgctcttggtaaggttgacatagtatatgtcaatttaaaa aataaaagtctgctttgtaaatagtaattttacccagtggtgcatgtttgagcaaacaaaaatgatgatttaagcacactacttattgcatcaaatat gtaccacagtaagtatagtttgcaagctttcaacaggtaatatgatgtaattggttccattatagtttgaagctgtcactgctgcatgtttatcttgc ctatgctgctgtatcttattccttccactgttcagaagtctaatatgggaagccatatatcagtggtaaagtgaagcaaattgttctaccaagacct cattcttcatgtcattaagcaataggttgcagcaaacaaggaagagcttcttgctttttattcttccaaccttaattgaacactcaatgatgaaaag cccgactgtacaaacatgttgcaagctgcttaaatctgtttaaaatatatggttagagttttctaagaaaatataaatactgtaaaaagttcattttat tttatttttcagccttttgtacgtaaaatgagaaattaaaagtatcttcaggtggatgtcacagtcactattgttagtttctgttcctagcacttttaa attgaagcacttcacaaaataagaagcaaggactaggatgcagtgtaggtttctgctttttttattagtactgtaaacttgcacacatttcaatgtgaa acaaatctcaaactgagttcaatgtttatttgctttcaatagtaatgccttatcattgaaagaggcttaaagaaaaaaaaaatcagctgatactctt ggcattgcttgaatccaatgtttccacctagtctttttattcagtaatcatcagtcttttccaatgtttgtttacacagatagatcttattgacccata tggcactagaactgtatcagatataatatgggatcccagctttttttcctctcccacaaaaccaggtagtgaagttatattaccagttacagcaaaat actttgtgtttcacaagcaacaataaatgtagattctttatactgaagctattgacttgtagtgtgttggtgaaatgcatgcaggaaaatgctgtta ccataaagaacggtaaacccacattacaatcaagccaaaagaataaaggtttcgcttttgtttttgtatttaattgttgtctttgtttctatctttgaaa tgccatttaaaggtagatttctatcatgtaaaaataatctatctgaaaaacaaatgtaaagaacacacattaattactataattcatctttcaattttt tcatggaatggaagttaattaagaagagtgtattggataactactttaatattggccaaaaagctagatatggcatcaggtagactagtggaaagt tacaaaaattaataaaaaaattgactaaca);
and SCN2A protein: NP_001035232.1 (SEQ ID NO: 8;
MAQSVLVPPGPDSFRFFTRESLAAIEQRIAEEKAKRPKQERKDEDDENGPKPNSDLEAGK

SLPFIYGDIPPEMVSVPLEDLDPYYINKKTFIVLNKGKAISRFSATPALYILTPFNPIRKLAI

KILVHSLFNMLIMCTILTNCVFMTMSNPPDWTKNVEYTFTGIYTFESLIKILARGFCLEDF

TFLRDPWNWLDFTVITFAYVTEFVDLGNVSALRTFRVLRALKTISVIPGLKTIVGALIQSV

KKLSDVMILTVFCLSVFALIGLQLFMGNLRNKCLQWPPDNSSFEINITSFFNNSLDGNGT

TFNRTVSIFNWDEYIEDKSHFYFLEGQNDALLCGNSSDAGQCPEGYICVKAGRNPNYGY

TSFDTFSWAFLSLFRLMTQDFWENLYQLTLRAAGKTYMIFFVLVIFLGSFYLINLILAVV

AMAYEEQNQATLEEAEQKEAEFQQMLEQLKKQQEEAQAAAAAASAESRDFSGAGGIG

VFSESSSVASKLSSKSEKELKNRRKKKKQKEQSGEEEKNDRVRKSESEDSIRRKGFRFSL

EGSRLTYEKRFSSPHQSLLSIRGSLFSPRRNSRASLESFRGRAKDIGSENDFADDEHSTFED

NDSRRDSLFVPHRHGERRHSNVSQASRASRVLPILPMNGKMHSAVDCNGVVSLVGGPS

TLTSAGQLLPEGTTTETEIRKRRSSSYHVSMDLLEDPTSRQRAMSIASILTNTMEELEESR

QKCPPCWYKFANMCLIWDCCKPWLKVKHLVNLVVMDPFVDLAITICIVLNTLFMAME

HYPMTEQFSSVLSVGNLVFTGIFTAEMFLKIIAMDPYYYFQEGWNIFDGFIVSLSLMELG

LANVEGLSVLRSFRLLRVFKLAKSWPTLNMLIKIIGNSVGALGNLTLVLAIIVFIFAVVGM

QLFGKSYKECVCKISNDCELPRWHMHDFFHSFLIVFRVLCGEWIETMWDCMEVAGQTM

CLTVFMMVMVIGNLVVLNLFLALLLSSFSSDNLAATDDDNEMNNLQIAVGRMQKGIDF

VKRKIREFIQKAFVRKQKALDEIKPLEDLNNKKDSCISNHTTIEIGKDLNYLKDGNGTTS

GIGSSVEKYVVDESDYMSFINNPSLTVTVPIAVGESDFENLNTEEFSSESDMEESKEKLNA

TSSSEGSTVDIGAPAEGEQPEVEPEESLEPEACFTEDCVRKFKCCQISIEEGKGKLWWNL

RKTCYKIVEHNWFETFIVFMILLSSGALAFEDIYIEQRKTIKTMLEYADKVFTYIFILEMLL

KWVAYGFQVYFTNAWCWLDFLIVDVSLVSLTANALGYSELGAIKSLRTLRALRPLRAL

SRFEGMRVVVNALLGAIPSIMNVLLVCLIFWLIFSIMGVNLFAGKFYHCINYTTGEMFDV

-continued

SVVNNYSECKALIESNQTARWKNVKVNFDNVGLGYLSLLQVATFKGWMDIMYAAVDS

RNVELQPKYEDNLYMYLYFVIFIIFGSFFTLNLFIGVIIDNFNQQKKKFGGQDIFMTEEQK

KYYNAMKKLGSKKPQKPIPRPANKFQGMVFDFVTKQVFDISIMILICLNMVTMMVETD

DQSQEMTNILYWINLVFIVLFTGECVLKLISLRYYYFTIGWNIFDFVVVILSIVGMFLAELI

EKYFVSPTLFRVIRLARIGRILRLIKGAKGIRTLLFALMMSLPALFNIGLLLFLVMFIYAIFG

MSNFAYVKREVGIDDMFNFETFGNSMICLFQITTSAGWDGLLAPILNSGPPDCDPDKDH

PGSSVKGDCGNPSVGIFFFVSYIIISFLVVVNMYIAVILENFSVATEESAEPLSEDDFEMFY

EVWEKFDPDATQFIEFAKLSDFADALDPPLLIAKPNKVQLIAMDLPMVSGDRIHCLDILF

AFTKRVLGESGEMDALRIQMEERFMASNPSKVSYEPITTTLKRKQEEVSAIIIQRAYRRY

LLKQKVKKVSSIYKKDKGKECDGTPIKEDTLIDKLNENSTPEKTDMTPSTTSPPSYDSVT

KPEKEKFEKDKSEKEDKGKDIRESKK),

NP_001035233.1 (SEQ ID NO: 9;
MAQSVLVPPGPDSFRFFTRESLAAIEQRIAEEKAKRPKQERKDEDDENGPKPNSDLEAGK

SLPFIYGDIPPEMVSVPLEDLDPYYINKKTFIVLNKGKAISRFSATPALYILTPFNPIRKLAI

KILVHSLFNMLIMCTILTNCVFMTMSNPPDWTKNVEYTFTGIYTFESLIKILARGFCLEDF

TFLRDPWNWLDFTVITFAYVTEFVNLGNVSALRTFRVLRALKTISVIPGLKTIVGALIQSV

KKLSDVMILTVFCLSVFALIGLQLFMGNLRNKCLQWPPDNSSFEINITSFFNNSLDGNGT

TFNRTVSIFNWDEYIEDKSHFYFLEGQNDALLCGNSSDAGQCPEGYICVKAGRNPNYGY

TSFDTFSWAFLSLFRLMTQDFWENLYQLTLRAAGKTYMIFFVLVIFLGSFYLINLILAVV

AMAYEEQNQATLEEAEQKEAEFQQMLEQLKKQQEEAQAAAAAASAESRDFSGAGGIG

VFSESSSVASKLSSKSEKELKNRRKKKKQKEQSGEEEKNDRVRKSESEDSIRRKGFRFSL

EGSRLTYEKRFSSPHQSLLSIRGSLFSPRRNSRASLFSFRGRAKDIGSENDFADDEHSTFED

NDSRRDSLFVPHRHGERRHSNVSQASRASRVLPILPMNGKMHSAVDCNGVVSLVGGPS

TLTSAGQLLPEGTTTETEIRKRRSSSYHVSMDLLEDPTSRQRAMSIASILTNTMEELEESR

QKCPPCWYKFANMCLIWDCCKPWLKVKHLVNLVVMDPFVDLAITICIVLNTLFMAME

HYPMTEQFSSVLSVGNLVFTGIFTAEMFLKIIAMDPYYYFQEGWNIFDGFIVSLSLMELG

LANVEGLSVLRSFRLLRVFKLAKSWPTLNMLIKIIGNSVGALGNLTLVLAIIVFIFAVVGM

QLFGKSYKECVCKISNDCELPRWHMHDFFHSFLIVFRVLCGEWIETMWDCMEVAGQTM

CLTVFMMVMVIGNLVVLNLFLALLLSSFSSDNLAATDDDNEMNNLQIAVGRMQKGIDF

VKRKIREFIQKAFVRKQKALDEIKPLEDLNNKKDSCISNHTTIEIGKDLNYLKDGNGTTS

GIGSSVEKYVVDESDYMSFINNPSLTVTVPIAVGESDFENLNTEEFSSESDMEESKEKLNA

TSSSEGSTVDIGAPAEGEQPEVEPEESLEPEACFTEDCVRKFKCCQISIEEGKGKLWWNL

RKTCYKIVEHNWFETFIVFMILLSSGALAFEDIYIEQRKTIKTMLEYADKVFTYIFILEMLL

KWVAYGFQVYFTNAWCWLDFLIVDVSLVSLTANALGYSELGAIKSLRTLRALRPLRAL

SRFEGMRVVVNALLGAIPSIMNVLLVCLIFWLIFSIMGVNLFAGKFYHCINYTTGEMFDV

SVVNNYSECKALIESNQTARWKNVKVNFDNVGLGYLSLLQVATFKGWMDIMYAAVDS

RNVELQPKYEDNLYMYLYFVIFIIFGSFFTLNLFIGVIIDNFNQQKKKFGGQDIFMTEEQK

KYYNAMKKLGSKKPQKPIPRPANKFQGMVFDFVTKQVFDISIMILICLNMVTMMVETD

DQSQEMTNILYWINLVFIVLFTGECVLKLISLRYYYFTIGWNIFDFVVVILSIVGMFLAELI

EKYFVSPTLFRVIRLARIGRILRLIKGAKGIRTLLFALMMSLPALFNIGLLLFLVMFIYAIFG

-continued

MSNFAYVKREVGIDDMFNFETFGNSMICLFQITTSAGWDGLLAPILNSGPPDCDPDKDH

PGSSVKGDCGNPSVGIFFFVSYIIISFLVVVNMYIAVILENFSVATEESAEPLSEDDFEMFY

EVWEKFDPDATQFIEFAKLSDFADALDPPLLIAKPNKVQLIAMDLPMVSGDRIHCLDILF

AFTKRVLGESGEMDALRIQMEERFMASNPSKVSYEPITTTLKRKQEEVSAIIIQRAYRRY

LLKQKVKKVSSIYKKDKGKECDGTPIKEDTLIDKLNENSTPEKTDMTPSTTSPPSYDSVT

KPEKEKFEKDKSEKEDKGKDIRESKK),
and

NP_066287.2 (SEQ ID NO: 1;
MAQSVLVPPGPDSFRFFTRESLAAIEQRIAEEKAKRPKQERKDEDDENGPKPNSDLEAGK

SLPFIYGDIPPEMVSVPLEDLDPYYINKKTFIVLNKGKAISRFSATPALYILTPFNPIRKLAI

KILVHSLFNMLIMCTILTNCVFMTMSNPPDWTKNVEYTFTGIYTFESLIKILARGFCLEDF

TFLRDPWNWLDFTVITFAYVTEFVDLGNVSALRTFRVLRALKTISVIPGLKTIVGALIQSV

KKLSDVMILTVFCLSVFALIGLQLFMGNLRNKCLQWPPDNSSFEINITSFFNNSLDGNGT

TFNRTVSIFNWDEYIEDKSHFYFLEGQNDALLCGNSSDAGQCPEGYICVKAGRNPNYGY

TSFDTFSWAFLSLFRLMTQDFWENLYQLTLRAAGKTYMIFFVLVIFLGSFYLINLILAVV

AMAYEEQNQATLEEAEQKEAEFQQMLEQLKKQQEEAQAAAAAASAESRDFSGAGGIG

VFSESSSVASKLSSKSEKELKNRRKKKKQKEQSGEEEKNDRVRKSESEDSIRRKGFRFSL

EGSRLTYEKRFSSPHQSLLSIRGSLFSPRRNSRASLFSFRGRAKDIGSENDFADDEHSTFED

NDSRRDSLFVPHRHGERRHSNVSQASRASRVLPILPMNGKMHSAVDCNGVVSLVGGPS

TLTSAGQLLPEGTTTETEIRKRRSSSYHVSMDLLEDPTSRQRAMSIASILTNTMEELEESR

QKCPPCWYKFANMCLIWDCCKPWLKVKHLVNLVVMDPFVDLAITICIVLNTLFMAME

HYPMTEQFSSVLSVGNLVFTGIFTAEMFLKIIAMDPYYYFQEGWNIFDGFIVSLSLMELG

LANVEGLSVLRSFRLLRVFKLAKSWPTLNMLIKIIGNSVGALGNLTLVLAIIVFIFAVVGM

QLFGKSYKECVCKISNDCELPRWHMHDFFHSFLIVFRVLCGEWIETMWDCMEVAGQTM

CLTVFMMVMVIGNLVVLNLFLALLLSSFSSDNLAATDDDNEMNNLQIAVGRMQKGIDF

VKRKIREFIQKAFVRKQKALDEIKPLEDLNNKKDSCISNHTTIEIGKDLNYLKDGNGTTS

GIGSSVEKYVVDESDYMSFINNPSLTVTVPIAVGESDFENLNTEEFSSESDMEESKEKLNA

TSSSEGSTVDIGAPAEGEQPEVEPEESLEPEACFTEDCVRKFKCCQISIEEGKGKLWWNL

RKTCYKIVEHNWFETFIVFMILLSSGALAFEDIYIEQRKTIKTMLEYADKVFTYIFILEMLL

KWVAYGFQVYFTNAWCWLDFLIVDVSLVSLTANALGYSELGAIKSLRTLRALRPLRAL

SRFEGMRVVVNALLGAIPSIMNVLLVCLIFWLIFSIMGVNLFAGKFYHCINYTTGEMFDV

SVVNNYSECKALIESNQTARWKNVKVNFDNVGLGYLSLLQVATFKGWMDIMYAAVDS

RNVELQPKYEDNLYMYLYFVIFIIFGSFFTLNLFIGVIIDNFNQQKKKFGGQDIFMTEEQK

KYYNAMKKLGSKKPQKPIPRPANKFQGMVFDFVTKQVFDISIMILICLNMVTMMVETD

DQSQEMTNILYWINLVFIVLFTGECVLKLISLRYYYFTIGWNIFDFVVVILSIVGMFLAELI

EKYFVSPTLFRVIRLARIGRILRLIKGAKGIRTLLFALMMSLPALFNIGLLLFLVMFIYAIFG

MSNFAYVKREVGIDDMFNFETFGNSMICLFQITTSAGWDGLLAPILNSGPPDCDPDKDH

PGSSVKGDCGNPSVGIFFFVSYIIISFLVVVNMYIAVILENFSVATEESAEPLSEDDFEMFY

EVWEKFDPDATQFIEFAKLSDFADALDPPLLIAKPNKVQLIAMDLPMVSGDRIHCLDILF

AFTKRVLGESGEMDALRIQMEERFMASNPSKVSYEPITTTLKRKQEEVSAIIIQRAYRRY

-continued

LLKQKVKKVSSIYKKDKGKECDGTPIKEDTLIDKLNENSTPEKTDMTPSTTSPPSYDSVT

KPEKEKFEKDKSEKEDKGKDIRESKK).

As used herein, the term “2'-deoxynucleoside” refers to a nucleoside comprising a 2'-H(H) deoxyfuranosyl sugar moiety. In certain embodiments, a 2'-deoxynucleoside is a 2'-β-D-deoxynucleoside and comprises a 2'-β-D-deoxyribosyl sugar moiety, which has the β-D ribosyl configuration as found in naturally occurring deoxyribonucleic acids (DNA). In certain embodiments, a 2'-deoxynucleoside may comprise a modified nucleobase or may comprise an RNA nucleobase (uracil).

As used herein, the term “2'-MOE” refers to a 2'-$OCH_2CH_2OCH_3$ group in place of the 2'-OH group of a furanosyl sugar moiety. A “2'-MOE sugar moiety” means a sugar moiety with a 2'-$OCH_2CH_2OCH_3$ group in place of the 2'-OH group of a furanosyl sugar moiety. Unless otherwise indicated, a 2'-MOE sugar moiety is in the β-D-ribosyl configuration. “MOE” means O-methoxyethyl.

As used herein, the term “2'-MOE nucleoside” refers to a nucleoside comprising a 2'-MOE sugar moiety.

As used herein, the term “5-methyl cytosine” refers to a cytosine modified with a methyl group attached at the 5 position. A 5-methyl cytosine is a modified nucleobase.

As used herein, the term “ameliorate”, used in reference to a treatment, refers to an improvement in at least one symptom or hallmark relative to the same symptom or hallmark in the absence of the treatment. In certain embodiments, amelioration is the reduction in the severity or frequency of a symptom or hallmark or the delayed onset or slowing of progression in the severity or frequency of a symptom or hallmark. In certain embodiments, the symptom or hallmark is seizures, hypotonia, sensory integration disorders, motor dysfunctions, intellectual and cognitive dysfunctions, movement and balance dysfunctions, visual dysfunctions, delayed language and speech, neurodevelopmental delays, sudden unexpected death in epilepsy, motor development delays, delayed social and language milestones, repetitive actions, uncoordinated oral movements, gastrointestinal disorders (for example, gastroesophageal reflux, diarrhea, constipation, dysmotility, and the like), or sleep problems. In certain embodiments, the seizures are focal, clonic, tonic, and generalized tonic and clonic seizures, prolonged seizures (often lasting longer than 10 minutes), or frequent seizures (for example, convulsive, myoclonic, absence, focal, obtundation status, or tonic seizures). In certain embodiments, the seizures are focal motor seizures, tonic seizures, generalized tonic-clonic seizures or myoclonic seizures.

As used herein, the term “cerebrospinal fluid” or “CSF” refers to the fluid filling the space around the brain and spinal cord. The term“artificial cerebrospinal fluid” or “aCSF” refers to a prepared or manufactured fluid that has certain properties of cerebrospinal fluid.

As used herein, the term “effective amount” of an oligomeric compound described herein refers to a quantity of the oligomeric compound sufficient to, when administered to the subject, including a human, effect beneficial or desired results, including clinical results. For example, in the context of treating a SCN2A-related disorder, e.g., a SCN2A-related disorder caused by a gain-of-function mutation, in a subject, an “effective amount” is an amount of an oligomeric compound that reduces the number of seizures experienced by the subject, as compared to the number of seizures experienced by the subject prior to the administration of the oligomeric compound. In some embodiments, an “effective amount” of an oligomeric compound is, when administered to a subject with a SCN2A-related disorder, e.g., a SCN2A-related disorder caused by a gain-of-function mutation, is sufficient to achieve a treatment response, such as a decrease in one or more symptoms, as compared to the response obtained without administration of the oligomeric compound.

As used herein, the term “gapmer” refers to a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the “gap” and the external regions may be referred to as the “wings” or “wing segments.” In certain embodiments, the internal region is a deoxy region. The positions of the internal region or gap refer to the order of the nucleosides of the internal region and are counted starting from the 5'-end of the internal region. Unless otherwise indicated, “gapmer” refers to a sugar motif. In certain embodiments, each nucleoside of the gap is a 2'-β-D-deoxynucleoside. In certain embodiments, the gap comprises one 2'-substituted nucleoside at position 1, 2, 3, 4, or 5 of the gap, and the remainder of the nucleosides of the gap are 2'-β-D-deoxynucleosides. As used herein, the term “MOE gapmer” refers to a gapmer having a gap comprising 2'-β-D-deoxynucleosides and wings comprising 2'-MOE nucleosides. As used herein, the term “mixed wing gapmer” refers to a gapmer having wings comprising modified nucleosides comprising at least two different sugar modifications. Unless otherwise indicated, a gapmer may comprise one or more modified internucleoside linkages and/or modified nucleobases and such modifications do not necessarily follow the gapmer pattern of the sugar modifications.

As used herein, the term “internucleoside linkage” refers to the covalent linkage between contiguous nucleosides in an oligonucleotide. As used herein, the term “modified internucleoside linkage” refers to any internucleoside linkage other than a phosphodiester internucleoside linkage. The term “phosphorothioate internucleoside linkage” or “PS internucleoside linkage” refers to a modified internucleoside linkage in which one of the non-bridging oxygen atoms of a phosphodiester internucleoside linkage is replaced with a sulfur atom.

As used herein, the term “linker-nucleoside” refers to a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, the term “nucleobase” refers to an unmodified nucleobase or a modified nucleobase. As used herein an “unmodified nucleobase” is adenine (A), thymine (T), cytosine (C), uracil (U), or guanine (G). As used herein, a “modified nucleobase” is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a target nucleic acid or oligonucleotide independent of any sugar or internucleoside linkage modification.

As used herein, the term "nucleoside" refers to a compound or a fragment of a compound comprising a nucleobase and a sugar moiety. The nucleobase and sugar moiety are each independently unmodified or modified. As used herein, the term "modified nucleoside" refers a nucleoside comprising a modified nucleobase and/or a modified sugar moiety. Modified nucleosides include abasic nucleosides, which lack a nucleobase. The term "linked nucleosides" refers to nucleosides that are connected in a contiguous sequence (i.e., no additional nucleosides are presented between those that are linked). An oligonucleotide may be described herein as comprising a sequence of linked oligonucleosides.

As used herein, the term "oligomeric compound" refers an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, the term "oligonucleotide" refers to a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, the term "modified oligonucleotide" refers to an oligonucleotide, wherein at least one nucleoside or internucleoside linkage is modified. As used herein, the term "unmodified oligonucleotide" refers to an oligonucleotide that does not comprise any nucleoside modifications or internucleoside modifications.

As used herein, the term "pharmaceutically acceptable carrier or diluent" refers to any substance suitable for use in administering to a subject. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein, the term "pharmaceutically acceptable salt" refers to any physiologically and pharmaceutically acceptable salt of a compound, e.g., an oligomeric compound. Pharmaceutically acceptable salts retain the desired biological activity of the parent compound and do not impart undesired toxicological effects thereto.

As used herein, the term "pharmaceutical composition" refers to a mixture of substances suitable for administering to a subject. For example, a pharmaceutical composition may comprise an oligomeric compound and a sterile aqueous solution.

As used herein, the term "subject" refers to any organism to which an oligomeric compound disclosed herein may be administered, e.g., for therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

In particular embodiments, a "subject" is a human subject. In further embodiments, a human subject is a pediatric subject. A pediatric subject is a child under the age of 18 years, such as under the age of 17 years, under the age of 16 years, under the age of 15 years, under the age of 14 years, under the age of 13 years, under the age of 12 years, under the age of 11 years, under the age of 10 years, under the age of 9 years, under the age of 8 years, under the age of 7 years, under the age of 6 years, under the age of 5 years, under the age of 4 years, under the age of 3 years, under the age of 2 years, under the age of 1 year, under the age of 6 months, under the age of 3 months or under the age of 1 month. In some embodiments, the pediatric subject may be 2-18 years old, e.g., 2 years old, 3 years old, 4 years old, 5 years old, 6 years old, 7 years old, 8 years old, 9 years old, 10 years old, 11 years old, 12 years old, 13 years old, 14 years old, 15 years old, 16 years old, 17 years old or 18 years old. In some embodiments, the pediatric subject may be 0-24 months old, e.g., 1 month old, 2 months old, 3 months old, 4 months old, 5 months old, 6 months old, 7 months old, 8 months old, 9 months old, 10 months old, 11 months old, 12 months old, 13 months old, 14 months old, 15 months old, 16 months old, 17 months old, 18 months old, 19 months old, 20 months old, 21 months old, 22 months old, 23 months old or 24 months old. In some embodiments, the pediatric subject is a newborn. In further embodiments, the pediatric subject is a premature newborn. In some embodiments, the newborn has low birth weight with or without prematurity.

As used herein, the term "sugar moiety" refers to an unmodified sugar moiety or a modified sugar moiety. As used herein, the term "unmodified sugar moiety" refers to a 2'-OH(H) β-D-ribosyl moiety, as found in RNA (an "unmodified RNA sugar moiety"), or a 2'-H(H) β-D-deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, the terms "modified sugar moiety" or "modified sugar" refer to a modified furanosyl sugar moiety or a sugar surrogate.

As used herein, the term "symptom or hallmark" refers to any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests. In certain embodiments, a hallmark is apparent on a brain MRI scan.

As used herein, the term "SCN2A-related disorder" refers to a class of neurological genetic diseases or disorders characterized by aberrant function of SCN2A. SCN2A-related disorders include, for example, epilepsy, pediatric epilepsy, benign familial neonatal/infantile seizures, severe early-onset epilepsy, epileptic encephalopathy, early infantile epileptic encephalopathy (i.e., early onset epileptic encephalopathy), late seizure onset epileptic encephalopathy, Ohtahara syndrome, infantile spasm syndrome (i.e., West syndrome), Lennox-Gastaut syndrome, generalized epilepsy with febrile seizures, migrating partial epilepsy of infancy (i.e., epilepsy of infancy with migrating focal seizures), infantile spasms, autism spectrum disorder, movement disorder, and drug-resistant epilepsies. In some embodiments, a SCN2A-related disorder may be caused by a gain-of-function SCN2A mutation. SCN2A-related disorders that may be caused by a gain-of-function SCN2A mutation include, for example, Ohtahara syndrome, epilepsy of infancy with migrating focal seizures, developmental and epileptic encephalopathy (DEE), including early seizure onset epileptic encephalopathy (EE). In some embodiments, a gain-of-function mutation in SCN2A that is associated with a SCN2A-related disorder includes a mutation selected from the group consisting of L210Q, A263V, E430A, R1882Q, G879R, Q1479H, V423L, G1593R, K1502N, V1601L, G211D, S1780I, D343H, and c.3986C>A p.(A1329D).

Oligomeric Compound

Methods of the present disclosure comprise administering to a subject with a SCN2A-related disorder an oligomeric compound that comprises a 6-10-4 MOE gapmer having a sequence (from 5' to 3') of CCACGACATATTTTTCTACA (SEQ ID NO: 3); wherein each of nucleosides 1-6 and 17-20 (from 5' to 3') are 2'-MOE nucleosides and each of nucleosides 7-16 are 2'-β-D-deoxynucleosides; wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages; and wherein each cytosine is a 5-methyl cytosine.

In some embodiments, the oligomeric compound comprises a modified oligonucleotide represented by the following chemical notation: ${}^{m}C_{es}{}^{m}C_{eo}A_{eo}{}^{m}C_{eo}G_{eo}A_{eo}{}^{m}C_{ds}A_{ds}T_{ds}A_{ds}T_{ds}T_{ds}T_{ds}T_{ds}T_{ds}{}^{m}C_{ds}T_{eo}A_{es}{}^{m}C_{es}A_{e}$ (SEQ ID NO: 3), wherein:

A=an adenine nucleobase, ${}^{m}C$=a 5-methyl cytosine nucleobase,

G=a guanine nucleobase,

T=a thymine nucleobase, e=a 2'-MOE sugar moiety, d=a 2'-β-D-deoxyribosyl sugar moiety, s=a phosphorothioate internucleoside linkage, and o=a phosphodiester internucleoside linkage.

In some embodiments, the oligomeric compound is a modified oligonucleotide represented by the following chemical structure:

(SEQ ID NO: 3)

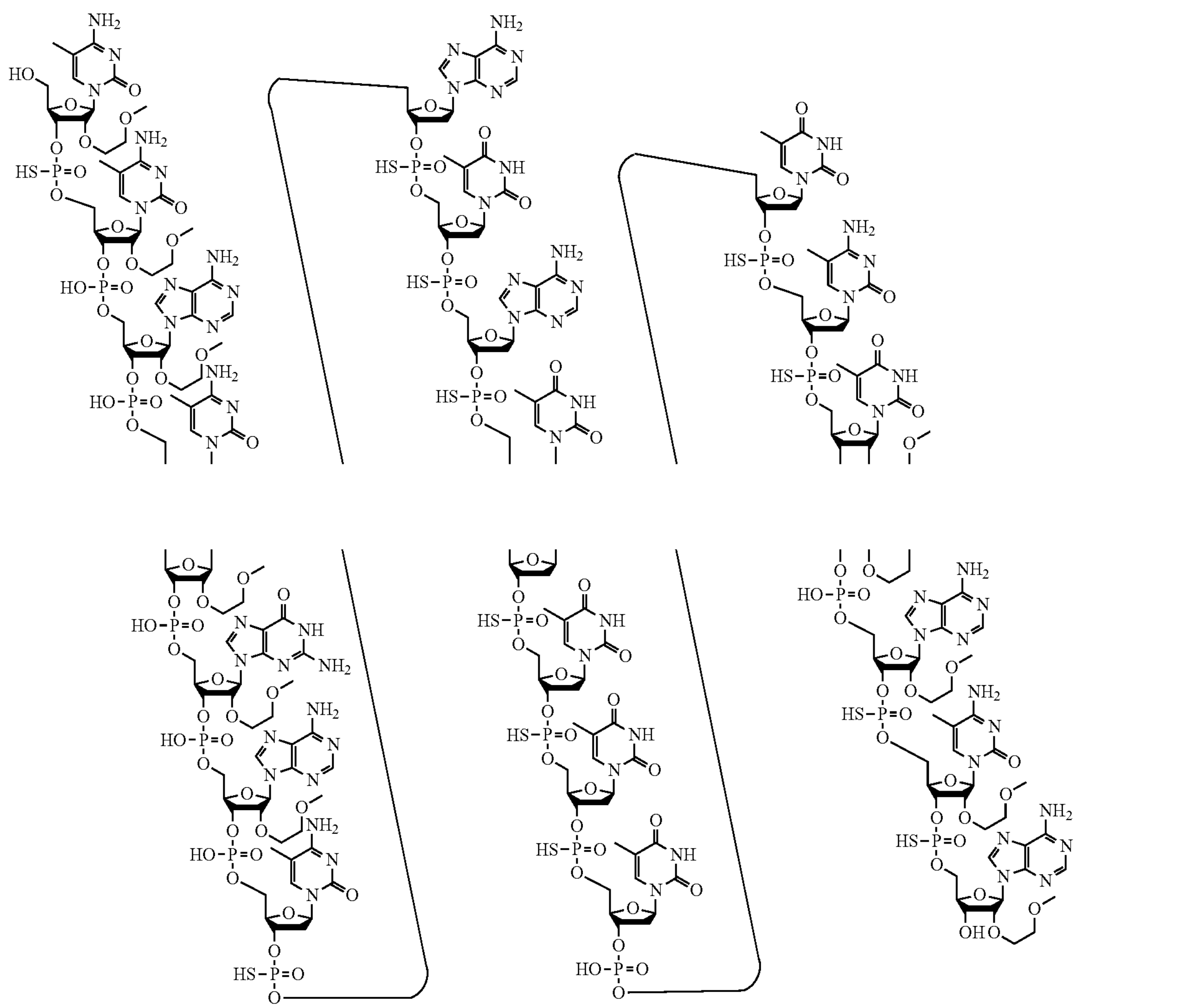

The modified oligonucleotide may be a sodium salt or a potassium salt. In one embodiment, the modified oligonucleotide is a sodium salt.

In some embodiments, the modified oligonucleotide may be represented by the following chemical structure:

(SEQ ID NO: 3)

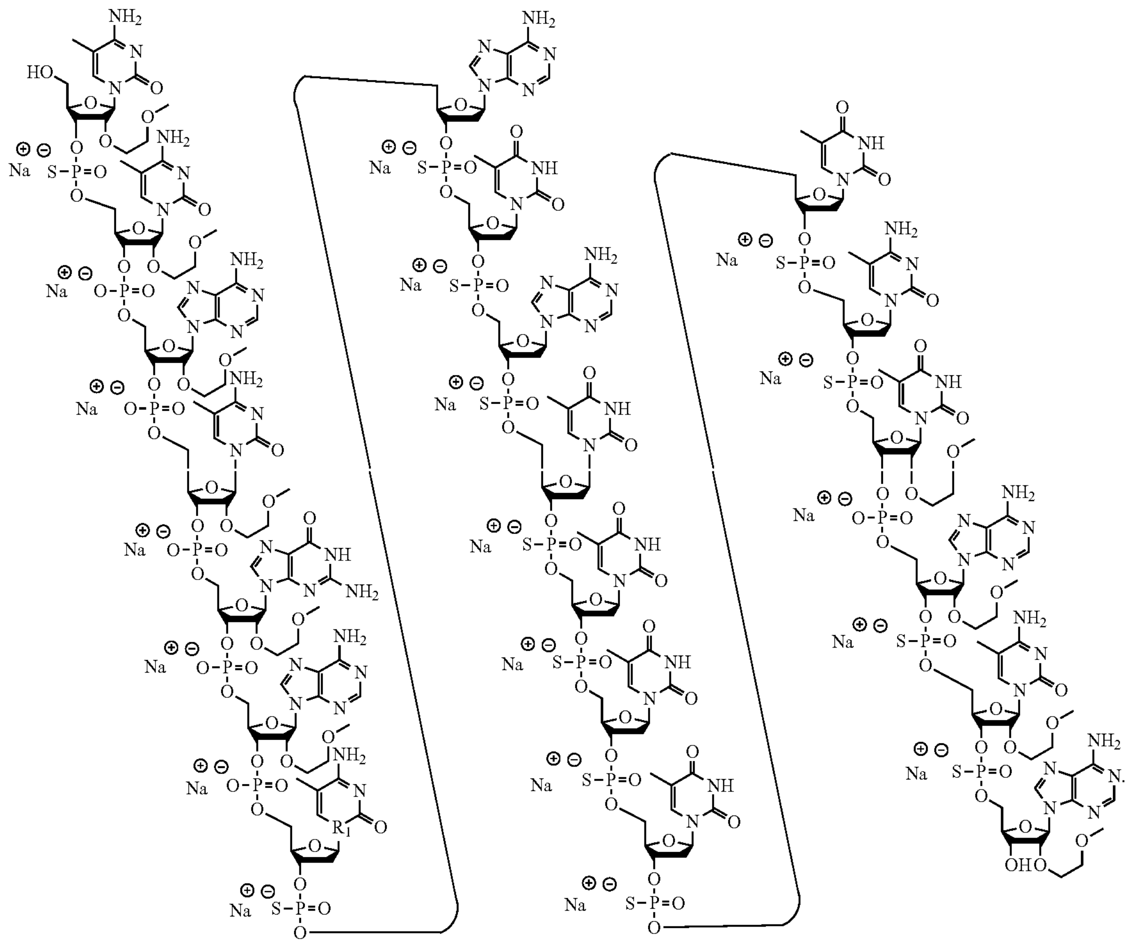

In some embodiments, the oligomeric compound of the present disclosure may also be referred to herein as "Compound 1" or "elsunursen".

In the context of the present disclosure, the oligomeric compound of the disclosure may be administered as a part of a pharmaceutical composition comprising the oligomeric compound and a pharmaceutically acceptable carrier or diluent. In certain embodiments, a pharmaceutical composition comprises or consists of a sterile saline solution and the oligomeric compound. In certain embodiments, the sterile saline is pharmaceutical grade saline. In certain embodiments, a pharmaceutical composition comprises or consists of the oligomeric compound and sterile water. In certain embodiments, the sterile water is pharmaceutical grade water. In certain embodiments, a pharmaceutical composition comprises or consists of the oligomeric compound and phosphate-buffered saline (PBS). In certain embodiments, the sterile PBS is pharmaceutical grade PBS. In certain embodiments, the pharmaceutical composition comprises or consists of the oligomeric compound and artificial cerebrospinal fluid ("artificial CSF" or "aCSF"). In certain embodiments, the artificial cerebrospinal fluid is pharmaceutical grade.

In certain embodiments, the pharmaceutical composition may comprise the oligomeric compound of the disclosure and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In the context of the present disclosure, the oligomeric compound may be administered to a subject by an injection (e.g., intravenously, subcutaneously, intramuscularly, intrathecally (IT), intracerebroventricularly (ICV), intraneurally, perineurally, etc.). In some embodiments, the oligomeric compound is administered to a subject intrathecally.

Methods of Treating SCN2A-Related Disorders

Disclosed herein are methods of reducing number of seizures experienced by a subject with a SCN2A-related disorder caused by a gain-of-function mutation in SCN2A gene that comprise administering to the subject an oligomeric compound of the present disclosure.

The present disclosure also provides methods of reducing frequency of seizures experienced by a subject with a SCN2A-related disorder that comprise administering to the subject an effective amount of an oligomeric compound of the present disclosure. In some embodiments, the term "frequency of seizures" refers to the number of seizures experienced by a subject in a given time period, e.g., a time period of a day, a week, 14 days, 28 days, a month, 3 months, 6 months or a year.

The present disclosure also provides methods of reducing the number of average daily seizures experienced by a subject with a SCN2A-related disorder that comprise administering to the subject an effective amount of an oligomeric compound of the present disclosure.

The present disclosure also provides methods of increasing the number of seizure-free days experienced by a subject with a SCN2A-related disorder that comprise administering to the subject an effective amount of an oligomeric compound of the present disclosure.

The present disclosure also provides methods of reducing seizure burden experienced by a subject with a SCN2A-related disorder or experienced by a caregiver of a subject with a SCN2A-related disorder that comprise administering to the subject an effective amount of an oligomeric compound of the present disclosure. In some embodiments, the term "seizure burden", as used herein, encompasses seizure frequency, seizure severity and burdens associated with seizure unpredictability. Burdens associated with seizures are discussed, e.g., in Berg et al., *Epilepsia Open* 2019, 4:293-301, the entire contents of which are hereby incorporated herein by reference.

In some embodiments, methods of the present disclosure allow achieving a reduction in seizures from baseline on top of, e.g., additional to the reduction in seizures based upon, best available standard of care. In some embodiments, a subject being administered Compound 1 in the context of the present disclosure in combination with standard of care therapy experiences a greater reduction in the number of seizures, e.g., the number of average daily seizures, than a subject who is administered standard of care therapy but is not administered Compound 1. In some embodiments, a subject being administered Compound 1 in the context of the present disclosure in combination with standard of care therapy experiences a greater reduction in the frequency of seizures than a subject who is administered standard of care therapy but is not administered Compound 1. In some embodiments, a subject being administered Compound 1 in the context of the present disclosure in combination with standard of care therapy experiences a greater increase in the number of seizures-free days than a subject who is administered standard of care therapy but is not administered Compound 1. In some embodiments, a subject being administered Compound 1 in the context of the present disclosure in combination with standard of care therapy experiences a greater decrease in seizure burden than a subject who is administered standard of care therapy but is not administered Compound 1.

The term "standard of care therapy", as used herein, encompasses any therapy (other than Compound 1) that is useful for treating a SCN2A-related disorder. In some embodiments, the standard of care therapy may comprise one or more sodium channel blocking medications, e.g., carbamazepine, oxcarbazepine, lamotrigine, valproate or topiramate.

Also disclosed herein are methods of treating a subject with a SCN2A-related disorder caused by a gain-of-function mutation in SCN2A gene that comprise administering to the subject an oligomeric compound of the present disclosure at a dose of about 0.1 mg to about 20 mg.

The methods disclosed herein may be used to ameliorate one or more symptoms of early-onset DEE, including, for example, seizures, limitations in communication, such as delayed language and speech; autonomic dysfunction; developmental delay; gastrointestinal abnormalities; movement disorders, such as choreoathetosis, dystonia, ataxia; anxiety; sensory issues; urinary retention problems; irritability; sleep problems (e.g., inability to fall asleep and inability to stay asleep); and behavior issues. Seizures include focal, clonic, tonic, and generalized tonic and clonic seizures, prolonged seizures (often lasting longer than 10 minutes), and frequent seizures.

The methods disclosed herein for treating a subject with a SCN2A-related disorder may have a disease-modifying effect on the subject. The disease-modifying effect may include one or more of, e.g., a reduction in seizure frequency experienced by a subject, an increase in the number of seizure-free days experienced by a subject; and an increase in survival of a subject, as compared to a subject who is administered standard of care therapy but is not administered Compound 1, or as compared to a subject who is not treated. In some embodiments, the disease modifying effect may also include a normalized developmental curve which includes one or more of, e.g., an increased ability of a subject to nurse, to interact socially, to process and/or manage outside stimuli, to grow and/or to develop language and/or speech, as compared to a subject who is administered standard of care therapy but is not administered Compound 1, or as compared to a subject who is not treated.

In some embodiments, methods of the present disclosure reduce the number of seizures experienced by the subject, as compared to the number of seizures experienced by the subject prior to the administration of the oligomeric compound. In some embodiments, seizures may include one or more of focal, clonic, tonic, and generalized tonic and clonic seizures, prolonged seizures (often lasting longer than 10 minutes), and frequent seizures. In some embodiments, seizures may include one or more of focal motor seizures, tonic seizures, generalized tonic-clonic seizures and myoclonic seizures.

In certain aspects, methods of the present disclosure comprise a dose escalation phase (or a titration phase) and a maintenance phase. Typically, the dose escalation phase is used to determine a maximum dose for the subject and the maintenance phase is used to administer the maximum dose to the subject on an ongoing basis. In certain aspects, the method does not include a dose escalation phase and a selected dose (also referred to herein as a maintenance dose) is administered to the subject on an ongoing basis.

In some embodiments, the oligomeric compound is administered to a subject in the context of the present disclosure at a dose of about 0.1 mg to about 20 mg, e.g., about 0.1 mg to about 0.5 mg, about 0.1 mg to about 1 mg, about 1 mg to about 5 mg, about 0.5 mg to about 8 mg, about 0.5 mg to about 10 mg, about 1 mg to about 8 mg, about 1 mg to about 10 mg, about 2 mg to about 10 mg or about 5 mg to about 15 mg. In some embodiments, the oligomeric compound is administered at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg or about 20 mg. In some embodiments, the oligomeric compound is administered at a dose of about 0.5 mg, about 1 mg, about 1.5 mg, about 2.0 mg, about 2.5 mg, about 3 mg, about 3.5 mg, about 4 mg, about 5 mg, about 8 mg, about 12 mg or about 15 mg.

In one embodiment, the oligomeric compound is administered at a dose of about 1 mg. In some embodiments, the oligomeric compound is administered at a dose of about 8 mg.

In some embodiments, the oligomeric compound is administered at a dose of at least 0.25 mg. In some embodiments, the oligomeric compound is administered at a dose of at least 0.5 mg. In some embodiments, the oligomeric compound is administered at a dose of at least 0.75 mg. In some embodiments, the oligomeric compound is administered at a dose of at least 1 mg. In some embodiments, the oligomeric compound is administered at a dose of at least 0.25 mg, at least 0.5 mg, at least 0.75 mg, at least 1 mg, at least 1.5 mg, at least 2 mg, at least 2.5 mg, at least 3 mg, at least 4 mg, at least 5 mg, at least 6 mg, at least 7 mg, at least 8 mg, at least 9 mg, at least 10 mg, at least 11 mg, at least 12 mg, at least 13 mg, at least 14 mg, at least 15 mg, at least 16 mg, at least 17 mg, at least 18 mg, at least 19 mg, or at least 20 mg.

In one aspect, the dosage of the oligomeric compound may be titrated one or more times. In certain embodiments, the dosage is increased 0.5-fold to 10-fold between each titrated dose, 1-fold to 10-fold or 1.25-fold to 5-fold between each titrated dose. In certain embodiments, the dosage is increased 1.25-fold to 2-fold, 1.5-fold to 3-fold, 1.5-fold to 2.5-fold, or 1.5-fold to 2-fold between each titrated dose. In certain embodiments, the dosage is increased 1.25-fold to 1.75-fold between each titrated dose. In certain embodiments, the dosage is increased 2-fold, up to 8 mg, followed by no more than a 1.5-fold increase for all subsequent doses.

In various embodiments, the dosage may be titrated upwardly or downwardly in the medical judgment of a clinician based upon any clinical factors such as for example, patient response, or lack of response, at a particular dosage, laboratory results (e.g., blood count, ECG results, brain scan results, results of pharmacokinetic assessments, etc.), patient illness or adverse events.

Downward titration may occur any number of times by any factor such as decreasing the dosage 0.5-fold to 10-fold between each downwardly titrated dose, decreasing the dosage 1-fold to 10-fold or 1.25-fold to 5-fold between each downwardly titrated dose. In certain embodiments, the dosage is decreased 1.25-fold to 2-fold, 1.5-fold to 3-fold, 1.5-fold to 2.5-fold, or 1.5-fold to 2-fold between each downwardly titrated dose. In certain embodiments, the dosage is decreased 1.25-fold to 1.75-fold between each titrated dose. In certain embodiments, the dosage is decreased 0.5-fold, 1-fold, or 2-fold. In an embodiment, downward titration may include immediate cessation of dosing or a pause in dosing.

In various embodiments upward titration may be followed by downward titration. In other embodiments, downward titration may be followed by upward titration.

In certain embodiments, during the dose escalation phase, the dosage of the oligomeric compound may be titrated from an initial dose of about 1 mg to a maximum dose of at least about 1.5 mg, about 2 mg, about 3 mg, about 3.5 mg, about 4 mg, about 5 mg, about 8 mg, about 10 mg, about 12 mg, about 15 mg, about 18 mg, about 20 mg, about 25 mg, about 30 mg, about 32 mg, about 35 mg, about 40 mg, about 45 mg, about 50 about mg, about 55 mg, about 60 mg, about 65 mg, about 70 mg, about 75 mg, about 80 mg, about 85 mg, about 90 mg, about 100 mg, or more. In certain embodiments, during the dose escalation phase, the dosage of the oligomeric compound is titrated from an initial dose of about 0.25 mg, about 0.5 mg, about 0.75 mg, about 1 mg, about 1.5 mg, about 2 mg, about 3 mg, about 4 mg, about 5 mg, about 6 mg, about 7 mg, about 8 mg, about 9 mg, about, 10 mg, about 11 mg, about 12 mg, about 13 mg, about 14 mg, or about 15 mg to a maximum dose of at least about 20 mg, about 25 mg, about 30 mg, about 35 mg, about 40 mg, about 45 mg, about 50 mg, about 60 mg, about 65 mg, about 70 mg, about 75 mg, about 80 mg, about 85 mg, about 90 mg, about 95 mg, about 100 mg, or more. In certain embodiments, the maximum dose is about 4-100 mg, about 4-50 mg, about 4-25 mg, about 4-15 mg, about 1-10 mg, about 1.5-10 mg, about 4-8 mg, about 1 to 5 mg, about 1.5 to 5 mg, about 1.5 to 8 mg, about 8-100 mg, about 8-75 mg, about 8-50 mg, about 8-25 mg, or about 8-15 mg. In certain embodiments, the maximum dose is about 15-100 mg, about 15-75 mg, about 15-50 mg, about 15-40 mg, about 15-30 mg, about 15-25 mg. In certain embodiments, during the dose escalation phase, the dosage of the oligomeric compound is titrated from an initial dose of about 1 mg to a maximum dose of at least about 15 mg. In certain embodiments, during the dose escalation phase, the dosage of the oligomeric compound is titrated from an initial dose of about 1 mg to a maximum dose of about 32 mg. In certain embodiments, during the dose escalation phase, the dosage of the oligomeric compound is titrated from an initial dose of about 1 mg to a maximum dose of about 32-64 mg. In certain embodiments, the dosage of the oligomeric compound is titrated from an initial dose of about 1 mg to a maximum dose of at least 64 mg.

In certain embodiments, the dosage of the oligomeric compound may be administered from an initial dose of about 1 mg to a cumulative dose of at least about 5 mg, about 7 mg, about 8 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 500 mg, about 1 g, about 10 g, or about 54 grams or more. In certain embodiments, the dosage of the oligomeric compound is administered from an initial dose of about 1 mg, about 1.5 mg, about 2 mg, about 2.5 mg, about 3 mg, about 3.5 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 25 mg, or about 30 mg to a cumulative dose of at least about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 500 mg, about 1 g, about 10 g, or about 54 grams or more.

In certain embodiments, the cumulative dose is about 40-200 mg, about 50-200 mg, about 50-175 mg, about 50-150 mg, about 50-125 mg, about 50-100 mg, about 50-75 mg, about 40-50 mg, about 75-200 mg, about 75-175 mg, about 75-150 mg, about 75-125 mg, about 75-100 mg, about 100-200 mg, about 100-175 mg, about 100-150 mg, about 100-125 mg, about 125-200 mg, about 125-175 mg, about 125-150 mg, about 150-200 mg, or about 150-175 mg. In certain embodiments, the dosage of the oligomeric compound is administered from an initial dose of about 1 mg to a cumulative dose of at least about 40 mg or 50 mg. In certain embodiments, the dosage of the oligomeric compound is administered from an initial dose of about 1 mg to a cumulative dose of at least about 100 mg. In certain embodiments, the dosage of the oligomeric compound is administered from an initial dose of about 1 mg to a cumulative dose of at least about 40-100 mg, 50-100 mg, 100 mg to 200 mg, 200 mg to 500 mg, about 500 mg to about 1 g, about 1 g to about 10 g, about 10 g to about 540 g.

In some embodiments, the dosing of the oligomeric compound, including dose escalations and reductions during treatment, is determined by a clinician in light of available information and relevant considerations. The relevant considerations may include any considerations deemed relevant by a clinician, such as, by way of non-limiting example, overall health of patient, response to drug treatment, infectious disease state and management, vital signs, seizure counts and/or test results, e.g., blood count, ECG results, brain scan results, results of pharmacokinetic assessments, etc.

In one aspect, the maximum dose is reached after administration of multiple titrated doses of the oligomeric compound. In certain embodiments, the maximum dose of the dose escalation phase is reached after administration of 2-20 titrated doses of the oligomeric compound, including after 2, 3, 4, 5, 6, 7, 8, 9, 10, 11, 12, 13, 14, 15, 16, 17, 18, 19, or 20 titrated doses of the oligomeric compound. In certain embodiments, the maximum dose of the dose escalation phase is reached after administration of 2-4, 2-10, 4-16, 4-12, 4-10, 4-8, 5-15, 5-12, 5-10, 5-8, 6-12, 6-10, 8-12, or 8-10 titrated doses of the oligomeric compound. In certain embodiments, the maximum dose of the dose escalation phase is reached after administration of up to about 4 to about 12 titrated doses of the oligomeric compound. In other embodiments, no titration is needed to reach the maximum dose, e.g., dose 1 is the maximum dose.

In one aspect, each administration of the titrated dose of the oligomeric compound is separated by about 3-20 weeks. In certain embodiments, each administration of the titrated dose of the oligomeric compound is separated by about 1 week, 2, 3, 4, 5, 6, 7, 8, 9, 10, 11, 12, 13, 14, 15, 16, 17, 18, 19, or 20 weeks. In certain embodiments of the dose escalation phase, the titrated dose of the oligomeric compound is administered about every 4-6 weeks. In certain embodiments, each administration of the titrated dose of the oligomeric compound is separated by at least about 6 weeks. In certain embodiments, each administration of the titrated dose of the oligomeric compound is separated by at least about 2-4 weeks. In other embodiments, each administration of the titrated dose of the oligomeric compound is separated by at least about 2 weeks, at least about 3 weeks, or at least about 4 weeks. In certain embodiments, a titrated dose of the oligomeric compound is administered no more frequently than every 6 weeks. In other embodiments, a titrated dose of the oligomeric compound is administered no more frequently than every 4 weeks. In other embodiments, a titrated dose of the oligomeric compound is administered no more frequently than every 3 weeks. In other embodiments, a titrated dose of the oligomeric compound is administered no more frequently than every 2 weeks.

In some embodiments, the oligomeric compound is administered to a subject every week. In some embodiments, the oligomeric compound is administered to a subject every 2 weeks. In some embodiments, the oligomeric compound is administered to a subject every 3 weeks. In some embodiments, the oligomeric compound is administered to a subject every 4 weeks. In some embodiments, the oligomeric compound is administered to a subject every 6 weeks. In some embodiments, the oligomeric compound is administered to a subject every 8 weeks. In some embodiments, the oligomeric compound is administered to a subject every 10 weeks. In some embodiments, the oligomeric compound is administered to a subject every 12 weeks. In some embodiments, the oligomeric compound is administered to a subject every month.

In certain embodiments, during the dose escalation phase, the dosage of the oligomeric compound is titrated from an initial dose of about 1 mg to a maximum dose of about 15 mg. In certain embodiments, during the dose escalation phase, the dosage of the oligomeric compound is titrated from a first dose of about 1 mg to a second dose of about 2 mg, and optionally to a third dose of about 4 mg, and optionally to a fourth dose of up to about 8 mg, and optionally to a fifth dose of up to about 12 mg, and optionally to a sixth dose of up to about 15 mg. In certain embodiments, the fourth dose of about 8 mg is titrated to a fifth dose of about 15 mg. In certain embodiments, 2-6 weeks separate the administration of each titrated dose. In other embodiments, the titration can continue up to a maximum dose of 100 mg.

In one aspect, the method of treatment further comprises administering a maintenance dose during a maintenance phase. In certain embodiments, the maintenance phase follows the dose escalation phase. In certain embodiments, the maintenance dose is the maximum dose following the dose escalation phase. In other embodiments, the maintenance dose is selected and administered to a subject without the subject undergoing a dose escalation phase.

In certain embodiments, the maintenance dose is administered about every 16-20 weeks or every 2-20 weeks. In certain embodiments, the maintenance dose is administered about every 1, 2, 3, 4, 5, 6, 7, 8, 9, 10, 11, 12, 13, 14, 15, 16, 17, 18, 19, or 20 weeks. In certain embodiments, the maintenance dose is administered about every 1-4 weeks, 1-6 weeks, 1-8 weeks, 1-16 weeks, 2-16 weeks, 2-8 weeks, 6-18 weeks, 6-16 weeks, 6-14 weeks, 6-12 weeks, 6-10 weeks, 8-18 weeks, 8-16 weeks, 8-14 weeks, 8-12 weeks, 8-10 weeks, 10-18 weeks, 10-16 weeks, 10-14 weeks, or 10-12 weeks. In certain embodiments, the maintenance dose is administered about every 12 weeks.

In one aspect of the methods of treatment, the maintenance dose is administered after the maximum dose, as described herein, has been reached during the dose escalation phase. In certain embodiments, the maintenance dose is administered after a maximum dose of about 1-15 mg, e.g., a maximum dose of about 1 mg, about 1.5 mg, about 2 mg, about 2.5 mg, about 3 mg, about 4 mg, about 5 mg, about 6 mg, about 7 mg, about 8 mg, about 10 mg, about 12 mg or about 15 mg has been reached. In certain embodiments, the maintenance dose is administered after the maximum dose of about 15 mg has been reached. In certain embodiments, the maintenance dose is administered after a maximum dose of greater than 15 mg has been reached. In certain embodiments, the maintenance dose is administered after a maximum dose of about 15-32 mg has been reached. In certain embodiments, the maintenance does is administered after a maximum dose of about 30-50 mg has been reached. In certain embodiments, the maintenance dose is administered after a maximum dose of greater than 50 mg has been reached.

In one aspect, multiple maintenance doses are administered. In certain embodiments each administration of the maintenance dose is separated by about 2-20 weeks. In certain embodiments, each administration of the maintenance dose is separated by about 2, 3, 4, 5, 6, 7, 8, 9, 10, 11, 12, 13, 14, 15, 16, 17, 18, 19, or 20 weeks. In various embodiments, each administration of the maintenance dose is separated by about a month. In certain embodiments, each administration of the maintenance dose is separated by about 8-16, 8-14, 8-12, 8-10, 10-16, 10-14, or 10-12 weeks. In certain embodiments, the maintenance dose is administered at least about every 12 weeks.

In one aspect, maintenance doses are administered over a period of 6 months or greater. In certain embodiments, maintenance doses are administered for the remainder of a subject's life. In certain embodiments, maintenance doses are administered for at least 1-50 years. In certain embodiments, maintenance doses are administered for at least 1, 2, 3, 4, 5, 6, 7, 8, 9, or 10 years. In certain embodiments, maintenance doses are administered for at least 2-50 years, 2-40 years, 2-35 years, 2-30 years, 2-25 years, 2-20 years, 2-15 years, 2-10 years, or 2-5 years. In certain embodiments, maintenance doses are administered for at least 2 years.

In one aspect, the method of treatment comprises inhibiting the expression of SCN2A in neuronal cells in the subject. In various aspects, the method of treatment comprises inhibiting the expression of SCN2A mRNA in the subject by about 10% to about 90%, about 35% to about 80%, about 20%, about 25%, about 30%, about 35%, about 40%, about 45%, about 50%, about 55%, about 60%, about 65%, about 70%, about 75%, about 80%, about 85%, about 90%, about 95%, or more than about 95% but less than 100%. In other aspects, about 25% to about 50% or about 35% to about 40% knockdown of SCN2A mRNA is achieved.

In an aspect, the subject has been diagnosed with early-onset DEE prior to one year of age. In another aspect, the subject has been diagnosed with early-onset DEE prior to three months of age. In certain embodiments, the subject has been diagnosed with early-onset DEE prior to two months or prior to one month of age. In certain embodiments, the subject has been diagnosed with early-onset DEE in utero. Typically, the diagnosis comprises determining that the subject carries an SCN2A mutation prior to administering the oligomeric compound. Any SCN2A mutation can be used to diagnose early-onset DEE, including any known SCN2A mutation and any SCN2A mutation identified in the future. In certain embodiments, the SCN2A mutation comprises one or more of A263V, E430A, E430G, R1882Q, G879R, G1593R, K1502N, V1601L, G211D, S1780I, D343H, R1626Q, G882E, M1545V, L210Q, Q1479H, N1662D, F1597L, V423L, A215T, I891T, A1329D, or a combination thereof. In some embodiments, the SCN2A mutation comprises one or more of Q1531K, L1563V, E1321K, Y1589C, M252V, R223E, L1330F, V208E, R36G, R1882G, D343G, V261L, F1651C, R1319Q, A263V, Q383E, V1325I, K908E, V261M, S987I, R1629H, R1882Q, M1338T, E999K, R856Q, V423L, S1336Y, R1626Q, G882E, N212D, E1211K, D195G, L1342P, R220Q, R853Q, R1435*, K503fs*, R937C, or a combination thereof. In some embodiments, the SCN2A mutation comprises one or more of L210Q, A263V, E430A, R1882Q, G879R, Q1479H, V423L, G1593R, K1502N, V1601L, G211D, S1780I, D343H and A1329D, or a combination thereof. In some embodiments, the SCN2A mutation comprises A1329D.

In one aspect, the subject is a human or non-human animal. In certain embodiments, the subject is a human. In certain embodiments, the subject is a human from 2 years old to 18 years old. In other embodiments, the subject is a human older than 2 years old or younger than 18 years old. In other embodiments, the subject is a human older than 18 years old.

In certain embodiments, the subject is a human younger than 2 years old. In certain embodiments, the subject is a human infant. In further embodiments, the infant is 6 months or younger, 5 months or younger, 4 months or younger, 3 months or younger, 2 months or younger or 1 month or younger.

In certain embodiments, the subject is a human newborn. In further embodiments, the newborn is a full term newborn, i.e., born after 39 or more weeks of gestation. In other embodiments, the newborn is a premature newborn, i.e., born after less than 39 weeks of gestation. In some embodiments, the subject is a human premature newborn born after less than 38 weeks, less than 37 weeks, less than 36 weeks, less than 35 weeks, less than 34 weeks, less than 33 weeks, less than 32 weeks, or less than 31 weeks, less than 30 weeks, or less than 28 weeks of gestation. In various embodiments, the newborn has a low birth weight regardless of gestational age.

An oligomeric compound described herein may be administered to a subject in the context of the present invention in combination with another agent or therapy, e.g., an antiepilepsy agent. Non-limiting examples of the anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide, and cannabidiol. In an embodiment, an oligomeric compound is administered in combination with carbamazepine.

In addition to intrathecal administration, the oligomeric compounds described herein may also be administered, for example, by oral, parenteral, intracerebroventricular, intraparenchymal, buccal, sublingual, nasal, rectal, patch, pump, or transdermal administration. Parenteral administration includes intravenous, intraperitoneal, subcutaneous, intramuscular, transepithelial, nasal, intrapulmonary, intrathecal, intracisternal, intracerebroventricular, intraparenchymal, rectal, and topical modes.

Other SCN2A disorders can be treated according to the methods disclosed in this application include developmental or epileptic encephalopathy (DEE), such as, Ohtahara Syndrome; epilepsy with migrating focal seizures of infancy (EIMFS); infantile and childhood DEE, for example West Syndrome and Lennon-Gastaut Syndrome; Dravet Syndrome; Idiopathic/Generic Generalized Epilepsies (IGE/GGE); Temporal Lobe Epilepsy; Myoclonic Astatic Epilepsy (MAE); Migrating Partial Epilepsy of Infancy (MMPSI); and familial hemiplegic migraines, with or without epilepsy. In certain embodiments, the SCN2A-related disorder is late seizure onset epileptic encephalopathy. In certain embodiments, the SCN2A-related disorder is Benign Familial Neonatal-Infantile Seizures. In certain embodiments, the SCN2A-related disorder is an intellectual disability (ID). In certain embodiments, the SCN2A-related disorder is an autism spectrum disorder (ASD).

The methods of treatment disclosed herein may be used to ameliorate one or more symptoms of SCN2A disorders, including seizures, hypotonia, sensory issues, such as sensory integration disorders, motor development delays and dysfunctions, intellectual and cognitive dysfunctions, movement and balance dysfunctions, visual dysfunctions, delayed language and speech, gastrointestinal disorders, neurodevelopmental delays, and sleep problems. Seizures include focal, clonic, tonic, and generalized tonic and clonic seizures, prolonged seizures (often lasting longer than 10 minutes), and frequent seizures.

In some embodiments, administration of an oligomeric compound to a subject in need thereof in the context of the present disclosure results in a decrease in the frequency of seizures experienced by the subject, as compared to the frequency of seizures experienced by the subject prior to the administration of the oligomeric compound. In some embodiments, administration of an oligomeric compound to a subject in need thereof in the context of the present disclosure results in a decrease of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% at least about 80%, at least about 85%, at least about 90% or at least about 95% in the frequency of seizures experienced by the subject, as compared to the frequency of seizures experienced by the subject prior to the administration of the oligomeric compound. In some embodiments, a decrease in the frequency of seizures in the subject is observed at least 1 week, at least 2 weeks, at least 4 weeks, at least 6 weeks, at least 8 weeks, at least 10 weeks, at least 12 weeks, at least 14 weeks or at least 16 or more weeks after the start of the administration of an oligomeric compound. In some embodiments, a decrease in frequency of seizures experienced by the subject is observed within 28 days after the start of administration of the oligomeric compound. In some embodiments, the term "frequency of seizures" refers to the number of seizures experienced by a subject in a given time period, e.g., a time period of 28 days.

In some embodiments, administering an oligomeric compound to a subject with a SCN2A-related disorder in the context of the present disclosure results in a decrease in the number of average daily seizures experienced by the subject, as compared to the number of average daily seizures experienced by the subject prior to administering the oligomeric compound. In some embodiments, administering an oligomeric compound to a subject in need thereof in the context of the present disclosure results in a decrease of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% in the number of average daily seizures experienced by the subject, as compared to the number of average daily seizures experienced by the subject prior to administering an oligomeric compound. In some embodiments, a decrease in the number of average daily seizures experienced by the subject is observed at least 1 week, at least 2 weeks, at least 4 weeks, at least 6 weeks, at least 8 weeks, at least 10 weeks, at least 12 weeks, at least 14 weeks or at least 16 or more weeks after the start of the administration of an oligomeric compound. In other embodiments, a decrease in the number of average daily seizures is observed within 24 hours after the start of administration of an oligomeric compound. In some embodiments, a decrease in the number of average daily seizures is observed within 28 days after the start of administration of the oligomeric compound. In some embodiments, a decrease in the number of average daily seizures is observed following administration of a single dose of the oligomeric compound. In some embodiments, a decrease in the number of average daily seizures is observed following administration of multiple doses of the oligomeric compound, i.e., two doses of the oligomeric compound, three doses of the oligomeric compound, or four or more doses of the oligomeric compound.

In some embodiments, administering of an oligomeric compound to a subject with a SCN2A-related disorder in the context of the present disclosure results in a decrease in the frequency of focal motor seizures experienced by the subject, as compared to the frequency of focal motor seizures experienced by the subject prior to the administration of the oligomeric compound. In some embodiments, administration of an oligomeric compound to a subject in need thereof in the context of the present disclosure results in a decrease of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% at least about 80%, at least about 85%, at least about 90% or at least about 95% in the frequency of focal motor seizures experienced by the subject, as compared to the frequency of focal motor seizures experienced by the subject prior to the administration of the oligomeric compound.

In some embodiments, administering of an oligomeric compound to a subject with a SCN2A-related disorder in the context of the present disclosure results in a decrease in the frequency of tonic seizures experienced by the subject, as compared to the frequency of tonic seizures experienced by the subject prior to the administration of the oligomeric compound. In some embodiments, administration of an oligomeric compound to a subject in need thereof in the context of the present disclosure results in a decrease of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% at least about 80%, at least about 85%, at least about 90% or at least about 95% in the frequency of tonic seizures experienced by the subject, as compared to the frequency of tonic seizures experienced by the subject prior to the administration of the oligomeric compound.

In some embodiments, administering of an oligomeric compound to a subject with a SCN2A-related disorder in the context of the present disclosure results in a decrease in the frequency of myoclonic seizures experienced by the subject, as compared to the frequency of myoclonic seizures experienced by the subject prior to the administration of the oligomeric compound. In some embodiments, administration of an oligomeric compound to a subject in need thereof in the context of the present disclosure results in a decrease of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% at least about 80%, at least about 85%, at least about 90% or at least about 95% in the frequency of myoclonic experienced by the subject, as compared to the frequency of myoclonic seizures experienced by the subject prior to the administration of the oligomeric compound.

Interictal epileptiform discharges (IEDs) are abnormal electrical brain activity patterns that occur between seizures in patients with epilepsy (Smith et al., *Elife.* 2022 Jan. 20; 11:e73541. doi: 10.7554/eLife.73541. PMID: 35050851; PMCID: PMC8813051). It has been reported that IEDs in children with idiopathic epilepsy can affect both cognitive function and academic performance. (Cheng et al., *BMC Neurol.* 2020 Jun. 6; 20(1):233. doi: 10.1186/s12883-020-01807-z. PMID: 32505173; PMCID: PMC7275426). IEDs can be measured non-invasively using electroencephalography (EEG), a technique that records electrical activity in the brain through electrodes placed on the scalp. This makes it possible to monitor changes in IED frequency in real-time without causing discomfort to the subject.

Without wishing to be bound by a specific theory, it is believed that IEDs may be used clinically, e.g., to test effects of various therapies in subjects with DEEs. For example, IEDs can serve as an objective biomarker for the presence and severity of epileptic activity. By measuring the frequency and distribution in the brain of IEDs before and after administering a drug treatment, the drug's effectiveness in reducing epileptic activity can be monitored. It is also believed that changes in IED frequency and distribution may be detectable before any significant changes in seizure frequency or other clinical signs. Thus, IEDs can provide an early indication of the drug's effectiveness in treating DEE in a clinical trial, and may be used to inform target engagement and dosing strategies. It is also believed that a decrease in IED frequency after drug treatment may be associated with improved seizure control and cognitive outcomes. Thus, monitoring IEDs during a clinical trial can provide valuable information on the potential long-term benefits of the treatment.

In some embodiments, administering an oligomeric compound to a subject in need thereof in the context of the present disclosure results in a decrease in the frequency of IEDs in the subject, as compared to the frequency of IEDs in the subject prior to administering an oligomeric compound. In some embodiments, administering an oligomeric compound to a subject in need thereof in the context of the present disclosure results in a decrease of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% or at least about 80% in frequency of IEDs in the subject, as compared to the frequency of IEDs in the subject prior to administering an oligomeric compound. In some embodiments, the decrease in the frequency of IEDs in the subject is observed at least 1 week, at least 2 weeks, at least 3 weeks, at least 4 weeks, at least 6 weeks, at least 8 weeks, at least 10 weeks, at least 12 weeks, at least 14 weeks or at least 16 or more weeks after the start of the administration of an oligomeric compound.

In some embodiments, administering an oligomeric compound to a subject in need thereof in the context of the present disclosure results in a decrease in the frequency of amplitude-integrated electroencephalography (aEEG) signals, as compared to the frequency of aEEG signals in the subject prior to administering an oligomeric compound. In some embodiments, administering an oligomeric compound to a subject in need thereof in the context of the present disclosure results in a decrease of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% or at least about 80% in frequency of aEEG signals in the subject, as compared to the frequency of aEEG signals in the subject prior to administering an oligomeric compound. In some embodiments, the decrease in the frequency of aEEG signals in the subject is observed at least 1 week, at least 2 weeks, at least 3 weeks, at least 4 weeks, at least 6 weeks, at least 8 weeks, at least 10 weeks, at least 12 weeks, at least 14 weeks or at least 16 or more weeks after the start of the administration of an oligomeric compound. In other embodiments, the decrease in frequency of aEEG signals in a subject is observed within 24 hours after the start of administration of an oligomeric compound.

EXEMPLIFICATION OF THE INVENTION

Example 1: A Seamless, Clinical Trial to Investigate the Safety and Efficacy of Multiple Doses of Compound 1 in Pediatric Participants with Early Onset SCN2A Developmental and Epileptic Encephalopathy This is a seamless, in part non-randomized, open label, and in part randomized, placebo procedure-controlled, double-blind, clinical trial to explore the safety, tolerability, PK, and efficacy of ascending doses of Compound 1 in pediatric participants with early onset SCN2A DEE, aged 2 to 18 years. The trial is being conducted in 4 parts: the preliminary safety Part 1 (open label), dose-escalation Part A (double blind), confirmatory Part B (double blind), followed by an open-label extension in Part C.

PART 1: PRELIMINARY SAFETY

| Objective | Endpoint |
| --- | --- |
| Primary | |
| To evaluate the safety and tolerability of Compound 1 administered by intrathecal (IT) injection in participants with early onset SCN2A DEE | Incidence and severity of treatment-emergent adverse events (TEAEs)<br>Changes in findings on physical and neurological examinations<br>Changes in video electroencephalogram (vEEG) characteristics as determined by a central reader<br>Changes in vital sign measurements<br>Changes in clinical laboratory results<br>Changes in electrocardiogram (ECG) parameters |
| Secondary | |
| To explore the preliminary efficacy of Compound 1 in participants with early onset SCN2A DEE | Seizure frequency per 28 days, as assessed by seizure diary, over the time period after the 4$^{th}$ dose administration<br>Seizure frequency per 28 days over the time period immediately after each dose administration |

-continued

| PART 1: PRELIMINARY SAFETY | |
|---|---|
| Objective | Endpoint |
| | Percent change from baseline in seizure frequency per 28 days over the time period immediately after each dose administration<br>Response, defined as ≥50% reduction in seizure frequency per 28 days over the time period immediately after each dose administration |
| PK | |
| To characterize the pharmacokinetics (PK) of Compound 1 | Plasma and cerebrospinal fluid (CSF) concentrations of Compound 1<br>Plasma Compound 1 PK parameters |
| Exploratory | |
| To explore additional preliminary efficacy of Compound 1 | Electroencephalogram (EEG) characteristics, including but not limited to electrographic seizures, interictal epileptiform discharges, background frequency, and features of sleep at each post dose timepoint |
| To evaluate the impact of Compound 1 on inflammatory markers | Levels of inflammatory markers (including C-reactive protein [CRP] and complement [test for total complement activity - CH50, C3a, Bb and C5a], fibrinogen) |
| To evaluate the potential for immunogenicity towards Compound 1 | Presence of anti-drug antibodies (ADA) in plasma |

| PART A: DOSE ESCALATION | |
|---|---|
| Objective | Endpoint |
| Primary | |
| To evaluate the safety and tolerability of ascending doses of Compound 1 administered by intrathecal (IT) injection in participants with early onset SCN2A DEE | Incidence and severity of TEAEs<br>Changes in findings on physical and neurological examinations<br>Changes in vEEG characteristics as determined by a central reader<br>Changes in vital sign measurements<br>Changes in clinical laboratory results<br>Changes in ECG parameters |
| Secondary | |
| To explore the preliminary efficacy of Compound 1 compared with placebo in participants with early onset SCN2A DEE | Seizure frequency per 28 days, as assessed by seizure diary, over the time period after the $6^{th}$ dose administration<br>Seizure frequency per 28 days over the time period immediately after each dose administration<br>Percent change from baseline in seizure frequency per 28 days over the time period immediately after each dose administration<br>Response, defined as ≥50% reduction in seizure frequency per 28 days over the time period immediately after each dose administration |
| PK | |
| To characterize the PK of Compound 1 | Plasma and CSF concentrations of Compound 1<br>Plasma Compound 1 PK parameters |
| Exploratory | |
| To explore additional preliminary efficacy of Compound 1 compared with placebo | EEG characteristics, including but not limited to electrographic seizures, interictal epileptiform discharges, background frequency, and features of sleep at each post dose timepoint<br>Clinical Global Impression-Severity (CGI-S) at baseline and Clinical Global Impression-Improvement (CGI-I) scores at each post dose timepoint |

-continued

| PART A: DOSE ESCALATION | |
|---|---|
| Objective | Endpoint |
| | Caregiver Global Impression-Severity (CgGI-S) at baseline and Caregiver Global Impression-Improvement (CgGI-I) scores at each post dose timepoint<br>Quality of life as assessed by Quality of Life Inventory-Disability (QI-Disability) at the end of Part A<br>evelopmental milestones as assessed by Bayley Scales of Infant Development - Third Edition (Bayley-3) domain and subtest scores<br>Behavior as assessed by Aberrant Behavior Checklist - 2nd Edition (ABC-2) total and subscale scores at the end of Part A<br>Sleep as assessed by Sleep Disturbance Scale for Children at the end of Part A |
| To evaluate the impact of Compound 1 on inflammatory markers | Levels of inflammatory markers (including CRP and complement [CH50, C3a, Bb and C5a], fibrinogen) |
| To evaluate the potential for immunogenicity towards Compound 1 | Presence of ADA in plasma |

| PART B: CONFIRMATORY | |
|---|---|
| Objective | Endpoint |
| Primary | |
| To assess the efficacy of Compound 1 administered by IT injections compared with placebo in participants with early onset SCN2A DEE | Seizure frequency per 28 days, as assessed by seizure diary, over the time period after the 6th dose administration |
| Secondary | |
| To assess the secondary efficacy of Compound 1 administered by IT injections compared with placebo in participants with early onset SCN2A DEE | Seizure frequency per 28 days during the time period immediately after each dose administration<br>Percent change from baseline in seizure frequency per 28 days over the time period immediately after each dose administration<br>Response, defined as ≥50% reduction in seizure frequency per 28 days, over the time period immediately after each dose administration<br>EEG characteristics, including but not limited to electrographic seizures, interictal epileptiform discharges, background frequency, and features of sleep at each post dose timepoint<br>CGI-S at baseline and CGI-I scores at each post dose timepoint<br>CgGI-S at baseline and CgGI-I scores at each post dose timepoint<br>Quality of life as assessed by Quality of Life Inventory-Disability (QI-Disability) at the end of Part B<br>Developmental milestones as assessed by Bayley Scales of Infant Development - Third Edition (Bayley-3) domain and subtest scores<br>Behavior as assessed by ABC-2 total and subscale scores at the end of Part B<br>Sleep as assessed by Sleep Disturbance Scale for Children at the end of Part B |
| Safety | |
| To evaluate the safety and tolerability of Compound 1 administered by IT injection in participants with early onset SCN2A DEE | Incidence and severity of TEAEs<br>Changes in findings on physical and neurological examinations<br>Changes in vEEG characteristics as determined by a central reader<br>Changes in vital sign measurements |

-continued

| PART B: CONFIRMATORY | |
|---|---|
| Objective | Endpoint |
| | Changes in clinical laboratory results<br>Changes in ECG parameters |
| PK | |
| To characterize the PK of Compound 1 | Plasma and CSF concentrations of Compound 1<br>Plasma Compound 1 PK parameters |
| Exploratory | |
| To evaluate the impact of Compound 1 on inflammatory markers | Levels of inflammatory markers (including CRP and complement [CH50, C3a, Bb and C5a], fibrinogen) |
| To evaluate the potential for immunogenicity towards Compound 1 | Presence of ADA in plasma |

| PART C: OPEN-LABEL EXTENSION | |
|---|---|
| Objective | Endpoint |
| Exploratory | |
| To evaluate the durability of efficacy of Compound 1 administered by IT injections at a maintenance dosing schedule | Seizure frequency per 28 days, as assessed by seizure diary, over the time period immediately after each dose administration<br>Percent change from baseline in seizure frequency per 28 days over the time period immediately after each dose administration<br>Response, defined as ≥50% reduction in seizure frequency per 28 days over the time period after each dose administration<br>EEG characteristics, including but not limited to electrographic seizures, interictal epileptiform discharges, background frequency, and features of sleep at each post dose timepoint<br>CGI-S at baseline and CGI-I scores at each post dose timepoint<br>CgGI-S at baseline and CgGI-I scores at each post dose timepoint<br>Quality of life as assessed by Quality of Life Inventory-Disability (QI-Disability) at the end of Part C<br>Developmental milestones as assessed by Bayley Scales of Infant Development - Third Edition (Bayley-3) domain and subtest scores<br>Behavior as assessed by ABC-2 total and subscale scores at the end of Part C<br>Sleep as assessed by Sleep Disturbance Scale for Children at the end of Part C |
| To evaluate the impact of Compound 1 on inflammatory markers | Levels of inflammatory markers (including CRP and complement [CH50, C3a, Bb and C5a], fibrinogen) |
| To evaluate the potential for immunogenicity towards Compound 1 | Presence of ADA in plasma |
| Safety | |
| To evaluate the safety and tolerability of Compound 1 administered by IT injection during maintenance dosing in participants with early onset SCN2A DEE | Incidence and severity of TEAEs<br>Changes in findings on physical and neurological examinations<br>Changes in vEEG characteristics as determined by a central reader<br>Changes in vital sign measurements<br>Changes in clinical laboratory results<br>Changes in ECG parameters |

-continued

| PART C: OPEN-LABEL EXTENSION | |
|---|---|
| Objective | Endpoint |
| | PK |
| To characterize the PK of Compound 1 during maintenance dosing | Plasma and CSF concentrations of Compound 1<br>Plasma Compound 1 PK parameters |

Part 1: Preliminary Safety

Part 1 is being conducted with the objective of obtaining clinical safety data which will further inform the dose escalation in Part A. In this open label, non-randomized part of the trial, at least 4 participants are enrolled and are receiving Compound 1 at 1 mg doses at ≥4-week intervals for up to 13 weeks.

Safety, along with available PK data, is being assessed by the sponsor on an ongoing basis along with scheduled quarterly Data Monitoring Committee (DMC) reviews after each interim analysis, and ad hoc reviews as needed based on emerging safety data. Preliminary efficacy in seizure reduction and safety was assessed after 4 doses.

Following their final dose, participants from Part 1 will have the potential to transition to long term extension, subject to the FDA's further review and approval of the trial continuation, and pending updated chronic toxicology data.

Part A: Dose Escalation

Part A will initiate upon completion of Part 1. The goal of Part A is to identify a cumulative dose of Compound 1 with a favorable benefit-risk profile for seizure reduction that can be further assessed in Part B. Part A will consist of up to 16 participants. Initially, 8 treatment-naïve participants will be randomized 3:1 to receive ascending doses of Compound 1 or a placebo procedure. The first 4 participants must reach at least 4 weeks after their first dose before additional participants can be administered study drug. Administrations will occur at ≥4-week intervals for the first 4 doses, and at ≥6-week intervals for the subsequent doses. Dose escalations will be within-participant. The starting dose will be 1 mg with ≤2-fold increase for subsequent doses with specific dose escalation criteria. The target is to reach a cumulative dose of up to 42 mg, which is predicted to correspond to approximately 35% knock down (KD), divided into 6 administrations.

Safety, along with available PK data, will be assessed by the sponsor on an ongoing basis along with scheduled quarterly DMC reviews and ad hoc reviews as needed based on emerging safety data. Preliminary efficacy in seizure reduction and safety will be assessed during the time period after the $6^{th}$ dose administration after up to 8 participants have reached a cumulative dose of up to 42 mg or a corresponding placebo procedure.

The dosing regimen may be revised based on the analysis of safety and efficacy. Maximum tolerated dose (MTD) in this trial is defined as 1 dose level below a single or cumulative dose associated with 2 or more Dose Limiting Toxicities (DLTs) in Part A or a 25% rate trial-wide. Up to 8 additional participants may be added (Group 2, randomized to active or placebo in a 3:1 ratio) to further assess the safety and efficacy of escalating doses of Compound 1. The starting dose for these additional participants will be up to the highest tolerated single dose previously administered. A second planned analysis assessing safety and efficacy during the time period after the $6^{th}$ dose will occur after up to 8 participants have reached up to 100 mg cumulatively. After the final dose (or placebo procedure), participants will subsequently have the opportunity to enter Part C/open-label extension.

Part B: Confirmatory Phase

Part B will further assess and confirm the safety and efficacy of the cumulative dose identified in Part A in a randomized, placebo procedure-controlled design. Up to 40 treatment-naïve participants will be randomized, with no more than 75% to receive Compound 1 over placebo treatment (3:1 randomization maximum). The final sample size and randomization scheme will be further confirmed based on the preliminary data and power calculations from Part A.

The cumulative dose and highest single dose will not exceed the respective MTD in Part A. The cumulative dose from Part A will be divided into ≤6 administrations of Compound 1 or placebo procedure and will be given no more frequently than every 6 weeks. If tolerability issues arise, participants may be titrated to safely reach the cumulative dose identified in Part A.

The primary endpoint will be seizure frequency over the time period after the $6^{th}$ dose as assessed by the seizure diary. Thus, the duration of participation in Part B is up to 30 weeks. After the final dose (or placebo procedure) participants will subsequently have the opportunity to enter the open-label extension of the trial, Part C.

Parts 1, A, and B will each consist of 3 periods: Screening Period, Intervention Period (open-label in Part 1, double-blind in Parts A and B), and Follow-up Period.

Screening Period

Prior to any clinical trial procedures, the participant/caregiver will provide written informed consent and satisfy inclusion/exclusion criteria. Key assessments during Screening will include medical and disease history, demographic data, body weight, height and head circumference, physical examination (including detailed neurological examination), clinical laboratory evaluations, magnetic resonance imaging (MRI) of the brain, vital signs measurements, 12-lead ECGs, and a review of concomitant medications/procedures.

Caregivers will complete a daily seizure diary for at minimum 4 weeks during the Baseline Observation period (prior to Baseline Dosing Visit) through EOT, including the days without visits. Other screening assessments may still occur during this 4-week period (and do not necessarily have to be completed prior to the start of the daily seizure diary). Each participant's eligibility will be reviewed and approved by an Eligibility Review Committee (ERC) before they are included into the trial. A baseline prolonged vEEG will be completed within the 4 weeks prior to Baseline Dosing Visit.

Intervention Period

Part 1 (Open-label Intervention): Participants will be admitted to the trial site on Day −1 for Baseline Dosing Visit. On Day 1, after confirmation of eligibility, they will receive Compound 1 via IT administration. Each participant will remain inpatient for a minimum of 24 hours, and up to 48 hours after dosing for physical examination (including detailed neurological examination), clinical laboratory evaluations, vital signs measurements, 12-lead ECGs, and any other trial assessments in this visit. The corresponding procedures and assessments including Compound 1 administration, will take place again in intervals of approximately (but not more frequent than) every 4 weeks, for up to 4 doses in total. Dosing in Part 1 may be less frequent based on the tolerability of the study drug.

Approximately 2 weeks after each Compound 1 administration, home-health visits, as well as home vEEG, will be conducted. Home-health visits may be conducted at home (i.e., remote to the investigational site) or in the clinic (at the investigational site), at the discretion of the participant together with the investigator. If there are any concerning AEs, or changes in the participant's examination, the participant may return at the discretion of the investigator for an unscheduled visit in the clinic for further evaluation.

Parts A and B (Double-blind Interventions): Participants will be admitted to the trial site on Day −1 for Baseline Dosing Visit. On Day 1, after confirmation of eligibility, they will receive Compound 1 via IT administration, or placebo procedure per the randomization schedule. Each participant will remain inpatient for a minimum of 24 hours, and up to 48 hours after dosing for physical examination (including detailed neurological examination), clinical laboratory evaluations, vital signs measurements, 12-lead ECGs, and any other trial assessments in this visit. The corresponding procedures and assessments including Compound 1 administration, or placebo procedure, will take place again in intervals of approximately (but not more frequent than) every 4 weeks for the first 4 doses and every 6 weeks for the subsequent doses in Part A, and every 6 weeks in Part B.

Approximately 2 weeks after each Compound 1 administration or placebo procedure, home-health visits, as well as home vEEG, will be conducted. Home-health visits may be conducted at home (i.e., remote to the investigational site) or in the clinic (at the investigational site), at the discretion of the participant together with the investigator. If there are any concerning AEs, or changes in the participant's examination, the participant may return at the discretion of the investigator for an unscheduled visit in the clinic for further evaluation.

Safety Follow-Up Period

During the 6-month follow-up period, home-health visits, as well as home vEEG, will be conducted. Home-health visits may be conducted at home (i.e., remote to the investigational site) or in the clinic (at the investigational site), at the discretion of the participant together with the investigator. If there are any concerning AEs or changes in the participant's examination (per caregiver report or noted at the home-health visit), the participant may return at the discretion of the investigator for an unscheduled visit in the clinic for further evaluation. A final visit to the clinic will occur for the end of trial assessments.

The Follow-up Period may be extended based on the results of the assessments at the end of study (EOS) visit and the investigator's best clinical judgement. Should it be considered necessary, the extended follow-up will include assessments for the presence of potential long-term and developmental effects.

Part C: Open-Label Extension

Participants Part C is an open-label extension of the trial that will assess the safety and durability of effect of Compound 1 on seizures and other outcomes measures of a maintenance dosing regimen over up to 2 years. The open label extension will be available for any patient with prior exposure to Compound 1 or if they are rolling over from an active Compound 1 trial.

Following Part 1

Following their final dose in Part 1, participants will have the potential to transition to the long-term extension in Part C, which will start ≥6 weeks after the final dose in Part 1, and after the FDA approval for dosing in Part C to proceed, whichever occurs later. Part C will have an initial titration period to allow for the maintenance dose to be reached safely. The starting dose in the titration period will be no more than the MTD in Part A, and the exact titration regimen will be determined following DMC's review of the interim analysis results from Part A. During the titration period, participants will receive 4 doses of Compound 1 at 4-week intervals, with the subsequent maintenance doses administered at ≥12-week intervals. All the doses in Part C for participants transitioning from Part 1 will be administered in an unblinded fashion.

If the results of the interim analysis from Part A do not become available within 6 weeks of the Part 1 completion and/or the FDA approval to proceed to Part C is not received within the same timeframe, participants may continue to be dosed with 1 mg of Compound 1, as an early Part C, at ≥6-week intervals in the interim, before commencing the titration period in Part C. This interim dosing may start ≥6 weeks after the final dose in Part 1 and continue until both the FDA approval for dosing in Part C is received and the titration regimen for this part is determined based on the results of the interim analysis from Part A.

Following Part A or B

Participants from Parts A and B will have the potential to enroll in Part C. Part C will have an initial titration period to allow participants which previously received placebo in Parts A or B to reach the Compound 1 maintenance dose safely, and to avoid breaking the study blind. During the titration period, participants who were on placebo in Part A or B will be administered 4 ascending doses of Compound 1 at 4-week intervals, with the fourth titration dose planned to be the MTD from Parts A and B. Participants who were on active in Part A or B will be administered the MTD of Compound 1 at the start (dose 1) and at the end of the titration period (dose 4); doses 2 and 3 of the titration regimen for these participants will comprise the placebo procedure. After the initial titration period, all the participants will receive Compound 1 maintenance doses at 12-week intervals. The first 3 titration doses in Part C for participants transitioning from Part A or B will be administered blinded; all other doses in Part C will be administered in an unblinded fashion.

The highest dose administered in Part C will be up to the maximum tolerated single dose from Part A and Part B. This dose level may change as Part A and Part B progress. It is expected that dosing every 12 weeks will be sufficient to maintain KD levels. Therefore, following the titration period, dosing will be at least 12 weeks apart for up to a total of 2 years. Participants may receive lower doses or less frequent dosing based on their tolerability.

The Follow-up Period may be extended based on the results of the assessments at the EOS visit and the investigator's best clinical judgement. Should it be considered necessary, the extended follow-up will include assessments for the presence of potential long-term and developmental effects.

Efficacy Assessments

Seizure Diary

An electronic device (e.g., tablet/phone, watch application, and/or other devices) was used to collect information about participant's seizures and daily concomitant medication use during the clinical trial. The diary was completed daily for at minimum 28 days prior to Baseline dosing visit, during the Baseline Observation Period (after the Screening visit) and daily throughout the remainder of the clinical trial. The diary from the Baseline Observation Period serves as an eligibility check, and to establish a baseline. Prompts were used to ensure adequate data capture in addition to spontaneous reporting. The diary was completed by the same caregiver as often as possible. Daily seizure diary data collected as part of an ongoing observation trial that falls within the Screening window per this protocol may be used without having to be repeated.

Video EEG

To the extent allowed by local regulations, a vEEG was performed by a trained technician throughout the trial in order to record brainwave activity and to evaluate for changes over time. Prolonged vEEG was completed at home or in a facility, ideally with a minimum of 12 hours of continuous recording and capturing periods of both wakefulness and sleep. vEEGs collected within the Screening window per this protocol, as part of an ongoing observational trial, would not have to be repeated during the Screening period.

Bayley Scales of Infant Development-Third Edition (Bayley-3)

The Bayley-3 is a standardized neurodevelopmental assessment measure used by clinicians to evaluate key domains in early childhood development for individuals between 16 days and 42 months after birth. These domains include adaptive behavior, cognition, language, motor function (gross and fine), and social-emotional development. The Bayley-3 assessments will be video recorded to the extent allowed by local regulations.

Sleep Disturbance Scale for Children

The parent-reported Sleep Disturbance Scale for Children (SDSC) is a 27-item scale rated on a 5-point Likert scale and designed to categorize sleep disorders in children. In addition to an overall score, the instrument provides 5 sub-scores for the following: disorders of initiating and maintaining sleep, sleep breathing disorders, disorders of arousal or sleep-wake transition disorders, disorders of excessive somnolence, and sleep hyperhidrosis.

Quality of Life Inventory-Disability (QI-Disability)

The QI-Disability is a parent-report measure for children with intellectual disabilities. It is a reliable and valid measure of the quality of life across the spectrum of intellectual disability. It has the potential to allow for clearer identification of support needs and measures responsiveness to interventions.

Aberrant Behaviors Checklist-2$^{nd}$ Edition (ABC-2)

The ABC-2 is a clinician-assessed rating scale that measures the severity of a range of problem behaviors commonly observed in individuals with intellectual disabilities.

Clinical Global Impression-Severity (CGI-S) and Clinical Global Impression-Improvement (CGI-I)

The CGI was developed for use in NIH-sponsored clinical trials in individuals with mental health disorders. The CGI provides an overall assessment of improvement over a specified period. The CGI includes two, 7-point Likert rating scales: the CGI-S and the CGI-I scale. The CGI will be anchored with reference to domains/symptoms experienced by participants with SCN2A-DEE. Participants will be assessed by the clinician at Baseline (Day 1) for the severity of SCN2A-DEE symptoms using the CGI-S. Change from baseline in SCN2A-DEE symptoms will be assessed by the clinician using the CGI-I.

Caregiver Global Impression-Severity (CgGI-S) and Caregiver Global Impression-Improvement (CgGI-I)

These scales are similar to the CGI-S and CGI-I. Participants will be assessed by the caregiver at Baseline (Day 1) for the severity of their SCN2A-DEE symptoms using the CgGI-S. Change from baseline in SCN2A-DEE symptoms will be assessed by the caregiver using the CgGI-I.

Results from Part 1: Preliminary Safety

In part 1, participants received Compound 1 intrathecally at ≥4 week intervals for up to 13 weeks. The incidence and severity of treatment-emergent adverse events was assessed, with preliminary efficacy and safety also assessed after 4 doses.

Four subjects participated in Part 1 of the trial as shown in Table 1 below.

TABLE 1

Subject Demographics

| Subject ID | Age at consent (years) | Gender | Race | Ethnicity | Number of dosing visits completed |
|---|---|---|---|---|---|
| 2001 | 3 | Female | White | Not Hispanic or Latino | 4 |
| 2002 | 14 | Male | White | Not Hispanic or Latino | 4 |
| 2003 | 2 | Female | White | Not Hispanic or Latino | 4 |
| 2004 | 2 | Male | Other (Hispanic) | Hispanic or Latino | 4 |

Each subject received 1 mg of Compound 1 every 4 weeks, or monthly. The schematic illustrating dosing of the subjects is shown in FIG. 1.

The subjects exhibited no clinically significant abnormalities in vital signs and physical and neurological signs upon examination.

Table 2 below shows the summary values of the seizure diary data for the subjects.

TABLE 2

Summary values of the seizure diary data

| | # of seizures | | | % reduction in the number of seizures from baseline | |
|---|---|---|---|---|---|
| Subject ID | Baseline | Dose Period 1 | Dose Period 2 | After 1$^{st}$ Dose | After 2$^{nd}$ dose |
| 2001 | 146 | 56 | 84 | 61.64 | 42.46 |
| 2002 | 41 | 21 | 22 | 48.78 | 46.34 |
| 2003 | 10 | 0 | 7 | 100 | 30 |
| 2004 | 345 | 331 | 134 | 4.05 | 61.16 |

TABLE 2-continued

| Summary values of the seizure diary data | | |
|---|---|---|
| | $1^{st}$ Dose | $2^{nd}$ Dose |
| % mean reduction in the number of seizures | 53.61 | 44.98 |
| % median reduction in the number of seizures | 55.21 | 44.00 |

Figure 2:
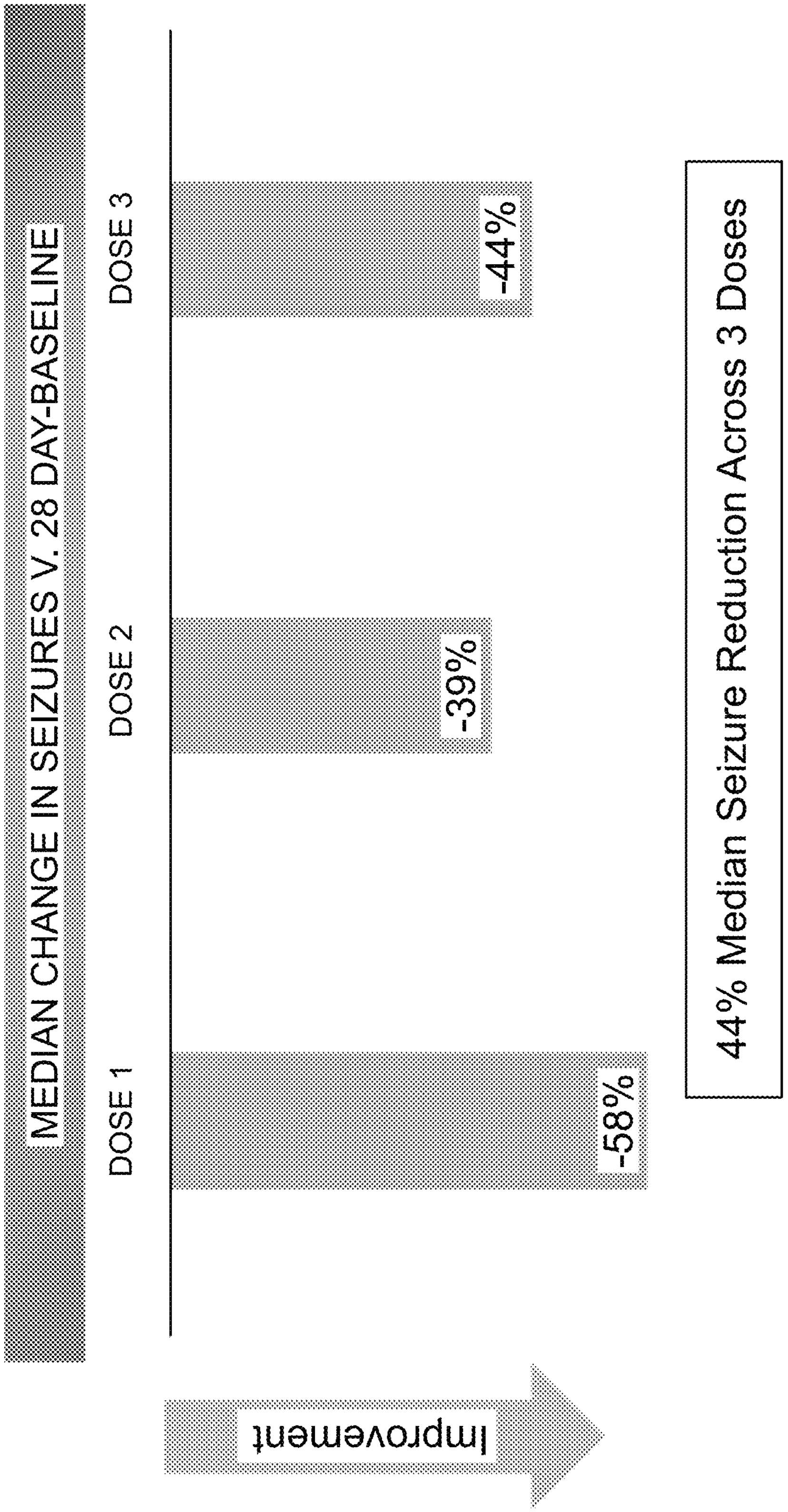
FIG. 2 is a bar graph showing median change in seizures vs. 28 day-baseline after 3 doses.

FIG. 2 is a bar graph showing median change in seizures vs. 28 day-baseline after 3 doses. The results shown in FIG. 2 indicate that Compound 1 exhibits efficacy in reducing seizures even after 1 dose.

Figure 3:
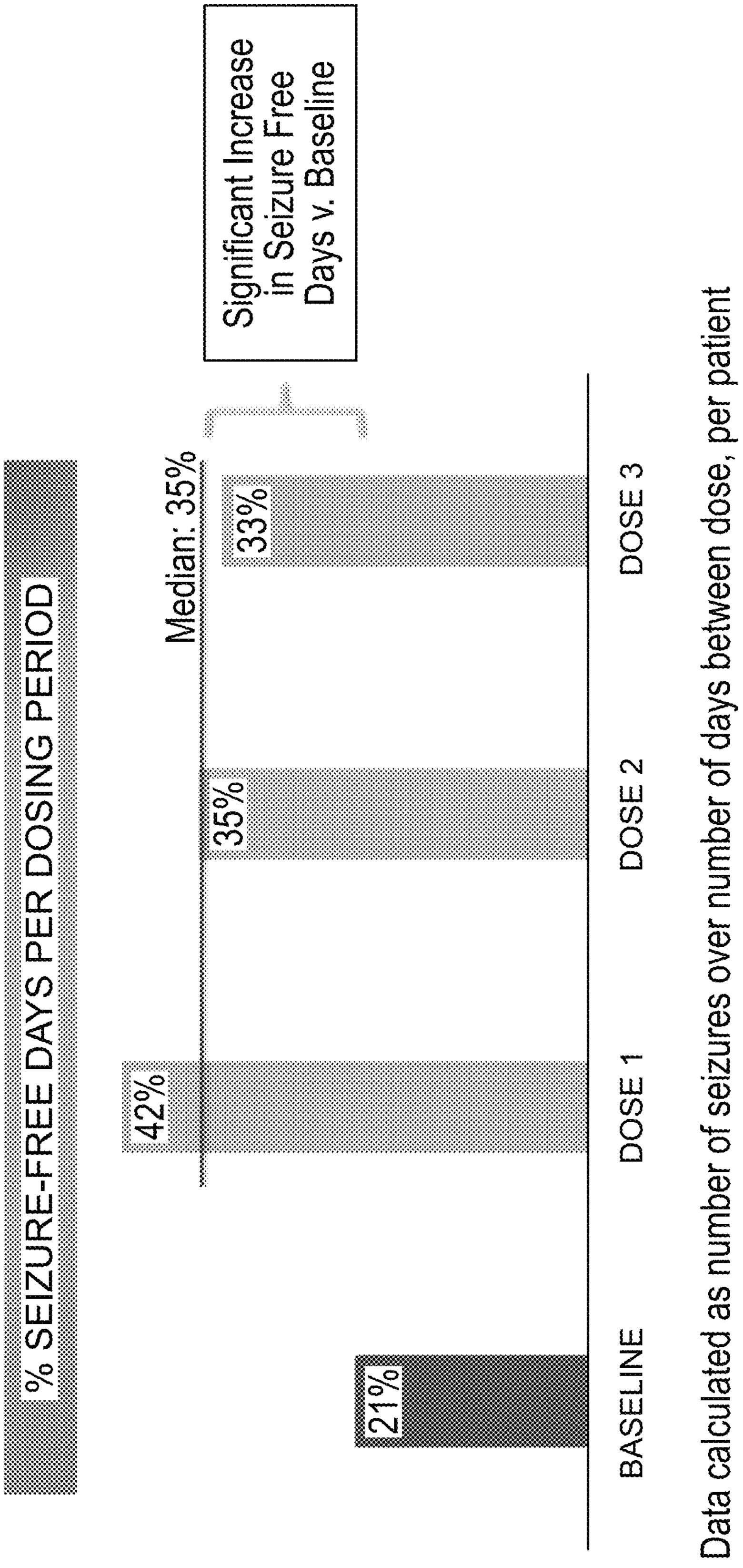
FIG. 3 is a bar graph showing % of seizure free day per dosing period, calculated as number of seizures over number of days between dose, per patient, after 3 doses.

FIG. 3 is a bar graph showing % of seizure free day per dosing period, calculated as number of seizures over number of days between dose, per patient, after 3 doses. The results shown in FIG. 3 indicate that there is a significant increase in seizure-free days vs. baseline, with improvements observed after one dose.

Figure 4:
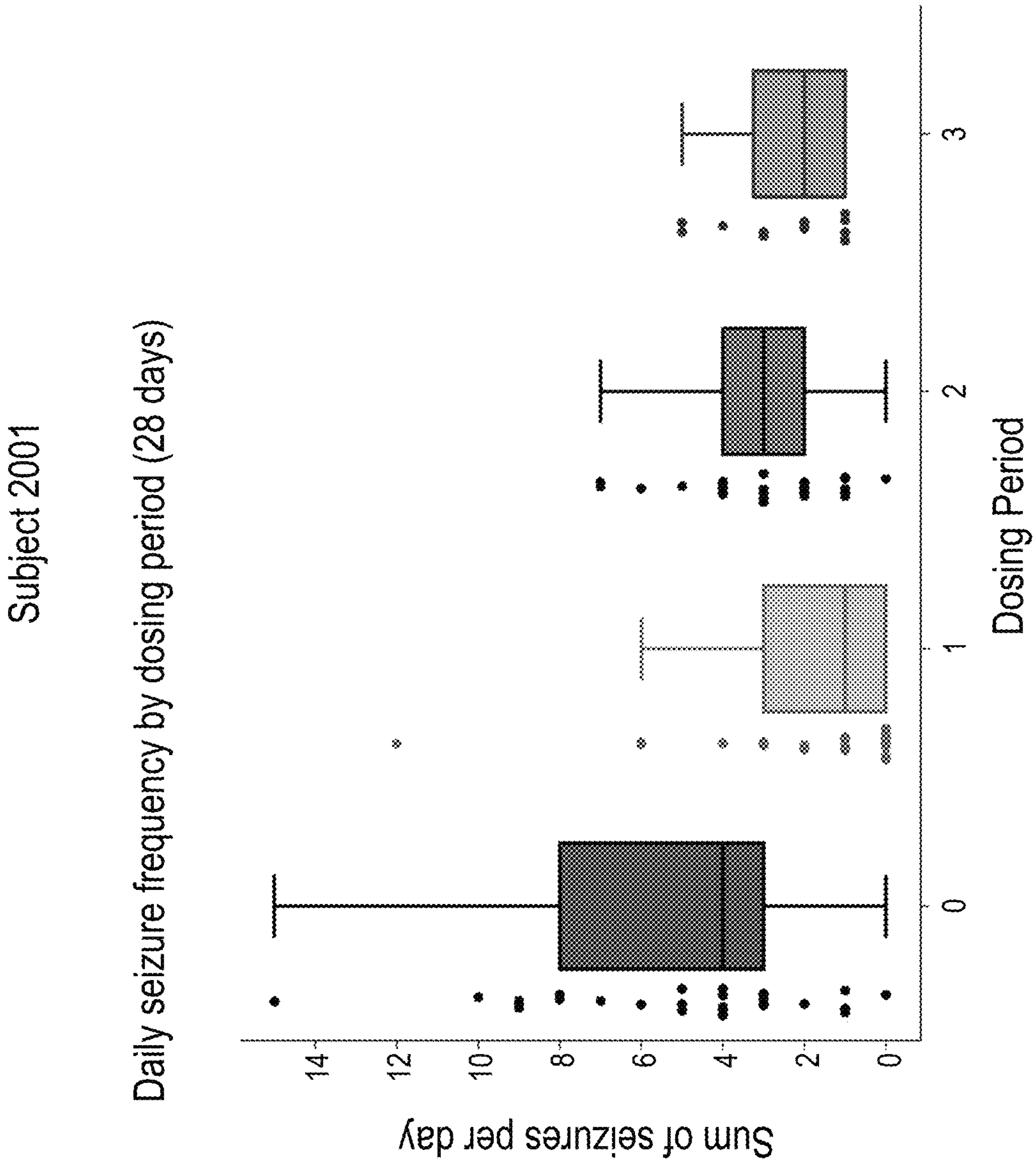
FIG. 4, Panel A is a boxplot showing daily seizure frequency by dosing period (28 days) for subject 2001 after 3 doses.
Figure 4:
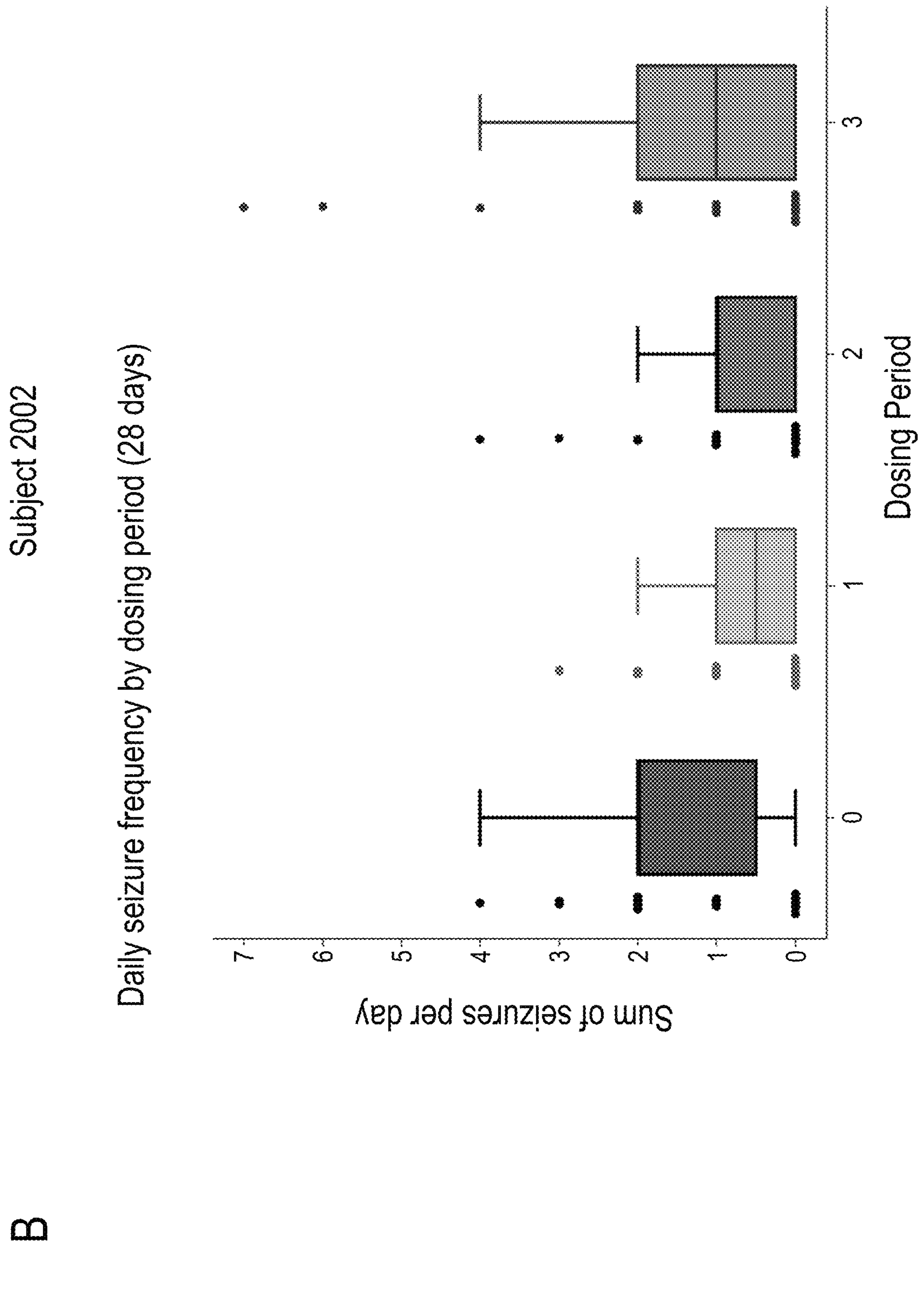
Figure 4:
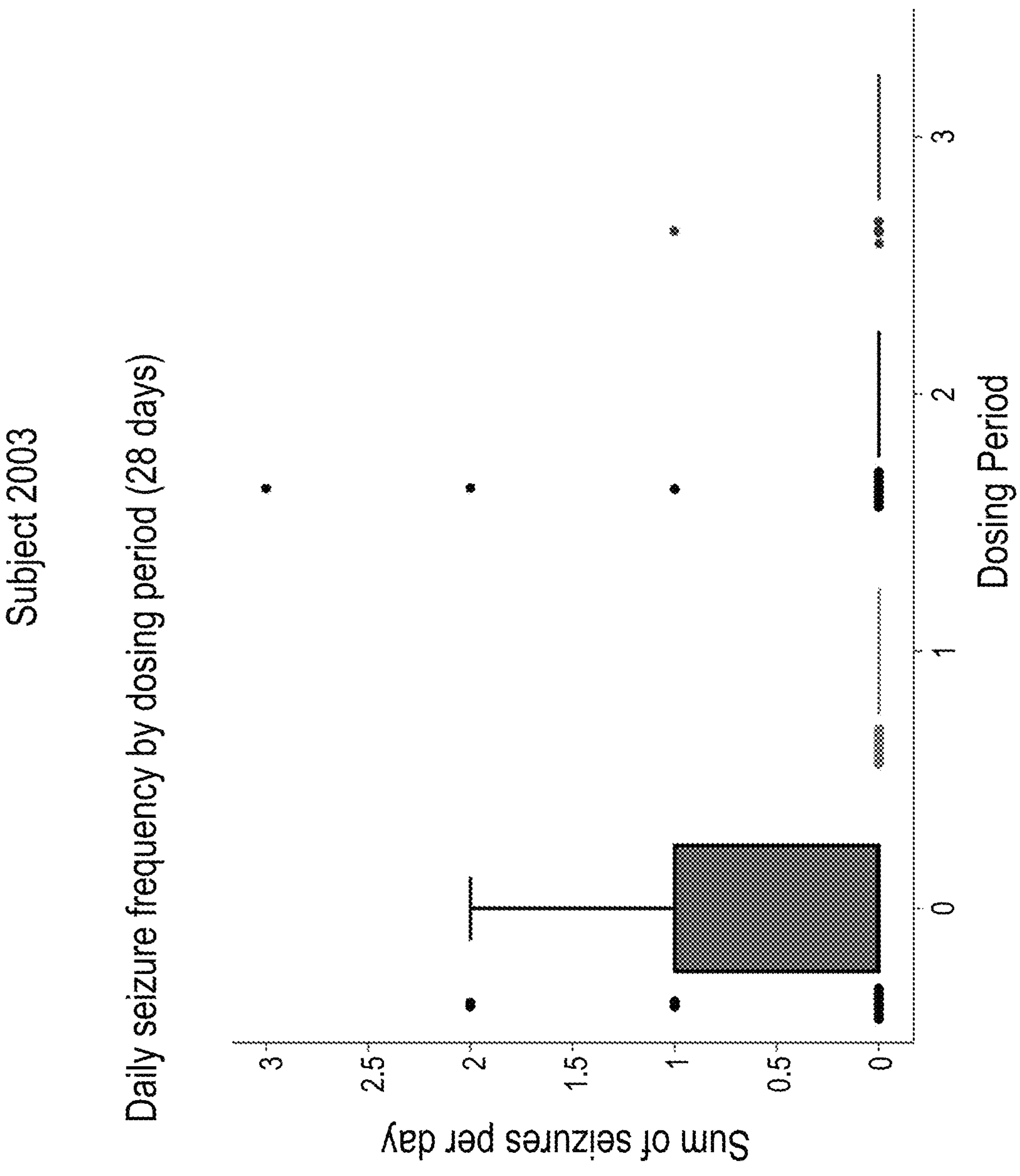
Figure 4:
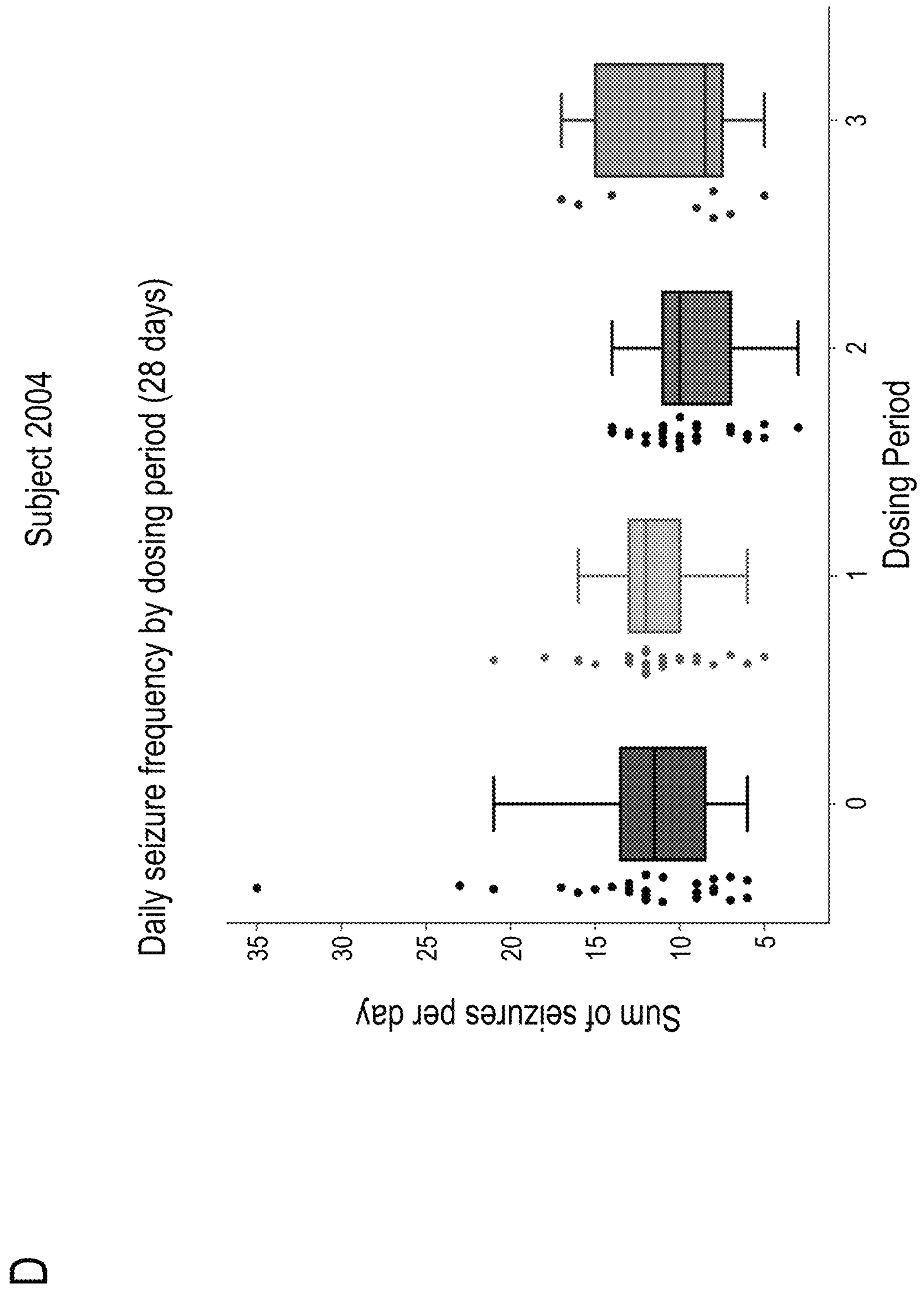

FIG. 4, Panel A is a boxplot showing daily seizure frequency by dosing period (28 days) for subject 2001 after 3 doses.

FIG. 4, Panel B is a boxplot showing daily seizure frequency by dosing period (28 days) for subject 2002 after 3 doses.

FIG. 4, Panel C is a boxplot showing daily seizure frequency by dosing period (28 days) for subject 2003 after 3 doses.

FIG. 4, Panel D is a boxplot showing daily seizure frequency by dosing period (28 days) for subject 2004 after 3 doses.

Figure 5:
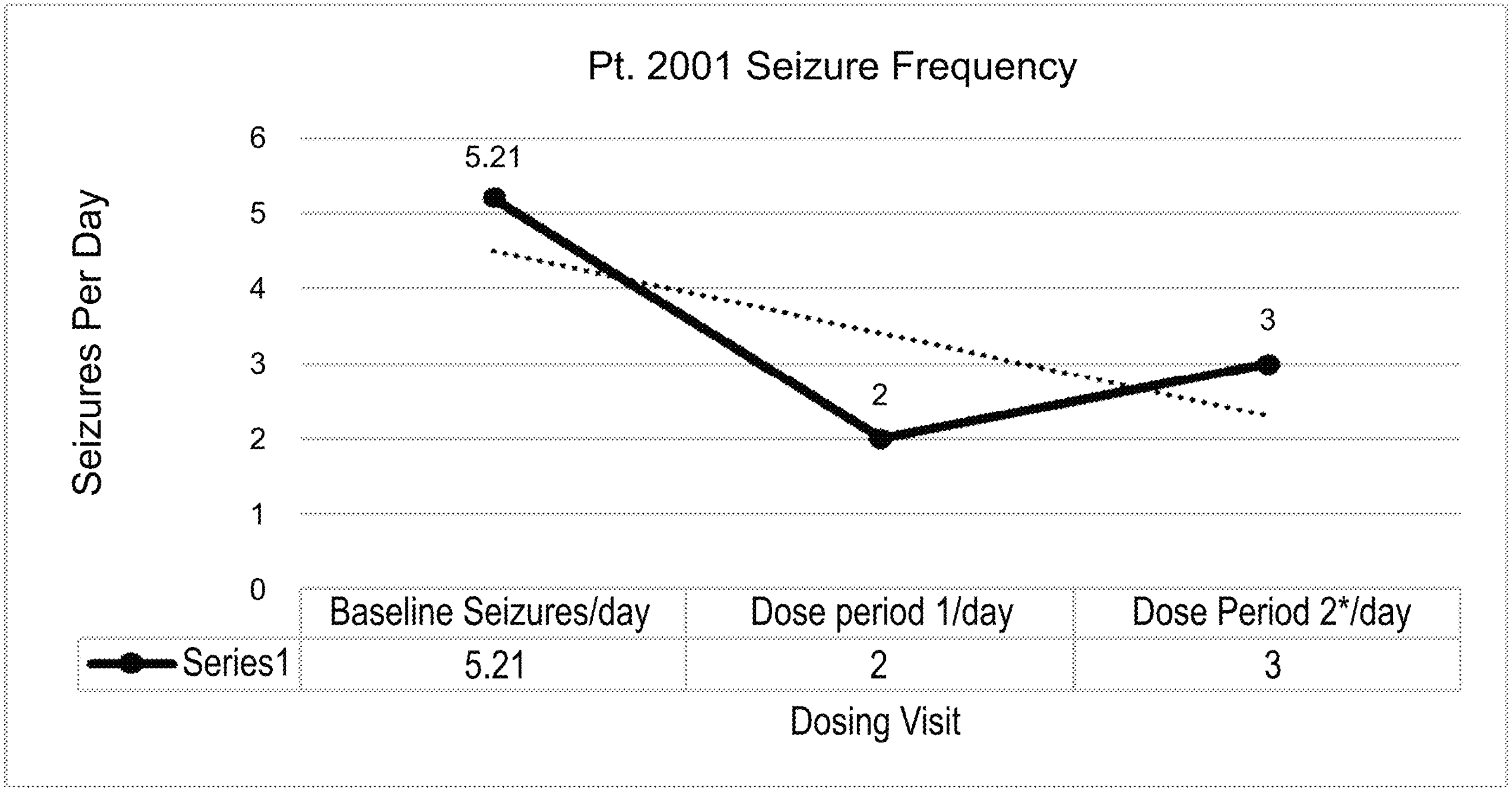
FIG. 5, Panel A is a graph showing daily seizure frequency per dose period for subject 2001 after 3 doses.
Figure 5:
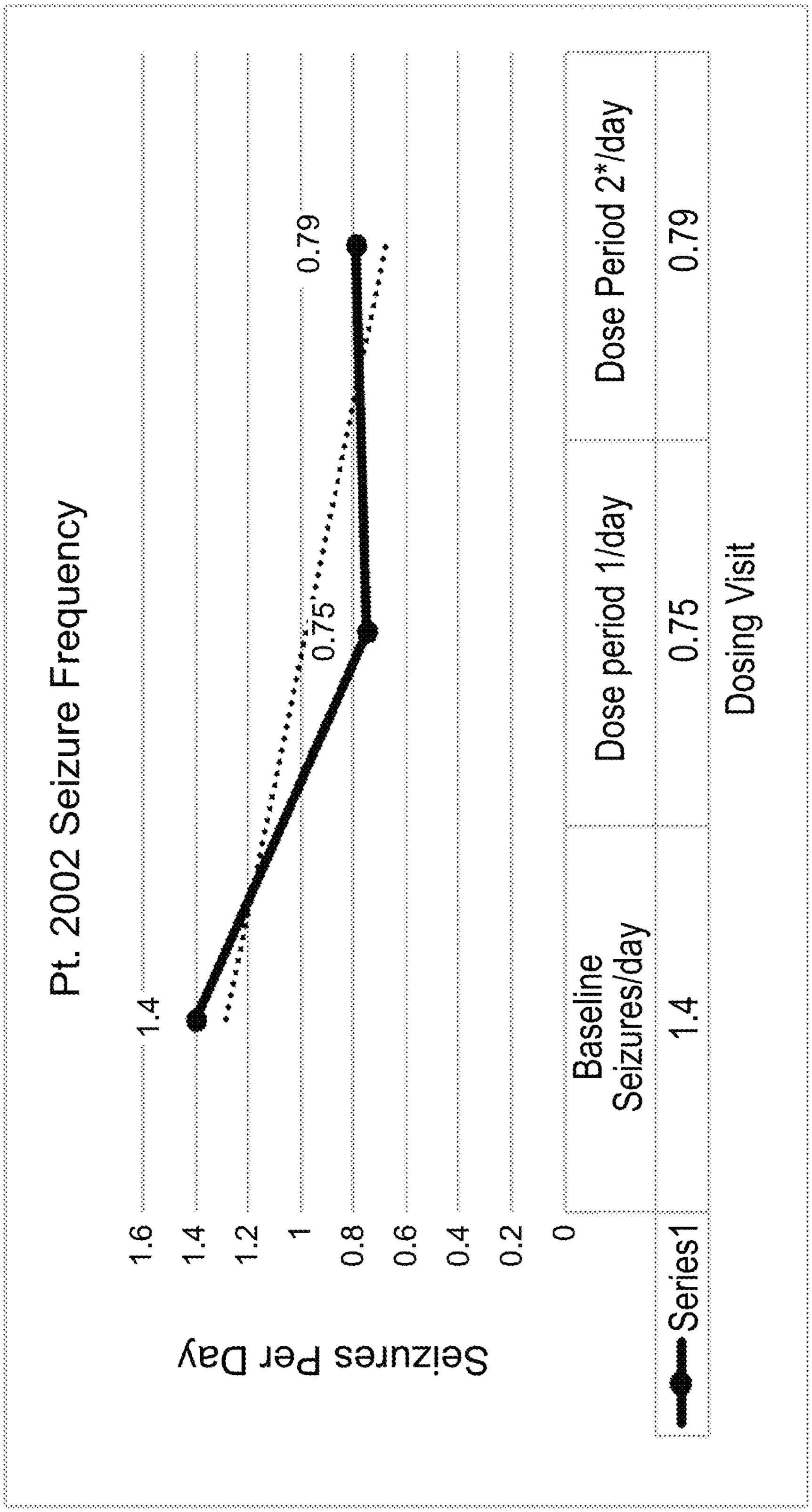
Figure 5:
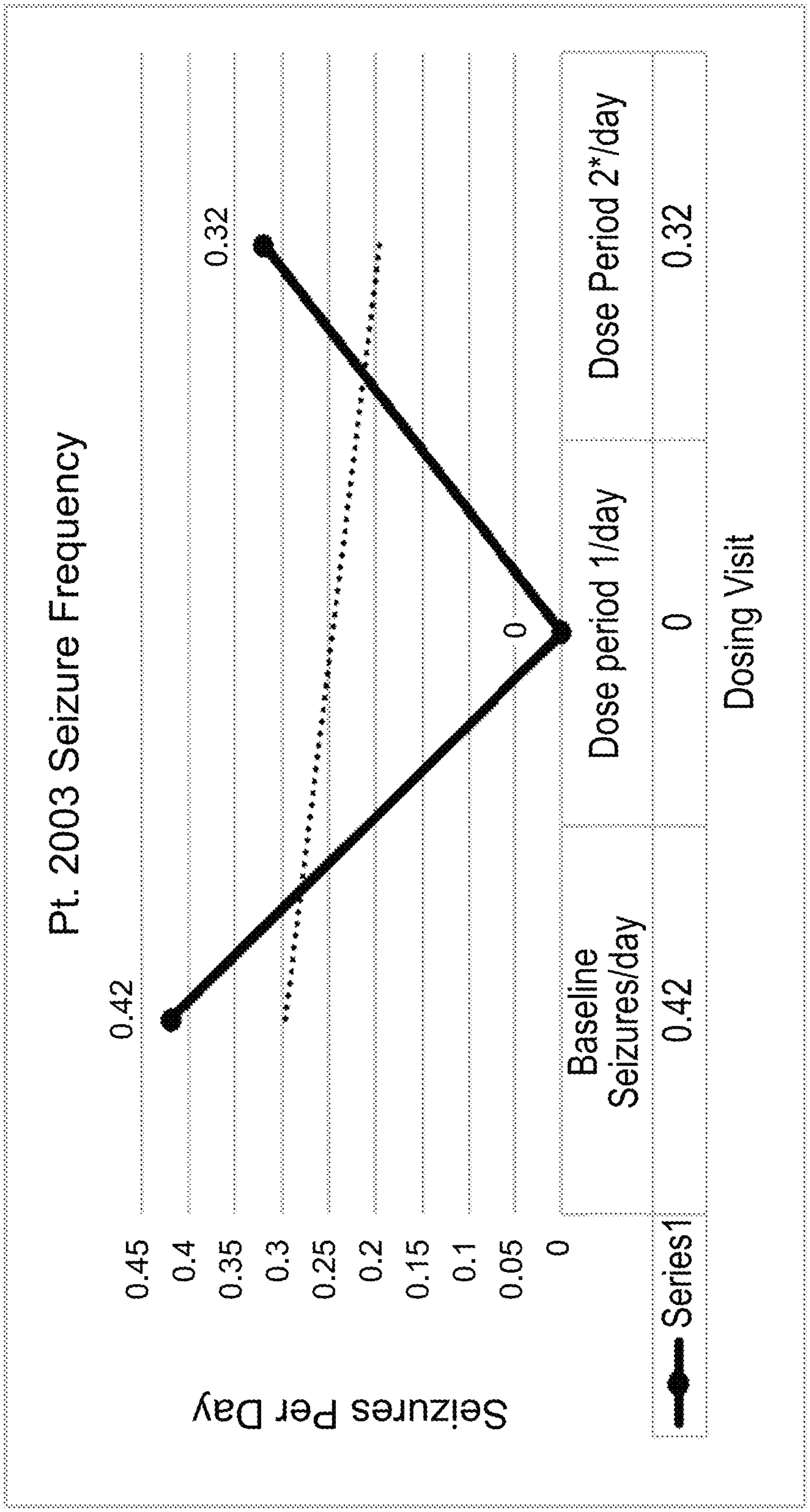
Figure 5:
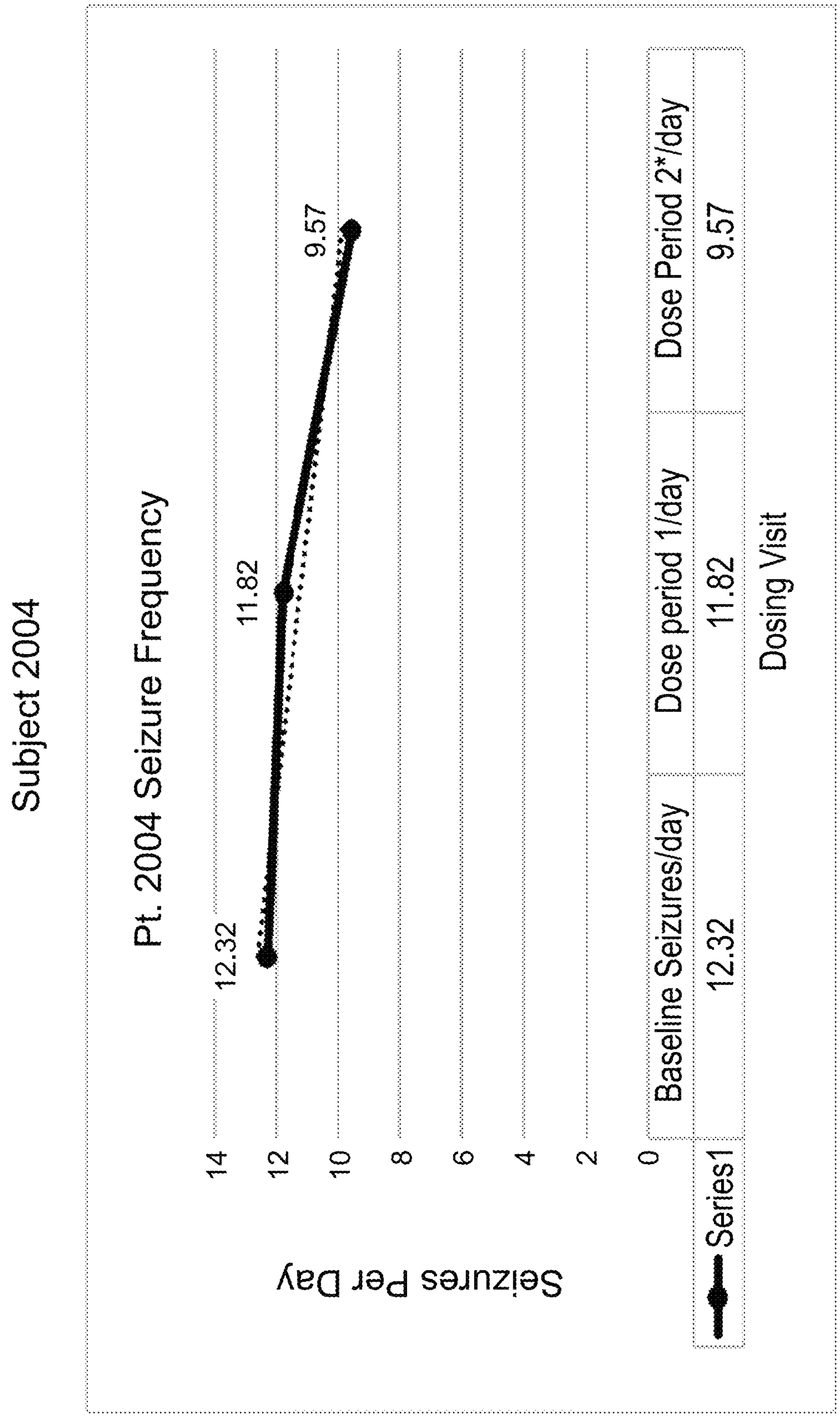

FIG. 5, Panel A is a graph showing daily seizure frequency per dose period for subject 2001 after 3 doses.

FIG. 5, Panel B is a graph showing daily seizure frequency per dose period for subject 2002 after 3 doses.

FIG. 5, Panel C is a graph showing daily seizure frequency per dose period for subject 2003 after 3 doses.

FIG. 5, Panel D is a graph showing daily seizure frequency per dose period for subject 2004 after 3 doses.

Table 3 below shows seizure diary summary data for Subject 2001 after 3 doses.

TABLE 3

Seizure summary data for subject 2001.

| | | Dosing Period | | |
|---|---|---|---|---|
| | Baseline | 1 | 2 | 3 |
| Number of days in the dosing period | 28 | 28 | 28 | 13 |
| Average daily seizures | 5.21 | 2.0 | 3 | 2.38 |
| Number of seizure free days | 1 | 9 | 1 | 0 |
| Number of focal motor seizures | 43 | 31 | 25 | 11 |
| Number of tonic seizures | 50 | 10 | 34 | 12 |
| Number of generalized tonic-clonic seizures | 0 | 0 | 0 | 0 |
| Number of myoclonic seizures | 50 | 6 | 19 | 8 |
| Number of times rescue medication was used | 5 | 5 | 12 | 4 |
| Average percentage rescue medication | 17.86% | 17.86% | 42.86% | 30.77% |

Table 4 below shows seizure type frequency data for subject 2001.

TABLE 4

Seizure type frequency data for subject 2001 after 2 doses.

| | Baseline | Dosing Period | | % reduction after | |
|---|---|---|---|---|---|
| | Seizures/month | 1 | 2 | 1 dose | 2 doses |
| Focal seizures | 43 | 31 | 25 | 27.90 | 41.86 |
| Tonic | 50 | 10 | 34 | 80 | 32 |
| GTC | No generalized T-C seizures in the period | No generalized T-C seizures in the period | No generalized T-C seizures in the period | No generalized T-C seizures in the period | No generalized T-C seizures in the period |
| Myoclonic | 50 | 6 | 19 | 88 | 62 |

Table 5 below shows seizure diary summary data for Subject 2002 after 3 doses.

TABLE 5

Seizure summary data for subject 2002.

| | | Dosing Period | | |
|---|---|---|---|---|
| | Baseline | 1 | 2 | 3 |
| Number of days in the dosing period | 28 | 28 | 28 | 8 |
| Average daily seizures | 1.46 | 0.75 | 0.79 | 0.25 |
| Number of seizure free days | 7 | 14 | 13 | 7 |
| Number of focal motor seizures | 0 | 0 | 1 | 0 |
| Number of tonic seizures | 40 | 21 | 21 | 2 |
| Number of generalized tonic-clonic seizures | 0 | 0 | 0 | 0 |
| Number of myoclonic seizures | 0 | 0 | 0 | 0 |
| Number of times rescue medication was used | 0 | 0 | 0 | 0 |
| Average percentage rescue medication | 0% | 0% | 0% | 0% |

Table 6 below shows seizure type frequency data for subject 2002.

TABLE 6

| Seizure type frequency data for subject 2002 after 2 doses. | | | | | |
|---|---|---|---|---|---|
| | Baseline | Dosing Period | | % reduction after | |
| | Seizures/month | 1 | 2 | 1 dose | 2 doses |
| Focal seizures | No focal seizures in the baseline | No focal seizures | 1 | No focal seizures | Increase of 1% |
| Tonic | 40 | 21 | 21 | 47.5 | 47.5 |
| GTC | No generalized T-C seizures in the period | No generalized T-C seizures in the period | No generalized T-C seizures in the period | No generalized T-C seizures in the period | No generalized T-C seizures in the period |
| Myoclonic | No myoclonic seizures in the baseline period | No myoclonic seizures in the period | No myoclonic seizures in the period | No myoclonic seizures in the period | No myoclonic seizures in the period |

Table 7 below shows seizure diary summary data for Subject 2003 after 3 doses.

TABLE 7

| Seizure summary data for subject 2003. | | | | |
|---|---|---|---|---|
| | | Dosing Period | | |
| | Baseline | 1 | 2 | 3 |
| Number of days in the dosing period | 28 | 28 | 28 | |
| Average daily seizures | 0.42 | 0 | 0.25 | |
| Number of seizure free days | 17 | 23 | 24 | |
| Number of focal motor seizures | 0 | 0 | 0 | |
| Number of tonic seizures | 9 | 0 | 4 | |
| Number of generalized tonic-clonic seizures | 0 | 0 | 0 | |
| Number of myoclonic seizures | 0 | 0 | 0 | |
| Number of times rescue medication was used | 2 | 0 | 1 | |
| Average percentage rescue medication | 4.17% | 0% | 3.57% | |

Table 8 below shows seizure type frequency data for subject 2003.

TABLE 8

| Seizure type frequency data for subject 2003 after 2 doses. | | | | | |
|---|---|---|---|---|---|
| | Baseline | Dosing Period | | % reduction after | |
| | Seizures/month | 1 | 2 | 1 dose | 2 doses |
| Focal seizures | No focal seizures in the baseline | No focal seizures in the period | No focal seizures in the period | No focal seizures in the period | No focal seizures in the period |
| Tonic | 9 | 0 | 4 | 100 | 55.56 |
| GTC | No generalized T-C seizures in the period | No generalized T-C seizures in the period | No generalized T-C seizures in the period | No generalized T-C seizures in the period | No generalized T-C seizures in the period |
| Myoclonic | No myoclonic seizures in the baseline period | No myoclonic seizures in the period | No myoclonic seizures in the period | No myoclonic seizures in the period | No myoclonic seizures in the period |

Table 9 below shows seizure diary summary data for Subject 2004.

TABLE 9

| Seizure summary data for subject 2004 after 3 doses. | | | | |
|---|---|---|---|---|
| | | Dosing Period | | |
| | Baseline | 1 | 2 | 3 |
| Number of days in the dosing period | 28 | 28 | 21 | |
| Average daily seizures | 12.32 | 11.82 | 9.81 | |
| Number of seizure free days | 0 | 0 | 0 | |
| Number of focal motor seizures | 0 | 0 | 0 | |
| Number of tonic seizures | 325 | 277 | 167 | |
| Number of generalized tonic-clonic seizures | 20 | 54 | 39 | |
| Number of myoclonic seizures | 0 | 0 | 0 | |
| Number of times rescue medication was used | 25 | 3 | 12 | |
| Average percentage rescue medication | 17.86% | 10.71% | 9.52% | |

Table 10 below shows seizure type frequency data for subject 2004.

TABLE 10

Seizure type frequency data for subject 2004 after 2 doses.

| | Baseline | Dosing Period | | % reduction after | |
|---|---|---|---|---|---|
| | Seizures/month | 1 | 2 | 1 dose | 2 doses |
| Focal seizures | No focal seizures in the baseline | No focal seizures in he period | No focal seizures in the period | No focal seizures in the period | No focal seizures in the period |
| Tonic | 325 | 277 | 109 | 14.76 | 66.46 |
| GTC | 20 | 54 | 25 | −170 (increase) | −25 (increase) |
| Myoclonic | No myoclonic seizures in the baseline period | No myoclonic seizures in the period | No myoclonic seizures in the period | No myoclonic seizures in the period | No myoclonic seizures in the period |

A vEEG scores were determined for each subject at base line and after each dosing period. In the vEEG scoring system, normal vEEG score=0, and a pathological vEEG score is greater than 0, with the worst score being 11. No changes in the vEEG scores throughout the dosing periods were observed for subject 2004, and an increase in the vEEG scores was observed for subjects 2001, 2002 and 2003 as shown in Table 11 below.

TABLE 11

VEEG scores for subjects during each dosing period after 2 doses.

| | | Dosing Period | |
|---|---|---|---|
| Subject ID | Baseline | 1 | 2 |
| 2001 | 7.8 | 11 | 9 |
| 2002 | 1.8 | 5.4 | 7.6 |
| 2003 | 2.2 | 7.6 | 7.6 |
| 2004 | 11 | 11 | 11 |

It is noted that there are limitations of the vEEG scoring system. Specifically, vEEG scores are highly impacted by numerous variables and represent a snapshot of one day. The vEEG scoring system is not yet validated, so caution is needed when interpreting the results.

During the study, subjects 2001 and 2004 experienced serious adverse events that were unrelated to the study drug. Subjects 2001, 2002 and 2004 also experienced non serious adverse events that were mild or moderate in severity. All TEAEs were resolved.

Figure 6:
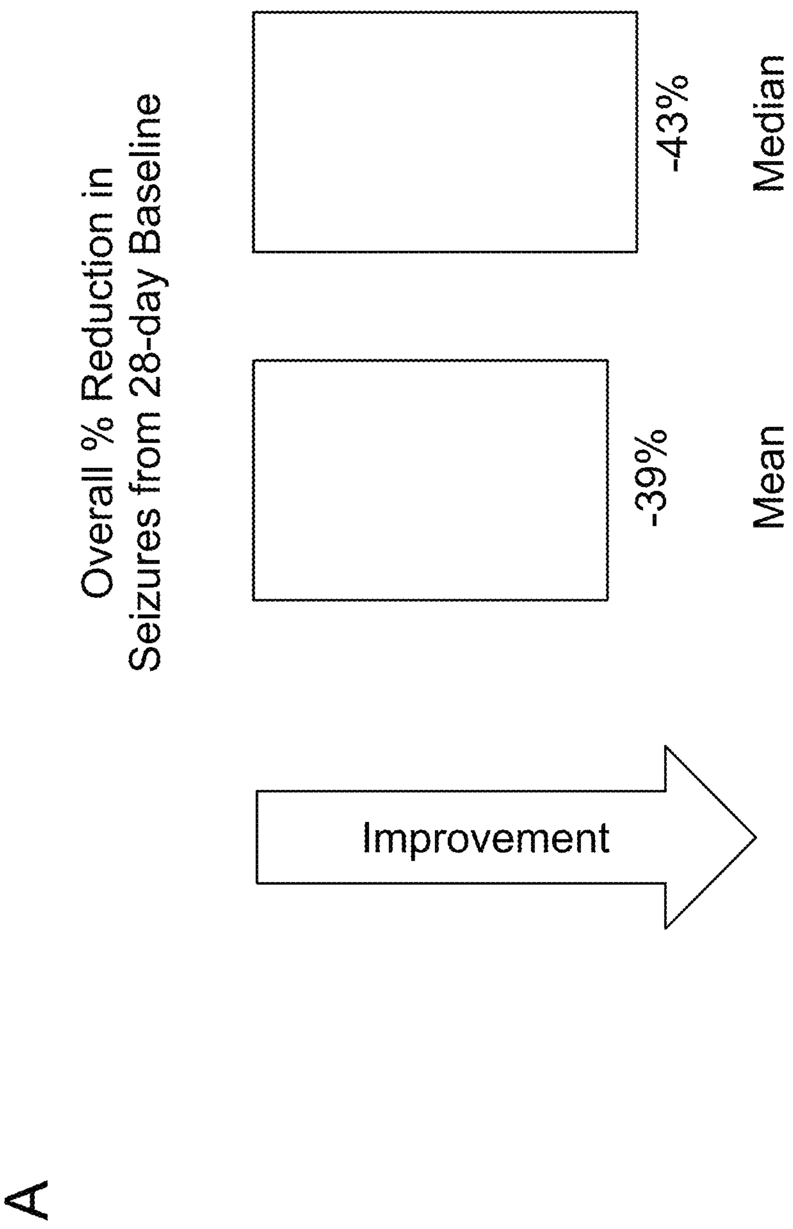
FIG. 6, Panel A is a bar graph showing mean and median change from baseline in seizure frequency for four subjects. The results represent overall percentage reduction from baseline observed through four 28-day periods for 4 subjects.
Figure 6:
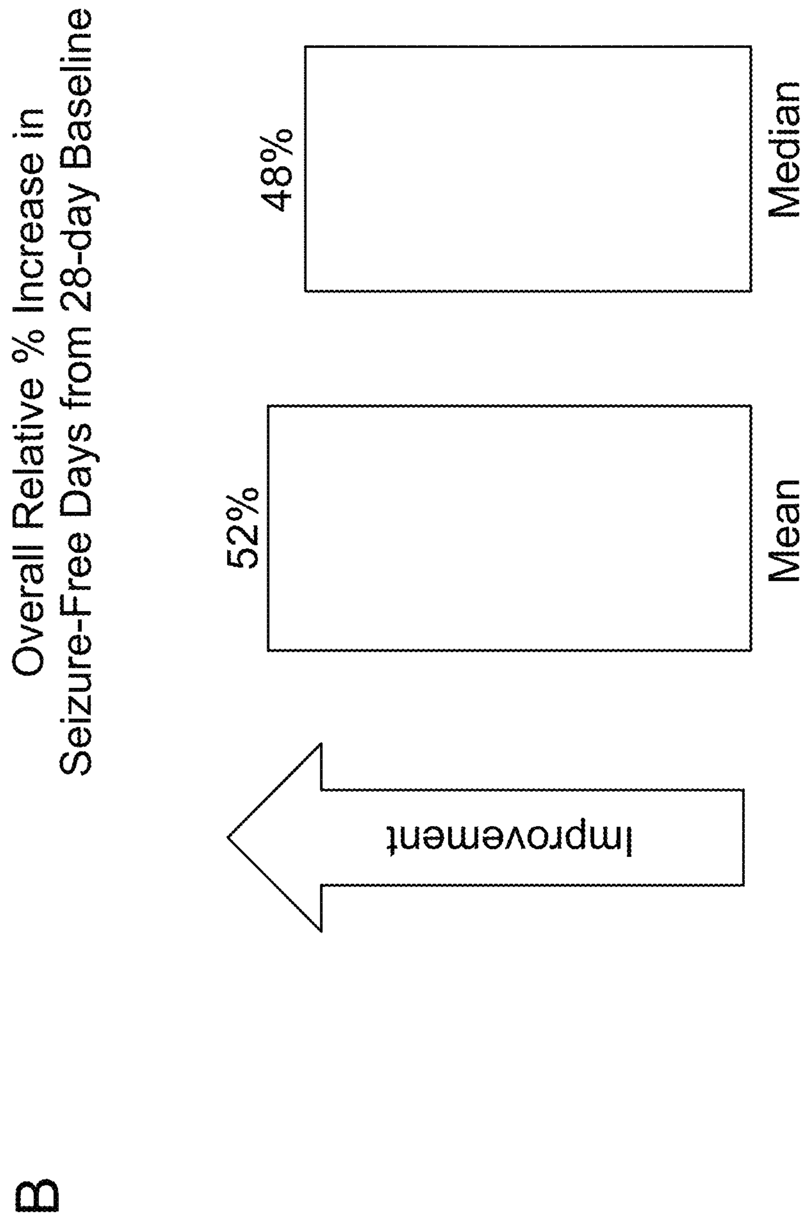

FIG. 6, Panel A is a bar graph showing mean and median change from baseline in seizure frequency for four subjects. The results represent overall percentage reduction from baseline observed through four 28-day periods for 4 subjects.

FIG. 6, Panel B is a bar graph showing mean and median relative percentage change from baseline in seizure-free days for 4 subjects. The results represent overall relative percentage increase in proportion of seizure-free days for 4 subjects.

Safety assessment after 4 doses showed that Compound 1 is well-tolerated with no drug-related AEs. Specifically, no TEAEs or SAEs were related to Compound 1, and all TEAEs were recovered or resolved. Assessments, such as physical and neurological examinations, vital sign measurements and electrocardiogram (ECG) parameters showed no clinically significant changes. Clinical laboratory results also showed no clinically significant changes, except for "elevated WBC" reported for 1 subject. There were 3 subjects with any TEAEs, of which 3 subjects had non-serious TEAEs and 2 subjects had any serious TEAEs. There were 10 individual TEAEs, of which 5 were non-serious TEAEs and 5 were any serious TEAEs. The any serious TEAEs included infection, which is common in this subject population.

Conclusions from Part 1

The preliminary results demonstrate that Compound 1 achieved significant and sustained seizure reduction at 1 mg dose levels, with unexpected benefits across all treated participants. Compound 1 was also well-tolerated with no drug-related AEs. Thus, preliminary results demonstrate tolerability of Compound 1 and its unprecedented efficacy in early onset SCN2A-DEE.

After administration of 4 doses of Compound 1, participants achieved a 43% median reduction in seizures from baseline on top of best available standard of care, and had an increased number of days without seizures, achieving a 48% relative median increase in seizure-free days from baseline. Treated participants were 1.6 times more likely to experience a seizure-free day. There were no TEAEs or SAEs considered related to study drug, and all TEAEs recovered/resolved.

Compound 1 has the potential to be the first disease-modifying treatment for early onset SCN2A GoF (gain-of-function) DEE.

Figure 7:
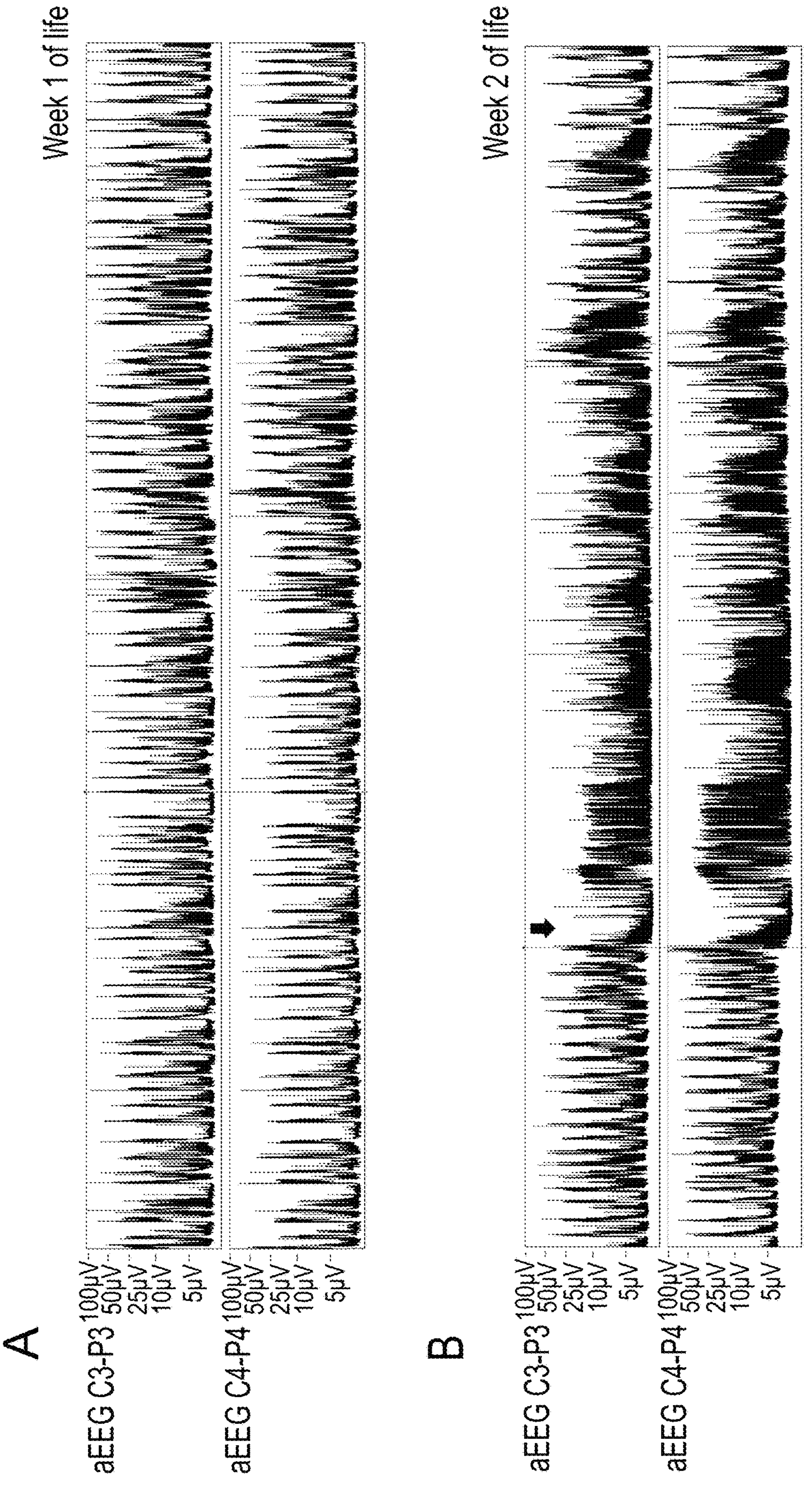
FIG. 7, Panel A shows representative aEEG traces in the subject showing a typical sawtooth pattern resembling EEG-status in week one.
Figure 7:
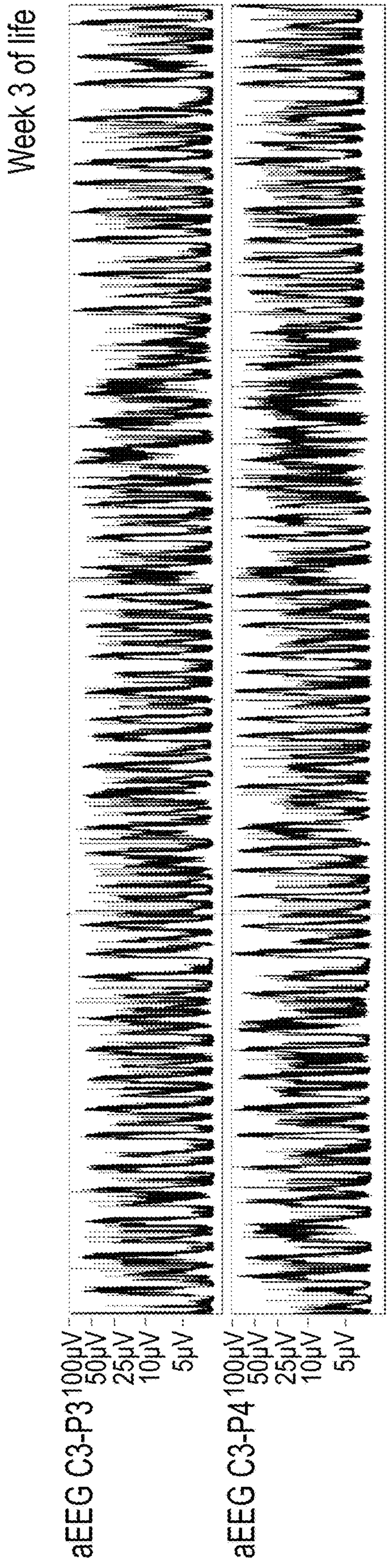

Example 2: Treatment of Early Onset SCN2A Developmental and Epileptic Encephalopathy Using Compound 1: A First-In-Patient Report in a Preterm Infant with Refractory Status Epilepticus Patient 1:

A preterm infant (29+4 weeks gestation; birthweight 1400 grams) was diagnosed prenatally using exome sequencing with a pathogenic SCN2A mutation. The pathogenic SCN2A variant identified was c.3986C>A p.(Ala1329Asp). The infant presented with status epilepticus (SE), as shown in FIG. 7. The infant had ongoing seizures since birth, confirmed by continuous EEG resembling SE, as well as a history of intrauterine seizures and arthrogryposis.

FIG. 7 shows representative aEEG traces demonstrating the subject's clinical course in the first weeks of life. Specifically, FIG. 7, Panel A shows representative aEEG traces in the subject showing a typical sawtooth pattern resembling EEG-status in week one. FIG. 7, Panel B shows representative aEEG traces in the subject demonstrating seizure reduction after several loading doses of phenytoin (arrow) in week three. FIG. 7, Panel C shows representative aEEG traces demonstrating that seizure reduction was not sustainable as status pattern reoccurred even when phenytoin levels were >40 μg/mL. Seizures were subclinical or motor seizures.

As shown in FIG. 7, anti-seizure treatment revealed only partial effect of high-dose sodium channel blockers (SCBs) and insufficient control of SE. Eligibility for Compound 1 treatment was evaluated using in silico protein structural modeling and in vitro electrophysiology studies aiming to ascertain GoF status and inform dosing strategies.

Results

Variant Characterization and GoF Confirmation

Voltage clamp experiments confirmed structural modeling predictions that the pathogenic p.Ala1329Asp variant interferes with binding of the inactivation motif that would lead to GoF via impaired inactivation and increased persistent current. Dynamic action potential clamp (DAPC) experiments, performed to assess the impact of the variant on intrinsic neuronal excitability, showed a large increase in action potential firing across the entire input range and significantly reduced rheobase compared to WT.

Figure 8:
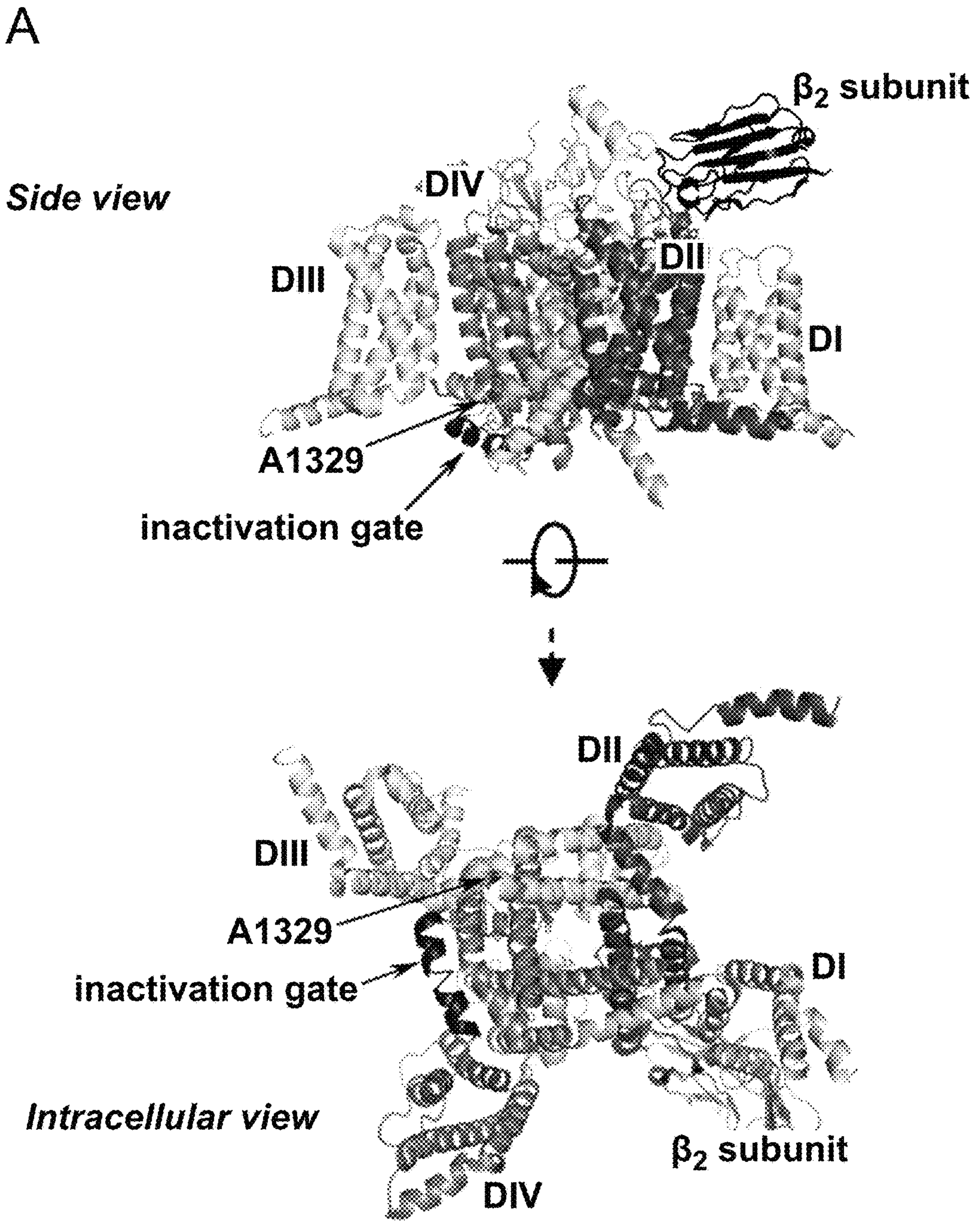
FIG. 8, Panel A shows side and intracellular views of the 3D structure of Nav1.2 highlighting the A1329 residue in the intracellular linker between transmembrane segments S4 and S5 in domain III (S4-$5_{DIII}$). Also indicated are the four domains (DI-DIV), the inactivation gate and the $\beta_2$ subunit.
Figure 8:
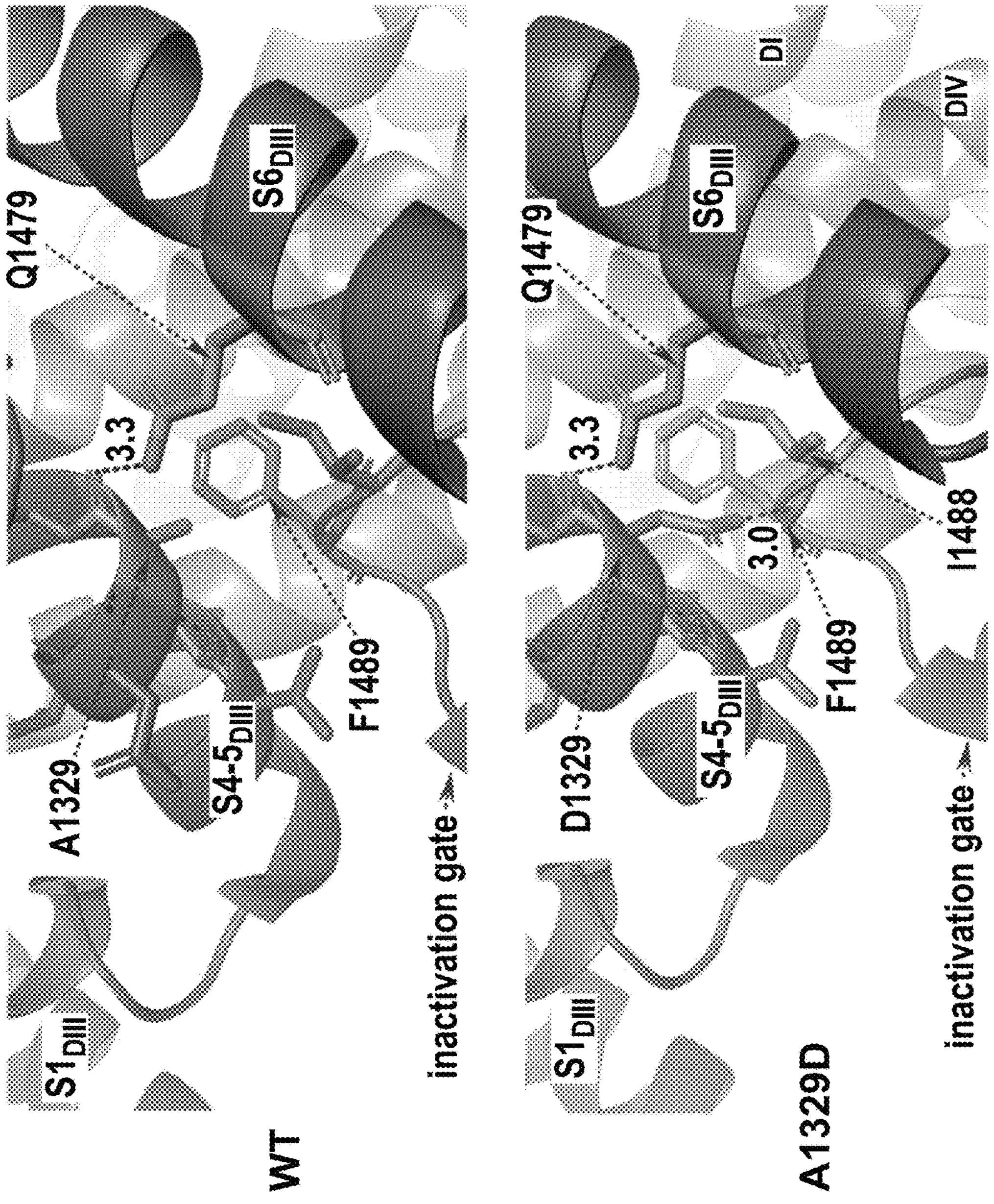

FIG. 8 shows the location of the A1329D Nav1.2 channel mutation. Specifically, FIG. 8, Panel A shows side and intracellular views of the 3D structure of Nav1.2 highlighting the A1329 residue in the intracellular linker between transmembrane segments S4 and S5 in domain III ($S4\text{-}5_{DIII}$). Also indicated are the four domains (DI-DIV), the inactivation gate and the $\beta_2$ subunit. FIG. 8, Panel B shows zoomed-in views of $S4\text{-}5_{DIII}$ region, before and after in silico mutagenesis (top, WT; bottom, A1329D). The D1329-F1489 interaction is likely to affect the binding of the IFM inactivation motif to its receptor pocket, resulting in delayed inactivation and persistent current.

Figure 9:
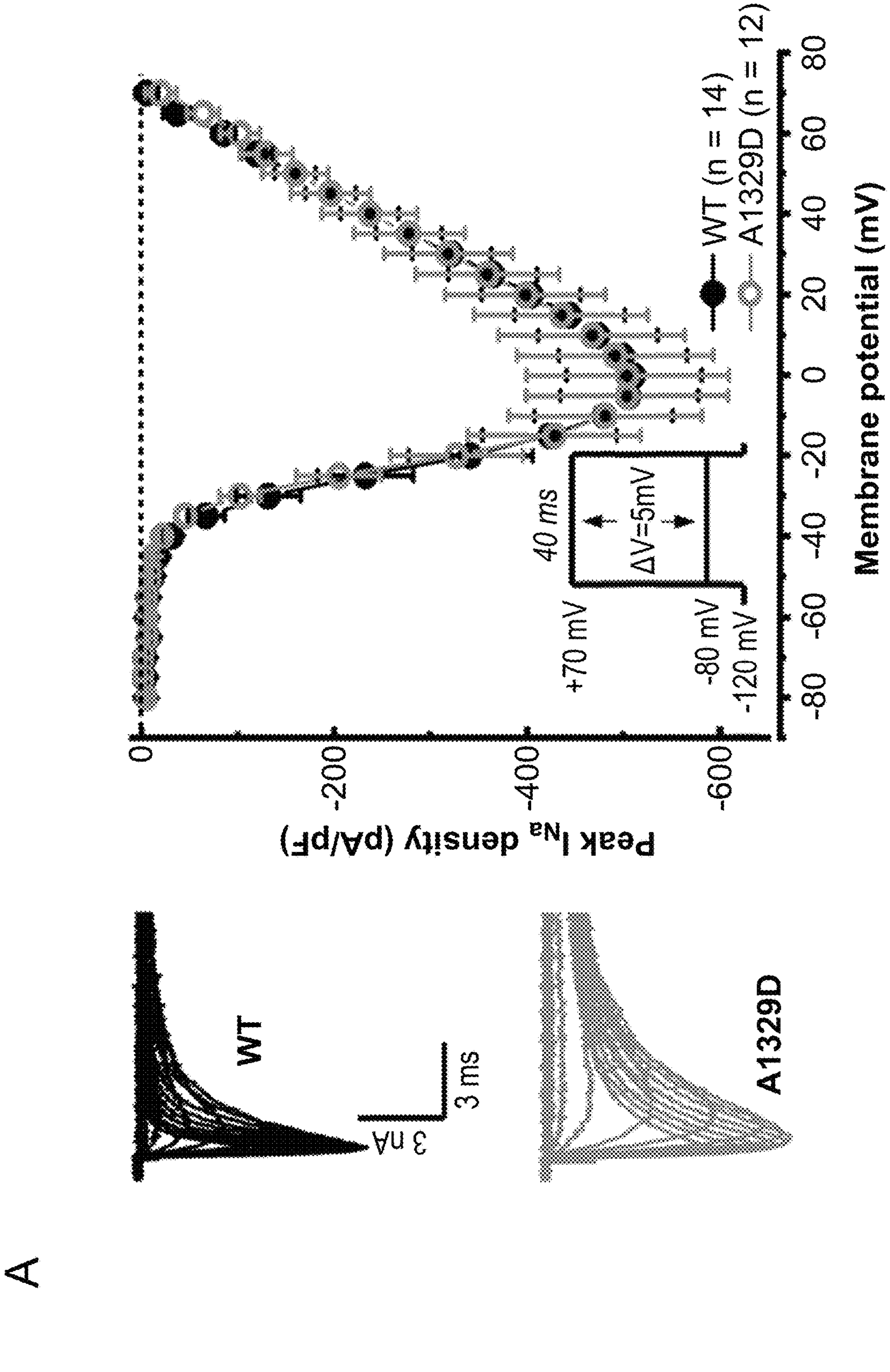
FIG. 9, Panel A shows sodium current ($I_{Na}$) density-voltage relationships (inset voltage protocol). Representative $I_{Na}$ traces are shown on the left.
Figure 9:
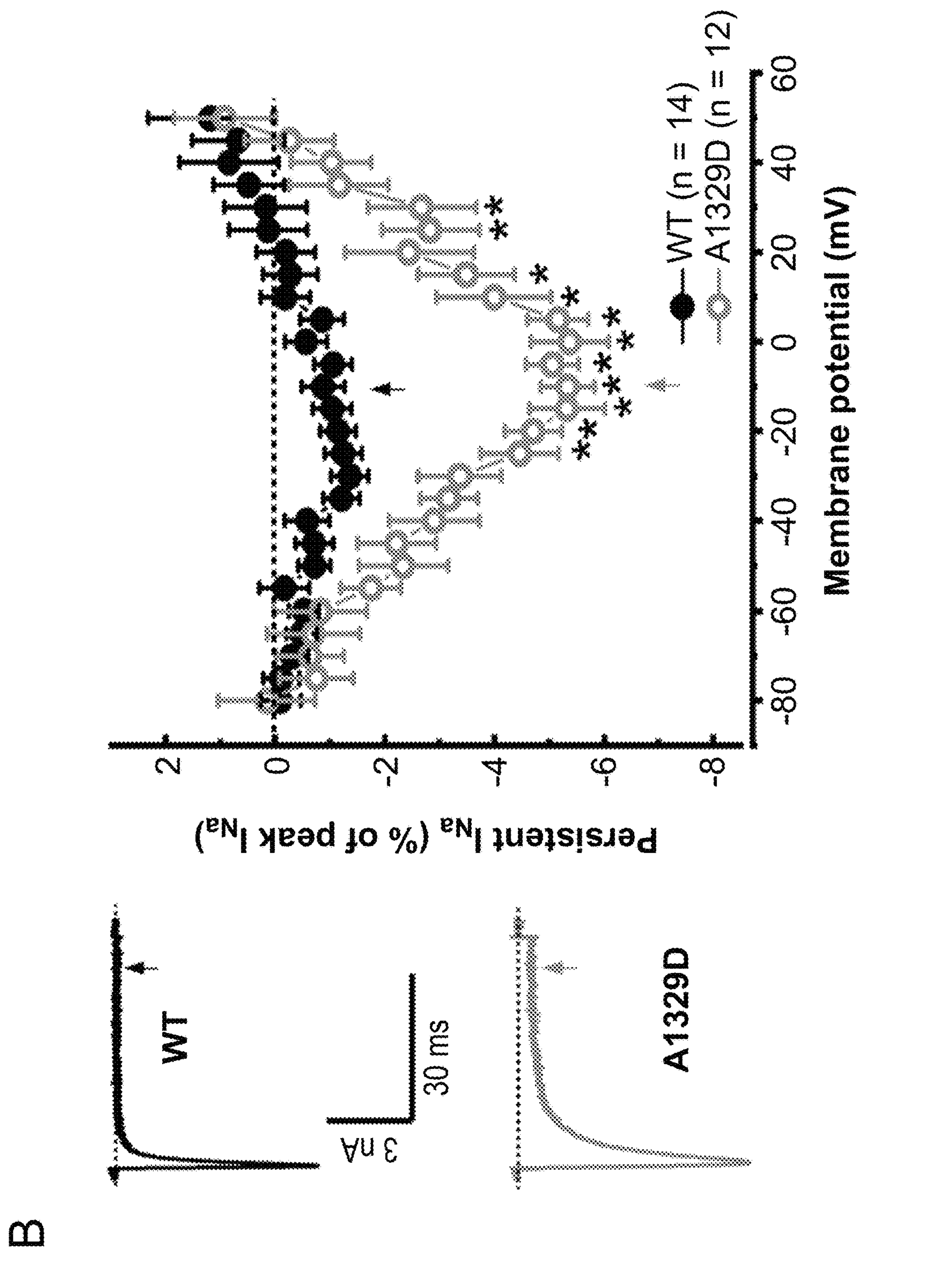
Figure 9:
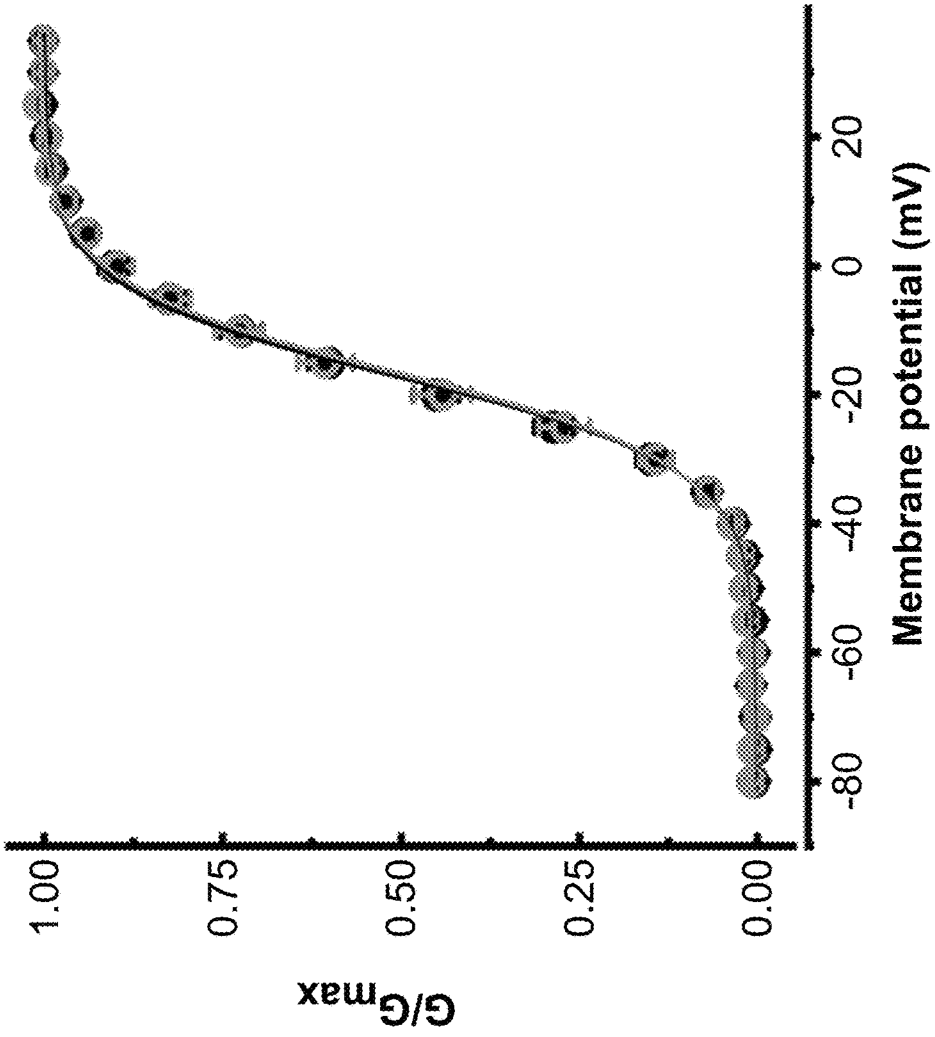
Figure 9:
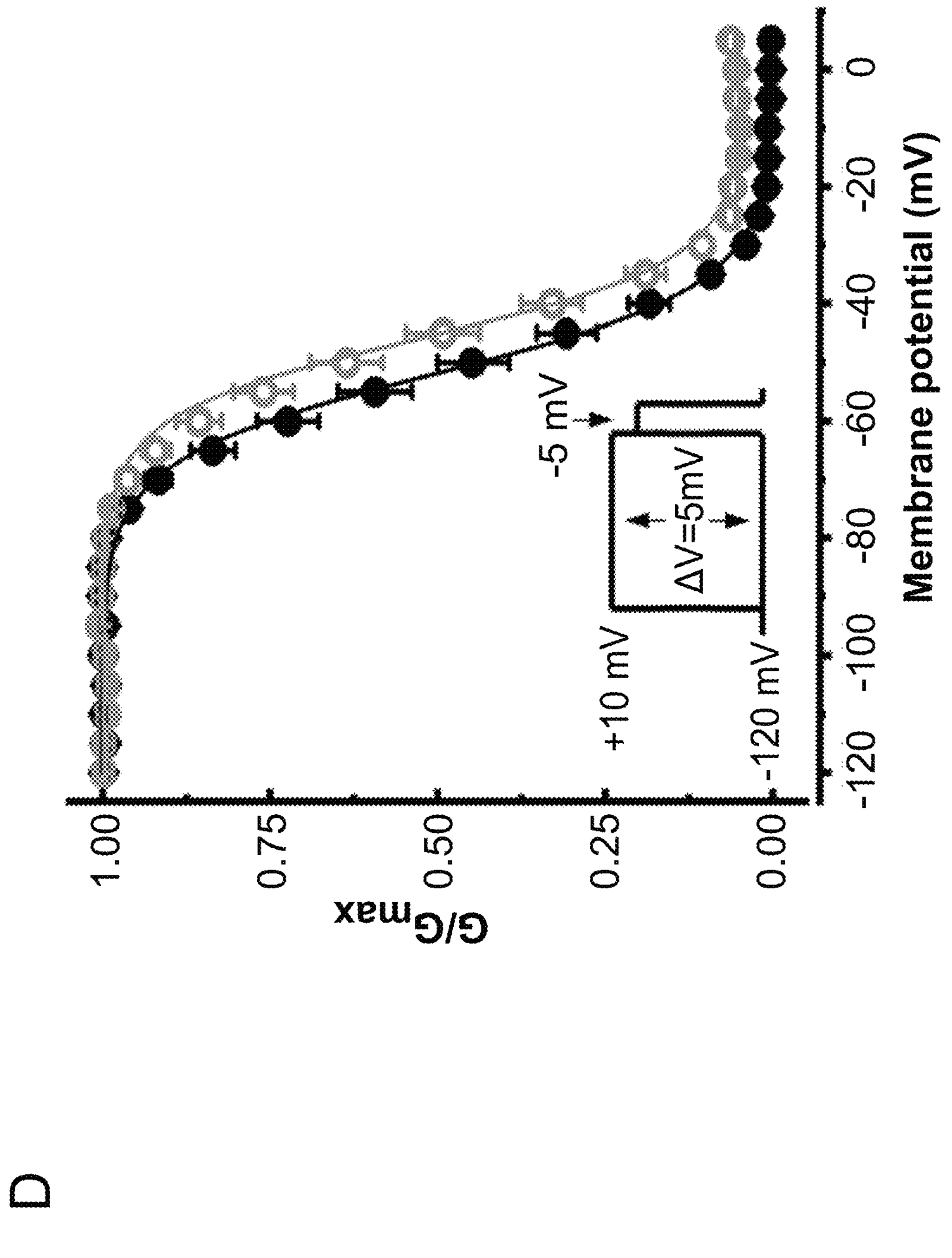
Figure 9:
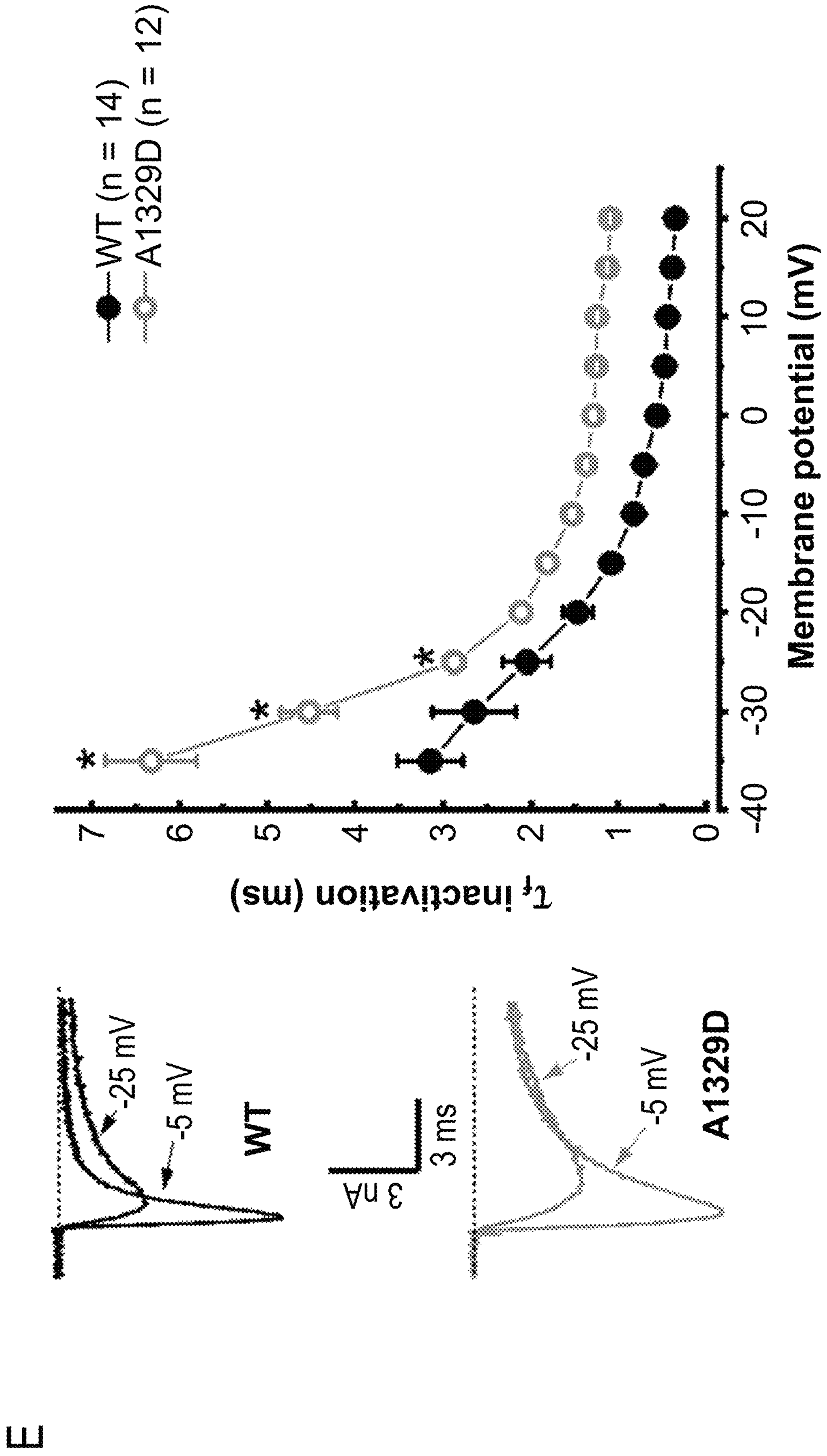
Figure 9:
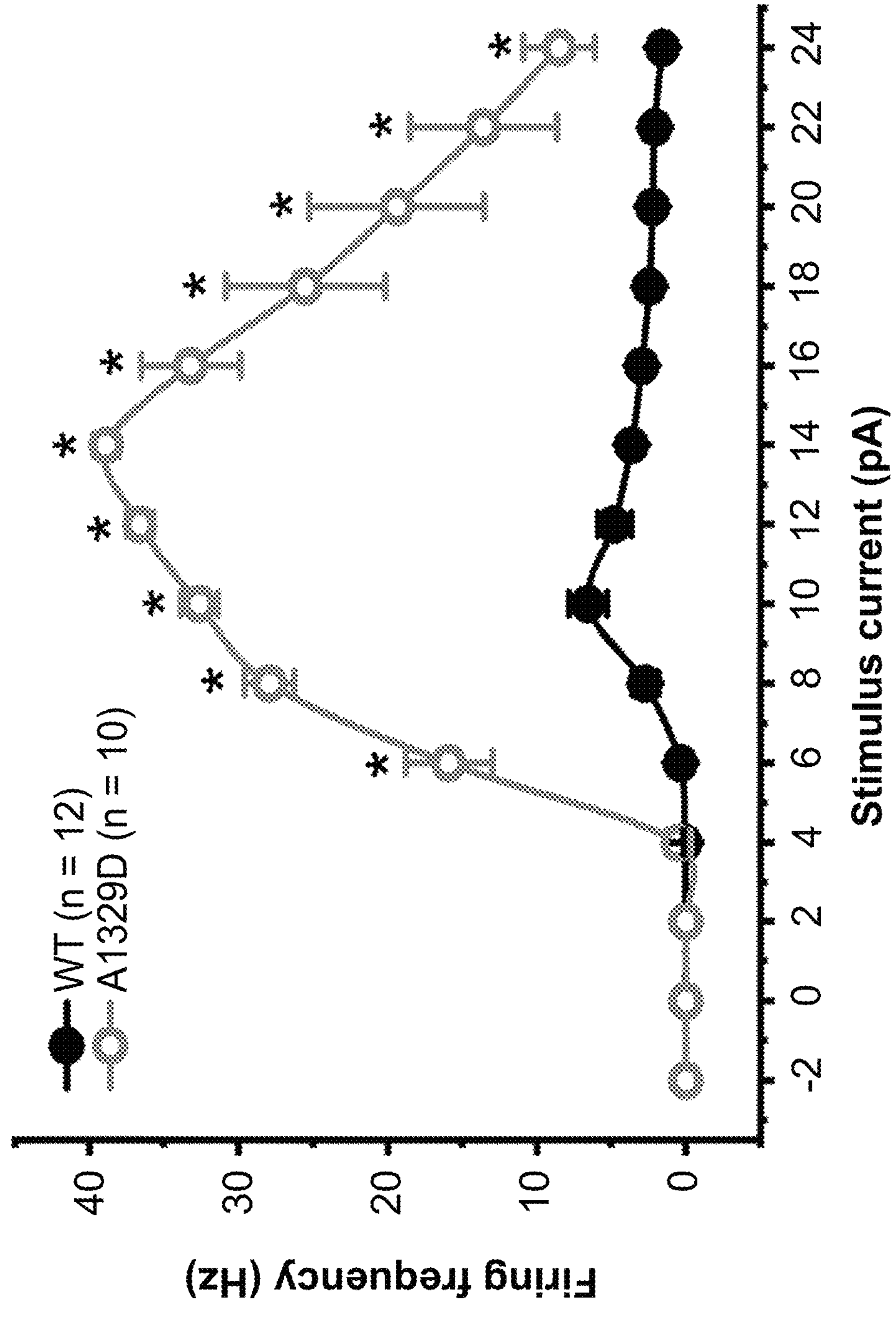

FIG. 9 shows biophysical characteristics of the A1329D variant and its impact on neuronal excitability relative to WT. In FIG. 9, data is presented as mean±SEM; *$P<0.05$ vs. WT. Specifically, FIG. 9, Panel A shows sodium current ($I_{Na}$) density-voltage relationships (inset voltage protocol). Representative $I_{Na}$ traces are shown on the left. FIG. 9, Panel B shows persistent inward $I_{Na}$-voltage relationships. Representative $I_{Na}$ traces elicited by −10 mV depolarizations are shown on the left. FIG. 9, Panel C shows voltage dependence of activation. FIG. 9, Panel D shows voltage dependence of inactivation. FIG. 9, Panel E shows dependence of the time course of $I_{Na}$ inactivation on the membrane potential. Representative WT and A1329D $I_{Na}$ traces elicited by −25 mV and −5 mV voltages are shown on the left. FIG. 9, Panel F shows input-output relationships for WT and A1329D variant.

Results Demonstrate Safety of Compound 1 and its Temporal Association with Seizure Reduction Following confirmation of GoF status, treatment with Compound 1 was initiated when patient was 1 month and 2 weeks old. Administration of a total of 15 doses have been reported. The first 6 doses, administered over 17 weeks, were (1 mg, 0.5 mg, 1 mg during the first 5 weeks; followed by 4 mg, 8 mg and 8 mg at intervals of about 4 weeks. The total cumulative dose of Compound 1 administered over 23 weeks was 22.5 mg, and the total cumulative dose of Compound 1 administered over 28 weeks and 5 days was 30.5 mg. The total cumulative dose administered after 12 doses was 70.5 mg. The total cumulative dose administered after 15 doses was 94.5 mg of Compound 1. The dosing, including drug escalations and reductions, was determined by clinician. A summary of the dosing for Patient 1 is summarized below in Table 12:

TABLE 12

Dosing Regime for Patient 1

| # | Dose Amount | Dose Date (days after initial dose) | Weight (kg) | Height (cm) | Cumulative |
|---|---|---|---|---|---|
| 1 | 1 mg | 0 days | 2.485 | | |
| 2 | 0.5 mg | 15 days | 2.915 | | |
| 3 | 1 mg | 31 days | 3.350 | 51 | |
| 4 | 4 mg | 80 days | 4.380 | 52 | |
| 5 | 8 mg | 122 days | 5.280 | 58 | |
| | N/A* | 131 days* | 5.622 | 61 | |
| 6 | 8 mg | 164 days | 5.955 | 61.5 | |
| 7 | 8 mg | 200 days | 5.8 | 62 | |
| 8 | 8 mg | 242 days | 7 | 64 | |
| 9 | 8 mg | 296 days | 8 | 66 | |
| 10 | 8 mg | 339 days | 8.7 | 70 | |
| 11 | 8 mg | 376 days | 8.9 | 73 | |
| 12 | 8 mg | 409 days | 9.08 | 74 | |
| 13 | 8 mg | 437 days | 9.3 | 75 | 78.5 mg |
| 14 | 8 mg | 466 days | 9.6 | 76 | |
| 15 | 8 mg | 495 days | 9.8 | 76 | 94.5 mg |

*No dose on this date. Ht/Wt are for plasma sample collection

Figure 10:
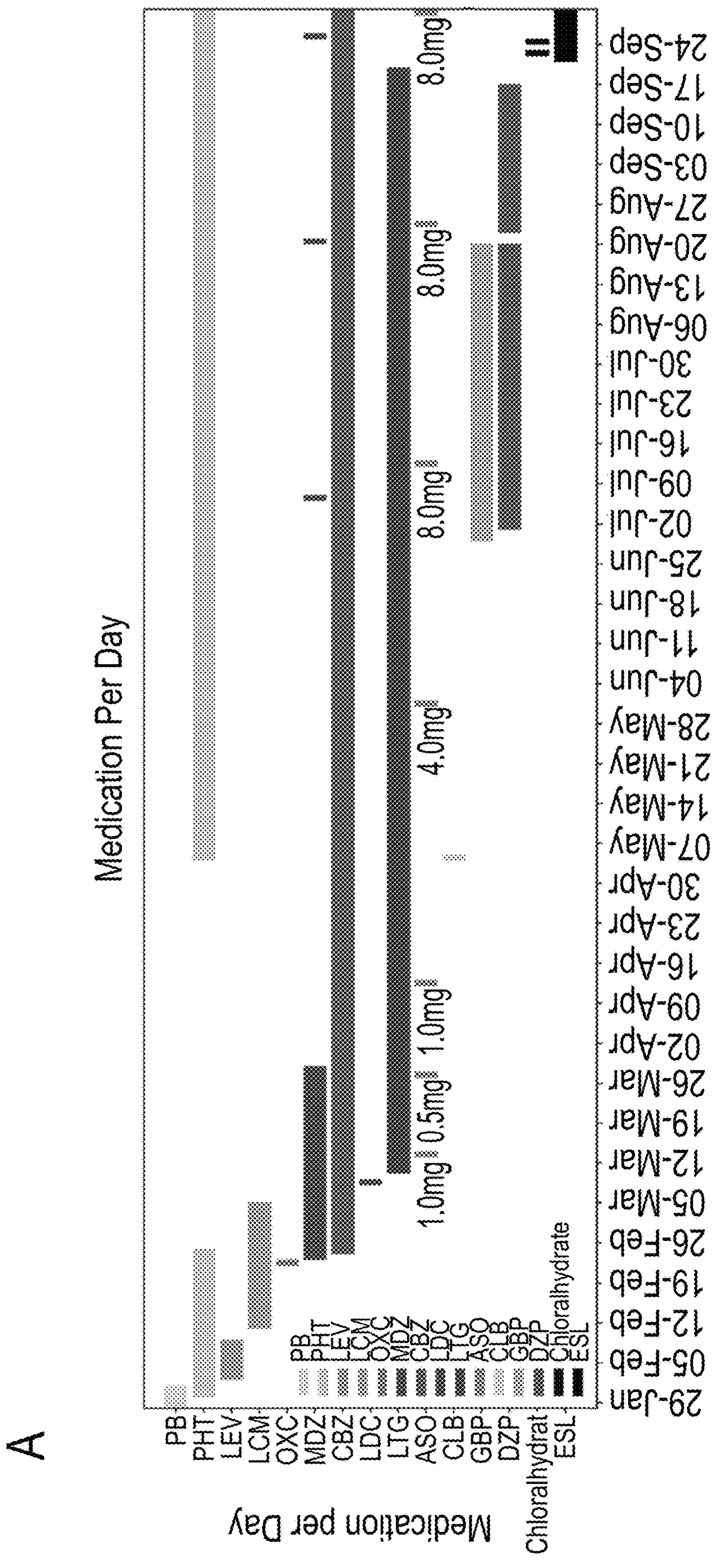
FIG. 10, Panel A shows patient clinical course including high-dose SCBs and introduction of Compound 1 dosing regimen. Associated reduction in seizure frequency is shown (bottom).
Figure 10:
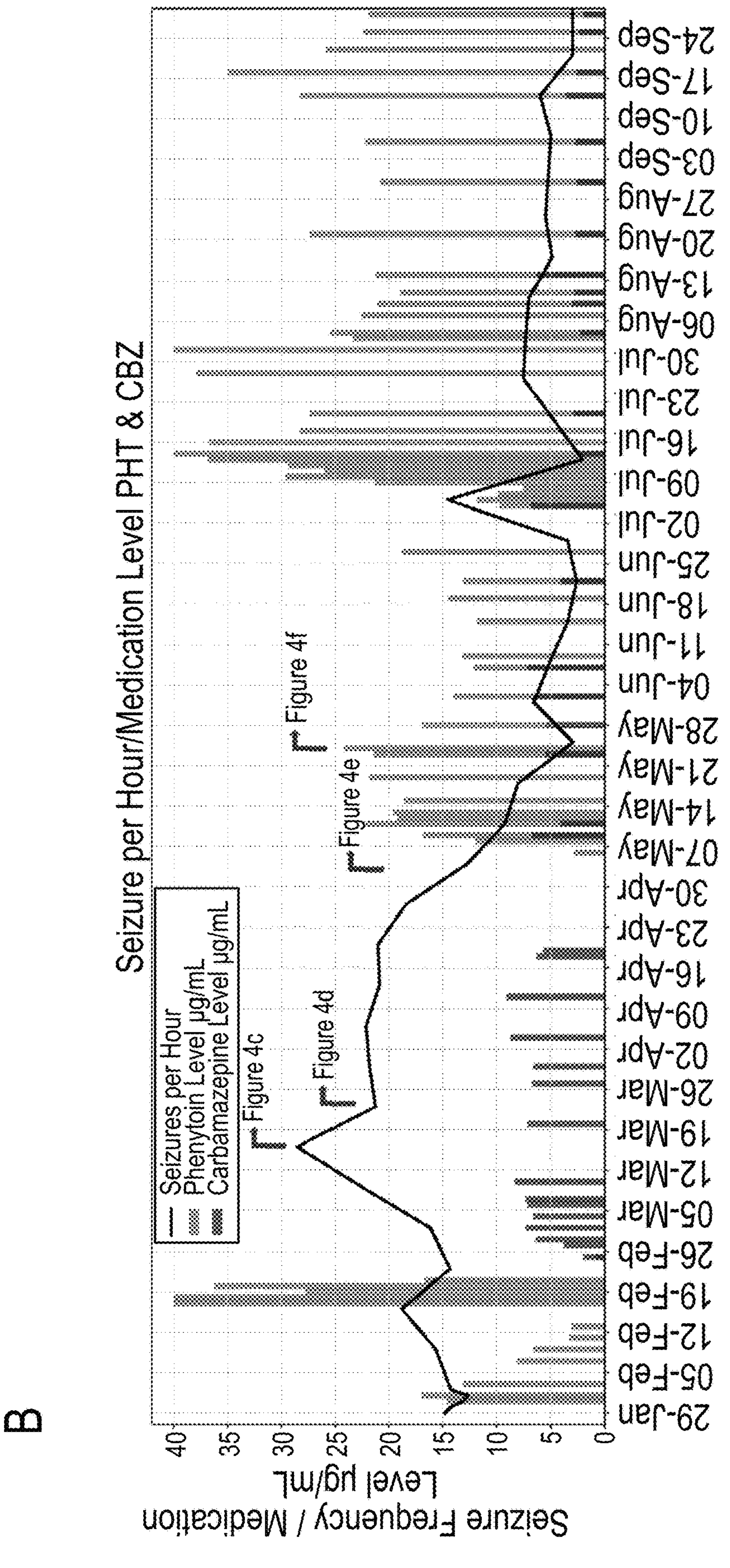
Figure 10:
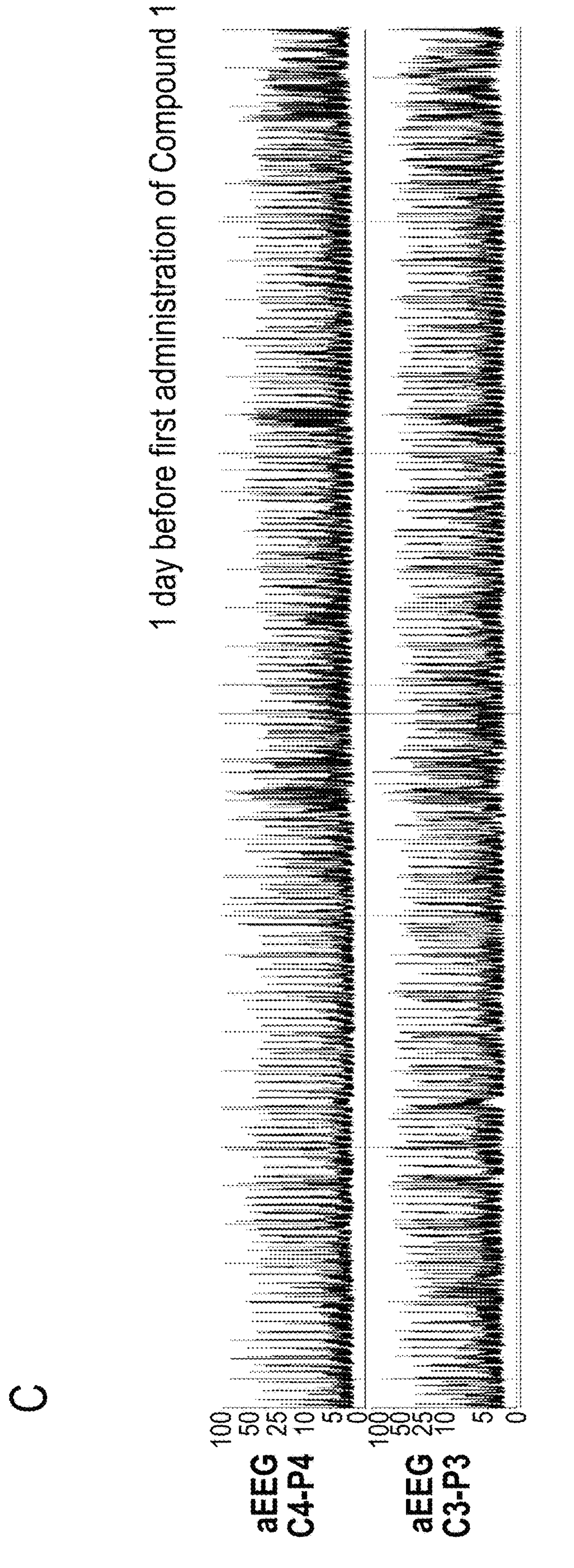
Figure 10:
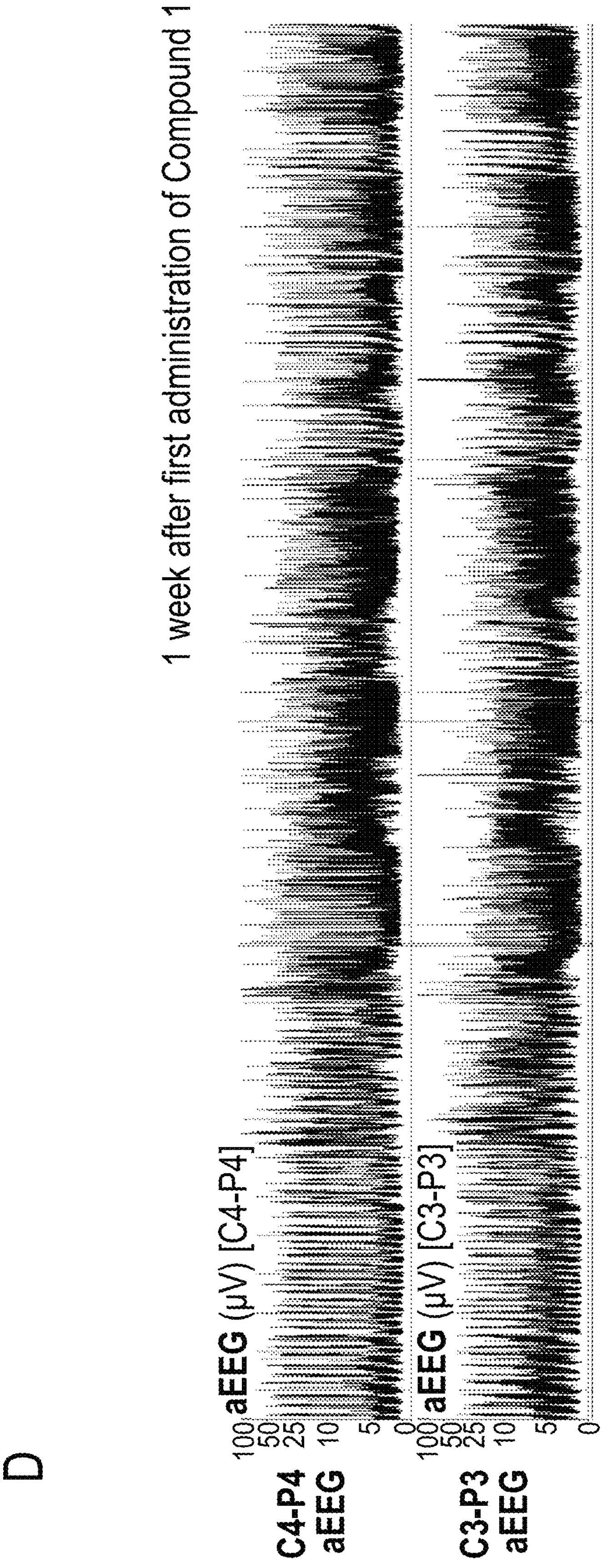
Figure 10:
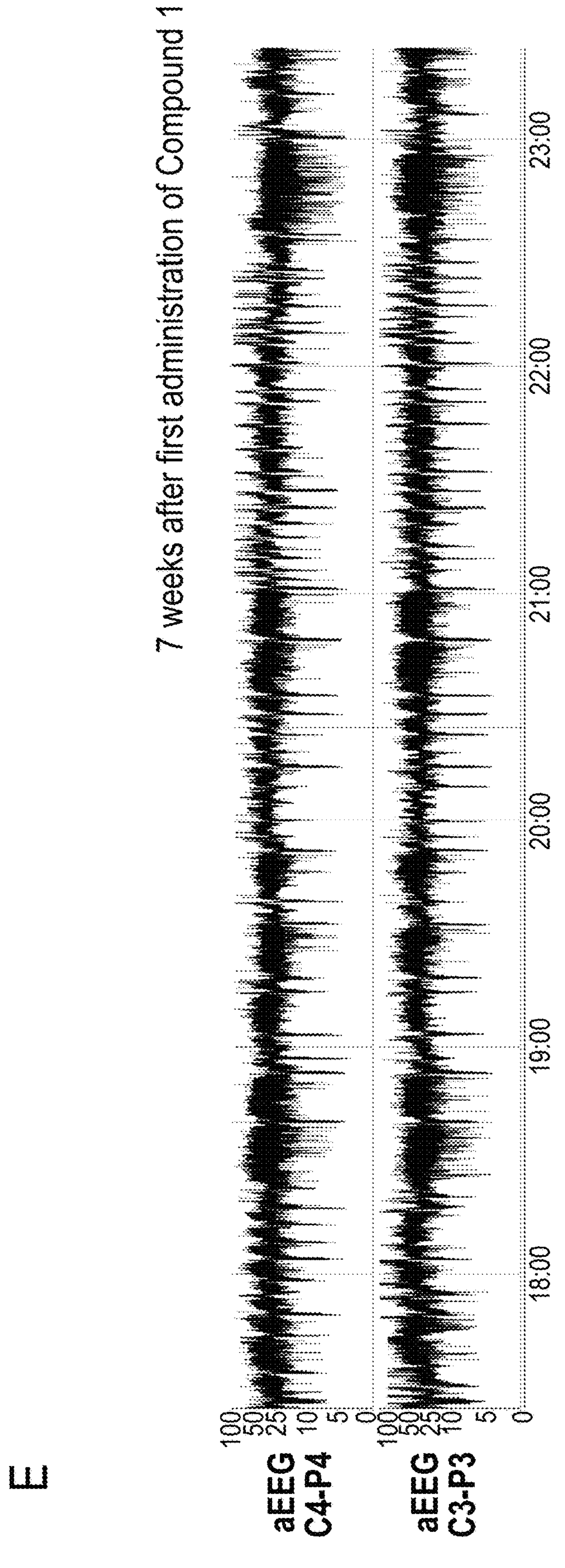
Figure 10:
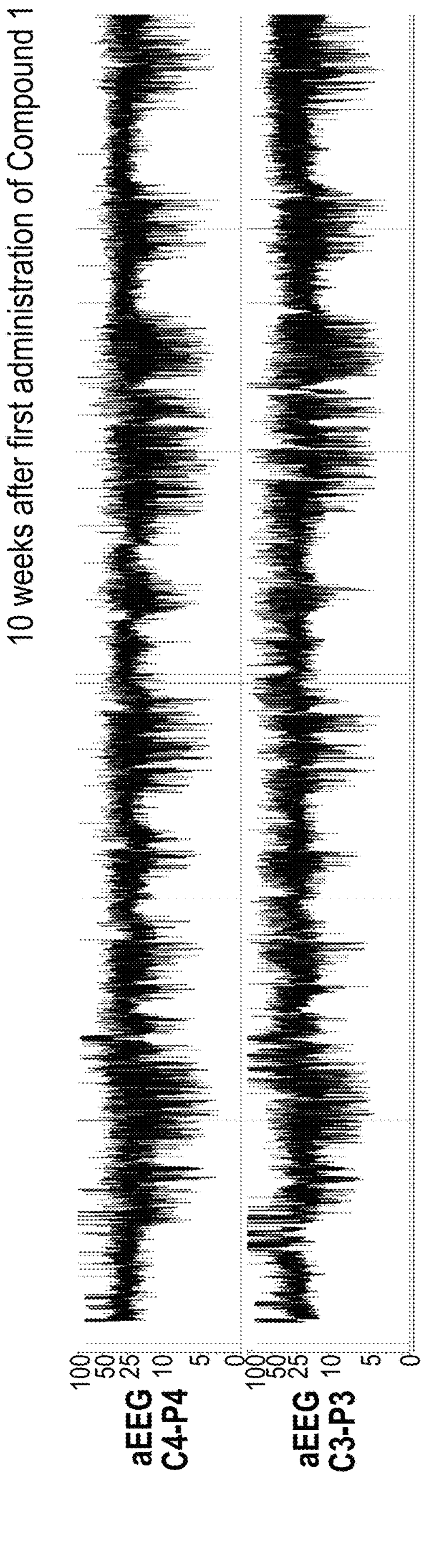

FIG. 10 shows patient clinical course following introduction of Compound 1 treatment regimen and effects on seizures. Specifically, FIG. 10, Panel A shows patient clinical course including high-dose SCBs and introduction of Compound 1 dosing regimen. Associated reduction in seizure frequency is shown (bottom). FIG. 10, Panel B is a bar graph showing the number of seizures per hour per medication level of phenytoin (PHT) and carbamazepine (CBZ). A total of 7 Compound 1 intrathecal doses were administered (30.5 mg total dose). FIG. 10, Panel C shows aEEG traces 1 day before the first administration of Compound 1 showing peak seizure frequency (status epilepticus). FIG. 10, Panel D shows aEEG traces 1 week after first administration of Compound 1. FIG. 10, Panel E shows aEEG traces 7 weeks after first administration of Compound 1. FIG. 10, Panel F shows aEEG traces 10 weeks after first administration of Compound 1.

The data shown in FIG. 10, Panels D-F demonstrate modulation and reduction of seizure activity (often in close timely relationship to SCB administration). It is also noted that seizure exacerbation between July 2 and 9 shown in the aEEG traces was due to urosepsis and concomitant decrease of SCB plasma levels.

A postnatal brain magnetic resonance imaging (MRI) at 5-weeks-old revealed T1 hyperintensities, periventricular thinning, prominent, extended lateral ventricles and periventricular medullary obliteration in addition to germinal matrix and periventricular leukomalacia possibly related to periventricular hemorrhagic infarction, demonstrating previous brain insults. A multitude of ASMs were administered immediately after birth and adjusted throughout the treatment period as deemed necessary by the treating physician, but the patient never adequately responded, sustaining refractory status epilepticus from birth until Compound 1 was administered.

Compound 1 treatment, in combination with best standard of care ASMs, was well tolerated with no severe or serious drug-related AEs up to a cumulative total of 94.5 mg over 16 months or 70 weeks.

To date, the patient has been administered a total of 15 doses of Compound 1 (1, 0.5, 1, 4, 8, 8, 8, 8, 8, 8, 8, 8, 8, 8, 8 mg) initiating at 6 weeks after birth, over a 70-week period. Dose levels were selected by the treating physician based on continuous evaluation of the infant's disease status while resident in the hospital. Compound 1 continues to be well tolerated, with no reported drug-related serious adverse events (SAEs) reported over the entire treatment period.

Importantly, no related AEs have been observed at the highest single doses of 8 mg (equivalent WT NHP dose of 0.8 mg with a total cumulative exposure of 3.05 mg). Following 6 doses with a cumulative exposure of 22.5 mg of dosing over 25 weeks, the CSF concentration of Compound 1 was determined to be 1.51 ng/mL. The exposures achieved demonstrate the safety and tolerability of Compound 1 in an infant, who had a bodyweight of 2 kg when the first dose was administered. Potential benefit of Compound 1 was evident soon after the first administration of Compound 1, where status epilepticus was interrupted intermittently 8 days after the first dose and ultimately ceased following continued dosing. Following the first administration of 4 mg of Compound 1, the patient stabilized, such that discharge from the intensive care unit for the first time was determined to be possible. A reduction in seizure frequency in excess of 50% was observed during follow-up assessments with seizure frequency and severity being markedly attenuated throughout the treatment period. Seizure frequence remains stable with ongoing dosing and was maintained after tapering phenytoin at age 14 months, with no worsening of neurodevelopment at age 18 months. Compound 1 was well-tolerated and no severe or serious adverse events were reported.

Patient 2:

Patient 2 is an 8-year old patient who was diagnosed with SCN2A-related Gain-of-Function DEE. The patient had a history of refractory seizures, global cerebral atrophy, global developmental delay, frequent oculogyric movement, and severe dystonia while awake.

The patient has received a total of 10 doses over a period of about 9 months at approximately monthly (about 3-4 week in this case) intervals with the highest dose of 5 mg and cumulative exposure of 22 mg to date. There have been no drug-related AEs reported, and the procedure and dosing have been well tolerated. A summary of the dosing for Patient 2 is summarized below in Table 13:

TABLE 13

Dosing Regime for Patient 2

| # | Dose Amount | Dose Date (days after initial dose) | Weight (kg) | Cumulative |
|---|---|---|---|---|
| 1 | 1 mg | 0 days | | |
| 2 | 1 mg | 22 days | | |
| 3 | 1 mg | 53 days | | |
| 4 | 1 mg | 83 days | | |
| 5 | 1.5 mg | 109 days | | 5.5 mg |
| 6 | 1.5 mg | 137 days | | |
| 7 | 3 mg | 166 days | | |
| 8 | 3 mg | 195 days | | |
| 9 | 4 mg | 223 days | | 17 mg |
| 10 | 5 mg | 250 days | | 22 mg |

Prior to the administration of Compound 1, the patient experienced urinary calcinosis, likely secondary to ethosuximide, and previous attempts to wean the medication led to worsening of facial myoclonus and inability to feed. Two weeks after the second dose of Compound 1, a 0.5 mL weekly reduction of ethosuximide was achieved and facial myoclonus subsided during waking hours.

Also, after the second dose, nystagmus was reportedly much less, tone was much improved, and administration of Botulinim toxin was ceased. Additionally, after administration of Dose 2, the patient was reported to have a drastic decrease in seizures and previous full tonic-clonic seizures appeared as subtle tongue movement with the jaw (reportedly how the tonic-clonic seizures previously began), but the tongue movement did not progress to tonic-clonic seizure. It was further reported by the care team that after Dose 2, the patient appeared happy and calm as compared to prior to treatment with Compound 1 when the patient was more agitated and exhibited more crying and screaming. After Dose 2, the patient was observed to make subtle hand movements not made before, and it was reported that she moved her arm to greet a visitor. The patient was also observed by teachers at school as being more alert than prior to treatment. Daily seizure counts are not currently being provided; however, a 24-hour EEG, conducted between Dose 2 and Dose 3, showed significantly fewer clinical and electrographic seizures; multifocal and generalized epileptic discharges remained abnormal.

In general, Compound 1 has been well tolerated over the administrations. Additionally, there have been several notable improvements in quality-of-life, as communicated by caregivers and medical personnel who provide support to the patient, including that:

- the family reported a reduction in tonic-clonic seizure intensity as well as improvement in attention and vocalization. The family reported that the patient is smiling more often;
- the family reported that the patient is more comfortable in a wheelchair and is more tolerant of sensory stimuli in general. As a result, they have begun going to restaurants;
- an occupational therapist reported improved range of motion and botulinic toxin administration was withheld;
- a speech therapist was able to provide liquids without thickening and reported that gazing communication and alertness improved;

Digestion has improved significantly, and suppositories are able to be withheld.

Patient 3:

Patient 3 is a patient from Example 1 (ID No. 2001) and was granted continued access to Compound 1. A summary of the continued dosing for Patient 3 is summarized below in Table 14:

TABLE 14

Dosing Regime for Patient 3

| # | Dose Amount | Dose Date (days after initial dose) | Weight (kg) | Cumulative |
|---|---|---|---|---|
| 1 | 1 mg | 0 days | 20 | |
| 2 | 1 mg | 35 days | 20 | |
| 3 | 1 mg | 63 days | 20 | 3 mg |
| 4 | 1 mg | 98 days | 20 | |
| 5 | 1 mg | 132 days | | 5 mg |

Compound 1 continues to be well tolerated by Patient 3.

Patient 4:

Patient 4 is a patient from Example 1 (ID No. 2004) and was granted continued access to Compound 1. A summary of the continued dosing for Patient 4 is summarized below in Table 15:

TABLE 15

| Dosing Regime for Patient 4 | | | | |
|---|---|---|---|---|
| # | Dose Amount | Dose Date (days after initial dose) | Weight (kg) | Cumulative |
| 1 | 1 mg | 0 days | 19 | |
| 2 | 1 mg | 31 days | 19 | |
| 3 | 1 mg | 79 days | 19 | 3 mg |
| 4 | 1 mg | 114 days | | 4 mg |
| 5 | 1 mg | 145 days | | |

Compound 1 continues to be well tolerated by Patient 4.

CONCLUSION

First-in-patient findings demonstrate Compound 1 to be the first disease-modifying treatment for early onset GoF SCN2A-DEE, with early clinical experience in combination with SCBs indicating safety and a temporal association with seizure reduction, including cessation of previous refractory SE.

What is claimed is:

1. A method of reducing frequency of seizures experienced by a subject with early onset SCN2A Developmental and Epileptic Encephalopathy (DEE) in need of treatment, said method comprising administering to said subject an effective amount of an oligomeric compound, wherein:

the SCN2A DEE is caused by a gain-of-function mutation in SCN2A gene;

the oligomeric compound comprises a 6-10-4 MOE gapmer having a sequence (from 5' to 3') of CCACGACATATTTTTCTACA (SEQ ID NO: 3);

wherein each of nucleosides 1-6 and 17-20 (from 5' to 3') are 2'-MOE nucleosides and each of nucleosides 7-16 are 2'-β-D-deoxynucleosides;

wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages; and each cytosine is a 5-methyl cytosine;

wherein the oligomeric compound is administered at a dose of about 0.5 mg to about 8 mg;

wherein the subject is a human and is a newborn to 18 years old; and wherein the oligomeric compound is administered intrathecally.

2. The method of claim 1, wherein the oligomeric compound is administered at a dose of about 0.5 mg, about 0.6 mg, about 0.7 mg, about 0.8 mg, about 0.9 mg, about 1 mg, about 2 mg, about 2.5 mg, about 3 mg, about 3.5 mg, about 4 mg, about 5 mg, about 6 mg, about 7 mg or about 8 mg.

3. The method of claim 1, wherein the oligomeric compound is administered at a dose of about 0.5 mg, about 1 mg, about 4 mg or about 8 mg.

4. The method of claim 3, wherein the oligomeric compound is administered at a dose of about 1 mg.

5. The method of claim 1, wherein the oligomeric compound is administered about once per month.

6. The method of claim 1, wherein the seizures are selected from the group consisting of focal motor seizures, tonic seizures, generalized tonic-clonic seizures and myoclonic seizures.

7. The method of claim 1, wherein administration of the oligomeric compound results in a decrease in the average number of daily seizures experienced by the subject in a 28-day period, as compared to the average number of daily seizures experienced by the subject prior to administration of the oligomeric compound.

8. The method of claim 1, wherein administration of the oligomeric compound results in a reduction in the number of seizures experienced by the subject in a 28-day period by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, as compared to the number of seizures experienced by the subject prior to administration of the oligomeric compound.

9. The method of claim 1, wherein the subject is between 2 and 18 years old.

10. The method of claim 1, wherein the subject is a newborn to 24 months old.

11. The method of claim 10, wherein the subject is a newborn.

12. The method of claim 11, wherein the newborn is a premature newborn.

13. The method of claim 1, wherein the gain-of-function mutation in SCN2A gene is selected from the group consisting of L210Q, A263V, E430A, R1882Q, G879R, Q1479H, V423L, G1593R, K1502N, V1601L, G211D, S1780I, D343H and A1329D.

14. The method of claim 13, wherein the gain-of-function mutation is A1329D.

15. The method of claim 1, wherein the oligomeric compound is a modified oligonucleotide represented by the following chemical structure:

(SEQ ID NO: 3)

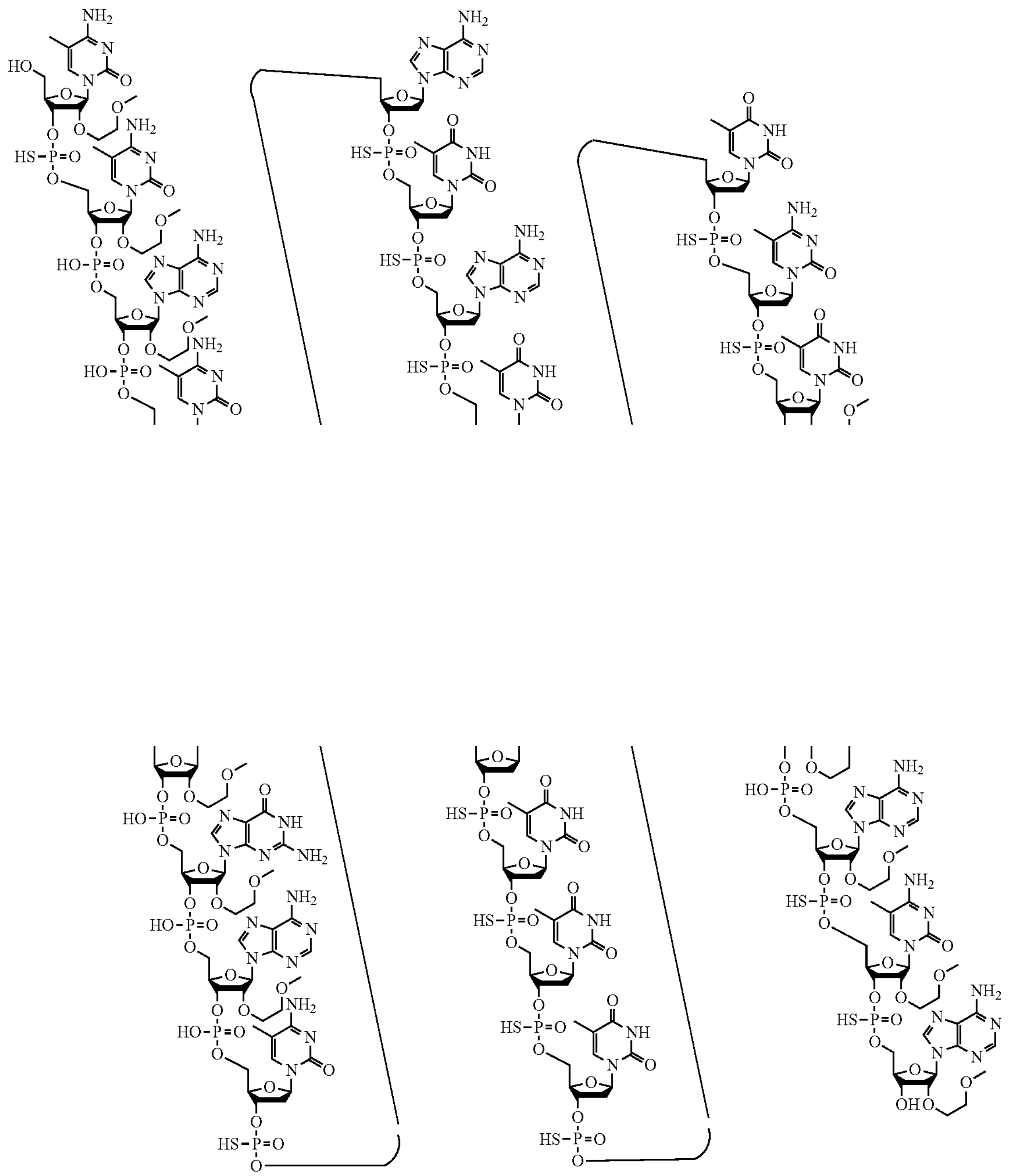

or a salt thereof.

16. The method of claim 15, wherein the modified oligonucleotide is a sodium salt or a potassium salt.

17. The method of claim 16, wherein the modified oligonucleotide is a sodium salt.

18. The method of claim 17, wherein the modified oligonucleotide represented by the following chemical structure:

(SEQ ID NO: 3)

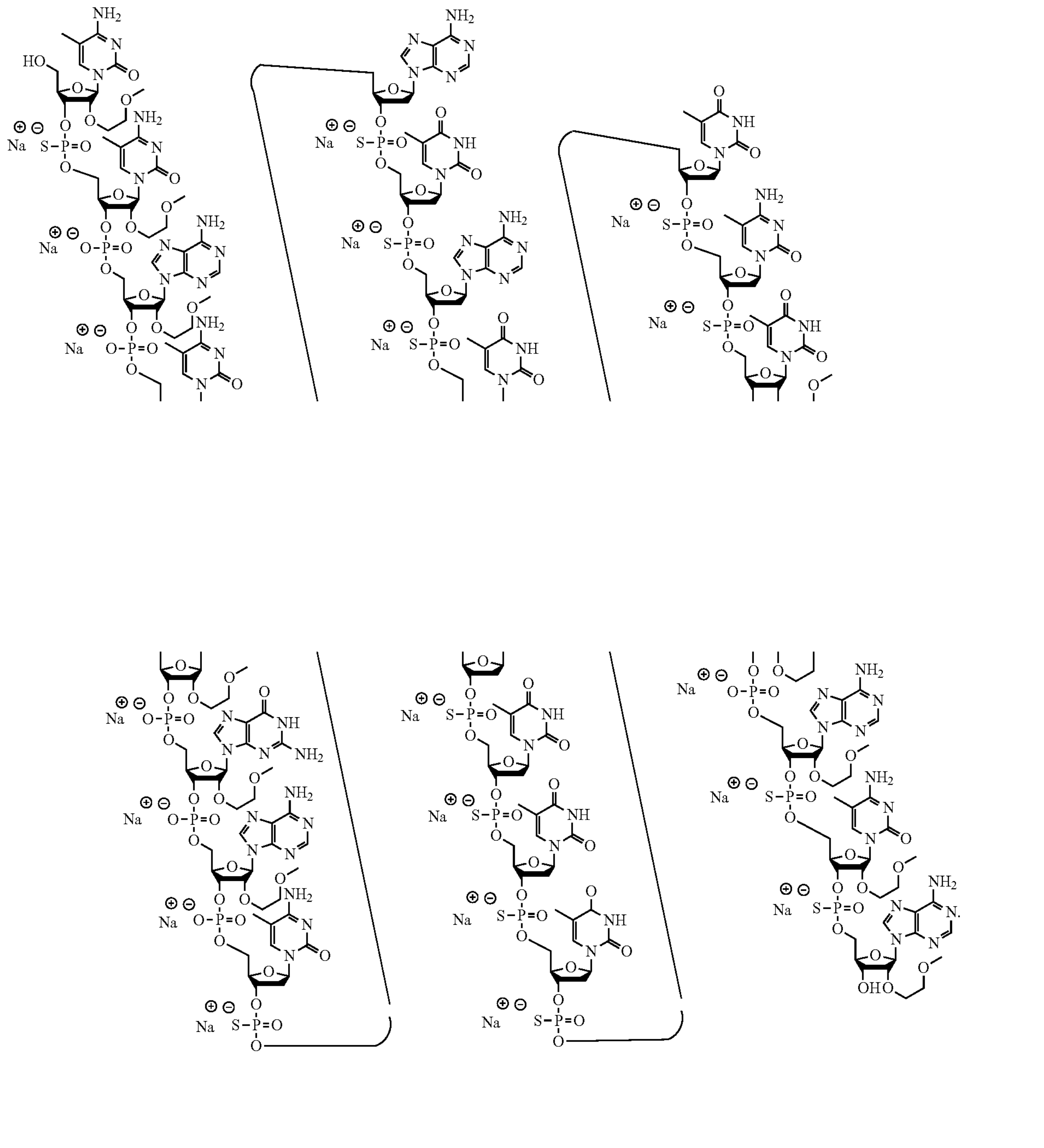

19. The method of claim 1, wherein the oligomeric compound is administered as a part of a pharmaceutical composition comprising the oligomeric compound and a pharmaceutically acceptable diluent or carrier.

20. The method of claim 19, wherein the pharmaceutically acceptable diluent is artificial CSF (aCSF) or phosphate-buffered saline (PBS).

21. The method of claim 20, wherein the pharmaceutically acceptable diluent is aCSF.

22. The method of claim 1, wherein the oligomeric compound is administered at a dose of about 1 mg to about 8 mg.

* * * * *

SEQUENCE LISTING

```
Sequence total quantity: 9
SEQ ID NO: 1            moltype = AA  length = 2005
FEATURE                 Location/Qualifiers
source                  1..2005
                        mol_type = protein
                        organism = Homo sapiens
SEQUENCE: 1
MAQSVLVPPG PDSFRFFTRE SLAAIEQRIA EEKAKRPKQE RKDEDDENGP KPNSDLEAGK  60
SLPFIYGDIP PEMVSVPLED LDPYYINKKT FIVLNKGKAI SRFSATPALY ILTPFNPIRK  120
LAIKILVHSL FNMLIMCTIL TNCVFMTMSN PPDWTKNVEY TFTGIYTFES LIKILARGFC  180
LEDFTFLRDP WNWLDFTVIT FAYVTEFVDL GNVSALRTFR VLRALKTISV IPGLKTIVGA  240
LIQSVKKLSD VMILTVFCLS VFALIGLQLF MGNLRNKCLQ WPPDNSSFEI NITSFFNNSL  300
DGNGTTFNRT VSIFNWDEYI EDKSHFYFLE GQNDALLCGN SSDAGQCPEG YICVKAGRNP  360
NYGYTSFDTF SWAFLSLFRL MTQDFWENLY QLTLRAAGKT YMIFFVLVIF LGSFYLINLI  420
LAVVAMAYEE QNQATLEEAE QKEAEFQQML EQLKKQQEEA QAAAAAASAE SRDFSGAGGI  480
GVFSESSSVA SKLSSKSEKE LKNRRKKKKQ KEQSGEEEKN DRVRKSESED SIRRKGFRFS  540
LEGSRLTYEK RFSSPHQSLL SIRGSLFSPR RNSRASLFSF RGRAKDIGSE NDFADDEHST  600
FEDNDSRRDS LFVPHRHGER RHSNVSQASR ASRVLPILPM NGKMHSAVDC NGVVSLVGGP  660
STLTSAGQLL PEGTTTETEI RKRRSSSYHV SMDLLEDPTS RQRAMSIASI LTNTMEELEE  720
SRQKCPPCWY KFANMCLIWD CCKPWLKVKH LVNLVVMDPF VDLAITICIV LNTLFMAMEH  780
YPMTEQFSSV LSVGNLVFTG IFTAEMFLKI IAMDPYYYFQ EGWNIFDGFI VSLSLMELGL  840
ANVEGLSVLR SFRLLRVFKL AKSWPTLNML IKIIGNSVGA LGNLTLVLAI IVFIFAVVGM  900
QLFGKSYKEC VCKISNDCEL PRWHMHDFFH SFLIVFRVLC GEWIETMWDC MEVAGQTMCL  960
TVFMMVMVIG NLVVLNLFLA LLLSSFSSDN LAATDDDNEM NNLQIAVGRM QKGIDFVKRK  1020
IREFIQKAFV RKQKALDEIK PLEDLNNKKD SCISNHTTIE IGKDLNYLKD GNGTTSGIGS  1080
SVEKYVVDES DYMSFINNPS LTVTVPIAVG ESDFENLNTE EFSSESDMEE SKEKLNATSS  1140
SEGSTVDIGA PAEGEQPEVE PEESLEPEAC FTEDCVRKFK CCQISIEEGK GKLWWNLRKT  1200
CYKIVEHNWF ETFIVFMILL SSGALAFEDI YIEQRKTIKT MLEYADKVFT YIFILEMLLK  1260
WVAYGFQVYF TNAWCWLDFL IVDVSLVSLT ANALGYSELG AIKSLRTLRA LRPLRALSRF  1320
EGMRVVVNAL LGAIPSIMNV LLVCLIFWLI FSIMGVNLFA GKFYHCINYT TGEMFDVSVV  1380
NNYSECKALI ESNQTARWKN VKVNFDNVGL GYLSLLQVAT FKGWMDIMYA AVDSRNVELQ  1440
PKYEDNLYMY LYFVIFIIFG SFFTLNLFIG VIIDNFNQQK KKFGGQDIFM TEEQKKYYNA  1500
MKKLGSKKPQ KPIPRPANKF QGMVFDFVTK QVFDISIMIL ICLNMVTMMV ETDDQSQEMT  1560
NILYWINLVF IVLFTGECVL KLISLRYYYF TIGWNIFDFV VVILSIVGMF LAELIEKYFV  1620
SPTLFRVIRL ARIGRILRLI KGAKGIRTLL FALMMSLPAL FNIGLLLFLV MFIYAIFGMS  1680
NFAYVKREVG IDDMFNFETF GNSMICLFQI TTSAGWDGLL APILNSGPPD CDPDKDHPGS  1740
SVKGDCGNPS VGIFFFVSYI IISFLVVVNM YIAVILENFS VATEESAEPL SEDDFEMFYE  1800
VWEKFDPDAT QFIEFAKLSD FADALDPPLL IAKPNKVQLI AMDLPMVSGD RIHCLDILFA  1860
FTKRVLGESG EMDALRIQME ERFMASNPSK VSYEPITTTL KRKQEEVSAI IIQRAYRRYL  1920
LKQKVKKVSS IYKKDKGKEC DGTPIKEDTL IDKLNENSTP EKTDMTPSTT SPPSYDSVTK  1980
PEKEKFEKDK SEKEDKGKDI RESKK                                        2005

SEQ ID NO: 2            moltype = DNA  length = 8630
FEATURE                 Location/Qualifiers
source                  1..8630
                        mol_type = genomic DNA
                        organism = Homo sapiens
SEQUENCE: 2
aagcatgatg gaattttagc tgcagtcttc ttggtgccag cttatcaatc ccaaactctg  60
ggtgtaaaag attctacagg gcactttctt atgcaaggag ctaaacagtg attaaaggag  120
caggatgaaa agatggcaca gtcagtgctg gtaccgccag gacctgacag cttccgcttc  180
tttaccaggg aatcccttgc tgctattgaa caacgcattg cagaagagaa agctaagaga  240
cccaaacagg aacgcaagga tgaggatgat gaaaatggcc caaagccaaa cagtgacttg  300
gaagcaggaa aatctcttcc atttatttat ggagacattc ctccagagat ggtgtcagtg  360
cccctggagg atctggaccc ctactatatc aataagaaaa cgtttatagt attgaataaa  420
gggaaagcaa tctctcgatt cagtgccacc cctgcccttt acattttaac tcccttcaac  480
cctattagaa aattagctat taagattttg gtacattctt tattcaatat gctcattatg  540
tgcacgattc ttaccaactg tgtatttatg accatgagta accctccaga ctggacaaag  600
aatgtggagt ataccttttac aggaatttat actttttgaat cacttattaa aatacttgca  660
aggggctttt gtttagaaga tttcacattt ttacgggatc catggaattg gttggatttc  720
acagtcatta cttttgcata tgtgacagag tttgtggacc tgggcaatgt ctcagcgttg  780
```

-continued

```
agaacattca gagttctccg agcattgaaa acaatttcag tcattccagg cctgaagacc  840
attgtggggg ccctgatcca gtcagtgaag aagctttctg atgtcatgat cttgactgtg  900
ttctgtctaa gcgtgtttgc gctaatagga ttgcagttgt tcatgggcaa cctacgaaat  960
aaatgtttgc aatggcctcc agataattct tcctttgaaa taaatatcac ttccttcttt  1020
aacaattcat tggatgggaa tggtactact ttcaatagga cagtgagcat atttaactgg  1080
gatgaatata ttgaggataa aagtcacttt tattttttag aggggcaaaa tgatgctctg  1140
ctttgtggca acagctcaga tgcaggccag tgtcctgaag gatacatctg tgtgaaggct  1200
ggtagaaacc ccaactatgg ctacacgagc tttgacacct ttagttgggc ctttttgtcc  1260
ttatttcgtc tcatgactca agacttctgg gaaaaccttt atcaactgac actacgtgct  1320
gctgggaaaa cgtacatgat attttttgtg ctggtcattt tcttgggctc attctatcta  1380
ataaatttga tcttggctgt ggtggccatg gcctatgagg aacagaatca ggccacattg  1440
gaagaggctg aacagaagga agctgaattt cagcagatgc tcgaacagtt gaaaaagcaa  1500
caagaagaag ctcaggcggc agctgcagcc gcatctgctg aatcaagaga cttcagtggt  1560
gctggtggga taggagtttt ttcagagagt tcttcagtag catctaagtt gagctccaaa  1620
agtgaaaaag agctgaaaaa cagaagaaag aaaaagaaac agaaagaaca gtctggagaa  1680
gaagagaaaa atgacagagt ccgaaaatcg gaatctgaag acagcataag aagaaaaggt  1740
ttccgttttt ccttggaagg aagtaggctg acatatgaaa agagattttc ttctccacac  1800
cagtccttac tgagcatccg tggctccctt ttctctccaa gacgcaacag tagggcgagc  1860
cttttcagct tcagaggtcg agcaaaggac attggctctg agaatgactt tgctgatgat  1920
gagcacagca cctttgagga caatgacagc cgaagagact ctctgttcgt gccgcacaga  1980
catggagaac ggcgccacag caatgtcagc caggccagcc gtgcctccag ggtgctcccc  2040
atcctgccca tgaatgggaa gatgcatagc gctgtggact gcaatggtgt ggtctccctg  2100
gtcgggggcc cttctaccct cacatctgct gggcagctcc taccagaggg cacaactact  2160
gaaacagaaa taagaaagag acggtccagt tcttatcatg tttccatgga tttattggaa  2220
gatcctacat caaggcaaag agcaatgagt atagccagta ttttgaccaa caccatggaa  2280
gaacttgaag aatccagaca gaaatgccca ccatgctggt ataaatttgc taatatgtgt  2340
ttgatttggg actgttgtaa accatggtta aaggtgaaac accttgtcaa cctggttgta  2400
atggacccat ttgttgacct ggccatcacc atctgcattg tcttaaatac actcttcatg  2460
gctatggagc actatcccat gacggagcag ttcagcagtg tactgtctgt tggaaacctg  2520
gtcttcacag ggatcttcac agcagaaatg tttctcaaga taattgccat ggatccatat  2580
tattactttc aagaaggctg gaatattttt gatggtttta ttgtgagcct tagtttaatg  2640
gaacttggtt tggcaaatgt ggaaggattg tcagttctcc gatcattccg gctgctccga  2700
gttttcaagt tggcaaaatc ttggccaact ctaaatatgc taattaagat cattggcaat  2760
tctgtggggg ctctaggaaa cctcaccttg gtattggcca tcatcgtctt catttttgct  2820
gtggtcggca tgcagctctt tggtaagagc tacaaagaat gtgtctgcaa gatttccaat  2880
gattgtgaac tcccacgctg gcacatgcat gactttttcc actccttcct gatcgtgttc  2940
cgcgtgctgt gtggagagtg gatagagacc atgtgggact gtatggaggt cgctggccaa  3000
accatgtgcc ttactgtctt catgatggtc atggtgattg gaaatctagt ggttctgaac  3060
ctcttcttgg ccttgctttt gagttccttc agttctgaca atcttgctgc cactgatgat  3120
gataacgaaa tgaataatct ccagattgct gtgggaagga tgcagaaagg aatcgatttt  3180
gttaaaagaa aaatacgtga atttattcag aaagcctttg ttaggaagca gaaagcttta  3240
gatgaaatta aaccgcttga agatctaaat aataaaaaag acagctgtat ttccaaccat  3300
accaccatag aaataggcaa agacctcaat tatctcaaag acggaaatgg aactactagt  3360
ggcataggca gcagtgtaga aaaatatgtc gtggatgaaa gtgattacat gtcatttata  3420
aacaacccta gcctcactgt gacagtacca attgctgttg gagaatctga ctttgaaaat  3480
ttaaatactg aagaattcag cagcgagtca gatatggagg aaagcaaaga gaagctaaat  3540
gcaactagtt catctgaagg cagcacggtt gatattggag ctcccgccga gggagaacag  3600
cctgaggttg aacctgagga atcccttgaa cctgaagcct gttttacaga agactgtgta  3660
cggaagttca agtgttgtca gataagcata gaagaaggca aagggaaact ctggtggaat  3720
ttgaggaaaa catgctataa gatagtggag cacaattggt tcgaaacctt cattgtcttc  3780
atgattctgc tgagcagtgg ggctctggcc tttgaagata tatacattga gcagcgaaaa  3840
accattaaga ccatgttaga atatgctgac aaggttttca cttacatatt cattctggaa  3900
atgctgctaa agtgggttgc atatggtttt caagtgtatt ttaccaatgc ctggtgctgg  3960
ctagacttcc tgattgttga tgtctcactg gttagcttaa ctgcaaatgc cttgggttac  4020
tcagaacttg gtgccatcaa atccctcaga acactaagag ctctgaggcc actgagagct  4080
ttgtcccggt ttgaaggaat gagggttgtt gtaaatgctc ttttaggagc cattccatct  4140
atcatgaatg tacttctggt ttgtctgatc ttttggctaa tattcagtat catgggagtg  4200
aatctctttg ctggcaagtt ttaccattgt attaattaca ccactggaga gatgtttgat  4260
gtaagcgtgg tcaacaacta cagtgagtgc aaagctctca ttgagagcaa tcaaactgcc  4320
aggtggaaaa atgtgaaagt aaactttgat aacgtaggac ttggatatct gtctctactt  4380
caagtagcca cgtttaaggg atggatggat attatgtatg cagctgttga ttcacgaaat  4440
gtagaattac aacccaagta tgaagacaac ctgtacatgt atctttattt tgtcatcttt  4500
attatttttg gttcattctt taccttgaat cttttcattg gtgtcatcat agataacttc  4560
aaccaacaga aaaagaagtt tggaggtcaa gacattttta tgacagaaga acagaagaaa  4620
tactacaatg caatgaaaaa actgggttca aagaaaccac aaaaacccat acctcgacct  4680
gctaacaaat tccaaggaat ggtctttgat tttgtaacca aacaagtctt tgatatcagc  4740
atcatgatcc tcatctgcct taacatggtc accatgatgg tggaaaccga tgaccagagt  4800
caagaaatga caaacattct gtactggatt aatctggtgt ttattgttct gttcactgga  4860
gaatgtgtgc tgaaactgat ctctcttcgt tactactatt tcactattgg atggaatatt  4920
tttgattttg tggtggtcat tctctccatt gtaggaatgt ttctggctga actgatagaa  4980
aagtattttg tgtcccctac cctgttccga gtgatccgtc ttgccaggat tggccgaatc  5040
ctacgtctga tcaaaggagc aaaggggatc cgcacgctgc tctttgcttt gatgatgtcc  5100
cttcctgcgt tgtttaacat cggcctcctt cttttcctgg tcatgttcat ctacgccatc  5160
tttgggatgt ccaattttgc ctatgttaag agggaagttg ggatcgatga catgttcaac  5220
tttgagacct ttggcaacag catgatctgc ctgttccaaa ttacaacctc tgctggctgg  5280
gatggattgc tagcacctat tcttaatagt ggacctccag actgtgaccc tgacaaagat  5340
caccctggaa gctcagttaa aggagactgt gggaacccat ctgttgggat tttctttttt  5400
gtcagttaca tcatcatatc cttcctggtt gtggtgaaca tgtacatcgc ggtcatcctg  5460
gagaacttca gtgttgctac tgaagaaagt gcagagcctc tgagtgagga tgactttgag  5520
```

-continued

```
atgttctatg aggtttggga gaagtttgat cccgatgcga cccagtttat agagtttgcc  5580
aaactttctg attttgcaga tgccctggat cctcctcttc tcatagcaaa acccaacaaa  5640
gtccagctca ttgccatgga tctgcccatg gtgagtggtg accggatcca ctgtcttgac  5700
atcttatttg cttttacaaa gcgtgttttg ggtgagagtg gagagatgga tgcccttcga  5760
atacagatgg aagagcgatt catggcatca aacccctcca aagtctctta tgagcccatt  5820
acgaccacgt tgaaacgcaa acaagaggag gtgtctgcta ttattatcca gagggcttac  5880
agacgctacc tcttgaagca aaaagttaaa aaggtatcaa gtatatacaa gaaagacaaa  5940
ggcaaagaat gtgatggaac acccatcaaa gaagatactc tcattgataa actgaatgag  6000
aattcaactc cagagaaaac cgatatgacg ccttccacca cgtctccacc ctcgtatgat  6060
agtgtgacca aaccagaaaa agaaaaattt gaaaaagaca aatcagaaaa ggaagacaaa  6120
gggaaagata tcagggaaag taaaaagtaa aaagaaacca agaattttcc attttgtgat  6180
caattgttta cagcccgtga tggtgatgtg tttgtgtcaa caggactccc acaggaggtc  6240
tatgccaaac tgactgtttt tacaaatgta tacttaaggt cagtgcctat aacaagacag  6300
agacctctgg tcagcaaact ggaactcagt aaactggaga aatagtatcg atgggaggtt  6360
tctattttca caaccagctg acactgctga agagcagagg cgtaatggct actcagacga  6420
taggaaccaa tttaaagggg ggagggaagt taaattttta tgtaaattca acatgtgaca  6480
cttgataata gtaattgtca ccagtgttta tgttttaact gccacacctg ccatattttt  6540
acaaaacgtg tgctgtgaat ttatcacttt tctttttaat tcacaggttg tttactatta  6600
tatgtgacta tttttgtaaa tgggtttgtg tttggggaga gggattaaag ggagggaatt  6660
ctacatttct ctattgtatt gtataactgg atatatttta aatggaggca tgctgcaatt  6720
ctcattcaca cataaaaaaa tcacatcaca aaagggaaga gtttacttct tgtttcagga  6780
tgtttttaga tttttgaggt gcttaaatag ctattcgtat ttttaaggtg tctcatccag  6840
aaaaaattta atgtgcctgt aaatgttcca tagaatcaca agcattaaag agttgtttta  6900
tttttacata acccattaaa tgtacatgta tatatgtata tatgtatatg tgcgtgtata  6960
tacatatata tgtatacaca catgcacaca cagagatata cacataccat tacattgtca  7020
ttcacagtcc cagcagcatg actatcacat ttttgataag tgtcctttgg cataaaataa  7080
aaatatccta tcagtccttt ctaagaagcc tgaattgacc aaaaaacatc cccaccacca  7140
ctttataaag ttgattctgc tttatcctgc agtattgttt agccatcttc tgctcttggt  7200
aaggttgaca tagtatatgt caatttaaaa aataaaagtc tgctttgtaa atagtaattt  7260
tacccagtgg tgcatgtttg agcaaacaaa aatgatgatt taagcacact acttattgca  7320
tcaaatatgt accacagtaa gtatagtttg caagctttca acaggtaata tgatgtaatt  7380
ggttccatta tagtttgaag ctgtcactgc tgcatgttta tcttgcctat gctgctgtat  7440
cttattcctt ccactgttca gaagtctaat atgggaagcc atatatcagt ggtaaagtga  7500
agcaaattgt tctaccaaga cctcattctt catgtcatta agcaataggt tgcagcaaac  7560
aaggaagagc ttcttgcttt ttattcttcc aaccttaatt gaacactcaa tgatgaaaag  7620
cccgactgta caaacatgtt gcaagctgct taaatctgtt taaaatatat ggttagagtt  7680
ttctaagaaa atataaatac tgtaaaaagt tcattttatt ttatttttca gccttttgta  7740
cgtaaaatga gaaattaaaa gtatcttcag gtggatgtca cagtcactat tgttagtttc  7800
tgttcctagc acttttaaat tgaagcactt cacaaaataa gaagcaagga ctaggatgca  7860
gtgtaggttt ctgcttttt attagtactg taaacttgca cacatttcaa tgtgaaacaa  7920
atctcaaact gagttcaatg tttatttgct ttcaatagta atgccttatc attgaaagag  7980
gcttaaagaa aaaaaaaatc agctgatact cttggcattg cttgaatcca atgtttccac  8040
ctagtctttt tattcagtaa tcatcagtct tttccaatgt ttgtttacac agatagatct  8100
tattgaccca tatggcacta gaactgtatc agatataata tgggatccca gcttttttc  8160
ctctcccaca aaaccaggta gtgaagttat attaccagtt acagcaaaat actttgtgtt  8220
tcacaagcaa caataaatgt agattcttta tactgaagct attgacttgt agtgtgttgg  8280
tgaaatgcat gcaggaaaat gctgttacca taaagaacgg taaaccacat tacaatcaag  8340
ccaaaagaat aaaggtttcg cttttgtttt tgtatttaat tgttgtcttt gtttctatct  8400
ttgaaatgcc atttaaaggt agatttctat catgtaaaaa taatctatct gaaaaacaaa  8460
tgtaaagaac acacattaat tactataatt catctttcaa ttttttcatg gaatggaagt  8520
taattaagaa gagtgtattg gataactact ttaatattgg ccaaaaagct agatatggca  8580
tcaggtagac tagtggaaag ttacaaaaat taataaaaaa ttgactaaca             8630

SEQ ID NO: 3            moltype = DNA  length = 20
FEATURE                 Location/Qualifiers
source                  1..20
                        mol_type = other DNA
                        organism = synthetic construct
modified_base           1
                        mod_base = OTHER
                        note = 2'-O-methoxyethyl modified 5-methyl cytosine with
                         phosphorothioate internucleoside linkage
modified_base           2
                        mod_base = OTHER
                        note = 2'-O-methoxyethyl modified 5-methyl cytosine
modified_base           3
                        mod_base = OTHER
                        note = 2'-O-methoxyethyl modified nucleotide
modified_base           4
                        mod_base = OTHER
                        note = 2'-O-methoxyethyl modified 5-methyl cytosine
modified_base           5
                        mod_base = OTHER
                        note = 2'-O-methoxyethyl modified nucleotide
modified_base           6
                        mod_base = OTHER
                        note = 2'-O-methoxyethyl modified nucleotide
modified_base           7
                        mod_base = OTHER
```

```
                        note = 5-methyl cytosine with phosphorothioate
                         internucleoside linkage
modified_base           8
                        mod_base = OTHER
                        note = Nucleotide with phosphorothioate internucleoside
                         linkage
modified_base           9
                        mod_base = OTHER
                        note = Nucleotide with phosphorothioate internucleoside
                         linkage
modified_base           10
                        mod_base = OTHER
                        note = Nucleotide with phosphorothioate internucleoside
                         linkage
modified_base           11
                        mod_base = OTHER
                        note = Nucleotide with phosphorothioate internucleoside
                         linkage
modified_base           12
                        mod_base = OTHER
                        note = Nucleotide with phosphorothioate internucleoside
                         linkage
modified_base           13
                        mod_base = OTHER
                        note = Nucleotide with phosphorothioate internucleoside
                         linkage
modified_base           14
                        mod_base = OTHER
                        note = Nucleotide with phosphorothioate internucleoside
                         linkage
modified_base           15
                        mod_base = OTHER
                        note = Nucleotide with phosphorothioate internucleoside
                         linkage
modified_base           16
                        mod_base = OTHER
                        note = 5-methyl cytosine with phosphorothioate
                         internucleoside linkage
modified_base           17
                        mod_base = OTHER
                        note = 2'-O-methoxyethyl modified nucleotide
modified_base           18
                        mod_base = OTHER
                        note = 2'-O-methoxyethyl modified nucleotide with
                         phosphorothioate internucleoside linkage
modified_base           19
                        mod_base = OTHER
                        note = 2'-O-methoxyethyl modified 5-methyl cytosine with
                         phosphorothioate internucleoside linkage
modified_base           20
                        mod_base = OTHER
                        note = 2'-O-methoxyethyl modified nucleotide
SEQUENCE: 3
ccacgacata tttttctaca                                              20

SEQ ID NO: 4            moltype = DNA  length = 8776
FEATURE                 Location/Qualifiers
source                  1..8776
                        mol_type = genomic DNA
                        organism = Homo sapiens
SEQUENCE: 4
aacagacatt gggtaccatc gaatgactgt cagaacagaa agctaaggca aaggagggag  60
gatgctgtgg tcatcctttc ttgttttttt cttctttaat gaggatagag cacatgtgag  120
attttacttt ctactccagt aaaaattctg aagaattgca ttggagactg ttatattcaa  180
cacatacgtg gattctgtgt tatgatttac atttttcttt atttcagcac tttcttatgc  240
aaggagctaa acagtgatta aaggagcagg atgaaaagat ggcacagtca gtgctggtac  300
cgccaggacc tgacagcttc cgcttcttta ccagggaatc ccttgctgct attgaacaac  360
gcattgcaga agagaaagct aagagaccca aacaggaacg caaggatgag gatgatgaaa  420
atggcccaaa gccaaacagt gacttggaag caggaaaatc tcttccattt atttatggag  480
acattcctcc agagatggtg tcagtgcccc tggaggatct ggacccctac tatatcaata  540
agaaaacgtt tatagtattg aataaaggga aagcaatctc tcgattcagt gccacccctg  600
ccctttacat tttaactccc ttcaacccta ttagaaaatt agctattaag attttggtac  660
attctttatt caatatgctc attatgtgca cgattcttac caactgtgta tttatgacca  720
tgagtaaccc tccagactgg acaaagaatg tggagtatac ctttacagga atttatactt  780
ttgaatcact tattaaaata cttgcaaggg gcttttgttt agaagatttc acatttttac  840
gggatccatg gaattggttg gatttcacag tcattacttt tgcatatgtg acagagtttg  900
tggacctggg caatgtctca gcgttgagaa cattcagagt tctccgagca ttgaaaacaa  960
tttcagtcat tccaggcctg aagaccattg tgggggccct gatccagtca gtgaagaagc  1020
tttctgatgt catgatcttg actgtgttct gtctaagcgt gtttgcgcta ataggattgc  1080
```

-continued

```
agttgttcat gggcaaccta cgaaataaat gtttgcaatg gcctccagat aattcttcct  1140
ttgaaataaa tatcacttcc ttctttaaca attcattgga tgggaatggt actactttca  1200
ataggacagt gagcatattt aactgggatg aatatattga ggataaaagt cacttttatt  1260
ttttagaggg gcaaaatgat gctctgcttt gtggcaacag ctcagatgca ggccagtgtc  1320
ctgaaggata catctgtgtg aaggctggta gaaaccccaa ctatggctac acgagctttg  1380
acacctttag ttgggccttt ttgtccttat ttcgtctcat gactcaagac ttctgggaaa  1440
acctttatca actgacacta cgtgctgctg ggaaaacgta catgatattt tttgtgctgg  1500
tcattttctt gggctcattc tatctaataa atttgatctt ggctgtggtg gccatggcct  1560
atgaggaaca gaatcaggcc acattggaag aggctgaaca gaaggaagct gaatttcagc  1620
agatgctcga acagttgaaa aagcaacaag aagaagctca ggcggcagct gcagccgcat  1680
ctgctgaatc aagagacttc agtggtgctg gtgggatagg agtttttttca gagagttctt  1740
cagtagcatc taagttgagc tccaaaagtg aaaaagagct gaaaaacaga agaaagaaaa  1800
agaaacagaa agaacagtct ggagaagaag agaaaaatga cagagtccga aaatcggaat  1860
ctgaagacag cataagaaga aaaggtttcc gtttttcctt ggaaggaagt aggctgacat  1920
atgaaaagag attttcttct ccacaccagt ccttactgag catccgtggc tccctttttct  1980
ctccaagacg caacagtagg gcgagccttt tcagcttcag aggtcgagca aaggacattg  2040
gctctgagaa tgactttgct gatgatgagc acagcacctt tgaggacaat gacagccgaa  2100
gagactctct gttcgtgccg cacagacatg gagaacggcg ccacagcaat gtcagccagg  2160
ccagccgtgc ctccagggtg ctccccatcc tgcccatgaa tgggaagatg catagcgctg  2220
tggactgcaa tggtgtggtc tccctggtcg gggggcccttc taccctcaca tctgctgggc  2280
agctcctacc agagggcaca actactgaaa cagaaataag aaagagacgg tccagttctt  2340
atcatgtttc catggattta ttggaagatc ctacatcaag gcaaagagca atgagtatag  2400
ccagtatttt gaccaacacc atggaagaac ttgaagaatc cagacagaaa tgcccaccat  2460
gctggtataa atttgctaat atgtgtttga tttgggactg ttgtaaacca tggttaaagg  2520
tgaaacacct tgtcaacctg gttgtaatgg acccatttgt tgacctggcc atcaccatct  2580
gcattgtctt aaatacactc ttcatggcta tggagcacta tcccatgacg gagcagttca  2640
gcagtgtact gtctgttgga aacctggtct tcacagggat cttcacagca gaaatgtttc  2700
tcaagataat tgccatggat ccatattatt actttcaaga aggctggaat atttttgatg  2760
gttttattgt gagccttagt ttaatggaac ttggtttggc aaatgtggaa ggattgtcag  2820
ttctccgatc attccggctg ctccgagttt tcaagttggc aaaatcttgg ccaactctaa  2880
atatgctaat taagatcatt ggcaattctg tgggggctct aggaaacctc accttggtat  2940
tggccatcat cgtcttcatt tttgctgtgg tcggcatgca gctctttggt aagagctaca  3000
aagaatgtgt ctgcaagatt tccaatgatt gtgaactccc acgctggcac atgcatgact  3060
ttttccactc cttcctgatc gtgttccgcg tgctgtgtgg agagtggata gagaccatgt  3120
gggactgtat ggaggtcgct ggccaaacca tgtgccttac tgtcttcatg atggtcatgg  3180
tgattggaaa tctagtggtt ctgaacctct tcttggcctt gcttttgagt tccttcagtt  3240
ctgacaatct tgctgccact gatgatgata acgaaatgaa taatctccag attgctgtgg  3300
gaaggatgca gaaaggaatc gattttgtta aaagaaaaat acgtgaattt attcagaaag  3360
cctttgttag gaagcagaaa gctttagatg aaattaaacc gcttgaagat ctaaataata  3420
aaaaagacag ctgtatttcc aaccatacca ccatagaaat aggcaaagac ctcaattatc  3480
tcaaagacgg aaatggaact actagtggca taggcagcag tgtagaaaaa tatgtcgtgg  3540
atgaaagtga ttacatgtca tttataaaca accctagcct cactgtgaca gtaccaattg  3600
ctgttggaga atctgacttt gaaaatttaa atactgaaga attcagcagc gagtcagata  3660
tggaggaaag caaagagaag ctaaatgcaa ctagttcatc tgaaggcagc acggttgata  3720
ttggagctcc cgccgaggga gaacagcctg aggttgaacc tgaggaatcc cttgaacctg  3780
aagcctgttt tacagaagac tgtgtacgga agttcaagtg ttgtcagata agcatagaag  3840
aaggcaaagg gaaactctgg tggaatttga ggaaaaacatg ctataagata gtggagcaca  3900
attggttcga aaccttcatt gtcttcatga ttctgctgag cagtggggct ctggcctttg  3960
aagatatata cattgagcag cgaaaaacca ttaagaccat gttagaatat gctgacaagg  4020
ttttcactta catattcatt ctggaaatgc tgctaaagtg ggttgcatat ggttttcaag  4080
tgtattttac caatgcctgg tgctggctag acttcctgat tgttgatgtc tcactggtta  4140
gcttaactgc aaatgccttg ggttactcag aacttggtgc catcaaatcc ctcagaacac  4200
taagagctct gaggccactg agagctttgt cccggtttga aggaatgagg gttgttgtaa  4260
atgctctttt aggagccatt ccatctatca tgaatgtact tctggtttgt ctgatctttt  4320
ggctaatatt cagtatcatg ggagtgaatc tctttgctgg caagttttac cattgtatta  4380
attacaccac tggagagatg tttgatgtaa gcgtggtcaa caactacagt gagtgcaaag  4440
ctctcattga gagcaatcaa actgccaggt ggaaaaatgt gaaagtaaac tttgataacg  4500
taggacttgg atatctgtct ctacttcaag tagccacgtt taagggatgg atggatatta  4560
tgtatgcagc tgttgattca cgaaatgtag aattacaacc caagtatgaa gacaacctgt  4620
acatgtatct ttattttgtc atctttatta tttttggttc attctttacc ttgaatcttt  4680
tcattggtgt catcatagat aacttcaacc aacagaaaaa gaagtttgga ggtcaagaca  4740
tttttatgac agaagaacag aagaaatact acaatgcaat gaaaaaactg ggttcaaaga  4800
aaccacaaaa acccatacct cgacctgcta acaaattcca aggaatggtc tttgattttg  4860
taaccaaaca agtctttgat atcagcatca tgatcctcat ctgccttaac atggtcacca  4920
tgatggtgga aaccgatgac cagagtcaag aaatgacaaa cattctgtac tggattaatc  4980
tggtgtttat tgttctgttc actggagaat gtgtgctgaa actgatctct cttcgttact  5040
actatttcac tattggatgg aatatttttg attttgtggt ggtcattctc tccattgtag  5100
gaatgtttct ggctgaactg atagaaaagt attttgtgtc cctaccctg ttccgagtga  5160
tccgtcttgc caggattggc cgaatcctac gtctgatcaa aggagcaaag gggatccgca  5220
cgctgctctt tgctttgatg atgtcccttc ctgcgttgtt taacatcggc ctccttcttt  5280
tcctggtcat gttcatctac gccatctttg ggatgtccaa ttttgcctat gttaagaggg  5340
aagttgggat cgatgacatg ttcaactttg agacctttgg caacagcatg atctgcctgt  5400
tccaaattac aacctctgct ggctgggatg gattgctagc acctattctt aatagtggac  5460
ctccagactg tgaccctgac aaagatcacc ctggaagctc agttaaagga gactgtggga  5520
acccatctgt tgggattttc ttttttgtca gttacatcat catatccttc ctggttgtgg  5580
tgaacatgta catcgcggtc atcctggaga acttcagtgt tgctactgaa gaaagtgcag  5640
agcctctgag tgaggatgac tttgagatgt tctatgaggt ttgggagaag tttgatcccg  5700
atgcgaccca gtttatagag tttgccaaac tttctgattt tgcagatgcc ctggatcctc  5760
ctcttctcat agcaaaaccc aacaaagtcc agctcattgc catggatctg cccatggtga  5820
```

-continued

```
gtggtgaccg gatccactgt cttgacatct tatttgcttt tacaaagcgt gttttgggtg  5880
agagtggaga gatggatgcc cttcgaatac agatggaaga gcgattcatg gcatcaaacc  5940
cctccaaagt ctcttatgag cccattacga ccacgttgaa acgcaaacaa gaggaggtgt  6000
ctgctattat tatccagagg gcttacagac gctacctctt gaagcaaaaa gttaaaaagg  6060
tatcaagtat atacaagaaa gacaaaggca aagaatgtga tggaacaccc atcaaagaag  6120
atactctcat tgataaactg aatgagaatt caactccaga gaaaaccgat atgacgcctt  6180
ccaccacgtc tccaccctcg tatgatagtg tgaccaaacc agaaaaagaa aaatttgaaa  6240
aagacaaatc agaaaaggaa gacaaaggga aagatatcag ggaaagtaaa aagtaaaaag  6300
aaaccaagaa ttttccattt tgtgatcaat tgtttacagc ccgtgatggt gatgtgtttg  6360
tgtcaacagg actcccacag gaggtctatg ccaaactgac tgtttttaca aatgtatact  6420
taaggtcagt gcctataaca agacagagac ctctggtcag caaactggaa ctcagtaaac  6480
tggagaaata gtatcgatgg gaggtttcta ttttcacaac cagctgacac tgctgaagag  6540
cagaggcgta atggctactc agacgatagg aaccaattta aagggggggag ggaagttaaa  6600
tttttatgta aattcaacat gtgacacttg ataatagtaa ttgtcaccag tgtttatgtt  6660
ttaactgcca cacctgccat atttttacaa aacgtgtgct gtgaatttat cacttttctt  6720
tttaattcac aggttgttta ctattatatg tgactatttt tgtaaatggg tttgtgtttg  6780
gggagaggga ttaaagggag ggaattctac atttctctat tgtattgtat aactggatat  6840
attttaaatg gaggcatgct gcaattctca ttcacacata aaaaaatcac atcacaaaag  6900
ggaagagttt acttcttgtt tcaggatgtt tttagatttt tgaggtgctt aaatagctat  6960
tcgtattttt aaggtgtctc atccagaaaa aatttaatgt gcctgtaaat gttccataga  7020
atcacaagca ttaaagagtt gttttatttt tacataaccc attaaatgta catgtatata  7080
tgtatatatg tatatgtgcg tgtatataca tatatatgta tacacacatg cacacacaga  7140
gatatacaca taccattaca ttgtcattca cagtcccagc agcatgacta tcacattttt  7200
gataagtgtc ctttggcata aaataaaaat atcctatcag tcctttctaa gaagcctgaa  7260
ttgaccaaaa aacatcccca ccaccacttt ataaagttga ttctgcttta tcctgcagta  7320
ttgtttagcc atcttctgct cttggtaagg ttgacatagt atatgtcaat ttaaaaaata  7380
aaagtctgct ttgtaaatag taattttacc cagtggtgca tgtttgagca aacaaaaatg  7440
atgatttaag cacactactt attgcatcaa atatgtacca cagtaagtat agtttgcaag  7500
ctttcaacag gtaatatgat gtaattggtt ccattatagt ttgaagctgt cactgctgca  7560
tgtttatctt gcctatgctg ctgtatctta ttccttccac tgttcagaag tctaatatgg  7620
gaagccatat atcagtggta aagtgaagca aattgttcta ccaagacctc attcttcatg  7680
tcattaagca ataggttgca gcaaacaagg aagagcttct tgctttttat tcttccaacc  7740
ttaattgaac actcaatgat gaaaagcccg actgtacaaa catgttgcaa gctgcttaaa  7800
tctgtttaaa atatatggtt agagttttct aagaaaatat aaatactgta aaaagttcat  7860
tttattttat ttttcagcct tttgtacgta aaatgagaaa ttaaaagtat cttcaggtgg  7920
atgtcacagt cactattgtt agtttctgtt cctagcactt ttaaattgaa gcacttcaca  7980
aaataagaag caaggactag gatgcagtgt aggtttctgc ttttttatta gtactgtaaa  8040
cttgcacaca tttcaatgtg aaacaaatct caaactgagt tcaatgttta tttgctttca  8100
atagtaatgc cttatcattg aaagaggctt aaagaaaaaa aaaatcagct gatactcttg  8160
gcattgcttg aatccaatgt ttccacctag tctttttatt cagtaatcat cagtcttttc  8220
caatgtttgt ttacacagat agatcttatt gacccatatg gcactagaac tgtatcagat  8280
ataaatatggg atcccagctt tttttcctct cccacaaaac caggtagtga agttatatta  8340
ccagttacag caaaatactt tgtgtttcac aagcaacaat aaatgtagat tctttatact  8400
gaagctattg acttgtagtg tgttggtgaa atgcatgcag gaaaatgctg ttaccataaa  8460
gaacggtaaa ccacattaca atcaagccaa aagaataaag gtttcgcttt tgtttttgta  8520
tttaattgtt gtctttgttt ctatctttga aatgccattt aaaggtagat ttctatcatg  8580
taaaaataat ctatctgaaa aacaaatgta aagaacacac attaattact ataattcatc  8640
tttcaatttt ttcatggaat ggaagttaat taagaagagt gtattggata actactttaa  8700
tattggccaa aaagctagat atggcatcag gtagactagt ggaaagttac aaaaattaat  8760
aaaaaattga ctaaca                                                    8776

SEQ ID NO: 5            moltype = DNA  length = 8895
FEATURE                 Location/Qualifiers
source                  1..8895
                        mol_type = genomic DNA
                        organism = Homo sapiens
SEQUENCE: 5
aacagacatt gggtaccatc gaatgactgt cagaacagaa agctaaggca aaggagggag  60
gatgctgtgg tcatcctttc ttgttttttt cttctttaat gaggatagag cacatgtgag  120
attttacttt ctactccagt aaaaattctg aagaattgca ttggagactg ttatattcaa  180
cacatacgtg gattctgtgt tatgatttac atttttcttt atttcagggg tttttctccc  240
tttgcttgac acttctctgt cctgacacct tgagaagaag gatgtgtttg cttacccttc  300
cgccatgatt gtaaatttcc tgaggccttc ccagccatgc agcactcact ttcttatgca  360
aggagctaaa cagtgattaa aggagcagga tgaaaagatg gcacagtcag tgctggtacc  420
gccaggacct gacagcttcc gcttctttac cagggaatcc cttgctgcta ttgaacaacg  480
cattgcagaa gagaaagcta agagacccaa acaggaacgc aaggatgagg atgatgaaaa  540
tggcccaaag ccaaacagtg acttggaagc aggaaaatct cttccattta tttatggaga  600
cattcctcca gagatggtgt cagtgcccct ggaggatctg gacccctact atatcaataa  660
gaaaacgttt atagtattga ataaagggaa agcaatctct cgattcagtg ccacccctgc  720
cctttacatt ttaactccct tcaaccctat tagaaaatta gctattaaga ttttggtaca  780
ttctttattc aatatgctca ttatgtgcac gattcttacc aactgtgtat ttatgaccat  840
gagtaaccct ccagactgga caaagaatgt ggagtatacc tttacaggaa tttatacttt  900
tgaatcactt attaaaatac ttgcaagggg cttttgttta gaagatttca catttttacg  960
ggatccatgg aattggttgg atttcacagt cattactttt gcgtatgtaa cagaatttgt  1020
aaacctaggc aatgtttcag ctcttcgaac tttcagagtc ttgagagctt tgaaaactat  1080
ttctgtaatt ccaggcctga agaccattgt gggggccctg atccagtcag tgaagaagct  1140
ttctgatgtc atgatcttga ctgtgttctg tctaagcgtg tttgcgctaa taggattgca  1200
gttgttcatg ggcaacctac gaaataaatg tttgcaatgg cctccagata attcttcctt  1260
tgaaataaat atcacttcct tctttaacaa ttcattggat gggaatggta ctactttcaa  1320
```

-continued

```
taggacagtg agcatattta actgggatga atatattgag gataaaagtc acttttattt  1380
tttagagggg caaaatgatg ctctgctttg tggcaacagc tcagatgcag gccagtgtcc  1440
tgaaggatac atctgtgtga aggctggtag aaaccccaac tatggctaca cgagctttga  1500
cacctttagt tgggcctttt tgtccttatt tcgtctcatg actcaagact tctgggaaaa  1560
cctttatcaa ctgacactac gtgctgctgg gaaaacgtac atgatatttt ttgtgctggt  1620
cattttcttg ggctcattct atctaataaa tttgatcttg gctgtggtgg ccatggccta  1680
tgaggaacag aatcaggcca cattggaaga ggctgaacag aaggaagctg aatttcagca  1740
gatgctcgaa cagttgaaaa agcaacaaga agaagctcag gcggcagctg cagccgcatc  1800
tgctgaatca agagacttca gtggtgctgg tgggatagga gtttttttcag agagttcttc  1860
agtagcatct aagttgagct ccaaaagtga aaaagagctg aaaaacagaa gaaagaaaaa  1920
gaaacagaaa gaacagtctg gagaagaaga gaaaaatgac agagtccgaa aatcggaatc  1980
tgaagacagc ataagaagaa aaggtttccg tttttccttg gaaggaagta ggctgacata  2040
tgaaaagaga ttttcttctc cacaccagtc cttactgagc atccgtggct cccttttctc  2100
tccaagacgc aacagtaggg cgagcctttt cagcttcaga ggtcgagcaa aggacattgg  2160
ctctgagaat gactttgctg atgatgagca cagcaccttt gaggacaatg acagccgaag  2220
agactctctg ttcgtgccgc acagacatgg agaacggcgc cacagcaatg tcagccaggc  2280
cagccgtgcc tccagggtgc tccccatcct gcccatgaat gggaagatgc atagcgctgt  2340
ggactgcaat ggtgtggtct ccctggtcgg gggcccttct accctcacat ctgctgggca  2400
gctcctacca gagggcacaa ctactgaaac agaaataaga aagagacggt ccagttctta  2460
tcatgtttcc atggatttat tggaagatcc tacatcaagg caaagagcaa tgagtatagc  2520
cagtattttg accaacacca tggaagaact tgaagaatcc agacagaaat gcccaccatg  2580
ctggtataaa tttgctaata tgtgtttgat ttgggactgt tgtaaaccat ggttaaaggt  2640
gaaacacctt gtcaacctgg ttgtaatgga cccatttgtt gacctggcca tcaccatctg  2700
cattgtctta aatacactct tcatggctat ggagcactat cccatgacgg agcagttcag  2760
cagtgtactg tctgttggaa acctggtctt cacagggatc ttcacagcag aaatgtttct  2820
caagataatt gccatggatc catattatta ctttcaagaa ggctggaata tttttgatgg  2880
ttttattgtg agccttagtt taatggaact tggtttggca aatgtggaag gattgtcagt  2940
tctccgatca ttccggctgc tccgagtttt caagttggca aaatcttggc caactctaaa  3000
tatgctaatt aagatcattg gcaattctgt gggggctcta ggaaacctca ccttggtatt  3060
ggccatcatc gtcttcattt ttgctgtggt cggcatgcag ctctttggta agagctacaa  3120
agaatgtgtc tgcaagattt ccaatgattg tgaactccca cgctggcaca tgcatgactt  3180
tttccactcc ttcctgatcg tgttccgcgt gctgtgtgga gagtggatag agaccatgtg  3240
ggactgtatg gaggtcgctg gccaaaccat gtgccttact gtcttcatga tggtcatggt  3300
gattggaaat ctagtggttc tgaacctctt cttggccttg cttttgagtt ccttcagttc  3360
tgacaatctt gctgccactg atgatgataa cgaaatgaat aatctccaga ttgctgtggg  3420
aaggatgcag aaaggaatcg attttgttaa aagaaaaata cgtgaattta ttcagaaagc  3480
ctttgttagg aagcagaaag ctttagatga aattaaaccg cttgaagatc taaataataa  3540
aaaagacagc tgtatttcca accataccac catagaaata ggcaaagacc tcaattatct  3600
caaagacgga aatggaacta ctagtggcat aggcagcagt gtagaaaaat atgtcgtgga  3660
tgaaagtgat tacatgtcat ttataaacaa ccctagcctc actgtgacag taccaattgc  3720
tgttggagaa tctgactttg aaaatttaaa tactgaagaa ttcagcagcg agtcagatat  3780
ggaggaaagc aaagagaagc taaatgcaac tagttcatct gaaggcagca cggttgatat  3840
tggagctccc gccgagggag aacagcctga ggttgaacct gaggaatccc ttgaacctga  3900
agcctgtttt acagaagact gtgtacggaa gttcaagtgt tgtcagataa gcatagaaga  3960
aggcaaaggg aaactctggt ggaatttgag gaaaacatgc tataagatag tggagcacaa  4020
ttggttcgaa accttcattg tcttcatgat tctgctgagc agtggggctc tggcctttga  4080
agatatatac attgagcagc gaaaaaccat taagaccatg ttagaatatg ctgacaaggt  4140
tttcacttac atattcattc tggaaatgct gctaaagtgg gttgcatatg gttttcaagt  4200
gtattttacc aatgcctggt gctggctaga cttcctgatt gttgatgtct cactggttag  4260
cttaactgca aatgccttgg gttactcaga acttggtgcc atcaaatccc tcagaacact  4320
aagagctctg aggccactga gagctttgtc ccggtttgaa ggaatgaggg ttgttgtaaa  4380
tgctctttta ggagccattc catctatcat gaatgtactt ctggtttgtc tgatcttttg  4440
gctaatattc agtatcatgg gagtgaatct ctttgctggc aagttttacc attgtattaa  4500
ttacaccact ggagagatgt ttgatgtaag cgtggtcaac aactacagtg agtgcaaagc  4560
tctcattgag agcaatcaaa ctgccaggtg gaaaaatgtg aaagtaaact ttgataacgt  4620
aggacttgga tatctgtctc tacttcaagt agccacgttt aagggatgga tggatattat  4680
gtatgcagct gttgattcac gaaatgtaga attacaaccc aagtatgaag acaacctgta  4740
catgtatctt tattttgtca tctttattat ttttggttca ttctttacct tgaatctttt  4800
cattggtgtc atcatagata acttcaacca acagaaaaag aagtttggag gtcaagacat  4860
ttttatgaca gaagaacaga agaaatacta caatgcaatg aaaaaactgg gttcaaagaa  4920
accacaaaaa cccataccte gacctgctaa caaattccaa ggaatggtct ttgattttgt  4980
aaccaaacaa gtctttgata tcagcatcat gatcctcatc tgccttaaca tggtcaccat  5040
gatggtggaa accgatgacc agagtcaaga aatgacaaac attctgtact ggattaatct  5100
ggtgtttatt gttctgttca ctggagaatg tgtgctgaaa ctgatctctc ttcgttacta  5160
ctatttcact attggatgga atatttttga ttttgtggtg gtcattctct ccattgtagg  5220
aatgtttctg gctgaactga tagaaaagta ttttgtgtcc cctaccctgt tccgagtgat  5280
ccgtcttgcc aggattggcc gaatcctacg tctgatcaaa ggagcaaagg ggatccgcac  5340
gctgctcttt gctttgatga tgtcccttcc tgcgttgttt aacatcggcc tccttctttt  5400
cctggtcatg ttcatctacg ccatctttgg gatgtccaat tttgcctatg ttaagaggga  5460
agttgggatc gatgacatgt tcaactttga gacctttggc aacagcatga tctgcctgtt  5520
ccaaattaca acctctgctg gctgggatgg attgctagca cctattctta atagtggacc  5580
tccagactgt gaccctgaca aagatcaccc tggaagctca gttaaaggag actgtgggaa  5640
cccatctgtt gggattttct tttttgtcag ttacatcatc atatccttcc tggttgtggt  5700
gaacatgtac atcgcggtca tcctggagaa cttcagtgtt gctactgaag aaagtgcaga  5760
gcctctgagt gaggatgact ttgagatgtt ctatgaggtt tgggagaagt ttgatcccga  5820
tgcgacccag tttatagagt ttgccaaact ttctgatttt gcagatgccc tggatcctcc  5880
tcttctcata gcaaaaccca acaaagtcca gctcattgcc atggatctgc ccatggtgag  5940
tggtgaccgg atccactgtc ttgacatctt atttgctttt acaaagcgtg ttttgggtga  6000
gagtggagag atggatgccc ttcgaataca gatggaagag cgattcatgg catcaaaccc  6060
```

```
ctccaaagtc tcttatgagc ccattacgac cacgttgaaa cgcaaacaag aggaggtgtc  6120
tgctattatt atccagaggg cttacagacg ctacctcttg aagcaaaaag ttaaaaaggt  6180
atcaagtata tacaagaaag acaaaggcaa agaatgtgat ggaacaccca tcaaagaaga  6240
tactctcatt gataaactga atgagaattc aactccagag aaaaccgata tgacgccttc  6300
caccacgtct ccaccctcgt atgatagtgt gaccaaacca gaaaaagaaa aatttgaaaa  6360
agacaaatca gaaaaggaag acaaagggaa agatatcagg gaaagtaaaa agtaaaaaga  6420
aaccaagaat tttccatttt gtgatcaatt gtttacagcc cgtgatggtg atgtgtttgt  6480
gtcaacagga ctcccacagg aggtctatgc caaactgact gtttttacaa atgtatactt  6540
aaggtcagtg cctataacaa gacagagacc tctggtcagc aaactggaac tcagtaaact  6600
ggagaaatag tatcgatggg aggtttctat tttcacaacc agctgacact gctgaagagc  6660
agaggcgtaa tggctactca gacgatagga accaatttaa aggggggagg gaagttaaat  6720
ttttatgtaa attcaacatg tgacacttga taatagtaat tgtcaccagt gtttatgttt  6780
taactgccac acctgccata tttttacaaa acgtgtgctg tgaatttatc acttttcttt  6840
ttaattcaca ggttgtttac tattatatgt gactattttt gtaaatgggt ttgtgtttgg  6900
ggagagggat taaagggagg gaattctaca tttctctatt gtattgtata actggatata  6960
ttttaaatgg aggcatgctg caattctcat tcacacataa aaaaatcaca tcacaaaagg  7020
gaagagttta cttcttgttt caggatgttt ttagattttt gaggtgctta aatagctatt  7080
cgtattttta aggtgtctca tccagaaaaa atttaatgtg cctgtaaatg ttccatagaa  7140
tcacaagcat taaagagttg ttttattttt acataaccca ttaaatgtac atgtatatat  7200
gtatatatgt atatgtgcgt gtatatacat atatatgtat acacacatgc acacacagag  7260
atatacacat accattacat tgtcattcac agtcccagca gcatgactat cacatttttg  7320
ataagtgtcc tttggcataa aataaaaata tcctatcagt cctttctaag aagcctgaat  7380
tgaccaaaaa acatccccac caccacttta taaagttgat tctgctttat cctgcagtat  7440
tgtttagcca tcttctgctc ttggtaaggt tgacatagta tatgtcaatt taaaaaataa  7500
aagtctgctt tgtaaatagt aattttaccc agtggtgcat gtttgagcaa acaaaaatga  7560
tgatttaagc acactactta ttgcatcaaa tatgtaccac agtaagtata gtttgcaagc  7620
tttcaacagg taatatgatg taattggttc cattatagtt tgaagctgtc actgctgcat  7680
gtttatcttg cctatgctgc tgtatcttat tccttccact gttcagaagt ctaatatggg  7740
aagccatata tcagtggtaa agtgaagcaa attgttctac caagacctca ttcttcatgt  7800
cattaagcaa taggttgcag caaacaagga agagcttctt gctttttatt cttccaacct  7860
taattgaaca ctcaatgatg aaaagcccga ctgtacaaac atgttgcaag ctgcttaaat  7920
ctgtttaaaa tatatggtta gagttttcta agaaaatata aatactgtaa aaagttcatt  7980
ttattttatt tttcagcctt ttgtacgtaa aatgagaaat taaaagtatc ttcaggtgga  8040
tgtcacagtc actattgtta gtttctgttc ctagcacttt taaattgaag cacttcacaa  8100
aataagaagc aaggactagg atgcagtgta ggtttctgct tttttattag tactgtaaac  8160
ttgcacacat ttcaatgtga aacaaatctc aaactgagtt caatgtttat ttgctttcaa  8220
tagtaatgcc ttatcattga aagaggctta aagaaaaaaa aaatcagctg atactcttgg  8280
cattgcttga atccaatgtt tccacctagt ctttttattc agtaatcatc agtcttttcc  8340
aatgtttgtt tacacagata gatcttattg acccatatgg cactagaact gtatcagata  8400
taatatggga tcccagcttt ttttcctctc ccacaaaacc aggtagtgaa gttatattac  8460
cagttacagc aaaatacttt gtgtttcaca agcaacaata aatgtagatt ctttatactg  8520
aagctattga cttgtagtgt gttggtgaaa tgcatgcagg aaaatgctgt taccataaag  8580
aacggtaaac cacattacaa tcaagccaaa agaataaagg tttcgctttt gtttttgtat  8640
ttaattgttg tctttgtttc tatctttgaa atgccattta aaggtagatt tctatcatgt  8700
aaaaataatc tatctgaaaa acaaatgtaa agaacacaca ttaattacta taattcatct  8760
ttcaattttt tcatggaatg gaagttaatt aagaagagtg tattggataa ctactttaat  8820
attggccaaa aagctagata tggcatcagg tagactagtg gaaagttaca aaaattaata  8880
aaaaattgac taaca                                                    8895

SEQ ID NO: 6            moltype = DNA  length = 8776
FEATURE                 Location/Qualifiers
source                  1..8776
                        mol_type = genomic DNA
                        organism = Homo sapiens
SEQUENCE: 6
aacagacatt gggtaccatc gaatgactgt cagaacagaa agctaaggca aaggagggag  60
gatgctgtgg tcatcctttc ttgttttttt cttctttaat gaggatagag cacatgtgag  120
attttacttt ctactccagt aaaaattctg aagaattgca ttggagactg ttatattcaa  180
cacatacgtg gattctgtgt tatgatttac atttttcttt atttcagcac tttcttatgc  240
aaggagctaa acagtgatta aaggagcagg atgaaaagat ggcacagtca gtgctggtac  300
cgccaggacc tgacagcttc cgcttcttta ccagggaatc ccttgctgct attgaacaac  360
gcattgcaga agagaaagct aagagaccca aacaggaacg caaggatgag gatgatgaaa  420
atggcccaaa gccaaacagt gacttggaag caggaaaatc tcttccattt atttatggag  480
acattcctcc agagatggtg tcagtgcccc tggaggatct ggacccctac tatatcaata  540
agaaaacgtt tatagtattg aataaaggga aagcaatctc tcgattcagt gccacccctg  600
ccctttacat tttaactccc ttcaacccta ttagaaaatt agctattaag attttggtac  660
attctttatt caatatgctc attatgtgca cgattcttac caactgtgta tttatgacca  720
tgagtaaccc tccagactgg acaaagaatg tggagtatac ctttacagga atttatactt  780
ttgaatcact tattaaaata cttgcaaggg gcttttgttt agaagatttc acatttttac  840
gggatccatg gaattggttg gatttcacag tcattacttt tgcgtatgta acagaatttg  900
taaacctagg caatgtttca gctcttcgaa ctttcagagt cttgagagct ttgaaaacta  960
tttctgtaat tccaggcctg aagaccattg tgggggccct gatccagtca gtgaagaagc  1020
tttctgatgt catgatcttg actgtgttct gtctaagcgt gtttgcgcta ataggattgc  1080
agttgttcat gggcaaccta cgaaataaat gtttgcaatg gcctccagat aattcttcct  1140
ttgaaataaa tatcacttcc ttctttaaca attcattgga tgggaatggt actactttca  1200
ataggacagt gagcatattt aactgggatg aatatattga ggataaaagt cacttttatt  1260
ttttagaggg gcaaaatgat gctctgcttt gtggcaacag ctcagatgca ggccagtgtc  1320
ctgaaggata catctgtgtg aaggctggta gaaaccccaa ctatggctac acgagctttg  1380
acacctttag ttgggccttt ttgtccttat ttcgtctcat gactcaagac ttctgggaaa  1440
```

-continued acctttatca actgacacta cgtgctgctg ggaaaacgta catgatattt tttgtgctgg 1500
tcattttctt gggctcattc tatctaataa atttgatctt ggctgtggtg gccatggcct 1560
atgaggaaca gaatcaggcc acattggaag aggctgaaca gaaggaagct gaatttcagc 1620
agatgctcga acagttgaaa aagcaacaag aagaagctca ggcggcagct gcagccgcat 1680
ctgctgaatc aagagacttc agtggtgctg gtgggatagg agtttttca gagagttctt 1740
cagtagcatc taagttgagc tccaaaagtg aaaaagagct gaaaaacaga agaaagaaaa 1800
agaaacagaa agaacagtct ggagaagaag agaaaaatga cagagtccga aaatcggaat 1860
ctgaagacag cataagaaga aaaggtttcc gtttttcctt ggaaggaagt aggctgacat 1920
atgaaaagag attttcttct ccacaccagt ccttactgag catccgtggc tcccttttct 1980
ctccaagacg caacagtagg gcgagccttt tcagcttcag aggtcgagca aaggacattg 2040
gctctgagaa tgactttgct gatgatgagc acagcacctt tgaggacaat gacagccgaa 2100
gagactctct gttcgtgccg cacagacatg gagaacggcg ccacagcaat gtcagccagg 2160
ccagccgtgc ctccagggtg ctccccatcc tgcccatgaa tgggaagatg catagcgctg 2220
tggactgcaa tggtgtggtc tccctggtcg gggcccttc taccctcaca tctgctgggc 2280
agctcctacc agagggcaca actactgaaa cagaaataag aaagagacgg tccagttctt 2340
atcatgtttc catggattta ttggaagatc ctacatcaag gcaaagagca atgagtatag 2400
ccagtatttt gaccaacacc atggaagaac ttgaagaatc cagacagaaa tgcccaccat 2460
gctggtataa atttgctaat atgtgtttga tttgggactg ttgtaaacca tggttaaagg 2520
tgaaacacct tgtcaacctg gttgtaatgg acccatttgt tgacctggcc atcaccatct 2580
gcattgtctt aaatacactc ttcatggcta tggagcacta tcccatgacg gagcagttca 2640
gcagtgtact gtctgttgga aacctggtct tcacagggat cttcacagca gaaatgtttc 2700
tcaagataat tgccatggat ccatattatt actttcaaga aggctggaat atttttgatg 2760
gttttattgt gagccttagt ttaatggaac ttggtttggc aaatgtggaa ggattgtcag 2820
ttctccgatc attccggctg ctccgagttt tcaagttggc aaaatcttgg ccaactctaa 2880
atatgctaat taagatcatt ggcaattctg tgggggctct aggaaacctc accttggtat 2940
tggccatcat cgtcttcatt tttgctgtgg tcggcatgca gctctttggt aagagctaca 3000
aagaatgtgt ctgcaagatt tccaatgatt gtgaactccc acgctggcac atgcatgact 3060
ttttccactc cttcctgatc gtgttccgcg tgctgtgtgg agagtggata gagaccatgt 3120
gggactgtat ggaggtcgct ggccaaacca tgtgccttac tgtcttcatg atggtcatgg 3180
tgattggaaa tctagtggtt ctgaacctct tcttggcctt gcttttgagt tccttcagtt 3240
ctgacaatct tgctgccact gatgatgata acgaaatgaa taatctccag attgctgtgg 3300
gaaggatgca gaaaggaatc gattttgtta aaagaaaaat acgtgaattt attcagaaag 3360
cctttgttag gaagcagaaa gctttagatg aaattaaacc gcttgaagat ctaaataata 3420
aaaaagacag ctgtatttcc aaccatacca ccatagaaat aggcaaagac ctcaattatc 3480
tcaaagacgg aaatggaact actagtggca taggcagcag tgtagaaaaa tatgtcgtgg 3540
atgaaagtga ttacatgtca tttataaaca accctagcct cactgtgaca gtaccaattg 3600
ctgttggaga atctgacttt gaaaatttaa atactgaaga attcagcagc gagtcagata 3660
tggaggaaag caaagagaag ctaaatgcaa ctagttcatc tgaaggcagc acggttgata 3720
ttggagctcc cgccgaggga gaacagcctg aggttgaacc tgaggaatcc cttgaacctg 3780
aagcctgttt tacagaagac tgtgtacgga agttcaagtg ttgtcagata agcatagaag 3840
aaggcaaagg gaaactctgg tggaatttga ggaaaacatg ctataagata gtggagcaca 3900
attggttcga aaccttcatt gtcttcatga ttctgctgag cagtggggct ctggcctttg 3960
aagatatata cattgagcag cgaaaaacca ttaagaccat gttagaatat gctgacaagg 4020
ttttcactta catattcatt ctggaaatgc tgctaaagtg ggttgcatat ggttttcaag 4080
tgtattttac caatgcctgg tgctggctag acttcctgat tgttgatgtc tcactggtta 4140
gcttaactgc aaatgccttg ggttactcag aacttggtgc catcaaatcc ctcagaacac 4200
taagagctct gaggccactg agagctttgt cccggtttga aggaatgagg gttgttgtaa 4260
atgctctttt aggagccatt ccatctatca tgaatgtact tctggtttgt ctgatctttt 4320
ggctaatatt cagtatcatg ggagtgaatc tctttgctgg caagttttac cattgtatta 4380
attacaccac tggagagatg tttgatgtaa gcgtggtcaa caactacagt gagtgcaaag 4440
ctctcattga gagcaatcaa actgccaggt ggaaaaatgt gaaagtaaac tttgataacg 4500
taggacttgg atatctgtct ctacttcaag tagccacgtt taagggatgg atggatatta 4560
tgtatgcagc tgttgattca cgaaatgtag aattacaacc caagtatgaa gacaacctgt 4620
acatgtatct ttattttgtc atctttatta tttttggttc attctttacc ttgaatcttt 4680
tcattggtgt catcatagat aacttcaacc aacagaaaaa gaagtttgga ggtcaagaca 4740
tttttatgac agaagaacag aagaaatact acaatgcaat gaaaaaactg ggttcaaaga 4800
aaccacaaaa acccatacct cgacctgcta acaaattcca aggaatggtc tttgattttg 4860
taaccaaaca agtctttgat atcagcatca tgatcctcat ctgccttaac atggtcacca 4920
tgatggtgga aaccgatgac cagagtcaag aaatgacaaa cattctgtac tggattaatc 4980
tggtgtttat tgttctgttc actggagaat gtgtgctgaa actgatctct cttcgttact 5040
actatttcac tattggatgg aatatttttg attttgtggt ggtcattctc tccattgtag 5100
gaatgtttct ggctgaactg atagaaaagt attttgtgtc ccctaccctg ttccgagtga 5160
tccgtcttgc caggattggc cgaatcctac gtctgatcaa aggagcaaag gggatccgca 5220
cgctgctctt tgctttgatg atgtcccttc ctgcgttgtt taacatcggc ctccttcttt 5280
tcctggtcat gttcatctac gccatctttg ggatgtccaa ttttgcctat gttaagaggg 5340
aagttgggat cgatgacatg ttcaactttg agacctttgg caacagcatg atctgcctgt 5400
tccaaattac aacctctgct ggctgggatg gattgctagc acctattctt aatagtggac 5460
ctccagactg tgaccctgac aaagatcacc ctggaagctc agttaaagga gactgtggga 5520
acccatctgt tgggattttc ttttttgtca gttacatcat catatccttc ctggttgtgg 5580
tgaacatgta catcgcggtc atcctggaga acttcagtgt tgctactgaa gaaagtgcag 5640
agcctctgag tgaggatgac tttgagatgt tctatgaggt ttgggagaag tttgatcccg 5700
atgcgaccca gtttatagag tttgccaaac tttctgattt tgcagatgcc ctggatcctc 5760
ctcttctcat agcaaaaccc aacaaagtcc agctcattgc catggatctg cccatggtga 5820
gtggtgaccg gatccactgt cttgacatct tatttgcttt tacaaagcgt gttttgggtg 5880
agagtggaga gatggatgcc cttcgaatac agatggaaga gcgattcatg gcatcaaacc 5940
cctccaaagt ctcttatgag cccattacga ccacgttgaa acgcaaacaa gaggaggtgt 6000
ctgctattat tatccagagg gcttacagac gctacctctt gaagcaaaaa gttaaaaagg 6060
tatcaagtat atacaagaaa gacaaaggca aagaatgtga tggaacaccc atcaaagaag 6120
atactctcat tgataaactg aatgagaatt caactccaga gaaaaccgat atgacgcctt 6180

-continued

```
ccaccacgtc tccaccctcg tatgatagtg tgaccaaacc agaaaaagaa aaatttgaaa  6240
aagacaaatc agaaaaggaa gacaaaggga aagatatcag ggaaagtaaa aagtaaaaag  6300
aaaccaagaa ttttccattt tgtgatcaat tgtttacagc ccgtgatggt gatgtgtttg  6360
tgtcaacagg actcccacag gaggtctatg ccaaactgac tgtttttaca aatgtatact  6420
taaggtcagt gcctataaca agacagagac ctctggtcag caaactggaa ctcagtaaac  6480
tggagaaata gtatcgatgg gaggtttcta ttttcacaac cagctgacac tgctgaagag  6540
cagaggcgta atggctactc agacgatagg aaccaattta aagggggggag ggaagttaaa  6600
tttttatgta aattcaacat gtgacacttg ataatagtaa ttgtcaccag tgtttatgtt  6660
ttaactgcca cacctgccat atttttacaa aacgtgtgct gtgaatttat cacttttctt  6720
tttaattcac aggttgttta ctattatatg tgactatttt tgtaaatggg tttgtgtttg  6780
gggagaggga ttaaagggag ggaattctac atttctctat tgtattgtat aactggatat  6840
attttaaatg gaggcatgct gcaattctca ttcacacata aaaaaatcac atcacaaaag  6900
ggaagagttt acttcttgtt tcaggatgtt tttagatttt tgaggtgctt aaatagctat  6960
tcgtattttt aaggtgtctc atccagaaaa aatttaatgt gcctgtaaat gttccataga  7020
atcacaagca ttaaagagtt gttttatttt tacataaccc attaaatgta catgtatata  7080
tgtatatatg tatatgtgcg tgtatataca tatatatgta tacacacatg cacacacaga  7140
gatatacaca taccattaca ttgtcattca cagtcccagc agcatgacta tcacattttt  7200
gataagtgtc ctttggcata aaataaaaat atcctatcag tcctttctaa gaagcctgaa  7260
ttgaccaaaa aacatcccca ccaccacttt ataaagttga ttctgcttta tcctgcagta  7320
ttgtttagcc atcttctgct cttggtaagg ttgacatagt atatgtcaat ttaaaaaata  7380
aaagtctgct ttgtaaatag taattttacc cagtggtgca tgtttgagca aacaaaaatg  7440
atgatttaag cacactactt attgcatcaa atatgtacca cagtaagtat agtttgcaag  7500
ctttcaacag gtaatatgat gtaattggtt ccattatagt ttgaagctgt cactgctgca  7560
tgtttatctt gcctatgctg ctgtatctta ttccttccac tgttcagaag tctaatatgg  7620
gaagccatat atcagtggta aagtgaagca aattgttcta ccaagacctc attcttcatg  7680
tcattaagca ataggttgca gcaaacaagg aagagcttct tgctttttat tcttccaacc  7740
ttaattgaac actcaatgat gaaaagcccg actgtacaaa catgttgcaa gctgcttaaa  7800
tctgtttaaa atatatggtt agagttttct aagaaaatat aaatactgta aaaagttcat  7860
tttattttat ttttcagcct tttgtacgta aaatgagaaa ttaaaagtat cttcaggtgg  7920
atgtcacagt cactattgtt agtttctgtt cctagcactt ttaaattgaa gcacttcaca  7980
aaataagaag caaggactag gatgcagtgt aggtttctgc ttttttatta gtactgtaaa  8040
cttgcacaca tttcaatgtg aaacaaatct caaactgagt tcaatgttta tttgctttca  8100
atagtaatgc cttatcattg aaagaggctt aaagaaaaaa aaaatcagct gatactcttg  8160
gcattgcttg aatccaatgt ttccacctag tctttttatt cagtaatcat cagtcttttc  8220
caatgtttgt ttacacagat agatcttatt gacccatatg gcactagaac tgtatcagat  8280
ataatatggg atcccagctt tttttcctct cccacaaaac caggtagtga agttatatta  8340
ccagttacag caaaatactt tgtgtttcac aagcaacaat aaatgtagat tctttatact  8400
gaagctattg acttgtagtg tgttggtgaa atgcatgcag gaaaatgctg ttaccataaa  8460
gaacggtaaa ccacattaca atcaagccaa aagaataaag gtttcgcttt tgtttttgta  8520
tttaattgtt gtctttgttt ctatctttaa aatgccattt aaaggtagat ttctatcatg  8580
taaaaataat ctatctgaaa aacaaatgta aagaacacac attaattact ataattcatc  8640
tttcaatttt ttcatggaat ggaagttaat taagaagagt gtattggata actactttaa  8700
tattggccaa aaagctagat atggcatcag gtagactagt ggaaagttac aaaaattaat  8760
aaaaaattga ctaaca                                                   8776
```

```
SEQ ID NO: 7            moltype = DNA  length = 8604
FEATURE                 Location/Qualifiers
source                  1..8604
                        mol_type = genomic DNA
                        organism = Homo sapiens
SEQUENCE: 7
atagcagtaa cacaattcac ctctagtgtg aacatatcag gatggcatag accagcactt  60
tcttatgcaa ggagctaaac agtgattaaa ggagcaggat gaaaagatgg cacagtcagt  120
gctggtaccg ccaggacctg acagcttccg cttctttacc agggaatccc ttgctgctat  180
tgaacaacgc attgcagaag agaaagctaa gagacccaaa caggaacgca aggatgagga  240
tgatgaaaat ggcccaaagc caaacagtga cttggaagca ggaaaatctc ttccatttat  300
ttatggagac attcctccag agatggtgtc agtgcccctg gaggatctgg acccctacta  360
tatcaataag aaaacgttta tagtattgaa taaagggaaa gcaatctctc gattcagtgc  420
cacccctgcc ctttacattt taactccctt caaccctatt agaaaattag ctattaagat  480
tttggtacat tctttattca atatgctcat tatgtgcacg attcttacca actgtgtatt  540
tatgaccatg agtaaccctc cagactggac aaagaatgtg gagtatacct ttacaggaat  600
ttatactttt gaatcactta ttaaaatact tgcaaggggc ttttgtttag aagatttcac  660
atttttacgg gatccatgga attggttgga tttcacagtc attactttttg catatgtgac  720
agagtttgtg gacctgggca atgtctcagc gttgagaaca ttcagagttc tccgagcatt  780
gaaaacaatt tcagtcattc caggcctgaa gaccattgtg ggggccctga tccagtcagt  840
gaagaagctt tctgatgtca tgatcttgac tgtgttctgt ctaagcgtgt ttgcgctaat  900
aggattgcag ttgttcatgg gcaacctacg aaataaatgt ttgcaatggc ctccagataa  960
ttcttccttt gaaataaata tcacttcctt ctttaacaat tcattggatg ggaatggtac  1020
tactttcaat aggacagtga gcatatttaa ctgggatgaa tatattgagg ataaaagtca  1080
cttttatttt ttagaggggc aaaatgatgc tctgctttgt ggcaacagct cagatgcagg  1140
ccagtgtcct gaaggataca tctgtgtgaa ggctggtaga aaccccaact atggctacac  1200
gagctttgac acctttagtt gggccttttt gtccttattt cgtctcatga ctcaagactt  1260
ctgggaaaac ctttatcaac tgacactacg tgctgctggg aaaacgtaca tgatattttt  1320
tgtgctggtc attttcttgg gctcattcta tctaataaat ttgatcttgg ctgtggtggc  1380
catggcctat gaggaacaga atcaggccac attggaagag gctgaacaga aggaagctga  1440
atttcagcag atgctcgaac agttgaaaaa gcaacaagaa gaagctcagg cggcagctgc  1500
agccgcatct gctgaatcaa gagacttcag tggtgctggt gggataggag ttttttcaga  1560
gagttcttca gtagcatcta agttgagctc caaaagtgaa aaagagctga aaaacagaag  1620
aaagaaaaag aaacagaaag aacagtctgg agaagaagag aaaaatgaca gagtccgaaa  1680
```

-continued

```
atcggaatct gaagacagca taagaagaaa aggtttccgt ttttccttgg aaggaagtag  1740
gctgacatat gaaaagagat tttcttctcc acaccagtcc ttactgagca tccgtggctc  1800
ccttttctct ccaagacgca acagtagggc gagccttttc agcttcagag gtcgagcaaa  1860
ggacattggc tctgagaatg actttgctga tgatgagcac agcacctttg aggacaatga  1920
cagccgaaga gactctctgt tcgtgccgca cagacatgga gaacggcgcc acagcaatgt  1980
cagccaggcc agccgtgcct ccagggtgct ccccatcctg cccatgaatg ggaagatgca  2040
tagcgctgtg gactgcaatg gtgtggtctc cctggtcggg ggcccttcta ccctcacatc  2100
tgctgggcag ctcctaccag agggcacaac tactgaaaca gaaataagaa agagacggtc  2160
cagttcttat catgtttcca tggatttatt ggaagatcct acatcaaggc aaagagcaat  2220
gagtatagcc agtattttga ccaacaccat ggaagaactt gaagaatcca gacagaaatg  2280
cccaccatgc tggtataaat ttgctaatat gtgtttgatt tgggactgtt gtaaaccatg  2340
gttaaaggtg aaacaccttg tcaacctggt tgtaatggac ccatttgttg acctggccat  2400
caccatctgc attgtcttaa atacactctt catggctatg gagcactatc ccatgacgga  2460
gcagttcagc agtgtactgt ctgttggaaa cctggtcttc acagggatct tcacagcaga  2520
aatgtttctc aagataattg ccatggatcc atattattac tttcaagaag gctggaatat  2580
ttttgatggt tttattgtga gccttagttt aatggaactt ggtttggcaa atgtggaagg  2640
attgtcagtt ctccgatcat tccggctgct ccgagttttc aagttggcaa aatcttggcc  2700
aactctaaat atgctaatta agatcattgg caattctgtg gggggctctag gaaacctcac  2760
cttggtattg gccatcatcg tcttcatttt tgctgtggtc ggcatgcagc tctttggtaa  2820
gagctacaaa gaatgtgtct gcaagatttc caatgattgt gaactcccac gctggcacat  2880
gcatgacttt ttccactcct tcctgatcgt gttccgcgtg ctgtgtggag agtggataga  2940
gaccatgtgg gactgtatgg aggtcgctgg ccaaaccatg tgccttactg tcttcatgat  3000
ggtcatggtg attggaaatc tagtggttct gaacctcttc ttggccttgc ttttgagttc  3060
cttcagttct gacaatcttg ctgccactga tgatgataac gaaatgaata atctccagat  3120
tgctgtggga aggatgcaga aaggaatcga ttttgttaaa agaaaaatac gtgaatttat  3180
tcagaaagcc tttgttagga agcagaaagc tttagatgaa attaaaccgc ttgaagatct  3240
aaataataaa aaagacagct gtatttccaa ccataccacc atagaaatag gcaaagacct  3300
caattatctc aaagacggaa atggaactac tagtggcata ggcagcagtg tagaaaaata  3360
tgtcgtggat gaaagtgatt acatgtcatt tataaacaac cctagcctca ctgtgacagt  3420
accaattgct gttggagaat ctgactttga aaatttaaat actgaagaat tcagcagcga  3480
gtcagatatg gaggaaagca aagagaagct aaatgcaact agttcatctg aaggcagcac  3540
ggttgatatt ggagctcccg ccgagggaga acagcctgag gttgaacctg aggaatccct  3600
tgaacctgaa gcctgtttta cagaagactg tgtacggaag ttcaagtgtt gtcagataag  3660
catagaagaa ggcaaaggga aactctggtg gaatttgagg aaaacatgct ataagatagt  3720
ggagcacaat tggttcgaaa ccttcattgt cttcatgatt ctgctgagca gtggggctct  3780
ggcctttgaa gatatataca ttgagcagcg aaaaaccatt aagaccatgt tagaatatgc  3840
tgacaaggtt ttcacttaca tattcattct ggaaatgctg ctaaagtggg ttgcatatgg  3900
ttttcaagtg tattttacca atgcctggtg ctggctagac ttcctgattg ttgatgtctc  3960
actggttagc ttaactgcaa atgccttggg ttactcagaa cttggtgcca tcaaatccct  4020
cagaacacta agagctctga ggccactgag agctttgtcc cggtttgaag gaatgagggt  4080
tgttgtaaat gctcttttag gagccattcc atctatcatg aatgtacttc tggtttgtct  4140
gatcttttgg ctaatattca gtatcatggg agtgaatctc tttgctggca agttttacca  4200
ttgtattaat tacaccactg gagagatgtt tgatgtaagc gtggtcaaca actacagtga  4260
gtgcaaagct ctcattgaga gcaatcaaac tgccaggtgg aaaaatgtga aagtaaactt  4320
tgataacgta ggacttggat atctgtctct acttcaagta gccacgttta agggatggat  4380
ggatattatg tatgcagctg ttgattcacg aaatgtagaa ttacaaccca agtatgaaga  4440
caacctgtac atgtatcttt attttgtcat ctttattatt tttggttcat tctttacctt  4500
gaatcttttc attggtgtca tcatagataa cttcaaccaa cagaaaaaga agtttggagg  4560
tcaagacatt tttatgacag aagaacagaa gaaatactac aatgcaatga aaaaactggg  4620
ttcaaagaaa ccacaaaaac ccatacctcg acctgctaac aaattccaag gaatggtctt  4680
tgattttgta accaaacaag tctttgatat cagcatcatg atcctcatct gccttaacat  4740
ggtcaccatg atggtggaaa ccgatgacca gagtcaagaa atgacaaaca ttctgtactg  4800
gattaatctg gtgtttattg ttctgttcac tggagaatgt gtgctgaaac tgatctctct  4860
tcgttactac tatttcacta ttggatggaa tattttgat tttgtggtgg tcattctctc  4920
cattgtagga atgtttctgg ctgaactgat agaaaagtat tttgtgtccc ctaccctgtt  4980
ccgagtgatc cgtcttgcca ggattggccg aatcctacgt ctgatcaaag gagcaaaggg  5040
gatccgcacg ctgctctttg ctttgatgat gtcccttcct gcgttgttta acatcggcct  5100
ccttcttttc ctggtcatgt tcatctacgc catctttggg atgtccaatt ttgcctatgt  5160
taagagggaa gttgggatcg atgacatgtt caactttgag acctttggca acagcatgat  5220
ctgcctgttc caaattacaa cctctgctgg ctgggatgga ttgctagcac ctattcttaa  5280
tagtggacct ccagactgtg accctgacaa agatcaccct ggaagctcag ttaaaggaga  5340
ctgtgggaac ccatctgttg ggattttctt ttttgtcagt tacatcatca tatccttcct  5400
ggttgtggtg aacatgtaca tcgcggtcat cctggagaac ttcagtgttg ctactgaaga  5460
aagtgcagag cctctgagtg aggatgactt tgagatgttc tatgaggttt gggagaagtt  5520
tgatcccgat gcgacccagt ttatagagtt tgccaaactt tctgattttg cagatgccct  5580
ggatcctcct cttctcatag caaaacccaa caaagtccag ctcattgcca tggatctgcc  5640
catggtgagt ggtgaccgga tccactgtct tgacatctta tttgctttta caaagcgtgt  5700
tttgggtgag agtggagaga tggatgccct tcgaatacag atggaagagc gattcatggc  5760
atcaaacccc tccaaagtct cttatgagcc cattacgacc acgttgaaac gcaaacaaga  5820
ggaggtgtct gctattatta tccagagggc ttacagacgc tacctcttga agcaaaaagt  5880
taaaaaggta tcaagtatat acaagaaaga caaaggcaaa gaatgtgatg gaacacccat  5940
caaagaagat actctcattg ataaactgaa tgagaattca actccagaga aaaccgatat  6000
gacgccttcc accacgtctc caccctcgta tgatagtgtg accaaaccag aaaaagaaaa  6060
atttgaaaaa gacaaatcag aaaaggaaga caaagggaaa gatatcaggg aaagtaaaaa  6120
gtaaaaagaa accaagaatt ttccattttg tgatcaattg tttacagccc gtgatggtga  6180
tgtgtttgtg tcaacaggac tcccacagga ggtctatgcc aaactgactg tttttacaaa  6240
tgtatactta aggtcagtgc ctataacaag acagagacct ctggtcagca aactggaact  6300
cagtaaactg gagaaatagt atcgatggga ggtttctatt ttcacaacca gctgacactg  6360
ctgaagagca gaggcgtaat ggctactcag acgataggaa ccaatttaaa ggggggaggg  6420
```

-continued

```
aagttaaatt tttatgtaaa ttcaacatgt gacacttgat aatagtaatt gtcaccagtg  6480
tttatgtttt aactgccaca cctgccatat ttttacaaaa cgtgtgctgt gaatttatca  6540
cttttctttt taattcacag gttgtttact attatatgtg actattttg taaatgggtt  6600
tgtgtttggg gagagggatt aaagggaggg aattctacat ttctctattg tattgtataa  6660
ctggatatat tttaaatgga ggcatgctgc aattctcatt cacacataaa aaaatcacat  6720
cacaaaaggg aagagtttac ttcttgtttc aggatgtttt tagatttttg aggtgcttaa  6780
atagctattc gtattttttaa ggtgtctcat ccagaaaaaa tttaatgtgc ctgtaaatgt  6840
tccatagaat cacaagcatt aaagagttgt tttattttta cataacccat taaatgtaca  6900
tgtatatatg tatatatgta tatgtgcgtg tatatacata tatatgtata cacacatgca  6960
cacacagaga tatacacata ccattacatt gtcattcaca gtcccagcag catgactatc  7020
acatttttga taagtgtcct ttggcataaa ataaaaatat cctatcagtc ctttctaaga  7080
agcctgaatt gaccaaaaaa catccccacc accactttat aaagttgatt ctgctttatc  7140
ctgcagtatt gtttagccat cttctgctct tggtaaggtt gacatagtat atgtcaattt  7200
aaaaaataaa agtctgcttt gtaaatagta attttaccca gtggtgcatg tttgagcaaa  7260
caaaaatgat gatttaagca cactacttat tgcatcaaat atgtaccaca gtaagtatag  7320
tttgcaagct ttcaacaggt aatatgatgt aattggttcc attatagttt gaagctgtca  7380
ctgctgcatg tttatcttgc ctatgctgct gtatcttatt ccttccactg ttcagaagtc  7440
taatatggga agccatatat cagtggtaaa gtgaagcaaa ttgttctacc aagacctcat  7500
tcttcatgtc attaagcaat aggttgcagc aaacaaggaa gagcttcttg ctttttattc  7560
ttccaacctt aattgaacac tcaatgatga aaagcccgac tgtacaaaca tgttgcaagc  7620
tgcttaaatc tgtttaaaat atatggttag agttttctaa gaaaatataa atactgtaaa  7680
aagttcattt tattttattt ttcagccttt tgtacgtaaa atgagaaatt aaaagtatct  7740
tcaggtggat gtcacagtca ctattgttag tttctgttcc tagcactttt aaattgaagc  7800
acttcacaaa ataagaagca aggactagga tgcagtgtag gtttctgctt ttttattagt  7860
actgtaaact tgcacacatt tcaatgtgaa acaaatctca aactgagttc aatgtttatt  7920
tgctttcaat agtaatgcct tatcattgaa agaggcttaa agaaaaaaaa aatcagctga  7980
tactcttggc attgcttgaa tccaatgttt ccacctagtc tttttattca gtaatcatca  8040
gtcttttcca atgtttgttt acacagatag atcttattga cccatatggc actagaactg  8100
tatcagatat aatatgggat cccagctttt tttcctctcc cacaaaacca ggtagtgaag  8160
ttatattacc agttacagca aaatactttg tgtttcacaa gcaacaataa atgtagattc  8220
tttatactga agctattgac ttgtagtgtg ttggtgaaat gcatgcagga aaatgctgtt  8280
accataaaga acggtaaacc acattacaat caagccaaaa gaataaaggt ttcgcttttg  8340
tttttgtatt taattgttgt ctttgtttct atctttgaaa tgccatttaa aggtagattt  8400
ctatcatgta aaaataatct atctgaaaaa caaatgtaaa gaacacacat taattactat  8460
aattcatctt tcaatttttt catggaatgg aagttaatta agaagagtgt attggataac  8520
tactttaata ttggccaaaa agctagatat ggcatcaggt agactagtgg aaagttacaa  8580
aaattaataa aaaattgact aaca                                         8604

SEQ ID NO: 8           moltype = AA  length = 2005
FEATURE                Location/Qualifiers
source                 1..2005
                       mol_type = protein
                       organism = Homo sapiens
SEQUENCE: 8
MAQSVLVPPG PDSFRFFTRE SLAAIEQRIA EEKAKRPKQE RKDEDDENGP KPNSDLEAGK  60
SLPFIYGDIP PEMVSVPLED LDPYYINKKT FIVLNKGKAI SRFSATPALY ILTPFNPIRK  120
LAIKILVHSL FNMLIMCTIL TNCVFMTMSN PPDWTKNVEY TFTGIYTFES LIKILARGFC  180
LEDFTFLRDP WNWLDFTVIT FAYVTEFVDL GNVSALRTFR VLRALKTISV IPGLKTIVGA  240
LIQSVKKLSD VMILTVFCLS VFALIGLQLF MGNLRNKCLQ WPPDNSSFEI NITSFFNNSL  300
DGNGTTFNRT VSIFNWDEYI EDKSHFYFLE GQNDALLCGN SSDAGQCPEG YICVKAGRNP  360
NYGYTSFDTF SWAFLSLFRL MTQDFWENLY QLTLRAAGKT YMIFFVLVIF LGSFYLINLI  420
LAVVAMAYEE QNQATLEEAE QKEAEFQQML EQLKKQQEEA QAAAAAASAE SRDFSGAGGI  480
GVFSESSSVA SKLSSKSEKE LKNRRKKKKQ KEQSGEEEKN DRVRKSESED SIRRKGFRFS  540
LEGSRLTYEK RFSSPHQSLL SIRGSLFSPR RNSRASLFSF RGRAKDIGSE NDFADDEHST  600
FEDNDSRRDS LFVPHRHGER RHSNVSQASR ASRVLPILPM NGKMHSAVDC NGVVSLVGGP  660
STLTSAGQLL PEGTTTETEI RKRRSSSYHV SMDLLEDPTS RQRAMSIASI LTNTMEELEE  720
SRQKCPPCWY KFANMCLIWD CCKPWLKVKH LVNLVVMDPF VDLAITICIV LNTLFMAMEH  780
YPMTEQFSSV LSVGNLVFTG IFTAEMFLKI IAMDPYYYFQ EGWNIFDGFI VSLSLMELGL  840
ANVEGLSVLR SFRLLRVFKL AKSWPTLNML IKIIGNSVGA LGNLTLVLAI IVFIFAVVGM  900
QLFGKSYKEC VCKISNDCEL PRWHMHDFFH SFLIVFRVLC GEWIETMWDC MEVAGQTMCL  960
TVFMMVMVIG NLVVLNLFLA LLLSSFSSDN LAATDDDNEM NNLQIAVGRM QKGIDFVKRK  1020
IREFIQKAFV RKQKALDEIK PLEDLNNKKD SCISNHTTIE IGKDLNYLKD GNGTTSGIGS  1080
SVEKYVVDES DYMSFINNPS LTVTVPIAVG ESDFENLNTE EFSSESDMEE SKEKLNATSS  1140
SEGSTVDIGA PAEGEQPEVE PEESLEPEAC FTEDCVRKFK CCQISIEEGK GKLWWNLRKT  1200
CYKIVEHNWF ETFIVFMILL SSGALAFEDI YIEQRKTIKT MLEYADKVFT YIFILEMLLK  1260
WVAYGFQVYF TNAWCWLDFL IVDVSLVSLT ANALGYSELG AIKSLRTLRA LRPLRALSRF  1320
EGMRVVVNAL LGAIPSIMNV LLVCLIFWLI FSIMGVNLFA GKFYHCINYT TGEMFDVSVV  1380
NNYSECKALI ESNQTARWKN VKVNFDNVGL GYLSLLQVAT FKGWMDIMYA AVDSRNVELQ  1440
PKYEDNLYMY LYFVIFIIFG SFFTLNLFIG VIIDNFNQQK KKFGGQDIFM TEEQKKYYNA  1500
MKKLGSKKPQ KPIPRPANKF QGMVFDFVTK QVFDISIMIL ICLNMVTMMV ETDDQSQEMT  1560
NILYWINLVF IVLFTGECVL KLISLRYYYF TIGWNIFDFV VVILSIVGMF LAELIEKYFV  1620
SPTLFRVIRL ARIGRILRLI KGAKGIRTLL FALMMSLPAL FNIGLLLFLV MFIYAIFGMS  1680
NFAYVKREVG IDDMFNFETF GNSMICLFQI TTSAGWDGLL APILNSGPPD CDPDKDHPGS  1740
SVKGDCGNPS VGIFFFVSYI IISFLVVVNM YIAVILENFS VATEESAEPL SEDDFEMFYE  1800
VWEKFDPDAT QFIEFAKLSD FADALDPPLL IAKPNKVQLI AMDLPMVSGD RIHCLDILFA  1860
FTKRVLGESG EMDALRIQME ERFMASNPSK VSYEPITTTL KRKQEEVSAI IIQRAYRRYL  1920
LKQKVKKVSS IYKKDKGKEC DGTPIKEDTL IDKLNENSTP EKTDMTPSTT SPPSYDSVTK  1980
PEKEKFEKDK SEKEDKGKDI RESKK                                        2005
```

-continued

```
SEQ ID NO: 9            moltype = AA  length = 2005
FEATURE                 Location/Qualifiers
source                  1..2005
                        mol_type = protein
                        organism = Homo sapiens
SEQUENCE: 9
MAQSVLVPPG PDSFRFFTRE SLAAIEQRIA EEKAKRPKQE RKDEDDENGP KPNSDLEAGK  60
SLPFIYGDIP PEMVSVPLED LDPYYINKKT FIVLNKGKAI SRFSATPALY ILTPFNPIRK  120
LAIKILVHSL FNMLIMCTIL TNCVFMTMSN PPDWTKNVEY TFTGIYTFES LIKILARGFC  180
LEDFTFLRDP WNWLDFTVIT FAYVTEFVNL GNVSALRTFR VLRALKTISV IPGLKTIVGA  240
LIQSVKKLSD VMILTVFCLS VFALIGLQLF MGNLRNKCLQ WPPDNSSFEI NITSFFNNSL  300
DGNGTTFNRT VSIFNWDEYI EDKSHFYFLE GQNDALLCGN SSDAGQCPEG YICVKAGRNP  360
NYGYTSFDTF SWAFLSLFRL MTQDFWENLY QLTLRAAGKT YMIFFVLVIF LGSFYLINLI  420
LAVVAMAYEE QNQATLEEAE QKEAEFQQML EQLKKQQEEA QAAAAAASAE SRDFSGAGGI  480
GVFSESSSVA SKLSSKSEKE LKNRRKKKKQ KEQSGEEEKN DRVRKSESED SIRRKGFRFS  540
LEGSRLTYEK RFSSPHQSLL SIRGSLFSPR RNSRASLFSF RGRAKDIGSE NDFADDEHST  600
FEDNDSRRDS LFVPHRHGER RHSNVSQASR ASRVLPILPM NGKMHSAVDC NGVVSLVGGP  660
STLTSAGQLL PEGTTTETEI RKRRSSSYHV SMDLLEDPTS RQRAMSIASI LTNTMEELEE  720
SRQKCPPCWY KFANMCLIWD CCKPWLKVKH LVNLVVMDPF VDLAITICIV LNTLFMAMEH  780
YPMTEQFSSV LSVGNLVFTG IFTAEMFLKI IAMDPYYYFQ EGWNIFDGFI VSLSLMELGL  840
ANVEGLSVLR SFRLLRVFKL AKSWPTLNML IKIIGNSVGA LGNLTLVLAI IVFIFAVVGM  900
QLFGKSYKEC VCKISNDCEL PRWHMHDFFH SFLIVFRVLC GEWIETMWDC MEVAGQTMCL  960
TVFMMVMVIG NLVVLNLFLA LLLSSFSSDN LAATDDDNEM NNLQIAVGRM QKGIDFVKRK  1020
IREFIQKAFV RKQKALDEIK PLEDLNNKKD SCISNHTTIE IGKDLNYLKD GNGTTSGIGS  1080
SVEKYVVDES DYMSFINNPS LTVTVPIAVG ESDFENLNTE EFSSESDMEE SKEKLNATSS  1140
SEGSTVDIGA PAEGEQPEVE PEESLEPEAC FTEDCVRKFK CCQISIEEGK GKLWWNLRKT  1200
CYKIVEHNWF ETFIVFMILL SSGALAFEDI YIEQRKTIKT MLEYADKVFT YIFILEMLLK  1260
WVAYGFQVYF TNAWCWLDFL IVDVSLVSLT ANALGYSELG AIKSLRTLRA LRPLRALSRF  1320
EGMRVVVNAL LGAIPSIMNV LLVCLIFWLI FSIMGVNLFA GKFYHCINYT TGEMFDVSVV  1380
NNYSECKALI ESNQTARWKN VKVNFDNVGL GYLSLLQVAT FKGWMDIMYA AVDSRNVELQ  1440
PKYEDNLYMY LYFVIFIIFG SFFTLNLFIG VIIDNFNQQK KKFGGQDIFM TEEQKKYYNA  1500
MKKLGSKKPQ KPIPRPANKF QGMVFDFVTK QVFDISIMIL ICLNMVTMMV ETDDQSQEMT  1560
NILYWINLVF IVLFTGECVL KLISLRYYYF TIGWNIFDFV VVILSIVGMF LAELIEKYFV  1620
SPTLFRVIRL ARIGRILRLI KGAKGIRTLL FALMMSLPAL FNIGLLLFLV MFIYAIFGMS  1680
NFAYVKREVG IDDMFNFETF GNSMICLFQI TTSAGWDGLL APILNSGPPD CDPDKDHPGS  1740
SVKGDCGNPS VGIFFFVSYI IISFLVVVNM YIAVILENFS VATEESAEPL SEDDFEMFYE  1800
VWEKFDPDAT QFIEFAKLSD FADALDPPLL IAKPNKVQLI AMDLPMVSGD RIHCLDILFA  1860
FTKRVLGESG EMDALRIQME ERFMASNPSK VSYEPITTTL KRKQEEVSAI IIQRAYRRYL  1920
LKQKVKKVSS IYKKDKGKEC DGTPIKEDTL IDKLNENSTP EKTDMTPSTT SPPSYDSVTK  1980
PEKEKFEKDK SEKEDKGKDI RESKK                                      2005
```